United States Patent [19]
Roberts et al.

[11] Patent Number: 6,051,549
[45] Date of Patent: *Apr. 18, 2000

[54] HEPARIN AND SULFATIDE BINDING PEPTIDES FROM THE TYPE-I REPEATS OF HUMAN THROMBOSPONDIN AND CONJUGATES THEREOF

[75] Inventors: David D. Roberts; Henry C. Krutzsch, both of Bethesda; Nenghua Guo, Gaithersburg, all of Md.

[73] Assignee: The United States of America as represented by the Department of Health and Human Services, Washington, D.C.

[*] Notice: This patent is subject to a terminal disclaimer.

[21] Appl. No.: 09/041,119

[22] Filed: Mar. 11, 1998

Related U.S. Application Data

[63] Continuation of application No. 08/487,568, Jun. 7, 1995, Pat. No. 5,770,563, which is a continuation-in-part of application No. 08/215,085, Mar. 21, 1994, abandoned, which is a continuation-in-part of application No. 07/801,812, Dec. 6, 1991, Pat. No. 5,357,041.

[51] Int. Cl.$^7$ .............................. A61K 38/00; C07K 7/00
[52] U.S. Cl. .................................. 514/2; 514/12; 514/13; 514/14; 514/15; 514/908; 530/300; 530/324; 530/326; 530/327; 435/4; 435/13
[58] Field of Search ............................... 514/2, 8, 12–18, 514/900; 530/300, 324–327; 435/4, 13

[56] References Cited

FOREIGN PATENT DOCUMENTS

| 0 443 404 | 8/1991 | European Pat. Off. . |
|---|---|---|
| Wo 90/01496 | 2/1990 | WIPO . |

OTHER PUBLICATIONS

CAPLUS AN 1995:487002 to J.Biol.Chem. vol. 270(13) pp. 7304–7310, Mar. 1995.
Cardin et al., "Molecular Modeling of Protein–Glycosaminoglycan Interactions" *Arteriosclerosis* 9(1):21–32 (1989).
Dixit et al., "Isolation and Characterization of a Heparin–binding Domain from the Amino Terminus of Platelet Thrombospondin", *J.Biol.Chem.*, 259 (16):10100–10105 (1984).
Schultz–Cherry et al., "Regulation of Transforming Grown Factor–αActivation by Discrete Sequences of Thrombospondin 1", *J. Biol. Chem.*, 270(13):7304–7310 (1995).
Sipes et al., "Inhibiion of Fibronectin Binding and Fibronectin–mediated Cell Adhesion to Collagen by Peptide from the Second Type I Repeat of Thrombospondin" *J. Cell Biol.*, 121(2):469–477 (1993).
Vogel et al., "Modulation of Endothelial Cell Proliferation, Adhesion, and Motility by Recombinant Heparin–Binding Domain and Synthetic Peptides from the Type I Repeats of Thrombospondin"*J. Cell Biochem.*, 53:74–84 (1993).
Weinstat–saslow et al., "Transfection of Thrombospindin 1 Complementary DNA into a Human Breast Carcinoma Cell Line Reduces Tumor Growth, Metastic Potential, and Angiogenesis", *Cancer Res.*, 54:6504–6511 (1994).
Kaesberg et al., "Chinese Hamster Ovary Cell Adhesion to Human Platelet Thrombospondin Is Dependent on Cell Surface Heparin Sulfate Proteoglycan", *J. Clin. invest.*, 83:994–1001 (1989).
Prater et al., "The Properdin–like Type I Repeats of Human Thrombospondin Contain a Cell Attachment Site", *J. Cell. Biol.*, 112(5):1031–1040 (1994).
Rich et al., "Cell–Adhesive Motif in Region II of Malarial Circumsporozoite Protein", *Science*, 249:1574–1577 (1990).
Roberts et al., "The Platelet Glycoprotein Thrombospondin Binds Specifically to Sulfated Glycolipids", *J. Biol. Chem.*, 260(16):9405–9411 (1985).
Roberts et al., "Platelet Thromsbospondin Mediates Attachment and Spreading of Human Melanoma Cells", *J. Cell Biol.*, 104:131–139 (1987).
Roberts et al., "Interaction of Thrombospondin with Sulfated Glycolipids and Proteoglycans of Human Melanoma Cells", *Cancer Res.*, 48:6785–6793 (1988).
Sturgeon et al., "Affinity Chromatography of Sialoglycoproteins, Utilising the Interaction of Serotonin with N–Acetylneuraminic Acid and Its Derivatives", *Carbohydr, Res.*, 103:213–219 (1982) .
Taroboletti et al., "Sulfatide–binding Domain of the Laminin A Chain", *J. Biol. Chem.*, 265(21) :12253–12258 (1990).
Todaro et al., Transforming growth factors produced by certain human tumor cells: Polypeptides that interact with epidermal growth factor receptors: , *Proc. Natl. Acad. SCi. USA*, 77(9):5258–5262 (1980).

(List continued on next page.)

*Primary Examiner*—Bennett Colba
*Attorney, Agent, or Firm*—Townsend and Townsend and Crew LLP

[57] ABSTRACT

This invention identifies a biologically active group of peptide sequences from Type I repeat units of the extracellular matrix protein, human thrombospondin-1, identical or homologous to the sequence, KRFKQDGGWSHWSP-WSSC (SEQ ID NO.30). The biological activities residing with the full sequences, portions thereof, and variants of the full or partial sequences are disclosed. The invention describes how biological activity may be enhanced by covalently linking these peptides to suitable carriers, preferably a branched, water-soluble polymer of low (or absent) toxicity and immunogenicity, such as polysucrose (Ficoll™). The invention describes (1) a method for preparing such conjugates, (2) the use of the defined peptides or their conjugates in blocking or modifying the action on cellular processes of heparin (e.g., proliferation, adhesion, motility, extravasation and neovascularization), sulfatides, related sulfated glycoconjugates, fibronectin, and basic fibroblast growth factor, involving malignant cell lines and normal endothelial cells. Use of the defined peptides, analogs or peptidomimetics and their conjugates for treatment of metastatic tumors, breast carcinomas, melanomas, Kaposi's sarcomas, hemangiomas, diabetic retinopathies, and various pathological conditions dependent upon neovascularization is also disclosed.

9 Claims, 63 Drawing Sheets

OTHER PUBLICATIONS

Tuszynski et al., Biolgical Activities of Peptides and Peptide Analogues Derived from Commonn Sequences Present in Thrombospondin, Properdin, and Malarial Proteins: , *J. Cell. Biol.,* 116(1):209–218 (1992).

Zabrenetzky et al., "Suramin Inhibits Laminin– and Thrombospondin–mediated Melanoma Cell Adhesion and Migration and Binding of These Adhesivr Proteins to Sulfatide", *Cancer Res.,* 50 :5937–5942 (1990).

Blackburn et al., The Heparin–binding Site of Antithrombin III:, *J. Biol. Chem.,* 259 (2) :939–941 (1984).

Bornstein, et al., "A Second, Expressed Thrombospondin Gene (Thbs2) Exists in the Mouse Genome", *J. Biol. Chem.,* 266(20) :12821–12824 (1991).

Cygler et al., "Recognition of a Cell–Surface Oligosaccharide of Pathogenic Salmonella by an Antibody Fab Fragment", *Science,* 253:442–445 (1991).

Danilov et al., "(Arg–Gly–Asp)$_n$–Albumin Conjugates as a Model Substratum for Integrin–Mediated Cell Adhesion", *Exp. Cell Res.,* 182:186–196 (1989).

Funahashi et al., "Preparation of Three Types of Heparin–Sepharose and Their Binding Activities to Thrombin and Antithrombin III", *Anal. Biochem.,* 126:414–421 (1982).

Guo et al., "Heparin– and Sulfatide–Binding Peptides from the Type I Repeats of Human Thrombospondin Promote Melanoma Cell Adhesion", *Proc. Natl. Acad. Sci. USA,* 89:3040–3044 (1992).

Guo et al.,Heparin–binding Peptides from the Type I Repeats of Thrombospondin: Structural Requirements for Heparin Binding and Promotion of Melanoma Cell Adhesion and Chemotaxis:, *J. Biol. Chem.,* 267(27):19349–19355 (1992).

Holt et al., "Antistasin, an Inhibitor of Coagulation and Metastasis, Binds to Sulfatide (Gal (3–$SO_4$)α1–1Cer and has a Sequence Homology with other Proteins that Bind Sulfated Glycoconjugates", *J. Biol. chem.,* 264(21): 12138–12140 (1989).

Jackson et al., "Glycosaminoglycans: Molecular Properties, Protein Interactions, and Role in Physiological Processes", *Physiol. Rev.,* 71(2) :481–539 (1991).

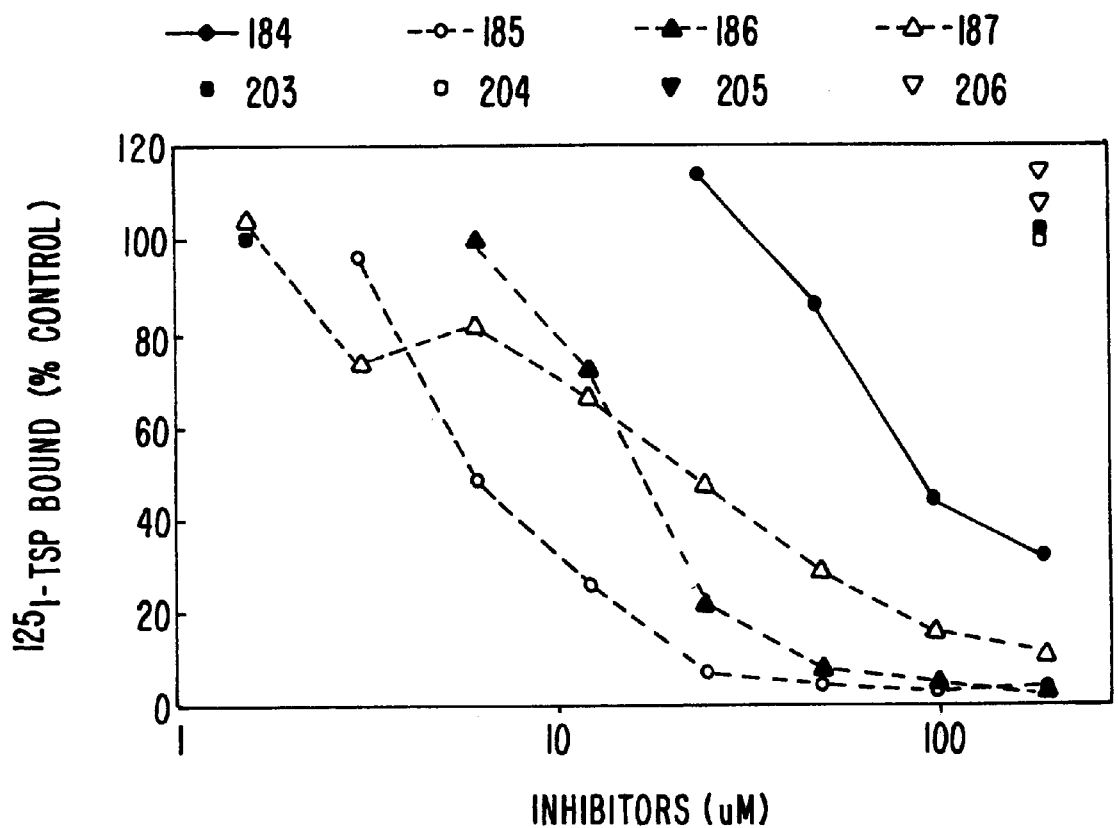
FIG. IA.

HEPARIN AND SULFATIDE BINDING PEPTIDES FROM THE TYPE-I REPEATS OF HUMAN THROMBOSPONDIN AND CONJUGATES THEREOF

This application is a continuation of and claims the benefit of U.S. application Ser. No. 08/487,568, filed Jun. 7, 1995, now U.S. Pat. No. 5,770,563, which is a continuation-in-part of U.S. patent application Ser. No. 08/215,085, filed Mar. 21, 1994, now abandoned, which is a continuation-in-part of U.S. patent application Ser. No. 07/801,812, filed Dec. 6, 1991, now U.S. Pat. No. 5,357,041.

BACKGROUND OF THE INVENTION

I. Technical Field

The present invention relates to peptides from the three type I repeats of human endothelial cell thrombospondin, and analogs and peptidomimetics based on these sequences which bind to sulfated glycoconjugates including heparin and sulfatide.

The invention also relates to conjugates of peptides from the three type I repeats of human endothelial cell thrombospondin with polysucrose or dextran.

The invention also relates to peptide mimetics and analogs based on the active thrombospondin sequences and conjugates thereof, and thiol derivatives thereof.

Additionally the invention relates to the use of the thrombospondin-derived peptides and conjugates as inhibitors of endothelial cell growth.

The invention also relates to the use of the peptides, analogs, and peptidomimetics, and conjugates derived from thrombospondin as inhibitors of tumor cell growth, including inhibition of breast cancer cell growth and melanoma cell growth.

The invention relates to the use of the peptides and conjugates of thrombospondin for treatment of Kaposi's sarcoma.

The invention relates to a method of treating a subject suffering from disease, involving abnormal vascular proliferation, including cancer, comprising administering to the subject peptides or peptide conjugates in a pharmaceutically acceptable carrier.

II. Background of the Invention

Heparin binding is critical for activities associated with many cellular growth factors, cell adhesion molecules, and certain enzymes involved in the blood clotting cascade. Agents to inhibit these interactions have found numerous uses in prevention of thrombosis. Heparin analogues have been shown to have anti-tumor and antimetastatic activities.

Peptides that bind to heparin have been identified or isolated from many heparin binding proteins (see, e.g., Cardin et al., *Arteriosclerosis*, Vol. 9, pages 21–32 (1989)). Examples of heparin binding peptides identified from adhesion molecules include type IV collagen, laminin, and fibronectin. All have clusters of basic amino acids which fit consensus sequences defined by comparison of many heparin binding proteins (see Cardin et al., as above). The binding constants of the Cardin et al peptides and other peptides described in this art area are in the general range of $10^4$ to $10^5$ molar$^{-1}$.

Peptides from malaria circumsporozoite protein have been disclosed to mediate cell adhesion (Rich et al., *Science*, Vol 249:1574–1577 (1990)). Such peptides suffer from the disadvantages of not binding heparin and the adhesion activity was ascribed to a sequence Val—Thr—Cys—Gly (SEQ ID NO:5), which is inactive for heparin binding.

Peptides from thrombospondin have been disclosed (Prater et al., *J. Cell Biol.* Vol 112, pages 1031–1040 (1992)). The sequences of Prater have a significant disadvantage since they are insufficient to bind to heparin or related sulfated glycoconjugates with high affinity.

Accordingly, there is a need in the present art for highly potent peptides that will bind to heparin or related sulfated glycoconjugates with high affinity. There is particularly a need for such peptides which are also useful to prevent interaction of heparin or related sulfated glyconjugates with adhesion molecules, growth factors, cells or heparin-dependent enzymes. Accordingly, it is an object of the present invention to overcome the difficulties in the prior art as described above.

SUMMARY OF THE INVENTION

In one aspect of the present invention to provide highly potent peptides having sequences which bind to heparin or related sulfated glycoconjugates with high affinity which are useful to prevent interaction of heparin or related sulfated glycoconjugates with adhesion molecules, growth factors, cells, or heparin dependent enzymes.

It is further an object to provide peptides which have binding constants which are unexpectedly superior to the binding constants of proteins (peptides) which are known in the art.

In a further aspect of the present invention is provided peptides which have a high binding affinity to heparin or related sulfated glycoconjugates and which lack a charge (essentially neutral peptides) in order to formulate more advantageous pharmaceutical agents for efficient delivery to the sites of action.

It is a still further object of the present invention to provide peptides having high potency for binding with heparin or related sulfated glycoconjugates in order to allow much smaller amounts of peptide to be effectively administered and thus reduce risk of toxicity and generation of immune responses against the peptides.

Another object is to provide a composition comprising peptide of the invention conjugated with a suitable carrier polymer or protein. The peptide is preferably covalently linked to polysucrose or dextran.

The invention also provides for a method of increasing the stability and of increasing the inhibitory activity for thrombospondin, basic fibroblast growth factor, or other heparin dependent factors binding to heparin, of a synthetic peptide comprising a type I repeat of thrombospondin by conjugating the synthetic peptide to polymeric carriers, including polysucrose or dextran.

It is an object to provide a method of increasing the stability and of increasing the inhibitory activity for thrombospondin binding to heparin, of a synthetic peptide comprising a type I repeat of thrombospondin or analogs thereof, wherein the step of conjugating the synthetic peptide to polysucrose such as FICOLL comprises the steps of:

(a) adding urea to a solution of N-iodoacetamidopropionyl-aminoethyl-carbamylmethylated FICOLL;

(b) reducing disulfide bonds in the synthetic peptide;

(c) adding the peptide of step (b) to resultant solution of step (a);

(d) adding 2-mercaptoethanol to product of step (c); and (e) isolating a conjugate of the synthetic peptide and FICOLL.

The invention also provides for a method of promoting the adhesion and growth of anchorage-dependent cells and a method of inhibiting eukaryotic cell proliferation by administering an effective amount of a composition comprising a synthetic peptide comprising a type I repeat of thrombospondin covalently linked to polysucrose or dextran to a eukaryotic cell.

The eukaryotic cell, in a preferred embodiment, is selected from the group consisting of corneal or aortic endothelial cells or human breast carcinoma or melanoma cells.

Additionally the invention provides use of the peptides and conjugates of thrombospondin as inhibitors of endothelial cell growth, tumor cell growth, including inhibition of breast cancer cell growth and melanoma cell growth, and as inhibitors of Kaposi's sarcoma cell proliferation in vitro and in vivo.

In an additional embodiment, the present invention provides substantially pure peptides which comprise from about 10 to about 30, amino acids in length, and the general amino acid sequence $(X_5—X_6—X_7—X_8)_i—X_9—X_{10}—(X_{11})_m—(G)_n—W—S—X_{12}—W—(S—X_{13}—W)_z$ (SEQ. ID. NO:57 through SEQ ID NO:72). In this embodiment, $X_5$ is selected independently from R, K, acR and acK, $X_6$ is selected independently form R or K, $X_8$ is selected independently from R or K, $X_7$ is F or A, i is 0 or 1, $X_9$ is Q or A, $X_{10}$ is D or A, $X_{11}$ is G or U (Dav) and m is 1 or 0, n is 1 or 0, $X_{12}$ is H or P; and $X_{13}$ is H or P and z is 1 or 0. These peptides may be free or conjugated to, e.g. a water soluble polymer. Preferred peptides will typically be from about 10, 11, 12, 13, 14, 15, 16, 17, or 18 to 30 amino acids in length.

In a related embodiment, the present invention provides a substantially pure retro-inverso peptide from about 10 to about 30 amino acids in length, wherein said retro-inverso peptide comprises the amino acids sequence, from C-terminal (left) to N-terminal (right), ri-$(X_5'—X_6'—X_7—X_8)_i—X_9—X_{10}—(X_{11})_m—(G)_n—W—S—X_{12}—W—(S—X_{13}—W)_z$. In this embodiment, ri denotes a retro-inverso peptide and all amino acids are D amino acids. Further, $X_5'$, $X_6'$ are selected independently from R, K, amR and amK, $X_8$ is selected independently from R or K, $X_7$ is F or A, i is 0 or 1, $X_9$ is Q or A, $X_{10}$ is D or A, $X_{11}$ is G or U (Dav) and m is 1 or 0, n is 1 or 0, $X_{12}$ is H or P and $X_{13}$ is H, P and z is 1 or 0. These peptides may be free or conjugated to, e.g. a water soluble polymer. Again, preferred peptides will typically be from about 10, 11, 12, 13, 14, 15, 16, 17, or 18 to 30 amino acids in length.

Also provided herein are pharmaceutical compositions comprising the peptides of the invention, in combination with a pharmaceutically acceptable carrier.

The present invention also provides methods of inhibiting heparin or heparan sulfate interaction in a sample, without activating latent TGF-β present in the sample. The methods comprise contacting the sample with an effective amount of a peptide of the invention.

Further provided by the instant invention are methods of inhibiting interaction of heparin or heparan sulfate with FGF-2 in a sample, comprising contacting the sample with an effective amount of the peptide of the invention.

Also provided are methods of inhibiting endothelial cell proliferation, comprising contacting the endothelial cells with an effective amount of the peptide of the invention.

In a further embodiment, the present invention also provides methods of inhibiting tumor growth in a patient, comprising administering to said patient, an effective amount of a peptide of the invention in a pharmaceutically acceptable carrier.

BRIEF DESCRIPTION OF THE DRAWINGS

FIGS. 1A and 1B are graphs illustrating the inhibition of $^{125}$I-thrombospondin binding to sulfated glycoconjugates by thrombospondin peptides.

Figure 1B:
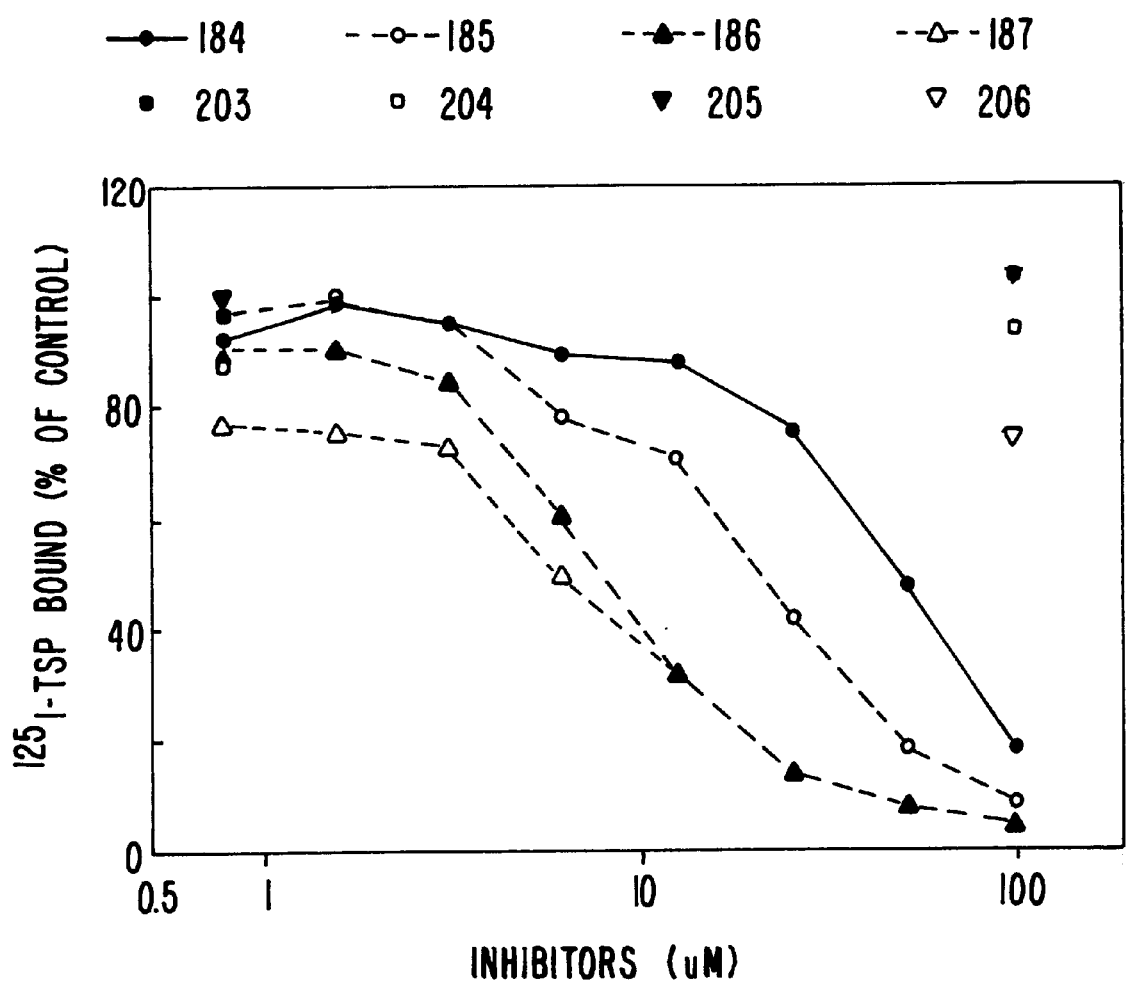

The primary inhibitory activity resides in an octapeptide sequence in each type I repeat that generally lacks basic amino acids but contain two conserved Trp residues and one conserved Ser residue. Substitutions with Ala demonstrate that at least one of the Trp residues and the Ser residue are essential for heparin or sulfatide binding and for promoting melanoma cell adhesion. The weak activity of SSCSVT (SEQ ID NO:13) and the enhanced activity of WSPWSSCSVT (SEQ ID NO:16) versus WSPWSSCS (SEQ ID NO:15) suggests that a second active sequence may be present. However, the tetrapeptides CSVT (SEQ ID NO:9) or the previously described VTCG (SEQ ID NO:5) are inactive. The peptide CSVTCG (SEQ ID NO:4) is active. Its activity may require disulfide mediated polymerization, however, since substitution of the first Cys with Ser to prevent polymerization eliminates most activity. It remains to be determined whether two subsites are present or whether the differences in activity of the peptides are due to variation in conformation of a single active sequence among the peptides. VTCG (SEQ ID NO:5) is proposed to be a potential adhesive sequence in the type I repeats that binds to protein receptors for thrombospondin (Rich et al., *Science* 249, 1574–1577 (1990); Prater et al., *J. Cell Biol.* 112, 1031–1040 (1991)). This sequence does not bind heparin, but the related peptide CSVTCG (SEQ ID NO:4) inhibits thrombospondin binding to heparin. Because CSVTCG (SEQ ID NO:4) also inhibits binding of laminin and apolipoprotein E, however, this peptide is not useful as a specific probe of thrombospondin binding to potential protein receptors recognizing the VTCG (SEQ ID NO:5) sequence.

A minimal consensus sequence of —Trp—Ser—Xaa—Trp— (SEQ ID NO:73) was derived by comparison of the sequences of the most active peptides. The amino acid residues absolutely conserved in this sequence are the two tryptophans and the serine following the first Trp. At least one of the two Trp residues is essential for activity as substitution of both residues with alanine abolished activity.

Thus, in contrast to previously defined hedarin binding peptides containing clusters of basic amino acid residues (Cardin et al., *Arteriosclerosis* 9, 21–32 (1989); Jackson et al., *Physiol. Rev.* 71, 481–539, (1991)), tryptophan is a major determinant for heparin binding to the type I repeats. Tryptophan has been implicated in heparin binding to antithrombin III (Blackburn et al., *J. Biol. Chem.* 259, 939–941 (1984)). Chemical modification of Trp 49 blocked heparin binding and heparin-enhanced inhibition of thrombin by antithrombin III. Tryptophan was shown by crystallographic analysis to be directly involved in carbohydrate binding to an anti-carbohydrate monoclonal antibody (Cygler et al., *Science* 252, 442–445, (1991)) and was shown to interact with carbohydrates via van der Waals interactions and hydrogen bonding. An analog of tryptophan, serotonin was also reported to specifically bind to sialyl oligosaccharides (Sturgeon et al., *Carbohydr. Res.* 103, 213–219 (1982)). Further characterization of the interactions of the thrombospondin peptides with heparin, including spectroscopic and crystallographic analysis, will be needed to determine the role of tryptophan in binding and to examine the contribution of other amino acids including the conserved serine.

Although heparin competes for sulfatide binding to laminin and thrombospondin, the type I repeat peptides reveal some differences between heparin and sulfatide binding activities. The previously defined heparin-binding consensus sequences from the amino terminal domain of thrombospondin weakly inhibit heparin binding. A similar sequence in the second type I repeat enhances inhibition of heparin binding when included with the tryptophan-containing heparin binding sequence. Peptides containing the heparin binding motif BBXB (SEQ ID NO:74) where B is Lys, Arg, or His and X is any amino acid reside, however, failed in all cases to interact with sulfatide. In fact, addition of the basic sequence in the second repeat decreased activity in sulfatide binding assays. A heparin binding motif in conjunction with VTCG (SEQ ID NO:5), which was proposed to mediate sulfatide binding by proteins sharing type I repeat homologies (Holt et al., *J. Biol. Chem.* 264, 12138–12140 (1989)), did not inhibit thrombospondin binding to heparin or sulfatide and weakly inhibited laminin binding only to heparin. These findings are consistent with previous reports that heparin binding consensus sequences in a denatured 30 Kd fragment of the A chain of laminin are sufficient for heparin but not for sulfatide binding (Taraboletti et al., *J. Biol. Chem.* 265, 12253–12258 (1990)).

Thrombospondin contains two potential heparin binding sites. Both direct binding and antibody inhibition indicate that the amino terminal domain is involved in some interactions with sulfated glycoconjugates on cells. Based on the present results, the type I repeats contain strong heparin binding sequences. Interaction of the 50–70 kD fragment of thrombospondin, which contains these sequences, with melanoma cells is partially heparin dependent (Prater et al., *J. Cell Biol.* 112, 1031–1040 (1991)). However, the larger 140 kD fragment containing the same sequences does not bind to heparin, sulfatide or heparan sulfate (Roberts, *Cancer Res.* 48, 6785–6793 (1988); Kaesberg et al., *J. Clin. Invest.* 83, 994–1001 (1989)). Thus, the sequences are cryptic in this fragment. The sequence is probably active in smaller thrombospondin fragments, since a 50 to 70 kDA fragment of thrombospondin containing this sequence binds to heparin (Guo et al.).

B. Endothelial cell growth inhibition

The current model for regulation of angiogenesis involves both stimulatory or angiogenic factors and inhibitory or anti-angiogenic factors (Folkman J, Shing Y (1992), *J. Biol. Chem.* 267:10931–10934; Folkman J, Klagsbrun M (1987), *Science* 235:442–447.) In normal adult endothelium, high expression of anti-angiogenic factors and limited availability of angiogenic factors maintains the endothelium in a nonproliferative state. Pathological states including wound repair, diabetic retinopathy or tumor growth may alter the balance of these simulators or inhibitors to allow neovascularization to proceed (Folkman J, Shing Y (1992), *J. Biol. Chem.* 267:10931–10934).

The major identified stimulators of angiogenesis produced by tumors are basic fibroblast growth factor (bFGF) and vascular endothelial cell growth factor (VEGF). These are potent stimulators of endothelial cell growth and motility in vitro. Several anti-angiogenic factors have also been identified, including thrombospondin (Good DJ, et al., (1990), *Proc. Natl. Acad. Sci. U.S.A.* 87:6624–6628; Taraboletti G, et al. (1990), *J. Cell Biol.* 111:765–772), interferon-alpha (Ezekowitz R A B, et al., (1992), *N. Engl. J. Med.* 326:1456–1463), platelet factor 4 (Maione T E, et al., (1990), *Science* 247:77–79), the $Ca^{2+}$ binding protein, SPARC (Funk S E, Sage H (1991), Proc. Natl. Acad. U.S.A. 88:2648–2652), apolipoprotein E and a proteolytic fragment of fibronectin (Homandberg, G A, et al.,(1986), *Biochim. Biophys. Acta* 874:61–71). The mechanism for action of angiogenesis inhibitors is less clear. Some of these proteins bind to heparin, and this binding activity may be responsible for some of the anti-angiogenic activities.

It has been shown that apolipoprotein E and heparin-binding recombinant fragments and synthetic peptides from thrombospondin can compete for binding of bFGF to endothelial cells or heparin and inhibit proliferative and migratory responses of endothelial cells to bFGF (Vogel T, et al., supra; and Vogel T. et al., (1993), J. Cell. Biochem. 53:74–84).

Thrombospondin is a major component of the α-granules of platelets and is a member of a gene family synthesized by many cell types in tissue culture (reviewed in Frazier W A (1991), *Curr. Opin. Cell Biol.* 3:792–799; and Mosher D F (1990), *Annu. Rev. Med.* 41:85–97). Thrombospondin-1 (TSP) is the product of the THBS1 gene (Wolf F W, et al., (1990), *Genomics* 6:685–691) and is the major form of this protein family in platelets and endothelial cells. In examining the role of thrombospondins in tumor metastasis, TSP from platelets has been used. Metastasis is a complex process involving escape of tumor cells from a primary tumor, local invasion of surrounding tissue, invasion through capillaries, arrest in specific target organs, extravasation, and colonization of the target organ (Aznavoorian S, et al., (1993), *Cancer* 71:1368–1383). Expression of oncogenes or loss of tumor suppressor genes presumably leads to expression of the many matrix degrading enzymes, adhesion molecules, motility factors, and growth factors that regulate tumor metastasis.

The role of TSP in development or progression of breast cancer is not known. Thrombospondin is synthesized by normal breast stromal cells in tissue culture (Baley P, et al., (1990), *J. Cell. Biochem.* 43:111–125) and is a normal component of human milk (Dawes J, et al., (1987), *Sem. Thromb. Hemost.* 13:378–384).

Immunohistochemical analyses of TSP expression in malignant breast tissues demonstrated strong staining in desmoplastic stroma and in the basement membrane associated with malignant ductal epithelium (Wong S Y, et al., (1992), *Am. J. Pathol.* 140:1473–1482). However, TSP is also expressed in the basement membrane of normal myoepithelial cells, and most invasive ductal carcinoma cells do not express TSP 920. High expression of TSP in breast carcinoma is restricted to invasive lobular carcinoma (Clezardin P, et al., (1993), *Cancer Res.* 53:1421–1430).

Thus, expression of TSP may be lost in some types of invasive breast carcinoma. This finding correlates with the in vitro observation that expression of TSP in hybrids of normal mammary epithelial cells with MCF-7 breast cancer cells was inversely related to their invasive behavior (Zajchoski D A, et al., (1990), *Proc. Natl. Acad. Sci. U.S.A.* 87:2314–2318).

TSP may play a role in several steps in the metastatic cascade. TSP promotes tumor cell adhesion and motility (Roberts D D, et al., (1987), *J. Cell. Biol.* 104:131–139; Taraboletti G, et al., (1987), *J. Cell. Biol.* 105:2409–2415), which are important in several steps of metastasis. Thrombospondin has also been reported to enhance melanoma cell interactions with platelets (Katagiri Y, et al., (1991), *Cancer Res.* 51:1286–1293.), which is critical to arrest and extravasation of circulating tumor cells during hematogenous metastasis. TSP is a tight binding inhibitor of several neutral proteases including plasmin, neutrophil elastase and cathepsin G (Hogg P J, et al., (1993), *J. Biol. Chem.* 268:21811–21818; Hogg P J, et al., (1993), *J. Biol. Chem.* 268:7139–7146), and so could potentially regulate tumor invasion through matrix. Finally, TSP has been identified as an inhibitor of angiogenesis (Good D J, et al., (1990), *Proc. Natl. Acad. Sci. U.S.A.* 87:6624–6628; Taraboletti G, et al., (1990), *J. Cell Biol.* 111:765–772; and Iruela-Arispe M L, et al., (1991), *Proc. Natl. Acad. Sci. U.S.A.* 88:5026–5030), which is critical for recruitment of blood vessels needed to support growth of the primary tumor and for development of hematogenous metastases. Because the ability to induce angiogenesis is associated with increased frequency of lymph node metastasis in breast cancer, the effects of TSP both on tumor cells and on endothelial cells was explored.

TSP is present at very low levels in plasma, but its concentration is elevated at sites of platelet activation. TSP is found in intracellular granules of endothelial cells and is enriched in the subendothelial matrix in vivo (Wight T N, et al., (1985), *J. Histochem. Cytochem.* 33:295–302; Munjal ID, et al., (1990), *Eur. J. Cell Biol.* 52:252–263). Thus, endothelial cells are exposed to significant concentrations of TSP in vivo. Endothelial cell responses to TSP are complex; the magnitude and direction of the responses depend upon the presence of additional matrix components and growth factors. Immobilized TSP promotes endothelial cell adhesion on some substrates but inhibits adhesion on others, including substrates coated with fibronectin (Lahav J, (1988), *Exp. Cell Res.* 177:199–204). Inhibition of adhesion to fibronectin is associated with disruption of focal adhesion contacts (Murphy-Ullrich J E, Höök M (1989), *J. Cell Biol.* 109:1309–1319). TSP promotes migration of endothelial cells in chemotaxis and haptotaxis assays but inhibits chemotaxis induced by bFGF (Taraboletti G, et al., (1990), *J. Cell Biol.* 111:765–772). TSP inhibits proliferation and spontaneous tube formation by endothelial cells in vitro (Iruela-Arispe M L, et al., (1991), *Proc. Natl. Acad. Sci. U.S.A.* 88:5026–5030) and inhibits angiogenesis in vivo. A 140 kD fragment of TSP has been identified as the anti-angiogenic factor in conditioned medium of hamster kidney cells.

Figure 28:
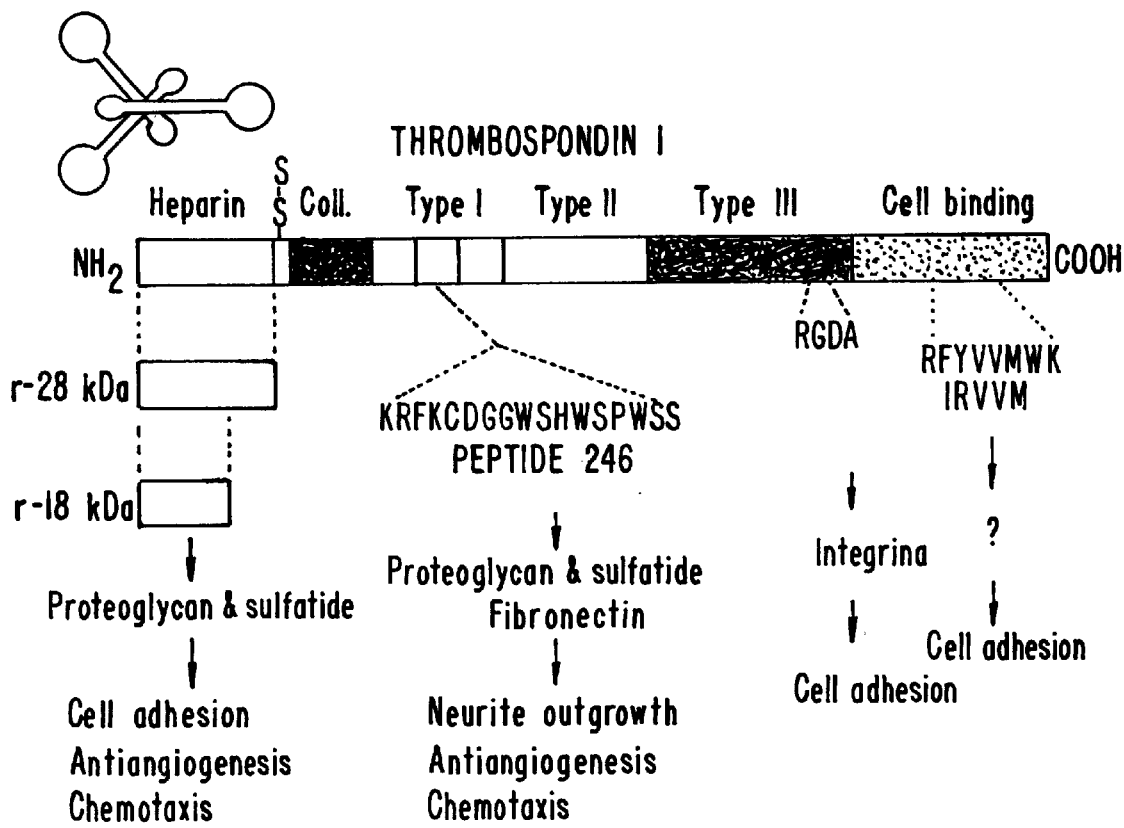

To understand the mechanism of these diverse and apparently conflicting effects of TSP on endothelial cell behavior, it was sought to define the domains of TSP that interact with the cells, the identity of the endothelial cell receptors that interact with TSP, and the intracellular responses in transduction and integration of the signals resulting from TSP binding to each receptor. At least three domains of TSP are implicated in interactions with endothelial cells. The structure of Thrombospondin is shown in FIG. 28. The trimeric structure of thrombospondin as visualized by rotary shadowing electron microscopy is depicted on the top left. The schematic structure of a thrombospondin subunit shows the major structural domains and three repeat regions. Recombinant fragments from the amino terminal domain (4–28 kDa and r-18 kDa) bind to sulfated glycoconjugates and inhibit angiogenesis. The other major active amino acid sequences identified in thrombospondin, their ligand binding specificities, and their functional activities are indicated.

Adhesion of bovine aortic endothelial cells on TSP is inhibited by peptides containing the Arg—Gly—Asp sequence in the type III region and may be mediated by a β3 integrin. TSP contains an Arg—Gly—Asp sequence that could potentially interact with this receptor (Lawler J, et al., (1988), *J. Cell Biol.* 107:2351–2361; Lawler J, Hynes R O, (1986) *J. Cell Biol.* 103:1635–1648; and Sun X, et al., (1992), *J. Cell Biol.* 118:693–701). A β3 integrin may also participate in chemotaxis and spreading of endothelial cells on TSP. Adhesion and migration of endothelial cells in a TSP gradient is inhibited by an antibody and ligands that bind to the amino terminal heparin-binding domain of TSP. The core region of TSP containing the type I repeats has also been shown to contain a cell-binding domain for endothelial cells (Dardik R, Lahav J, (1991), *Biochemistry* 30:9378–9386).

The domains of TSP that account for its antiproliferative activity are unclear. Based on inhibition by monoclonal antibodies and sulfated polysaccharides, it appears that the heparin-binding domain at the amino-terminus of TSP may be responsible for regulation of endothelial proliferation (Taraboletti G, et al., (1990) *J. Cell Biol.* 111:765–772). However, a 140 kDa fragment of TSP that lacks the amino-terminal region also suppresses endothelial cell growth. Thus, multiple sites on the TSP molecule may modulate endothelial cell growth and motility. Moreover, based on recent studies by Murphy-Ullrich et al. ((1992), *Molec. Biol. Cell* 3:181–188), inhibition of bovine endothelial cell growth by TSP is at least partly due to the inhibitory activity of transforming growth factor β (TGFβ), which complexes with TSP and contaminates most TSP preparations. Two parts of TSP that have antiproliferative activity in isolation have been identified (Vogel T, et al., (1993), *J. Cell. Biochem.* 53:74–84). Recombinant amino-terminal domain of TSP also inhibits endothelial growth and motility induced by serum or bFGF.

Synthetic peptides from the type I repeats also inhibited proliferation to bFGF and showed a biphasic effect on motility of endothelial cells in the presence of bFGF that mimicked the activity of intact thrombospondin. Recently Tolsma et al. ((1993), *J. Cell Biol.* 122) reported that additional peptides from the type I repeats have antiangiogenic activity and identified an additional sequence in the procollagen domain with antiangiogenic activity. Thus, as least three isolated regions of thrombospondin have antiangiogenic activities, and some of these activities are expressed in synthetic or recombinant constructs without contaminating TGFβ.

Interactions of thrombospondin with tumor cells are also complex. Two regions of the TSP molecule have been identified that mediate adhesive and migratory responses of cultured human melanoma cells to TSP (Roberts D D, et al., (1987), *J. Cell. Biol.* 104:131–139; Taraboletti G, et al., (1987), *J. Cell. Biol.* 105:2409–2415). The carboxyl-terminal domain mediates attachment and haptotaxis, and the amino-terminal domain mediates cell spreading and chemotaxis. Sulfated glycoconjugates, including heparan sulfate proteoglycans and sulfated glycolipids, interact with the amino-terminal domain of TSP. A sulfated glycolipid, present only in melanoma cell lines that spread on TSP, binds to TSP and participates in melanoma cell spreading on TSP but not on fibronectin (Roberts D D, (1988), *Cancer Res.* 48:6785–6793). Integrin and non-integrin receptors for the carboxyl-terminus of TSP have been characterized in several types of tumor and normal cells (Yabkowitz R, et al., (1993), *J. Immunol.* 151:149–158; Yabkowitz R, Dixit V M, (1991), *Cancer Res.* 51:3648–3656; and Asch A S, et al., (1991), *J. Biol. Chem.* 266:1740–1745).

At least two regions of thrombospondin interact with sulfated glycoconjugates. Proteolytic or recombinant fragments from the amino terminus of thrombospondin were identified that bind specifically to heparin or sulfatide. Basic consensus sequences occur in the amino terminal domain of TSP (Cardin A D, Weintraub H J R, (1989), *Arteriosclerosis* 9:21–32; and Jackson R L, et al., (1991), *Physiol. Rev.* 71:481–539) and were shown to be active using recombinant fragments containing these sequences. A second putative heparin binding site was identified in the type I repeats of TSP (Prater, C A, et al., (1991), *J. Cell Biol.* 112:1031–1040). Synthetic peptides from TSP were used to further define this heparin binding site in the type I repeats. These studies led to the discovery of a novel heparin binding sequence (Guo N, et al., (1992), Proc. Natl. Acad. Sci. U.S.A. 89:3040–3044; Guo N, et al., (1992), *J. Biol. Chem.* 267:19349–19355).

Surprisingly, it has been discovered that peptides from the three type I repeats of human endothelial cell TSP, containing the consensus sequence —Trp—Ser—Xaa—Trp (SEQ ID NO:73), but not adjacent peptides from the TSP sequence containing the previously identified adhesive motif Val—Thr—Cys—Gly (SEQ ID NO:5) (Asch A S, et al., (1992), Biochem. *Biophys. Res. Commun.* 182:1208–1217), that bind to sulfated glycoconjugates including heparin and sulfatide and inhibit TSP binding, also promote melanoma binding of TSP or laminin to human melanoma cells. The active peptides lack any previously identified heparin-binding consensus sequences and several do not contain any basic amino acids. Studies with homologous peptides showed that the tryptophan residues are important for binding. Adjacent basic residues in the second type I repeat enhance binding to heparin but not to sulfatide. Using defined oligosaccharides from heparin, the two heparin binding sequences from TSP have different binding specificities. The type I peptides of TSP thus define a new class of heparin-binding peptides.

Further studies using these peptides demonstrated that the two Trp residues and the Ser residue are important for activity (Guo N, et al., (1992), *J. Biol. Chem.* 267:19349–19355). The Trp residues generally are spaced less than three residues apart. The Pro residue appears to be important for proper conformation and activity of the pentapeptide Trp—Ser—Pro—Trp—Ser (SEQ ID NO:55), but some larger peptides with substitutions of the Pro residue are active. Peptides containing the consensus sequence and basic amino acids are chemotactic for A2058 human melanoma cells. The functional importance of this novel heparin and sulfatide binding motif is suggested by its conservation in other members of the TSP gene family, complement components, and in many members of the cytokine receptor and transforming growth factor B superfamilies (Bazan J F, (1990), *Proc. Natl. Acad. Sci. U.S.A.* 87:6934–6938).

Based on its effects on tumor cell adhesion, growth, and motility, expression of TSP by tumor cells may regulate their metastatic phenotype. It was found that TSP mRNA and protein expression were decreased in subclones of K1735 melanoma cells selected for high metastatic potential in mice and in human lung epithelial cell lines transfected with ras and selected for tumor formation by growth in nude mice (Zabrenetzky V S, et al., (1992), *Proc. Am. Assoc. Cancer Res.* 33:A404). Overexpression of thrombospondin-I in breast carcinoma cells suppresses tumor growth in nude mice (Weinstat-Saslow D, et al., (1993), *Proc. Am. Assoc. Cancer Res.* 34:A394), identifying THBS as a potential tumor and metastasis suppressor gene.

Data demonstrates that TSP peptides inhibit endothelial cell growth in vitro and angiogenesis in vivo. The synthetic peptides from the type I repeats and recombinant amino-terminal heparin-binding domain from TSP mimic the inhibitory activities of intact TSP on endothelial cell proliferation and motility. Without being bound to a particular theory, it is believed that these fragments and peptides act, at least in part, by competing with bFGF for binding to heparan sulfate proteoglycan receptors on the endothelial cells, which are essential for presentation of bFGF to its signalling receptor. This appears to be a general mechanism for inhibition of angiogenesis by heparin-binding proteins, given that the heparin-binding protein apolipoprotein E has been found to be a potent inhibitor of endothelial cell proliferation., and motility in vitro (II) and in vivo.

Establishing the molecular mechanisms involved in adhesion and metastatic migration of tumor cells also has led to development of inhibitory agents to prevent tumor invasion and metastasis. Accordingly, the peptides of the present invention, are particularly useful in this application, since they are active in vitro at relatively low concentrations. The strong antiproliferative activity of the TSP peptides suggest that these are also useful for inhibition of pathological angiogenesis in vivo. Free peptides, however, often have short half lives in circulation. They are subject to rapid clearance due to their small size and susceptible to proteolytic degradation. In several cases, use of polymer conjugates of peptides has overcome these limitations. There have been several successful applications of this technique for peptides from extracellular matrix proteins. Conjugation of Arg—Gly—Asp peptides from fibronectin to a soluble polyurethane produced conjugates which retained their biological activity to inhibit cell adhesion while increasing the circulating half life from less than 2 minutes to greater than 10 hours (Braatz J A, Yashuda Y, Olden K, Yamada K M, Heifetz A H (1993): Functional peptide-polyurethane conjugates with extended circulatory half lives. *Bioconjugate Chem* 4:262–267).

Conjugates of the fibronectin peptide R—G—D—S (SEQ ID NO:55) to the water soluble polymer poly(carboxyethylmethacrylamide) were also active and inhibited lung and liver metastasis of B16 melanoma and L5178 lymphoma cells, respectively, in mice (Komazawa H, et al., (1993), *J. Bioactive Compat. Polymers* 8:258–274). The antimetastatic activity of RGDS peptides was also increased by conjugation to 6-O-carboxymethyl chitin (Komazawa H, et al., (1993), *Carbohydr. Polymers* 21:299–307). Thus, in vivo activities of active adhesion sequences from extracellular matrix proteins can be enhanced by conjugation to water soluble polymers.

Figure 29:
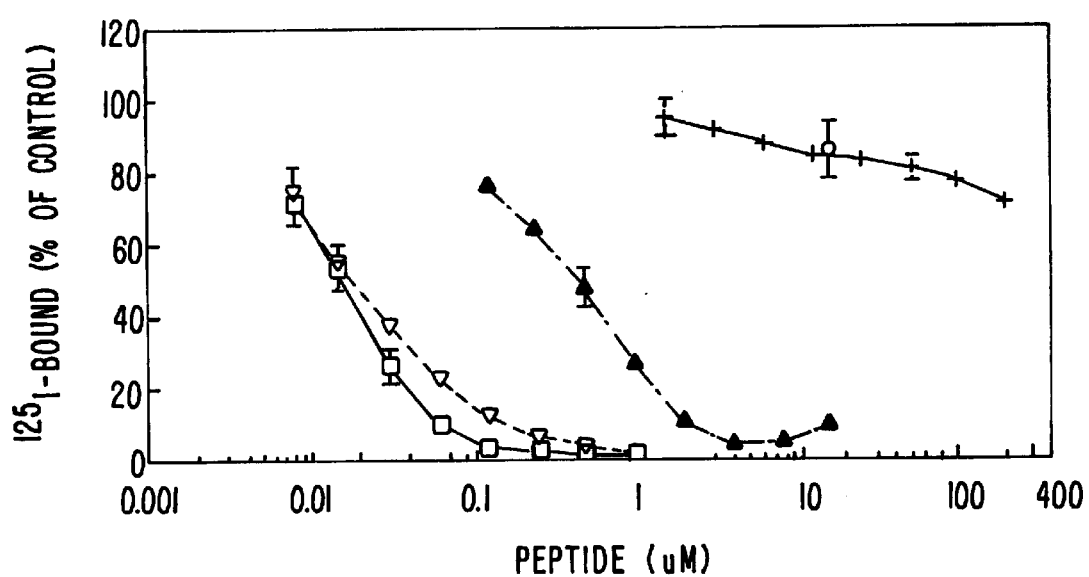
Figure 30:
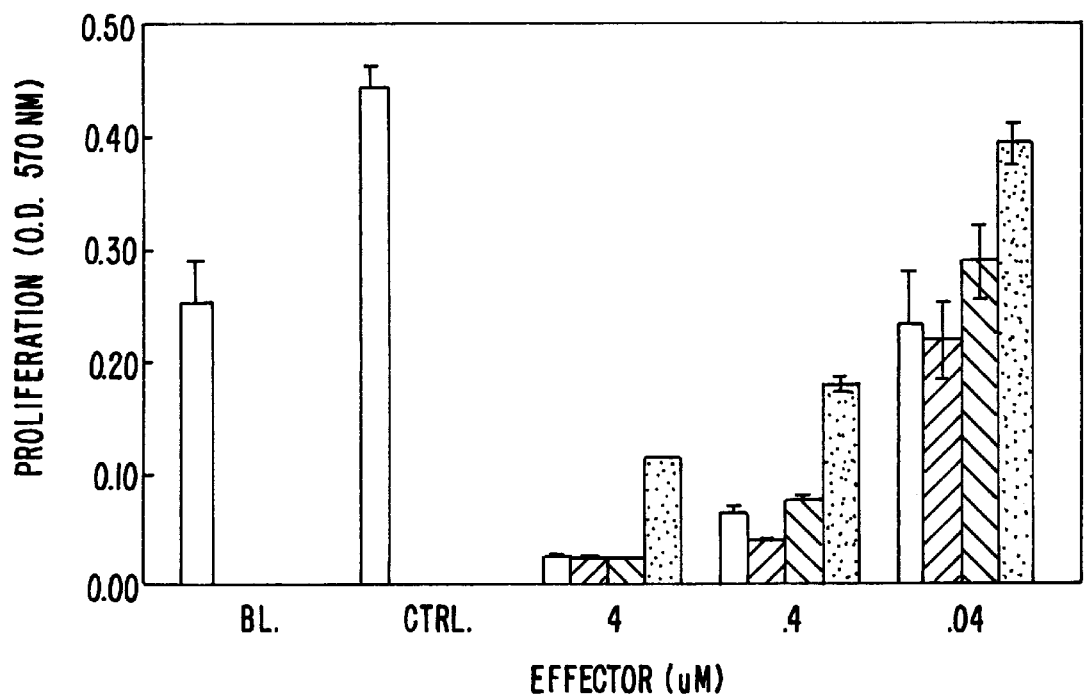
Figure 31:
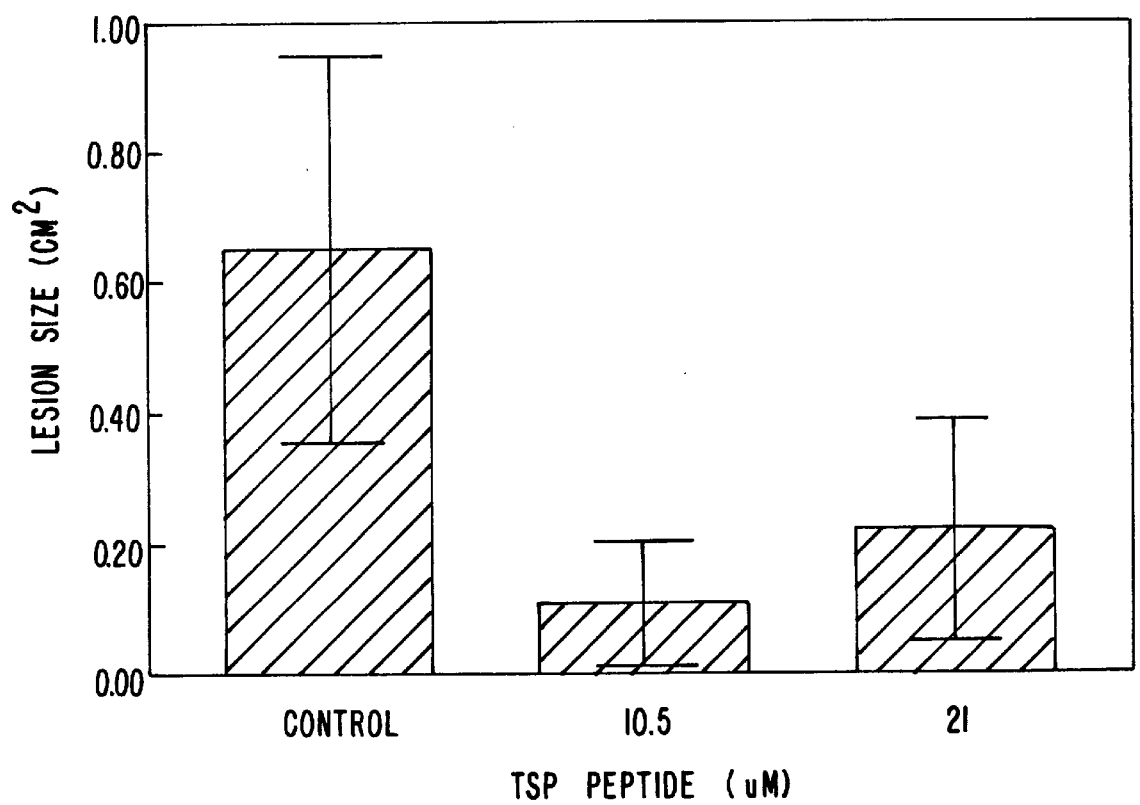

The peptides from the type I repeats of thrombospondin have therefore been conjugated to a FICOLL carrier to increase their stability in vivo. These conjugates retain the heparin-binding activity of the free peptides (FIG. 29) and are more potent than the free peptides for inhibiting proliferation of endothelial cells and breast carcinoma cells in vitro (FIG. 30). The conjugates have shown antitumor and antimetastatic activities in animal models. Data using Kaposi's sarcoma in nude mice and intravenous injection of the conjugates show marked inhibition of angiogenic lesion formation (FIG. 31). FICOLL conjugates of the invention were further characterized and their activities examined in animal models of breast carcinoma tumorigenesis and metastasis.

C. Inhibition of tumor cell growth

Growth of many solid tumors is strongly dependent on recruitment of neovascularization. Increased vascularization of primary breast tumors has been associated with increased rates of metastasis to lymph nodes and poorer prognosis (Weidner N, et al., (1991), *N. Eng. J. Med.* 324:1–8; Horak E R, et al., (1992), *Lancet* 340:1120–1124). Since normal endothelium is non-proliferating, neovascularization of tumors requires specific induction of endothelial cell growth and migration. The factors that are produced by tumors and their mechanism of regulation of angiogenesis are poorly understood.

Cell-cell and cell-matrix interactions are important regulators of normal cell growth and differentiation and play crucial roles in pathological conditions including tumor growth and metastasis. Accordingly, the molecular basis for cell-cell and cell-matrix interactions in breast tumor metastasis was investigated. Specifically tumor-matrix interactions mediated by the glycoprotein thrombospondin was examined. It was hypothesized that thrombospondin plays a significant role in regulating neovascularization of breast and some other tumors. As such, the ability of the peptides of the the invention to mimic or inhibit thrombospondin interactions is particularly useful in the regulation of this neovascularization, both in vitro and in vivo.

D. Inhibition of Kanosi's sarcoma

Kaposi's sarcoma (KS) is the most common tumor associated with patients that have acquired immunodeficiency syndrome (AIDS)(Gross, D. J. et al., *Int. J. Dermatol.,* (1989) 28:571; Safai, B., *Semin. Oncol.,* (1987) 14:7; Safai, B., et al., *Ann. Intern. Med.,* (1985b 103:744; Proceedings. *J. Acquir. Immune. Defic. Syndro.,* 3:21; and Farizo, K. M. et al., *JAMA* (1992), 267:1798). Current therapeutic approaches for the treatment of AIDS-KS using chemotherapeutic agents is frequently associated with intolerable side effects that may severely compromise the immune status of patients already immunocompromised due to infection with HIV-1 (Heagy, W. et al., *Infect. Immun.,* (1989) 57:3619; Gill, P.S. et al., *AIDS,* (1992) 6:1477; Gill, P.S. et al., *Am. J. Med.,* (1991) 90:427; and Lane, H. C. et al. *J. Clin. Immunol.* 9:351). In vitro and in vivo model systems have been developed to study the pathogenesis of AIDS-KS in order to gain an understanding of the requirements of this neovascular process which may lead to the development of useful therapeutic agents (Nakamura, S. et al., *Science,* (1988) 242:426; and Salahuddin, S. Z. et al., *Science* (1988) 242:430) .

Antiangiogenic molecules can be grouped into several classes to include polysaccharides, proteins, peptides, steroids, and microbial products (Folkman, J. et al., *J. Biol. Chem.,* (1992) 267:10931; and Folkman, J. et al., *Nature,* (1987) 329:671). Two novel agents have shown promise as anti-angiogenic agents for the treatment of AIDS-KS using this model system. One molecule is a bacterial-derived peptidoglycan termed (DS-4152) (Nakamura, S. et al., *Science,* (1992) 255:1437) and the second is a heparin binding plasma protein termed Apolipoprotein E (Busch, C. et al., *J. Invest. Dermatol,* (1992) 99:795). As a result of these studies, other molecules derived from the extracellular matrix that have been reported to regulate angiogenesis were investigated (Folkman, J. et al., *J. Biol. Chem.,* (1992) 267:10931; and Folkman, J. et al., *Nature,* (1987) 329:671).

As previously described, thrombospondin-1 (TSP) is a 450 kDa extracellular matrix protein that binds heparin and heparan sulfate proteoglycans and has been shown to have major effects on the proliferation, migration, and adhesion of endothelial cells. TSP has been shown to inhibit the growth of endothelial cells in vitro and exhibit potent antiangiogenic activity in vivo. These in vitro results suggest that the AIDS-KS cell strains have properties with respect to TSP very similar to endothelial cells.

The peptides of the present invention, which were derived from the sequence of the type I repeats of TSP, possess the ability to strongly inhibit endothelial cell proliferation, adhesion, and motility in vitro. Accordingly, because the autocrine and growth factor stimulated proliferation of the AIDS-KS cells appears to involve the interaction of heparin-binding growth factors, the peptides of the present invention were tested for the ability to inhibit KS cell proliferation and migration in vitro, and KS-like lesion formation in vivo. Specifically, experiments were performed to 1) determine if TSP would inhibit the AIDS-KS cells ability to proliferate, and migrate in response to growth factors; 2) determine the functional domains of TSP responsible this inhibition; and 3) use fragments or peptides derived from the functional domains of TSP to inhibit KS-like lesion formation in vivo. Surprisingly, it has been shown that peptide conjugates of TSP evolved from the type I repeat units can function as a novel agents for the treatment for AIDS-KS.

II. Peptides of the invention

A. Generally

The present invention generally provides a family of peptides, peptide analogs and peptidomimetics (hereinafter referred to as "peptides") having high binding affinity to heparin or related sulfated glycoconjugates and containing an active binding sequence that is essentially lacking a charge. The invention also relates to the use of these peptides to prevent interaction of heparin or related sulfated glycoconjugates with adhesion molecules, growth factors, cells, or heparin-dependent enzymes.

The peptides of the present invention will typically have high binding affinities to heparin or related sulfated glycoconjugates, e.g., which have a heparin binding constant in the range of $10^8$ to $10^5$ molar$^{-1}$. The term "related sulfated glycoconjugates" as used above and in the application as follows is defined as sulfated glycoconjugates which have binding characteristics similar to heparin.

The peptides according to the invention are based upon the functional sequences defined in the adhesive glycoprotein thrombospondin. The peptides according to the present invention, whose sequences are set forth herein, may generally be produced by art recognized methods, such as recombinant and synthetic methods that are well known in the art. Recombinant techniques are generally described in Sambrook, et al., *Molecular Cloning: A Laboratory Manual*, (2nd ed.) Vols. 1–3, Cold Spring Harbor Laboratory, (1989). Techniques for the synthesis of polypeptides are generally described in Merrifield, *J. Amer. Chem. Soc.* 85:2149–2456 (1963), Atherton, et al., *Solid Phase Peptide Synthesis: A Practical Approach*, IRL Press (1989), and Merrifield, *Science* 232:341–347 (1986). Alternatively, in some cases, the peptides described herein may be isolated from portions of the adhesive glycoprotein thrombospondin.

The peptides described herein are also provided in substantially pure form. By "substantially pure" is meant that the peptides are provided separated from proteins or other contaminants with which they are naturally associated. A protein or polypeptide is considered substantially pure when that protein makes up greater than about 50% of the total protein content of the composition containing that protein, and typically, greater than about 60% of the total protein content. More typically, a substantially pure protein will make up from about 75 to about 90% of the total protein. Preferably, the protein will make up greater than about 90%, and more preferably, greater than about 95% of the total protein in the composition.

Some of these peptides lack the clusters of basic amino acids which fit the consensus sequences present in many heparin binding proteins and further have binding constants of approximately 10 to 100-fold higher than the proteins having the basic amino acids consensus sequences. Further, the substantial lack of an electrical charge for a preferred sub-sequence (having four to fifteen amino acid residues) present in preferred peptides within the family of peptides according to the present invention will be advantageous in formulating pharmaceutical agents based on these peptides for efficient delivery to their sites of action.

For certain applications where lack of charge is not required, including use as an adhesive peptide to culture anchorage-dependent cells, modification of the peptide described in the present invention with basic amino acid sequences (such as in SEQ ID NO:19) can increase activity and increase the specificity of the peptide for heparin over other sulfated glycoconjugates.

A further advantage of the present family of peptides is that their higher potency will allow much smaller amounts of peptide to be administered than those required by the prior art peptides and thus will reduce risk of toxicity and cost and possibly decrease generation of immune responses against the peptides.

Peptides from the three type I repeat regions of human thrombospondin were prepared by solid phase synthesis. The peptides used to define heparin binding specificity are listed in Tables 2 and 3.

Peptides of the invention will typically range in length from 4 to 150 amino acids, and will in some embodiments, preferably have a length of from 4 to 100 amino acids. Alternatively, the peptides of the present invention may have a length of 2–150 amino acids and will preferably have a length of 4–100 amino acids. Still more preferred peptides will range in length from about 10 to about 150 amino acids, with the most preferred peptides being from about 10, 11, 12, 13, 14, 15, 16, 17 and 18 to about 30 amino acids in length.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. Peptides that are acetylated at the amino terminal group will possess the prefix "ac". Similarly, carboxamide amino acids at the C-terminal will possess the suffix "am". The abbreviation "tp" denotes thiopropionyl.

In addition to peptides consisting only of naturally-occuring amino acids, peptidomimetics of the heparin binding peptides are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) *TINS* p.392; and Evans et al. (1987) *J. Med. Chem* 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH (OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., *Trends Pharm Sci* (1980) pp. 463–468 (general review); Hudson, D. et al., *Int J Pept Prot Res* (1979) 14:177–185 (—CH$_2$NH—, CH$_2$CH$_2$—); Spatola, A. F. et al., *Life Sci* (1986) 38:1243–1249 (—CH$_2$—S); Hann, M. M., *J Chem Soc Perkin Trans I* (1982) 307–314 (—CH—CH—, cis and trans); Almquist, R. G. et al., *J Med Chem* (1980) 23:1392–1398 (—COCH$_2$—); Jennings-White, C. et al., *Tetrahedron Lett* (1982) 23:2533 (—COCH$_2$—); Szelke, M. et al., European Appln. EP 45665 (1982) CA: 97:39405 (1982) (—CH(OH)CH$_2$—); Holladay, M. W. et al., *Tetrahedron Lett* (1983) 24:4401–4404 (—C(OH)CH$_2$—); and Hruby, V. J., *Life Sci* (1982) 31:189–199 (—CH$_2$—S—); each of which is incorporated herein by reference.

Preferred peptides include those having a sub-sequence of four or five amino acid residues, which sub-sequence essentially lacks a charge. More preferred is a peptide according to the invention having a subsequence —Trp—X$_1$—X$_2$—Trp— (SEQ ID NO:75), wherein X$_1$ is an amino acid selected from the group consisting of Ser, Thr, Ala and —X$_2$— is an amino acid selected from the group consisting of Pro, Glu, Ala, His, and Ser. Even more preferred is a peptide according to the invention having a sequence —Trp—Ser—X$_2$—Trp— (SEQ ID NO:78) wherein X$_2$ is defined as described above and further having a sequence selected from the formulae consisting of —B$_1$—B$_2$—X$_3$—B$_3$— (SEQ ID NO:74) or —B$_1$—X$_3$—B$_2$—X$_4$—B$_3$— (SEQ ID NO:76), wherein X$_3$ and X$_4$ are independently any amino acid and B$_1$, B$_2$ and B$_3$ are independently selected from Lys, Arg and His.

In a particularly preferred embodiment of the invention, the peptides described above are peptides having a sequence independently selected from the group consisting of 184 (SEQ ID NO:1), 185 (SEQ ID NO:2), 186 (SEQ ID NO:3), 239 (SEQ ID NO:14), and 246 (SEQ ID NO:19). Peptides 387 (SEQ ID NO:30), 392 (SEQ ID NO:32), 416, and 419 (SEQ ID NO:34) are also preferred.

In a related aspect, the present invention provides peptides having the general sequence of amino acids (X$_5$—X$_6$—X$_7$—X$_8$)$_i$—X$_9$—X$_{10}$—(X$_{11}$)$_m$—(G)$_n$—W—S—X$_{12}$—W—(S—X$_{13}$—W)$_z$, (SEQ ID NO:57 through SEQ ID NO:72), where X$_5$ is selected independently from R, K, acR and acK, X$_6$ is selected independently from R or K, X$_8$ is selected independently from R or K, X$_7$ is F or A, i is 0 or 1, X$_9$ is Q or A, X$_{10}$ is D or A, X$_{11}$ is G or U (Dav) and m is 1 or 0, n is 1 or 0, X$_{12}$ is H or P and X$_{13}$ is H or P and z is 1 or 0.

The present invention also provides retro-inverso peptides, similar to those described above, and having the general sequence of amino acids ri-(X$_5$'—X$_6$'—X$_7$—X$_8$)$_i$—X$_9$—X$_{10}$—(X$_{11}$)$_m$—(G)$_n$—W—S—X$_{12}$—W—(S—X$_{13}$—W)$_z$, where ri denotes a retro-inverso peptide and all amino acids are D amino acids, X$_5$' and X$_6$' are selected independently from R, K or amides thereof, X$_8$ is selected from R or K, X$_7$ is F or A, i is 0 or 1, X$_9$ is Q or A, X$_{10}$ is D or A, X$_{11}$ is G or U (Dav) and m is 1 or 0, n is 1 or 0; X$_{12}$ is H or P; and X$_{13}$ is H and P, and z is 1 or 0.

A. Initial Peptide Identification

Tables 1 and 2, below, list the sequences in a single letter format, which are discussed above and referred to in FIGS. 1–39. The tables list these sequences by a designated peptide number or abbreviation and include a corresponding sequence-listing identification number.

TABLE 1

Inhibition of $^{125}$I-Thrombospondin Binding to Heparin or Sulfatide

| | | | IC$_{50}$ | |
|---|---|---|---|---|
| Peptide | SEQ ID NO: | Sequence | Haparin Binding | Sulfatide Binding |
| 184 | 1 | SPWSEWTSCSTS | 47 | 14 |
| 186 | 3 | GPWSPWDICSVT | 8.5 | 27 |
| 185 | 2 | SHWSPWSSCSVT | 20 | 5.8 |
| 239 | 14 | SHWSPWSS | 5.2 | 10 |
| 244 | 17 | SHASPASS | >200 | >200 |
| 240 | 15 | WSPWSSCS | 60 | 100 |
| 241 | 16 | WSPWSSCSVT | 35 | 34 |
| 246 | 19 | KRFKQDGGWSHWSPWSS | 2.1 | >100 |
| 203 | 5 | VTCG | >200 | >200 |
| 204 | 6 | VTCGGGVQKR | >200 | >200 |
| 245 | 18 | VTCGGGVQKRSRL | >200 | >200 |
| 205 | 7 | VTCGDGVITR | >200 | >200 |
| 187 | 4 | CSVTCG | 6 | 14 |
| 237 | 12 | SSVTCG | 58 | 30 |
| 238 | 13 | SSCSVT | 85 | >100 |
| 234 | 9 | CSVT | >200 | >200 |
| 235 | 10 | SSVT | >200 | >200 |
| 236 | 11 | ASVT | >200 | >200 |
| 206 | 8 | TSCGNGIQQR | >200 | >200 |
| P1 | 20 | RQMKKTR | >200 | >2 |
| P2 | 21 | RKGSGRRLVK | 60 | >2 |

TABLE 2

Inhibition of $^{125}$I-Laminin or Apolipoprotein E Binding to Heparin or Sulfatide

| | | IC$_{50}$ | | |
|---|---|---|---|---|
| | | Laminin Binding to: | | APO E Binding to |
| Peptide | SEQ ID NO: | Heparin | Sulfatide | Heparin |
| 184 | 1 | 36 | 42 | 4.2 |
| 186 | 3 | 15 | 35 | 52 |
| 185 | 2 | 5 | 15 | 8 |
| 239 | 14 | 11 | 12 | 250 |
| 244 | 17 | >200 | | >200 |
| 240 | 15 | 100 | 100 | 150 |
| 241 | 16 | 34 | 50 | 180 |
| 246 | 19 | 3 | >100 | |
| 203 | 5 | >200 | >200 | |
| 245 | 18 | ~200 | >200 | |
| 204 | 6 | >200 | >200 | |
| 205 | 7 | >200 | >200 | |
| 187 | 4 | 3 | 3.9 | 84 |
| 237 | 12 | 100 | 85 | |
| 234 | 9 | >200 | >200 | |
| 235 | 10 | >200 | >200 | |
| 236 | 11 | >200 | >200 | |
| 238 | 13 | >200 | >200 | |
| 206 | 8 | >200 | >200 | |
| P1 | 20 | >200 | >200 | |
| P2 | 21 | 60 | >200 | |

Also included in the present invention are peptides which have the sequences described herein, but which have been modified to include an amino-terminal N-acyl or aryl group and/or a carboxyl-terminal amide or alkyl amide group.

Several peptides from the type I repeats were tested for inhibition of thrombospondin binding to heparin and sulfatide (FIGS. 1 and 2). The peptides chosen flanked the VTCG sequence (SEQ ID NO:5) previously identified as an adhesive motif but lacked clusters of basic amino acids needed for the predicted heparin binding consensus sequence. Surprisingly, only the sequences amino-terminal to the VTCG sequence (SEQ ID NO:15) were active (SEQ ID NO:1, SEQ ID NO:2 and SEQ ID NO:3). Dodecapeptides from all three repeats inhibited heparin and sulfatide binding with $IC_{50}$ values from 6 to 100 μM (SEQ ID NO:1, SEQ ID NO:2 and SEQ ID NO:3). Flanking peptides adjacent to each active peptide were inactive (SEQ ID NO:6, SEQ ID NO:7 and SEQ ID NO:8). The peptide from repeat 2 (SEQ ID NO:2) was the most active followed by repeat 3 (SEQ ID NO:3) then repeat 1 (SEQ ID NO:1).

The three repeat peptides were comparable inhibitors of binding to heparin with $IC_{50}$ values between 10 and 20 μM. Two peptides from the amino terminal heparin binding domain of thrombospondin containing predicted consensus sequences for heparin binding also inhibited thrombospondin binding to heparin but were much weaker than the type I repeat peptides with $IC_{50}$ values greater than 100 μM. These peptides, however, did not inhibit binding to sulfatide.

Figure 3:
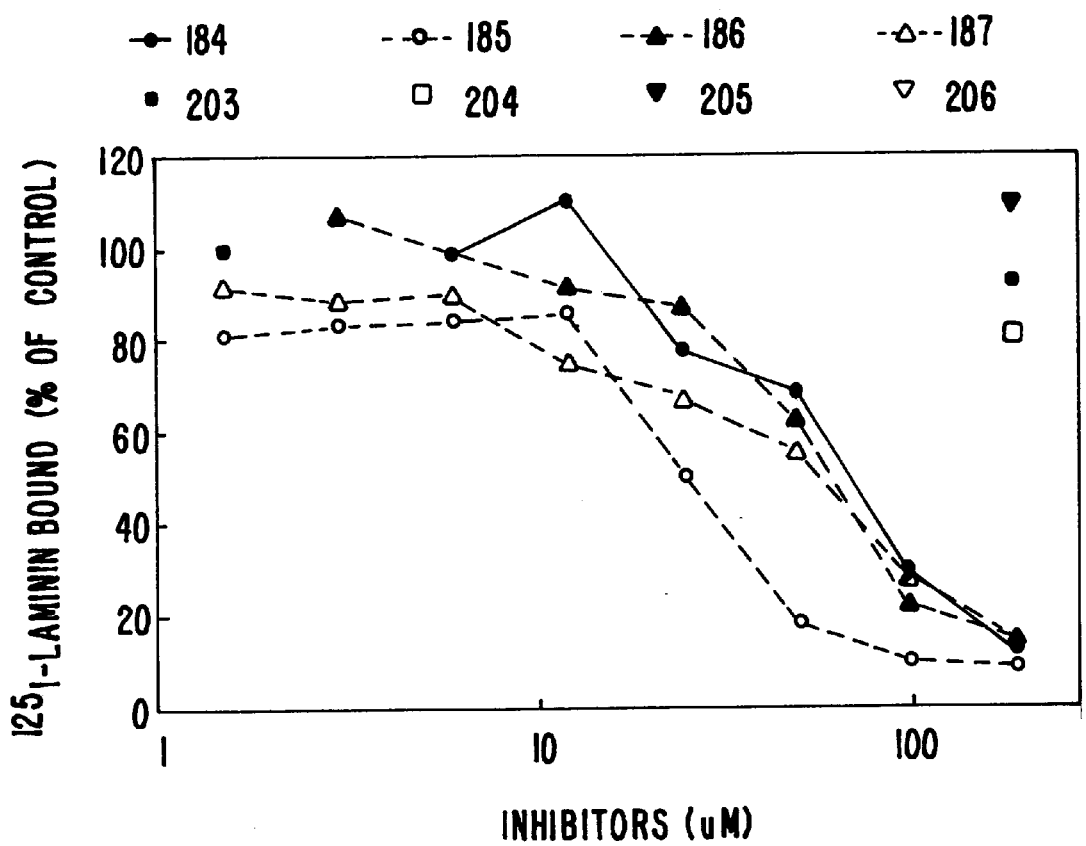
FIG. 3 is a graph showing the inhibition of $^{125}$I-laminin binding to sulfated glycoconjugates by thrombospondin peptides.

Since the most active peptides contained few or no basic amino acids, the possibility existed that the peptides were inhibiting by binding to a heparin binding site on thrombospondin rather than to the sulfated glycoconjugates. To examine this hypothesis, the peptides were tested as inhibitors of laminin and apolipoprotein E binding to heparin or sulfatide (FIG. 3 and Table 2). The same peptides were active as inhibitors of both proteins and inhibited laminin binding to both substrates. Since it is highly unlikely that the same peptides could bind specifically to heparin binding sites on three unrelated proteins, the activity of the peptides is due to binding to the sulfated glycoconjugates rather than the protein. Lack of binding of the peptides to laminin or thrombospondin was confirmed by the failure of labeled thrombospondin or laminin to bind to the peptides immobilized directly on plastic or as BSA conjugates.

Several peptides containing portions of the most active sequence from the second type I repeat were synthesized and tested as inhibitors of thrombospondin and laminin binding to further define the active sequence for heparin binding (Tables 1 and 2). VTCG (SEQ ID NO:5) was inactive, although a larger peptide containing this sequence, CSVTCG (SEQ ID NO:4), was active. However, this peptide rapidly formed disulfide oligomers in solution, based on reversed phase HPLC analysis. The inhibition curve was much more shallow than those for the other active peptides (FIG. 3), suggesting heterogeneous binding or that inhibition may be an artifact due to aggregation of the peptide. An analog of this peptide where the first cysteine was replaced with a serine, SSVTCG (SEQ ID NO:12), was a very weak inhibitor, except of thrombospondin binding to sulfatide where it was 2-fold less active than CSVTCG (SEQ ID NO:4). CSVT (SEQ ID NO:9) was also inactive, but addition of two residues on the amino terminus to give SSCSVT (SEQ ID NO:13) produced weak inhibition of thrombospondin binding.

Several smaller peptides derived from the active sequence of the second type I repeat were also potent inhibitors (Tables 1 and 2). The peptide containing the first eight residues, SHWSPWSS (SEQ ID NO:14), was more active than the intact dodecapeptide for inhibiting thrombospondin binding. A decapeptide lacking the first two amino acids of the dodecapeptide was also a potent inhibitor, but a peptide comprising the center eight residues was much less active. By comparison with the sequences in the other two type I repeats, a minimal consensus sequence for binding may be defined: WSXW (SEQ ID NO:73). The two Trp residues and the Ser residue were entirely conserved. To test the function of tryptophan in binding, an octapeptide was synthesized where the Trp residues were substituted with Ala, SHASPASS (SEQ ID NO:17). This peptide was more than 100-fold less active than the natural sequence in thrombospondin, SHWSPWSS (SEQ ID NO:19). Thus, at least one of the two Trp residues appears to be important to activity.

Effects of peptides on tumor cell binding to thrombospondin or laminin were also examined. Peptides from the second and third repeat significantly inhibited laminin binding to A2058 melanoma cells (FIG. 5). As was observed for binding to heparin and sulfatide binding, the peptide from the first repeat was weaker. Thrombospondin binding to A2058 melanoma cells was inhibited by peptide 184 (SEQ ID NO:1) from the first repeat (FIG. 6A). Inhibition was dose dependent and occurred at comparable concentrations as inhibited thrombospondin binding to heparin or sulfatide. Part of thrombospondin binding to melanoma cells is inhibitable by heparin (FIG. 6A). Addition of peptide 184 (SEQ ID NO:1) in the presence of heparin did not further inhibit binding of thrombospondin, indicating that inhibition by the peptide was due to competition with a sulfated glycoconjugate rather than a heparin-resistant protein receptor for thrombospondin on the melanoma cells.

The putative heparin binding consensus sequence to the right of the VTCG (SEQ ID NO:5) sequence in the third repeat and a similar sequence to the left of the active sequence in the second repeat were also tested for activity (Tables 2 and 3). A peptide containing VTCG (SEQ ID NO:5) and extending through the BBXB motif (SEQ ID NO:74) (VTCGGGVQKRSRL) (SEQ ID NO:18) was inactive. Addition of the flanking BBXB motif (SEQ ID NO:74) to the second repeat (KRFKQDGGWSHWSPWSS) (SEQ ID NO:19), however, enhanced activity approximately 3-fold for inhibiting thrombospondin or laminin binding to heparin but markedly decreased activity for inhibiting binding of both proteins to sulfatide.

The role of the third Trp residue, the conserved Ser residue, and the spacing between the Trp residues in heparin binding activity was examined using synthetic analogs of the type I consensus sequence (see Table 2, below). Addition of a third Trp residue (peptide 256, SEQ ID NO:22) increased activity for laminin binding but decreased activity for thrombospondin slightly. Spacing between the two required Trp residues of two residues was critical for optimum activity as removal of both residues between the two Trp residues decreased activity (peptide 257, SHWWSS SEQ ID NO:23), and the analog with only one residue between the Trp residues (peptide 258, SHWSWSS SEQ ID NO:24) was active only for inhibiting laminin binding. Increasing to three residues between the Trp residues (peptide 260, SHWSSPWSS SEQ ID NO:26) or 5 residues (peptide 259, GGWSHASPWSS SEQ ID NO:25) also abolished activity. Substitution of the conserved Ser residue also caused loss of activity (peptide 261, SHWAPWSS SEQ ID NO:27). Therefore, at least two Trp residues with two residues between appear to be important for strong activity. The first spacing residue preferably Ser, but the second spacing residue is not conserved. In contrast to the requirement of Ser for binding to heparin, binding of this motif in the context of the second type I repeat to fibronectin is maintained when Ser is substituted with Ala or Thr at $X_1$ (Sipes et al., *J. Cell Biol.*, (1993) 121:469–477).

Figure 8:
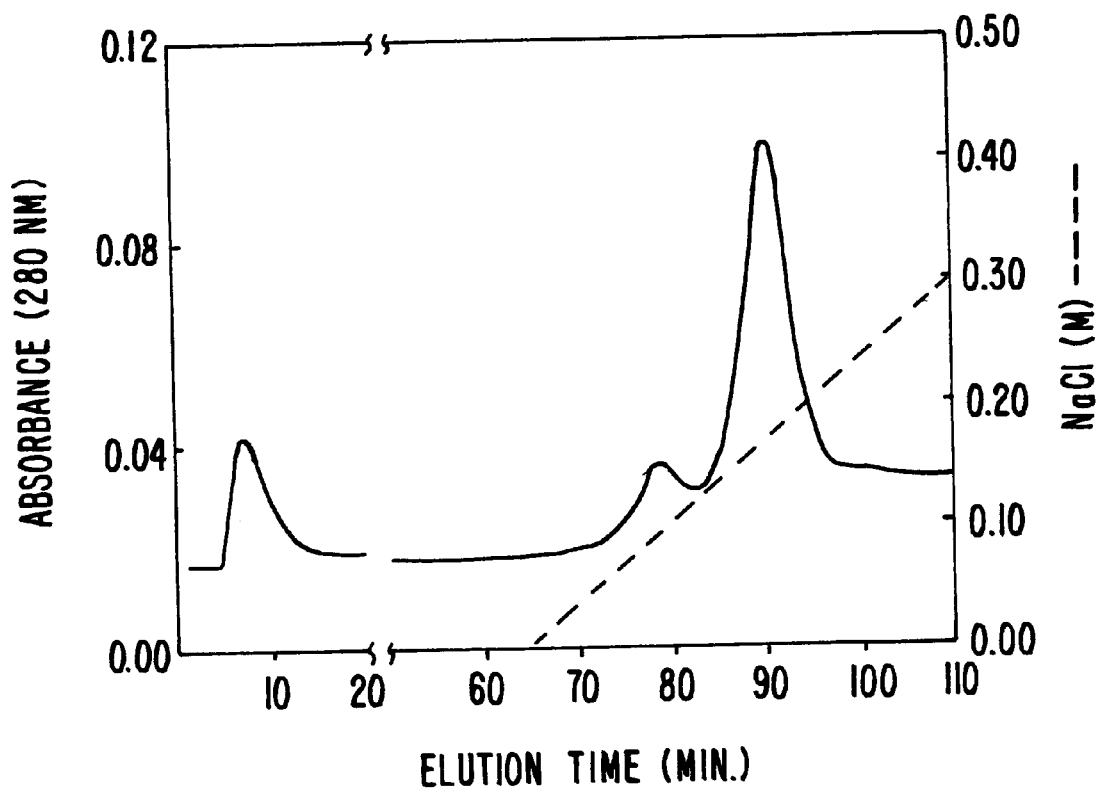
FIG. 8 is a graph showing the binding of a peptide from the second type I repeat of thrombospondin (SEQ ID NO:19) to heparin agarose. Peptide 246 (KRFKQDGGWSHWSPWSS, 100 μg) was applied to a 0.7×7 cm heparin agarose column in 20 mM tris buffer, pH 7.4 and eluted at a flow rate of 0.7 ml/min with a gradient to 0.5 M NaCl in the same buffer. Absorbance was monitored at 280 nm. NaCl concentration was determined by conductivity.

To directly demonstrate binding of the active peptides to heparin, the peptide from the second repeat (246, SEQ ID NO:19) was applied to a heparin affinity column (FIG. 8).

The peptide was quantitatively bound when applied in tris buffer and eluted on a NaCl gradient in three experiments at 0.13 to 0.16 M NaCl (FIG. 8).

Figure 5A:
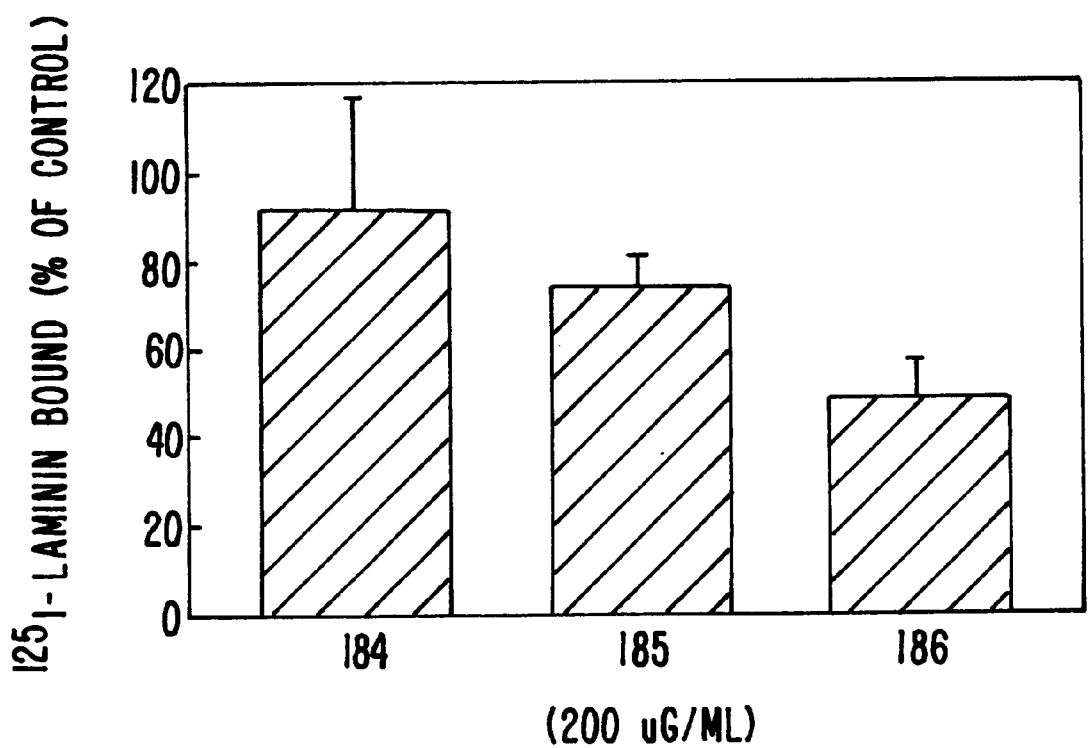
FIG. 5A is a graph representing the inhibition of $^{125}$I-laminin binding to A2058 melanoma cells by thrombospondin peptides.
Figure 5B:
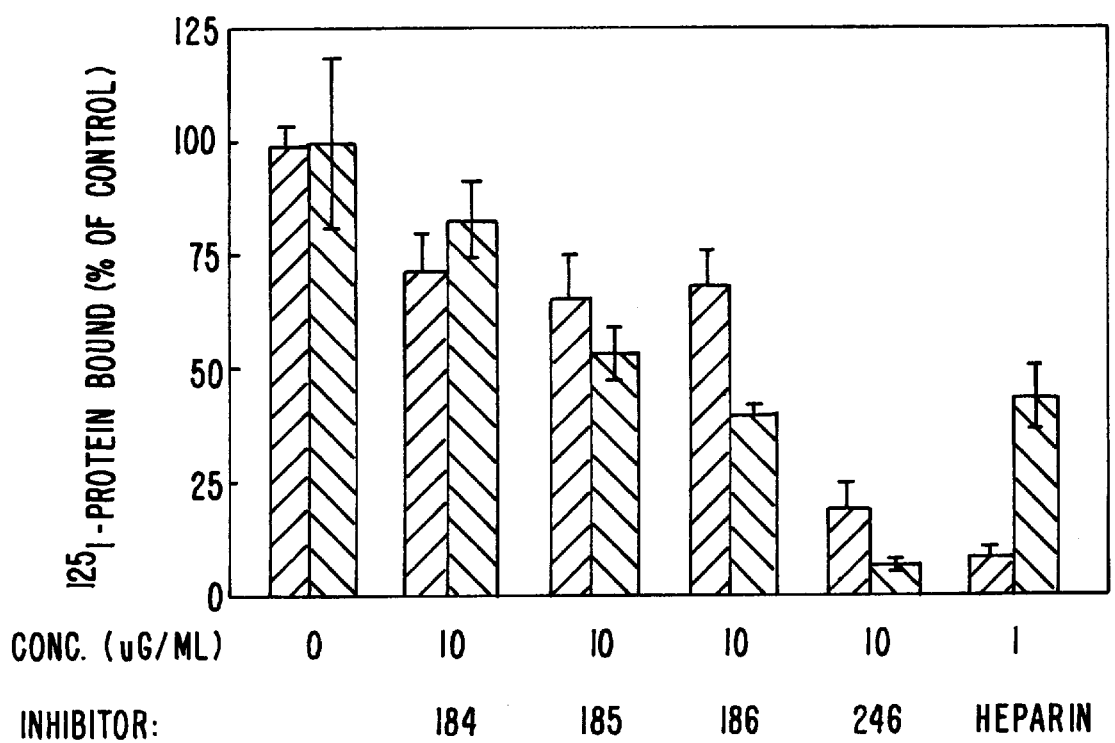
FIG. 5B is a graph which illustrates the inhibition of $^{125}$I-laminin and $^{125}$I-thrombospondin binding to A2058 melanoma cells by thrombospondin peptides.
Figure 6A:
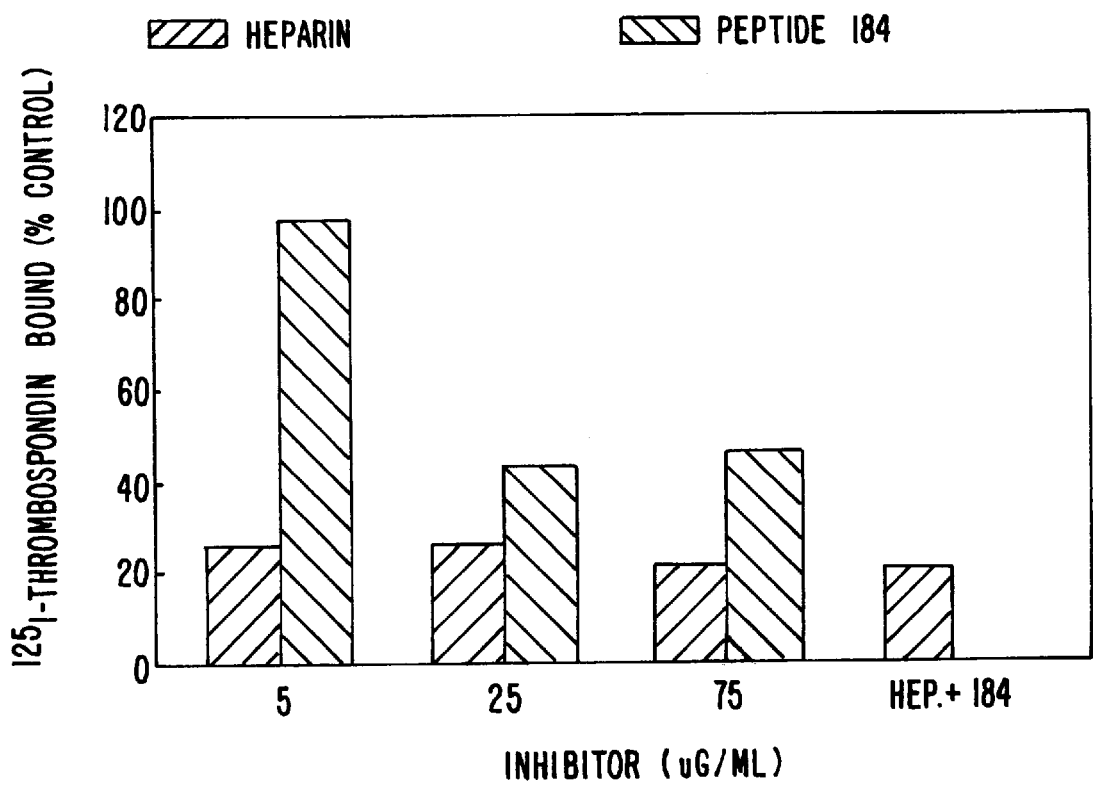
FIGS. 6A and 6B are graphs representing the inhibition of $^{125}$I-thrombospondin binding to A2058 melanoma cells by heparin and thrombospondin peptide 184 (SEQ ID NO:1), and peptide 246 (SEQ ID NO:19), respectively.

Peptides from the type I repeats significantly inhibited thrombospondin and laminin binding to A2058 melanoma cells (FIGS. 5A–B). The order of activities for the peptides was the same as was observed for binding of the respective proteins to heparin. The peptide containing the extended second repeat (246 (SEQ ID NO:19)) was most active, inhibiting thrombospondin binding more than 90% at 10 µg/ml. At the concentrations used, inhibition of binding to melanoma cells by the dodecapeptides from all three type I repeats was partial. In additional experiments, inhibition was found to be dose dependent and occurred at comparable concentrations to those needed to inhibit binding of the proteins to heparin.

Heparin inhibited both thrombospondin and laminin binding to the A2058 melanoma cells (FIGS. 5A–B). Thrombospondin binding was inhibited approximately 90%, but approximately 50% of laminin binding was resistant to inhibition by excess heparin. Laminin binding to A2058 melanoma cells was shown previously to be partially heparin dependent (Taroboletti et al., *J. Biol. Chem.* 265, 12253–12258 (1990)). Addition of 1 µg/ml peptide 246 (SEQ ID NO:19) in the presence of heparin did not further inhibit binding of laminin (FIG. 6B), indicating that inhibition by the peptide was due to competition for binding to a sulfated glycoconjugate rather than to a heparin-resistant protein receptor for laminin on the melanoma cells. At 10 µg/ml of peptide, the inhibition of laminin binding was partially reversed by addition of heparin, probably due to binding of the heparin to the peptide.

Figure 9:
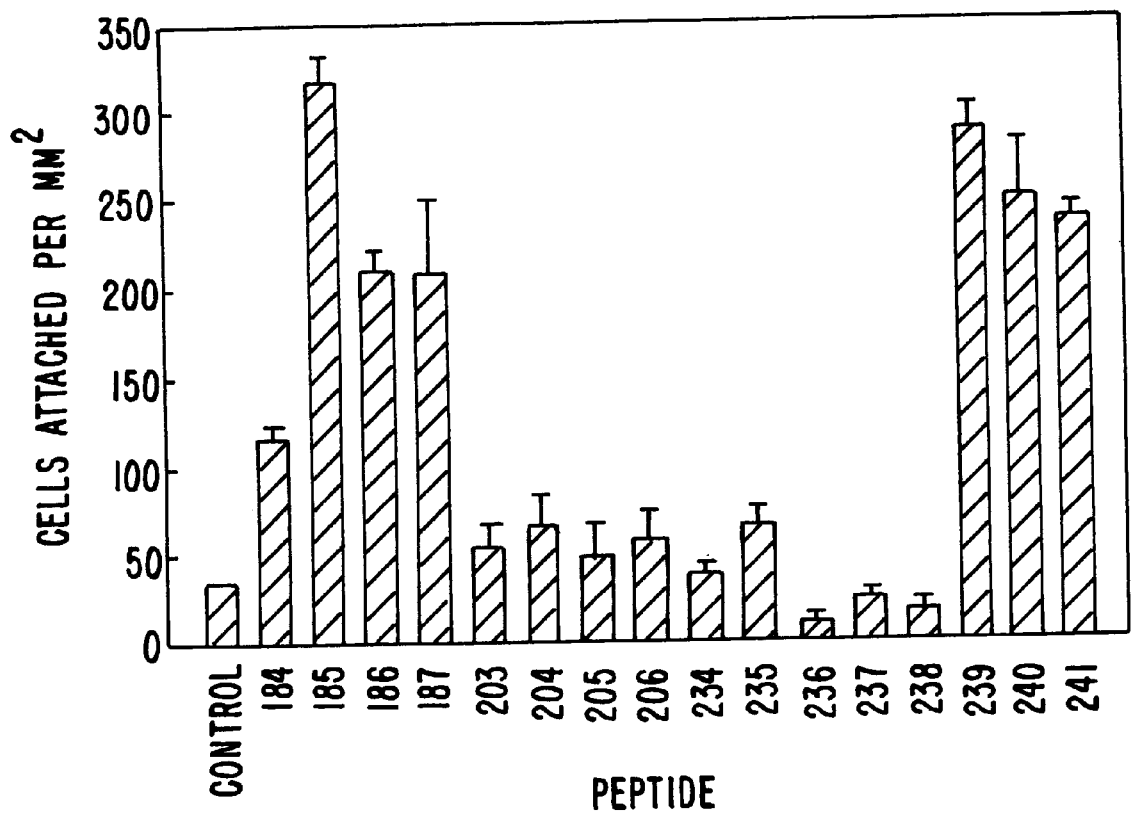
FIG. 9 is a histogram shows the degree of adhesion of A2058 melanoma cells on a control peptide and 16 thrombospondin peptides.

Several of the peptides when adsorbed on plastic strongly promoted melanoma cell adhesion (FIG. 9). Activity in the adhesion assay was correlated with the ability of the peptides to inhibit thrombospondin binding to heparin or sulfatide. Peptide 185 (SEQ ID NO:2) was more active than 184 (SEQ ID NO:1) or 186 (SEQ ID NO:3) in both assays. The active subfragments of 185 (SEQ ID NO:4) also promoted cell adhesion. None of the peptides containing VTCG (SEQ ID NO:5) promoted significant cell adhesion above background except CSVTCG (SEQ ID NO:4). As was observed for inhibition of heparin binding substitution of the first cys residue in CSVTCG (SEQ ID NO:4) with Ser abolished activity in promoting melanoma cell adhesion (SEQ ID NO:2). The two peptides from the amino terminal domain of thrombospondin SEQ ID Nos:20 and 21 did not promote melanoma cell adhesion.

Figure 10:
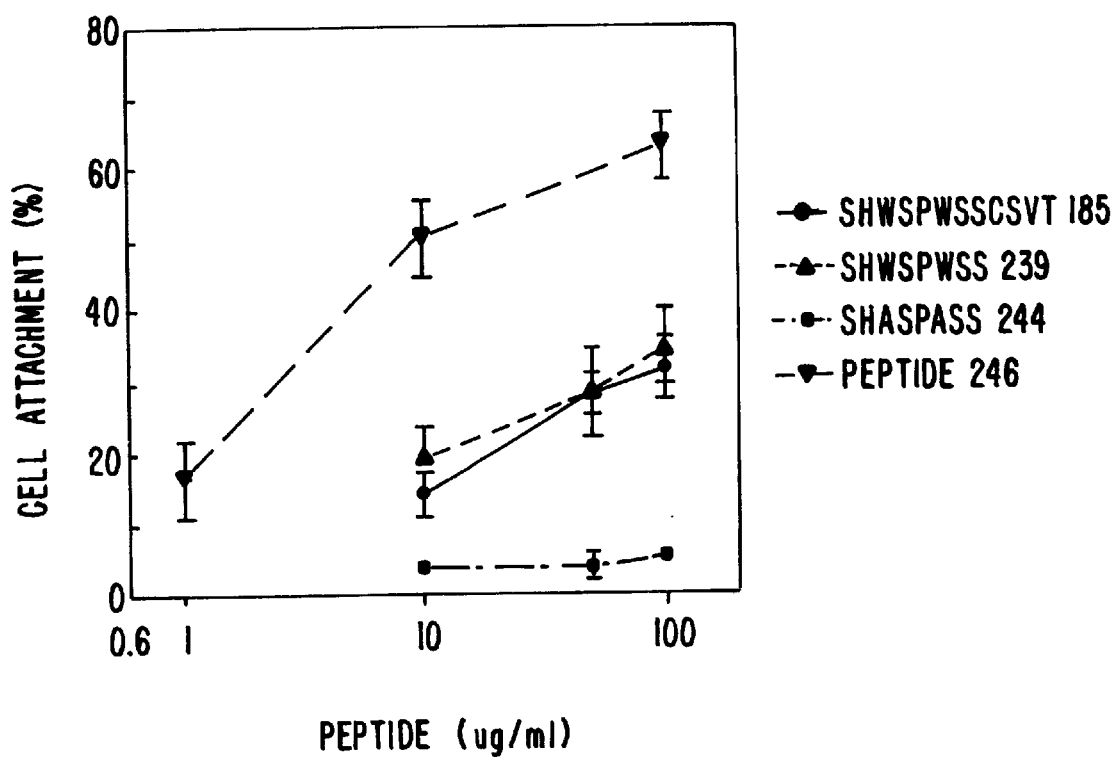
FIG. 10 is a graph showing the concentration dependence for A2058 melanoma cell adhesion to 4 thrombospondin peptides. Adhesion determined microscopically is presented as percent of cells applied (mean ±SD, n=6) to plastic disks coated with the indicated concentrations of peptides: 185, 239, 244 or 246 (SEQ ID NO:2, SEQ ID NO:14, SEQ ID NO:17, or SEQ ID NO:19, respectively). Nonspecific adhesion was 1.9±0.9%.

Adhesion to the peptides was dose dependent (FIG. 10). The extended peptide from the second repeat (246 SEQ ID NO:19)) was most active and, at 10 µg/ml, promoted extensive spreading of melanoma cells. Trp residues were required for adhesion, as the octapeptide containing Ala replacements for Trp was inactive.

Figure 11:
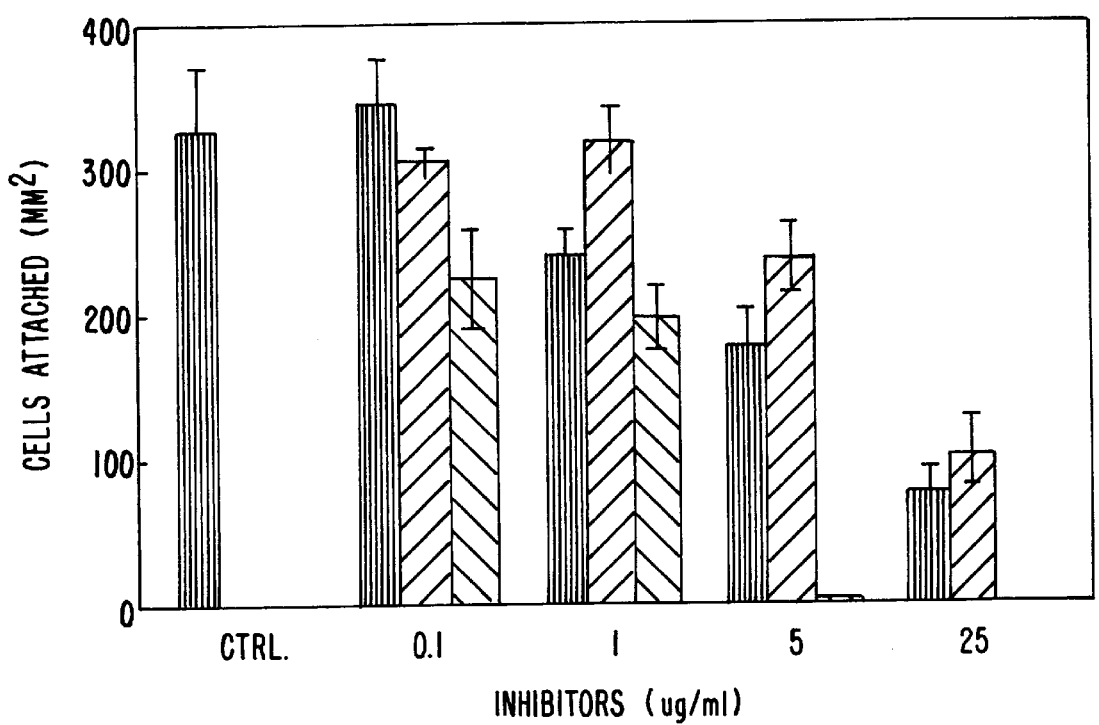
FIG. 11 is a histogram representing the inhibition of melanoma cell adhesion to thrombospondin peptides by heparin binding peptides. Melanoma cells (1×10$^3$/mm$^2$) in RPMI medium or medium containing the indicated concentrations of 18 kD thrombospondin fragment (solid bars), 28 kD thrombospondin fragment (gray bars), or apolipoprotein E (striped bars) were allowed to attach to polystyrene disks coated with 200 μg/ml peptide 185 (SEQ ID NO:2). Results are presented as mean ±SD, n=6.

An 18 kD recombinant heparin-binding fragment of thrombospondin and apolipoprotein E inhibited adhesion of A2058 melanoma cells to the peptides (FIG. 11). Inhibition was greater by apolipoprotein E than by the thrombospondin fragment. This order of activity is consistent with the greater affinity of apolipoprotein E for heparin. Because both proteins bind to heparan sulfate, this result suggests that the peptides are promoting cell adhesion by binding to heparan sulfate proteoglycans on the melanoma cells.

C. Analoging of Lead Peptides

Amino acid substitution analysis identified the minimal consensus sequence Trp—Ser—Xaa—Trp (SEQ ID NO:73) as essential for heparin binding activity in the thrombospondin type I repeat peptides. The activity of this minimal sequence is increased by a basic motif Lys—Arg—Phe—Lys (SEQ ID NO:36) which is present in the second type I repeat. An 18 amino acid peptide, containing these sequences and the native C-terminal Cys residue to allow conjugation to a polymeric carrier (KRFKQDGGWSHWSPWSSC) (SEQ ID NO:30) (Peptide nos. 364, 387 and 407), was taken as the starting sequence for further substitution analysis. The Asp—Gly sequence in this peptide is susceptible to acidic cleavage, and may decrease the yield of full length peptide during synthesis and conjugation to carriers. The analog with an Ala residue in place of the Asp was prepared and showed identical activity to the native sequence for inhibition of endothelial cell proliferation (see FIG. 25, peptide 392, SEQ ID NO:32). Further substitutions were made to examine the role of the Gln residue and to determine which basic residues are required for activity. Conjugate 419 (SEQ ID NO:34) in Table 2 above is a potent inhibitor of heparin binding (FIG. 22) and of endothelial (FIG. 25) and melanoma (FIG. 26A–C) cell proliferation. Therefore Gln is not essential.

Several conjugates have been prepared containing the WSXW motifs (SEQ ID NO:73) but lacking the basic amino acids. These have been shown to be inhibitors of corneal endothelial cell (FIG. 17A–B) and breast carcinoma cell proliferation (FIG. 18) but not aortic endothelial cell proliferation (FIG. 24B) at high serum. The prototype sequence for these peptides is the sequence GGWSHWSPWSSC (SEQ. ID NO: 28). Conjugates containing this peptide also bound to heparin and inhibited endothelial cell proliferation, but transposition of the Cys residue to the amino terminus (CGGWSHWSPWSS) (SEQ ID NO:29) and coupling through this residue produced an inactive conjugate.

In preliminary studies using short peptides, the Pro residue was found to be essential for heparin-binding activity of the sequence WSXWS (SEQ ID NO:77) (Guo N, et al., (1992), *J. Biol. Chem.* 267:19349–19355). Without being bound to a particular theory, it is believed that pro-residues may limit the conformational freedom of short peptides. Derivatives in which both WSXW motifs contain a Pro residue may therefore increase heparin-binding activity and would be expected to eliminate the fibronectin-binding activity of this peptide which requires the sequence GGW-SHW (SEQ ID NO:52). Several derivatives of Pro may be used to further limit the conformational freedom of the residues linked to Pro, including the rigid cis and trans proline analogs based on 2-aminocyclopentane carboxylic acid (Mierke D F, et al., (1990), *Int. J. Pept. Protein Res.* 35:35–45) and thioproline.

The peptide derived from the second type I repeat of TSP-1, KRFKQDGGWSHWSPWSS, (SEQ ID NO:19) inhibits heparin binding to TSP, activates latent TGFβ (Schultz-Cherry, et al., *J. Biol. Chem.* (1995) 270:7304–7310), see also U.S. patent application Ser. No. 08/105,900, filed Aug. 12, 1993, and incorporated herein by reference, and inhibits proliferation of endothelial cells stimulated by FGF-2 (Vogel, et al., *J. Cell. Biochem.* (1993) 53:74–84). The potency of these peptides and their strong effects on endothelial cell behavior suggest that stable analogues based on this sequence could be useful therapeutic agents to control pathological angiogenesis. A number of analogues based on the L-forward peptides were synthesized to maximize heparin binding activity:

TABLE 4

Epitope Mapping and Structure-Function on Inhibition of
Binding of Heparin to Thrombospondin by L-Forward Peptides

| | IC50 Inhibitory Activity (uM) | |
|---|---|---|
| Peptide Sequence (#) | Free Peptide | Conjugated Peptide |
| KRFKQDGGWSWHSPWSSC | — | 3.5 |
| KRFKQAGGWSHWSPWSSC (392) | 0.3 | 0.14 |
| KRFKAAGGWSHWSPWSSCam (419) | 0.028 | 0.04 |
| KRAKAAGGWSHWSPWSSC | 0.03 | 0.025 |
| KRFKQDGGASHASPASSC (389) | — | >5 |
| acKRAKQAGGWSHWAACam | 0.045 | 0.02 |
| KRAKQDUWSHWSP | 0.32 | — |
| KRAKQDGGWSHWSP | 0.13 | — |

From the above analoging data, a number of trends become apparent. Substitution of the Asp residue at position 6 and the Gln and Asp residues at position 5 and 6 by Ala residues yielded peptides with higher activity and better solubilities (Table 4). Substitution of the Phe at position 3 by Ala, primarily to eliminate the TGF-Beta activating activity possessed by the parent peptide, resulted in an even more active peptide KRAKAAGGWSHWSPWSSC (SEQ ID NO:42). Deletion of the second Trp motif from a peptide containing the Ala substitution for Phe, KRAKQDGGW-SHWSP (SEQ ID NO:46), produced a highly active peptide for inhibiting TSP binding to Heparin. Finally, terminal modifications with acetyl and amide substituents are also envisioned, e.g., acKRAKAAGGWSHWASCam (SEQ ID NO:75) (ac=N-acetyl, am=C-terminal primary amide). This peptide also showed good activity and solubility characteristics. The Ala—Ala substitution also helped facilitate the coupling to polysucrose. These results are summarized in Table 4.

Preferred peptides of the present invention are ascertained from the above data. In particular, these peptides are characterized, as described previously, by the subsequence of amino acids —Trp—$X_1$—$X_2$—Trp—, wherein $X_1$ is an amino acid selected from the group consisting of Ser, Thr, Ala and —$X_2$— is an amino acid selected from the group consisting of Pro, Glu, Ala, His, and Ser. Even more preferred is a peptide according to the invention having a sequence —Trp—Ser—$X_2$—Trp— (SEQ ID NO:75) wherein $X_2$ is defined as described above and further having a sequence selected from the formulae consisting of —$B_1$—$B_2$—$X_3$—$B_3$— (SEQ ID NO:74) or —$B_1$—$X_4$—$B_2$—$B_3$— (SEQ ID NO:74), wherein $X_3$ and $X_4$ are independently any amino acid and $B_1$, $B_2$ and $B_3$ are independently selected from Lys, Arg and His.

Still more preferred are peptides having the sequence ($X_5$—$X_6$—$X_7$—$X_8$)$_i$—$X_9$—$X_{10}$—($X_{11}$)$_m$—(G)$_n$—W—S—$X_{12}$—W—(S—$X_{13}$—W)$_z$ (SEQ ID NO:57 through SEQ ID NO:72), where $X_5$ is selected independently from R, K, acR and acK, $X_6$ is selected independently from R or K, $X_8$ is selected from R or K, $X_7$ is F or A, i is 0 or 1, $X_9$ is Q or A, $X_{10}$ is D or A, $X_{11}$ is G or U (Dav) and m is 1 or 0, n is 1 or 0, $X_{12}$ is H or P, and $X_{13}$ is H or P and z is 1 or 0. Still more preferred are peptides which have the N-terminal sequence (K or acK) —K—F—K— (SEQ ID NO:80), and thus include the general sequence of amino acids $X_5$—K—F—K—$X_9$—$X_{10}$—($X_{11}$)$_m$—(G)$_n$—W—S—$X_{12}$—W—(S—$X_{13}$—W)$_z$ (SEQ ID NO:81 through SEQ ID NO:88); where $X_5$ is selected from K and acK. Also preferred are peptides which include the N-terminal sequence (K or acK)—R—A—K— (SEQ ID NO:89), and thus have the amino acid sequence $X_5$—R—A—K—$X_9$—$X_{10}$—($X_{11}$)$_m$—(G)$_n$—W—S—$X_{12}$—W—(S—$X_{13}$—W)$_z$ (SEQ ID NO:90 through SEQ ID NO:97), where $X_5$ is selected from K and acK.

In some embodiments, preferred peptides will comprise the above described sequences but will have additional sequences at the C-terminal. In particular, the peptides may additionally comprise an additional —Ser—Ser (or S—S) sequence at the C-terminal, and may also comprise a C terminal thio containing acid, e.g., cysteine or thiopropionyl (tp). Additionally, the preferred peptides may comprise one or two trp motifs (e.g., W—S—X—W (SEQ ID NO:73), as well as zero, one or two glycine residues in the central portion (e.g., $X_{11}$—G).

Particularly preferred peptides of this embodiment include those selected from the following group consisting of: KRFKQDGGWSWHSPWSSC (SEQ ID NO:41); KRFKQAGGWSHWSPWSSC (SEQ ID NO:32); KRFKAAGGWSHWSPWSSCam (SEQ ID NO:33); KRAKAAGGWSHWSPWSSC (SEQ ID NO:42); KRFKQDGGASHASPASSC (SEQ ID NO:31); acKRAKQAGGWSHWAACam (SEQ ID NO:44); KRAKQDUWSHWSP (SEQ ID NO:45); and KRFKQAGGWSHWSPW (SEQ ID NO:48).

D. Retro-Inverso Peptides

Retro-inverso peptides have been successfully applied to increase the stability and biological activity of peptide sequences for therapeutic applications (reviewed in Chorev M, Goodman M (1993), *Acc. Chem. Res.* 26:266–273. See also Goodman, M, and Chorev, M (1979), *Acc. Chem. Res.* 12:1–7.). The methods of Chorev M and Goodman M were used to prepare retro-inverso peptides of the present invention. Of particular relevance to the thrombospondin peptides, an all D-amino acid peptide analog of a peptide from the A chain of the extracellular matrix protein laminin replicated the activity of the natural sequence to influence tumor cell adhesion and growth in vitro and in vivo (Nomizu M, Utani A, Shiraishi N, Kibbey M C, Yamada Y, Roller P P (1992): The all-D-configuration segment containing the IKVAV (SEQ ID NO:56) sequence of laminin A chain has similar activities to the all-L-peptide in vitro and in vivo. *J. Biol. Chem.* 267:14118–14121).

Accordingly, in further preferred aspects, the peptides of the present invention may be modified to include full or partial retro-inverso sequences. Such retro-inverso peptides will typically comprise the same amino acid sequence as the peptide sequences described herein, but the sequence will be composed partially or entirely of D-amino acids, thus having a reversed stereochemistry from a peptide which is synthesized using L-amino acids. Use of retro-inverso peptide sequences minimizes enzymatic degradation and, therefore, extends biological half-life of the peptide moiety. Also, these sequences may favorably alter potential immunogenic properties of the analogous conjugates prepared from normal L-amino acid sequences. The retro-inverso sequences (as free peptides or conjugates) are particularly useful in those applications which require or prefer orally active agents (due to resistance to enzymolysis).

The retro-inverso analog of the thrombospondin type 1 peptide sequences, e.g., KRFKQDGGWSHWSPWSSC (SEQ ID NO:30) and the peptides identified in Tables 3 and 4) were prepared by conventional methods and were generally modified by acetylation of the N-terminus and amidation of the C-terminal carboxyl group to eliminate the inappropriate charges at the corresponding termini. The free peptides and FICOLL conjugates were tested for inhibition of TSP binding to heparin in vitro (FIGS. 21 and 39A–C).

The peptide analogs were conjugated to FICOLL and compared to conjugates containing the native sequences for inhibition of bovine aortic endothelial and MDA435 cell proliferation induced by serum or bFGF and melanoma cell proliferation (FIGS. 26A–D). The peptide was further tested in the in vivo assays.

For the purposes of the present invention, retro-inverso peptides are denoted by "ri", and are written, from left to right, from the C-terminal to the N-terminal amino acid, e.g. the opposite of typical L-peptide notation. Where the peptides comprise all D-amino acids, the notation will be "all D". Typically, the retro-inverso peptides of the present invention incorporate all D isomer amino acids.

The first D-reverse or retro-inverso peptide was synthesized based on the native TSP sequence, all D-acCSSWPSWHSWGGDQKFRKam. This construct retained full activity. Analogues of the above peptide were prepared, based on the data obtained with the L-forward peptides described above. Ala substitutions for Phe, Phe and Asp, Phe, Asp, and Gln, and Ala for Asp showed a fairly direct correlation with the activities of L-forward peptides, except that the Ala for Gln substitution in the retro-inverso analog led to a decrease in specific activity. In general, the substitution of these amino acids did lead to increases in specific activity and to greater solubility, possibly due to the induction of some alpha-helical configuration in the peptides. Similar results, with retention or increases in activity, were obtained for elimination of the second Trp motif, and for substitution of Ser—Ser with Ala—Ala.

Using the peptide "all D-acAAWHSWGGAQKARKam," or ri-amKRAKQAGGWSHWAACam (ri=retro-inverso), for convenience of comparison, as a starting point to further investigate the roles of the basic trp motif and single trp motif in activity (Table 5, peptide 483). The effect of changing from the first to the second overlapping motif in the original peptide, that is by substituting Pro for His, was also investigated and found to have no effect upon heparin binding activity. Substitution of delta-aminovaleric acid ("Dav" or "U") for the Gly—Gly sequence, which eliminates the last protease susceptible peptide bond by replacing it with two methylene groups, yielded a species with full inhibitory activity toward heparin binding (Peptide 486). Shortening the gap between the basic and Trp motifs by elimination of one Gly residue produced a peptide and polysucrose conjugate with the highest inhibitory activity (peptide 517). Eliminating both Gly residues decreased activity two fold relative to the former peptide (peptide 526).

Inserting a Ser residue in the sequence of the peptide resulted in an increase of inhibitory activity when the peptide contained a Dav residue. In contrast to the peptide without the Ser insertion, shortening the space between the two motifs resulted in a loss of specific activity in regards to inhibition of heparin binding (Table 4). When the peptides in this group were conjugated to polysucrose, through a thio-ether bond to a Cys residue included in their sequence, specific activity for inhibition of heparin binding and endothelial cell proliferation was retained, indicating that these constructs were of potential in vivo use. Substituting the AcCys with thiopropionyl (tp) increased the coupling yields for conjugation of the peptides to polysucrose with the expected retention of activity. These results are summarized in Table 5, below.

TABLE 3

Epitope Mapping and Structure-Function on Inhibition of Binding of Heparin to Thrombospondin by Retro-Inverso Peptides

| | IC50 Inhibitory Activity (uM) | |
| --- | --- | --- |
| Peptide Sequence | Free Peptide | Conjugated Peptide |
| ri-amKRFKQDGGWSHWSPWSSCac | 0.4 | 1.0 |
| ri-amKRFKQDGGWSHWSPWSStp | 0.16 | 0.12 |
| ri-amKRAKQDGGWSHWSPWSSCac | 0.1 | 0.3 |
| ri-amKRAKQAGGWSHWSPWSSCac | 0.03 | 0.05 |
| ri-amKRAKAAGGWSHWSPWSSCac | 0.15 | — |
| ri-amKRFKQDGGASHASPASSCac | 10 | >5 |
| ri-amKRAKQDGGASHASPASSCac | 6.2 | >5 |
| ri-amKRAKQAGGWSHWAAtp | 0.13 | 0.1 |
| ri-amGGWSHWSPWAAtp | >20 | >5 |
| ri-amKRAKQUWSHWAAtp | 0.046 | 0.025 |
| ri-amKRAKQAUWSPWAAtp | 0.005 | 0.03 |
| ri-amKRAKQAUWSHWSAAtp | 0.001 | 0.03 |
| ri-amKRAKQAGWSHWAAtp | 0.001 | 0.012 |
| ri-amKRAKQAGWSHWSAAtp | 0.035 | — |
| ri-amKRAKQAWSHWAAtp | 0.07 | — |

Based upon the above data, preferred retro-inverso peptides can be ascertained. In particular, as with the L-forward peptides, particularly preferred retro-inverso peptides will have a core sequence of amino acids: ri-($X_5'$—$X_6'$—$X_7$—$X_8$)$_i$—$X_9$—$X_{10}$—$(X_{11})_m$—$(G)_n$—W—S—$X_{12}$—W—(S—$X_{13}$—W)$_z$, where $X_5'$ is independently selected from R, K, amR and amK, $X_6'$ is independently selected from R or K, $X_8$ is selected independently from R or K, $X_7$ is F or A, i is 0 or 1, $X_9$ is Q or A, $X_{10}$ is D or A, $X_{11}$ is G or U (Dav) and m is 1 or 0, n is 1 or 0, $X_{12}$ is H or P, and $X_{13}$ is H or P and z is 1 or 0. Still more preferred are peptides which have the C-terminal sequence ri-(K or amK)—R—F—K—, and thus include the general sequence of amino acids ri—$X_5'$—R—F—K—$X_9$—$X_{10}$—$(X_{11})_m$—$(G)_n$—W—S—$X_{12}$—W—(S—$X_{13}$—W)$_z$; where $X_5'$ is selected from K and acK. Also preferred are peptides which include the C-terminal sequence ri-(K or amK)—R—A—K—, and thus have the amino acid sequence $X_5'$—R—A—K—$X_9$—$X_{10}$—$(X_{11})_m$—$(G)_n$—W—S—$X_{12}$—W—(S—$X_{13}$—W)$_z$, where ri—$X_5'$ is selected from K and amK.

Particularly preferred retro-inverso peptides include: ri-amKRFKQDGGWSHWSPWSSCac; ri-amKRFKQDGGWSHWSPWSStp; ri-amKRAKQDGGWSHWSPWSSCac; KRAKQAGGWSHWSPWSSCac; ri-amKRAKAAGGWSHWSPWSSCac; ri-amKRFKQDGGASHASPASSCac; ri-amKRAKQDGGASHASPASSCac; ri-amKRAKQAGGWSHWAAtp; ri-amGGWSHWSPWAAtp; ri-amKRAKQUWSHWAAtp; ri-amKRAKQAUWSPWAAtp; ri-amKRAKQAUWSHWSAAtp; ri-amKRAKQAGWSHWAAtp; ri-amKRAKQAGWSHWSAAtp; ri-amKRAKQAWSHWAAtp; ri-amKRAKQAGWSHWAAac; ri-amKRFKQAGWSHWAAac; ri-amKRARQAGWSHWAAac; and ri-amKKAKQAGWSHWAAac.

E. Studies on inhibition of heparin binding to basic fibroblast growth factor

The above peptides were subjected to testing for inhibitory capabilities. Inhibition of heparin binding using FGF-2 as the ligand differed in several ways when compared to those involving TSP as the labeled ligand. Inhibition of binding of FGF-2 binding to Heparin by these peptides required that both the basic motifs and one of the trp motifs be present (Table 5). Peptides containing only Trp motifs were uniformly inactive. Variations on the spacing between the motifs involving changes in the Gly—Gly sequence, and various substitutions by Ala for various residues did not cause significant changes in inhibitory activity, nor did substitution of the first Trp motif with the second motif, which involved a His to Pro interchange. Changes in the basic motif had more influence on specific activity, as changes from Phe to Ala or from Arg to Lys increased inhibitory activity toward heparin binding, providing further evidence for a specific role of the basic residues. The results of these experiments are shown in Tables 6 and 7, below.

TABLE 5

Epitope Mapping and Structure-Function on Inhibition of Binding of Heparin to Basic Fibroblast Growth Factor by L-Forward Peptides

| Peptide Sequence | IC50 Inhibitory Activity (uM) |
|---|---|
| KRFKQDGGWSHWSPWSS (499) | 3.2 |
| KRFKDDGGWSHWSPWSSC | 3.8 |
| KRFKQDGGWSHW | 2.5 |
| KRFKQDGG | >40 |
| GGWSHWSPWSS | >40 |
| GGWSHW | >40 |
| SHWSPWSSC | >40 |
| KRFKQDGGASHASPASSC (389) | >40 |
| KRFKQAGGWSHWSPW | 0.45 |
| KRFKAAGGWSHWSPWSSCam | 0.18 |
| KRAKAAGGWSHWSPWSSC | 0.22 |
| acKRAKQAGGWSHWAACam | 0.41 |
| KRAKQDUWSHWSP | 1.5 |
| TRIRQDGGWSHW | 13 |

TABLE 6

Binding to Basic Fibroblast Growth Factor by Retro-Inverso Peptides

| Peptide Sequence | IC50 for Inhibition of Binding |
|---|---|
| ri-amKRFKQDGGWSHWSPWSStp (521) | 1.5 |
| ri-amKRAKQDGGWSHWSPWSSCac (474) | 0.95 |
| ri-amKRAKQAGGWSHWSPWSSCac (476) | 0.22 |
| ri-amKRAKAAGGWSHWSPWSSCac (473) | 1.9 |
| ri-amKRAKQDGGASHASPASSCac (513) | 18 |
| ri-amKRFKQDGGASHASPASSCac (475) | >20 |
| ri-amGGWSHWSPWAAtp (493) | |
| ri-amKRAKQAGGWSHWAAtp (483) | >20 |
| ri-amKRAKQAUWSHWAAtp (486) | 0.45 |
| ri-amKRAKQAUWSPWAAtp (515) | 0.38 |
| ri-amKRAKQAUWSHWSAAtp (516) | 1.0 |
| ri-amKRAKQAGWSHWAAtp (517) | 3.0 |
| ri-amKRAKQAGWSHWSAAtc (525) | 0.28 |
| ri-amKRAKQAWSHWAAtp (526) | 0.43 |
| ri-amKRAKQAGWSHWAAac (529) | 0.37 |
| ri-amKRFKQAGWSHWAAac (530) | 0.65 |
| ri-amKRARQAGWSHWAAac (536) | 0.95 |
| ri-amKKAKQAGWSHWAAac (537) | 0.1 |

F. Studies on inhibition of endothelial cell Proliferation

Similar structure-function and epitope mapping studies were carried out with regard to inhibition of bovine endothelial cell proliferation. The results in general showed the same trends that were observed when these peptides were tested for inhibition of heparin binding to TSP or FGF-2. As with the TSP binding studies, the polysucrose conjugates showed activities similar to those of the free peptide in most cases. In the case where they differ, the conjugates showed higher activity. This may be due either to a lower tendency of the conjugates to stick to the microtiter wells or a greater tendency to disrupt binding of the cells to the substratum in the wells. The results of this study are summarized in Table 8.

TABLE 7

| Peptide | $IC_{50}$ Inhibitory Activity ($\mu$M) Free Peptide | Conjugate |
|---|---|---|
| KRFKQDGGWSHWSPWSSC (364, 387, 407) (SEQ ID NO: 30) | — | >5 |
| KRFKAAGGWSHWSPWSSCam (419) SEQ ID NO: 33) | — | 0.12 |
| ri-amKRFKQDGGWSHWSPWSSCac (416) | — | 0.13 |
| ri-amKRFKQDGGWSHWSPWSStp (521) | 40 | 35 |
| ri-amKRAKQAGGWSHWSPWSSCac (474) | — | 0.1 |
| ri-amKRFKQDGGASHASPASSCac (475) | — | 4 |
| ri-amKRAKQDGGASHASPASSCac (513) | 18 | 17 |
| ri-amKRAKQAGGWSHWAAtp (483) | 4 | 0.06 |
| ri-amKRAKQAUWSHWAAtp (486) | 1.6 | 0.12 |
| ri-amKRAKQAUWSPWAAtp (515) | 15 | 15 |
| ri-amKRAKQAUWSHWSAAtp (516) | 10 | 9 |
| ri-amKRAKQAGWSHWAAtp (517) | 3 | 2.8 |

Based on retro-inverso peptides with the basic single Trp motif, the effect of changing from the first to the second overlapping Trp motif in the original peptide, that is by substituting Pro for His was investigated on the free peptide and on the polysucrose conjugate, as with the L-forward peptides. In this case, the effect on the inhibition of heparin binding was not affected. Studies were also carried out on the influence of shortening the gap between the basic and Trp motifs by elimination of one Gly residue or both. When this was done, the peptide and polysucrose conjugate with the most inhibitory activity had one Gly residue in its sequence. In another set of related experiments, the effect of inserting a Ser residue in the sequence of the peptide resulted in an increase of inhibitory activity when the peptide contained a Dav residue, but now, in contrast to the peptide without the Ser insertion, shortening the space between the two motifs resulted in a loss of specific activity in regards to inhibition of heparin binding.

Figure 26A:
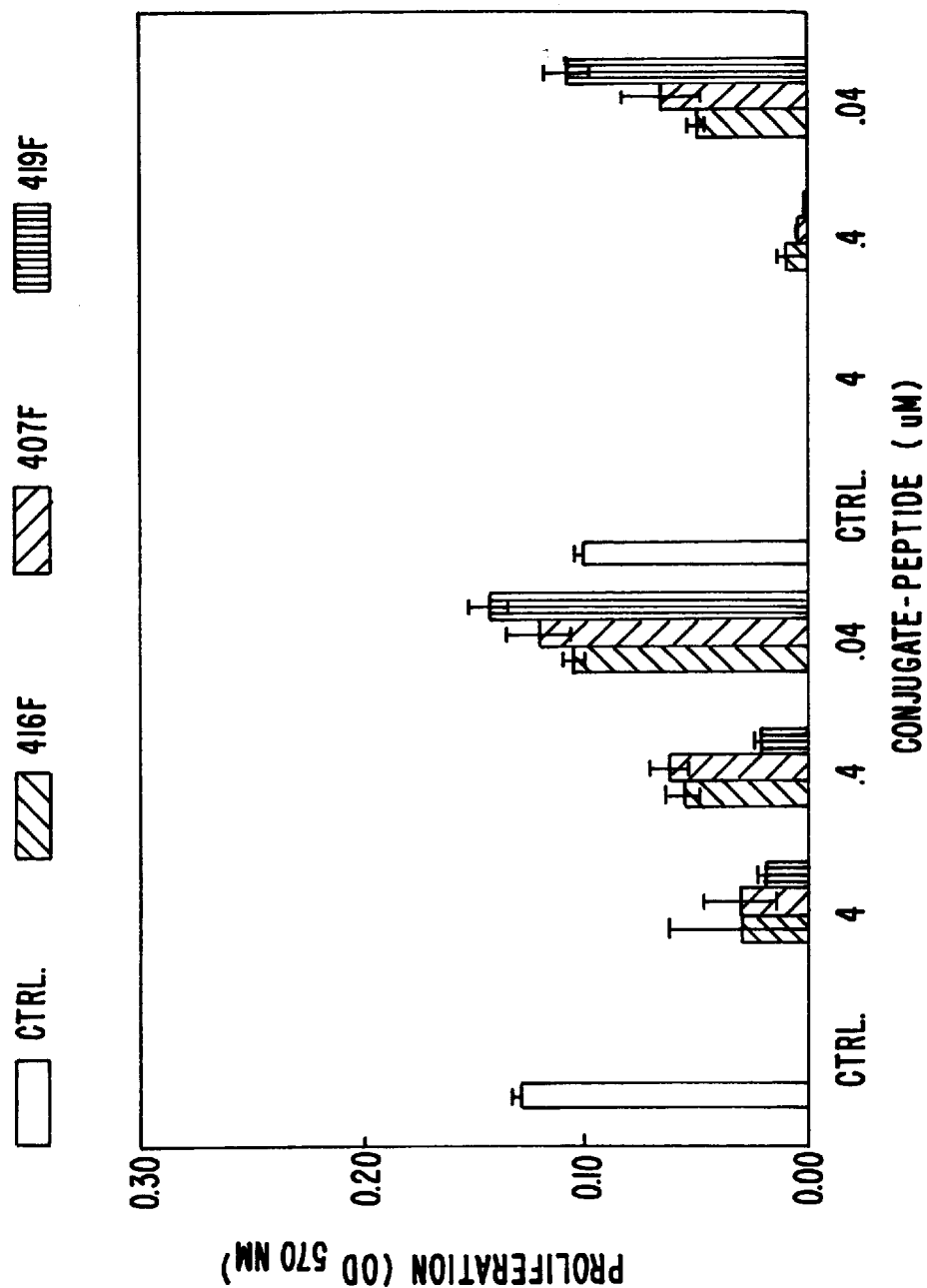
Figure 26B:
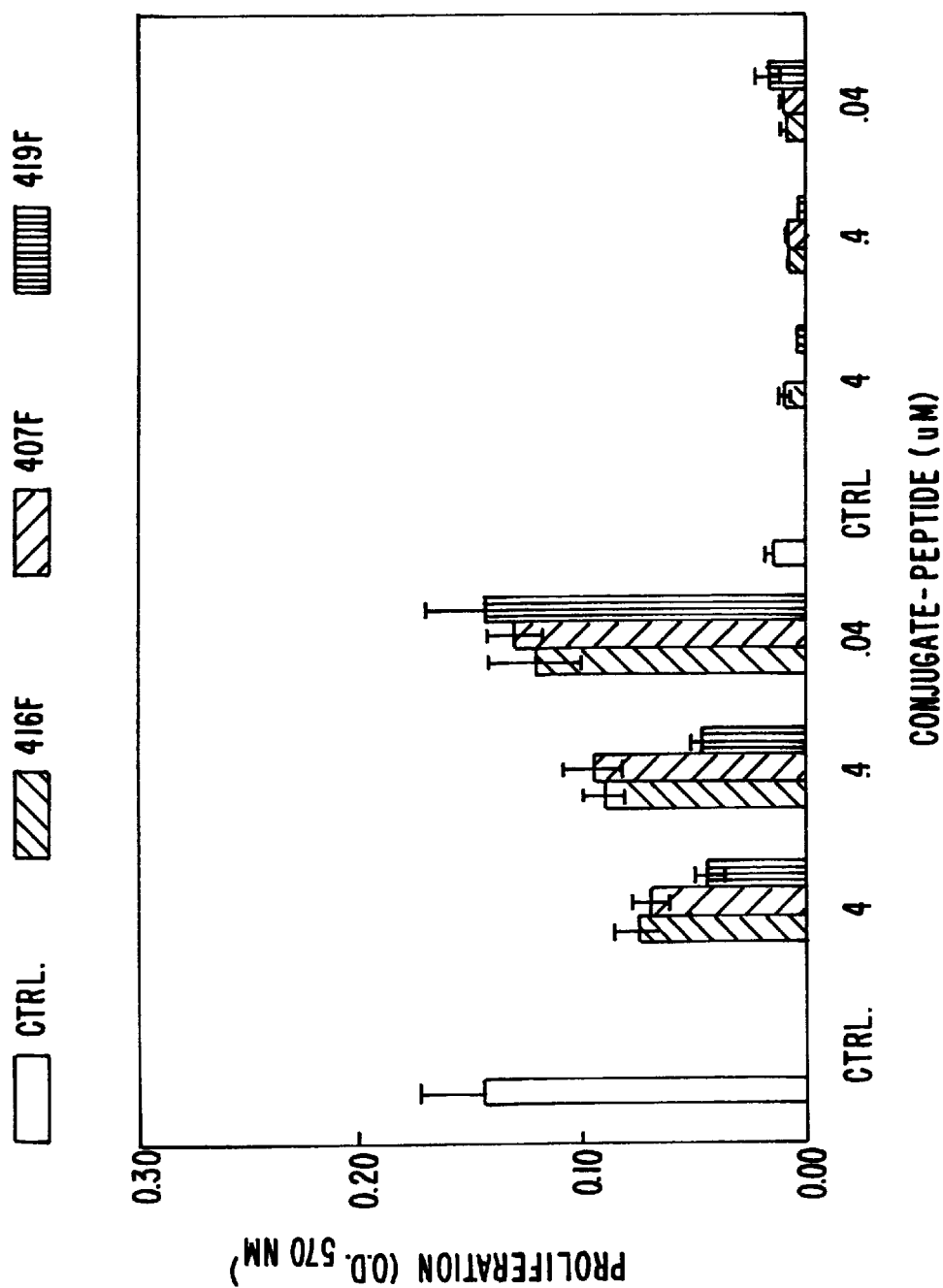
Figure 26C:
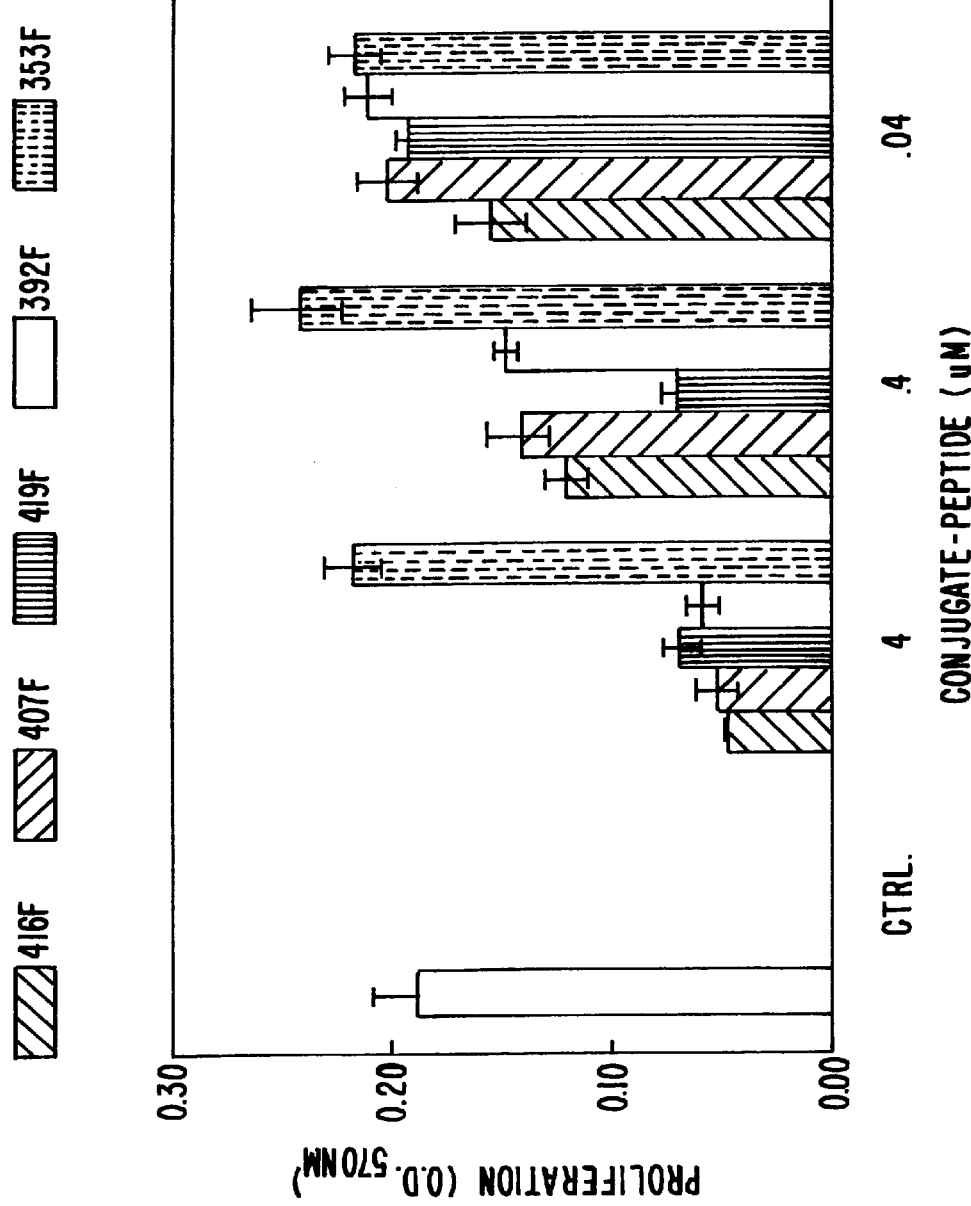
Figure 26D:
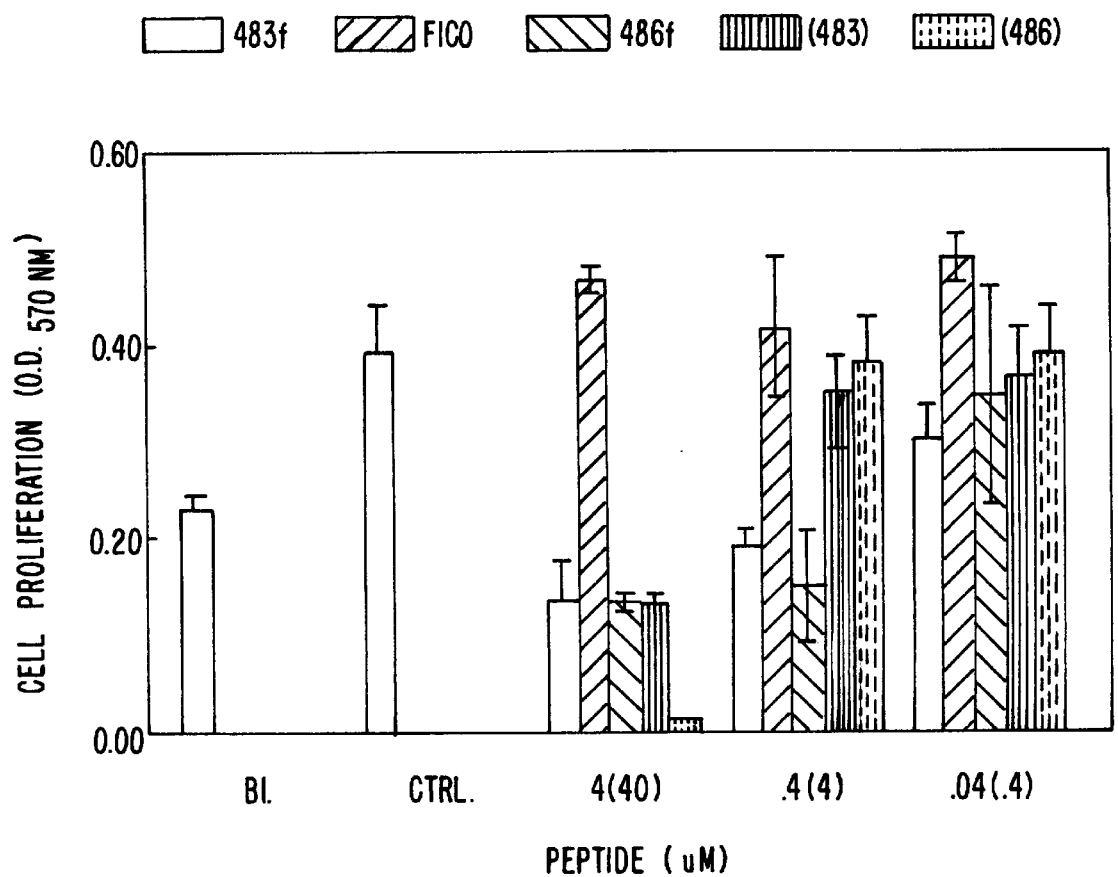

The retro-inverso peptides also inhibited proliferation of human breast carcinoma cell line MDA MB435 (FIG. 26D). The free peptides ri-amKRAKQAGGWSHWAAtp (peptide 483) and ri-amKRAKQAUWSHWAAtp (peptide 486) were both active. Conjugation of the latter peptide to polysucrose increased its potency of inhibition approximately 10-fold, but the polysucrose alone, was inactive. In general, the free peptides and conjugates had less activity to inhibit breast carcinoma cell proliferation than to inhibit endothelial cell proliferation.

Due to the strong inhibitory effect of the peptides on aortic endothelial cells, the possibility that the peptides induced programmed cell death in endothelial cells was examined. Several of the peptides as polysucrose conjugates induced DNA fragmentation in endothelial cells (See FIG. 43). No DNA fragmentation was observed in MDA cells following the same treatment.

Figure 27A:
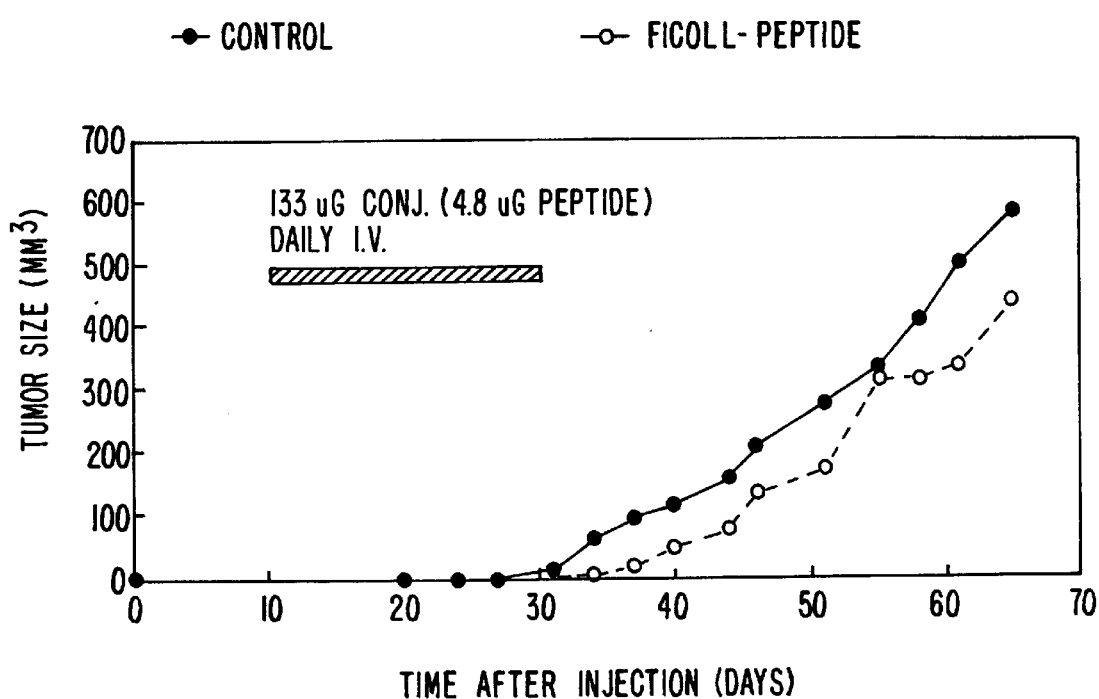
Figure 27B:
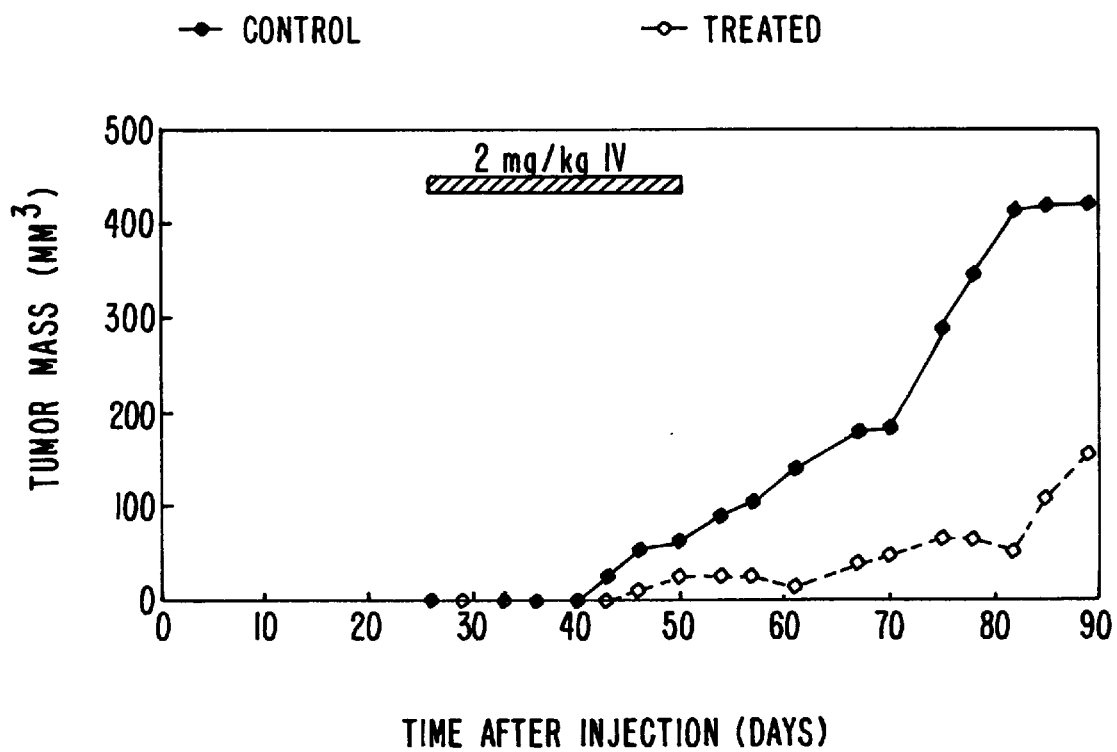
Figure 27C:
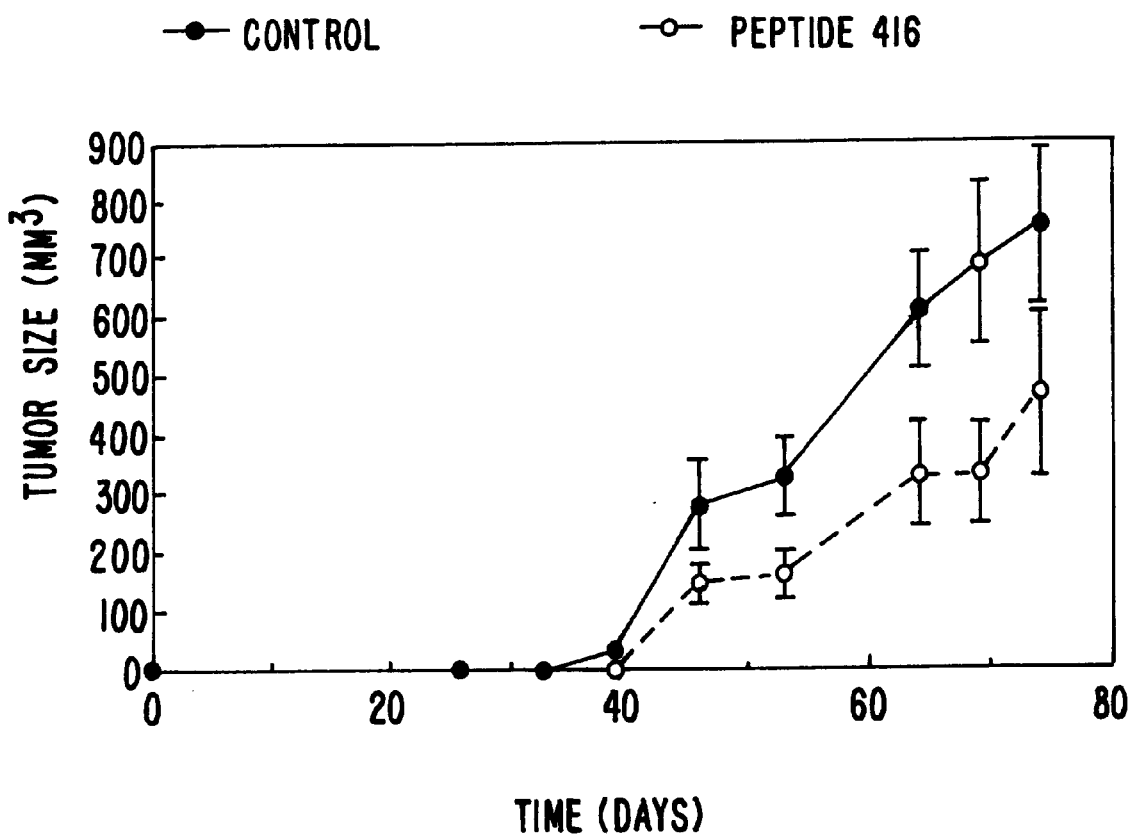
Figure 27D:
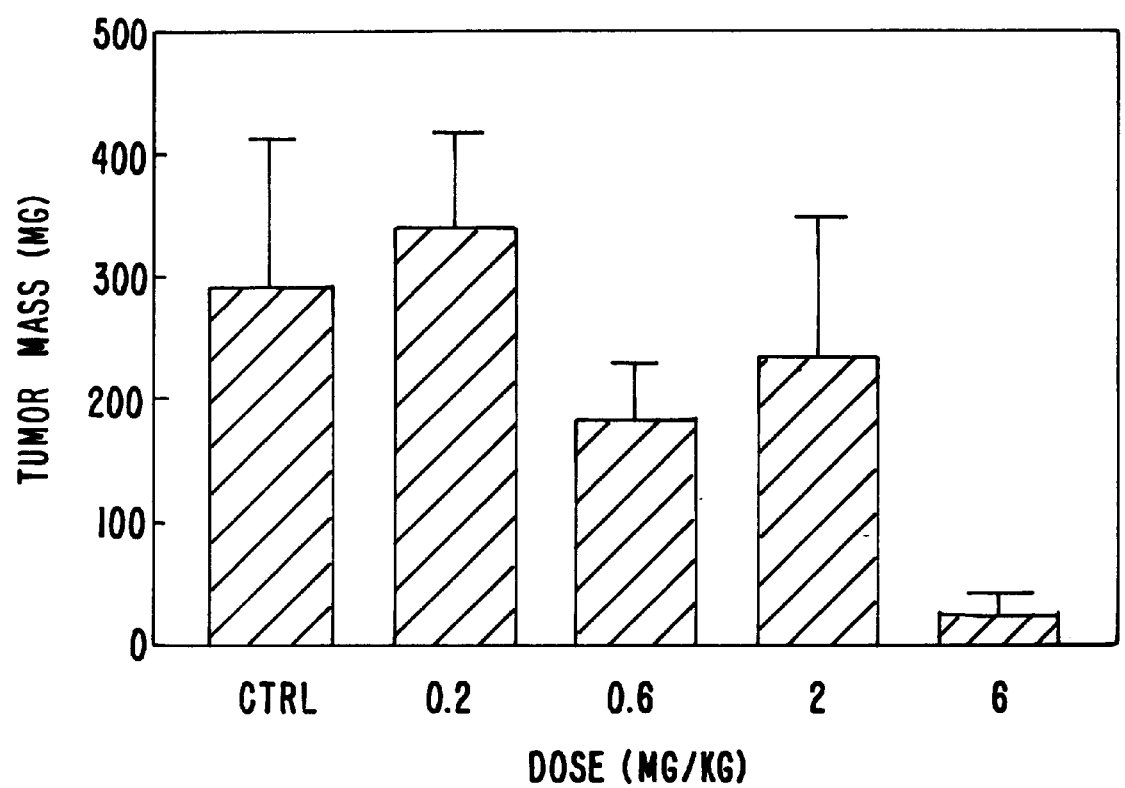

The retro-inverso analog of the native TSP sequence was also tested for inhibition of MDA MB435 tumor growth in an orthotopic nude mouse model demonstrated previously to be inhibited by over-expression of a TSP cDNA in the tumor cells. Tumor cells were allowed to implant for approximately one to three weeks prior to administering the peptide analog or a polysucrose conjugate. No significant inhibition of tumor growth was observed in the animals treated with 6 mg/kg of the peptide conjugated to 400,000 MW polysucrose containing 0.2 mg/kg of bound peptide (FIG. 27D). In contrast, daily intravenous treatment with the free peptide at 2 mg/kg significantly inhibited tumor growth (FIGS. 27B and 27C). The inhibitory effect persisted beyond the treatment period, although the growth of the tumors eventually resumed. Histological examination showed increased infiltration of the treated tumors with mononuclear cells. A dose response using 0.2 to 6 mg/kg of the peptides showed maximal inhibition of tumor growth following treatment with 6 mg/kg of peptide (FIG. 27D). Animals were treated with up to 10 mg/kg without overt toxicity.

G. Inhibition of Proliferation of Kaposi's Sarcoma Cells

Figure 36:
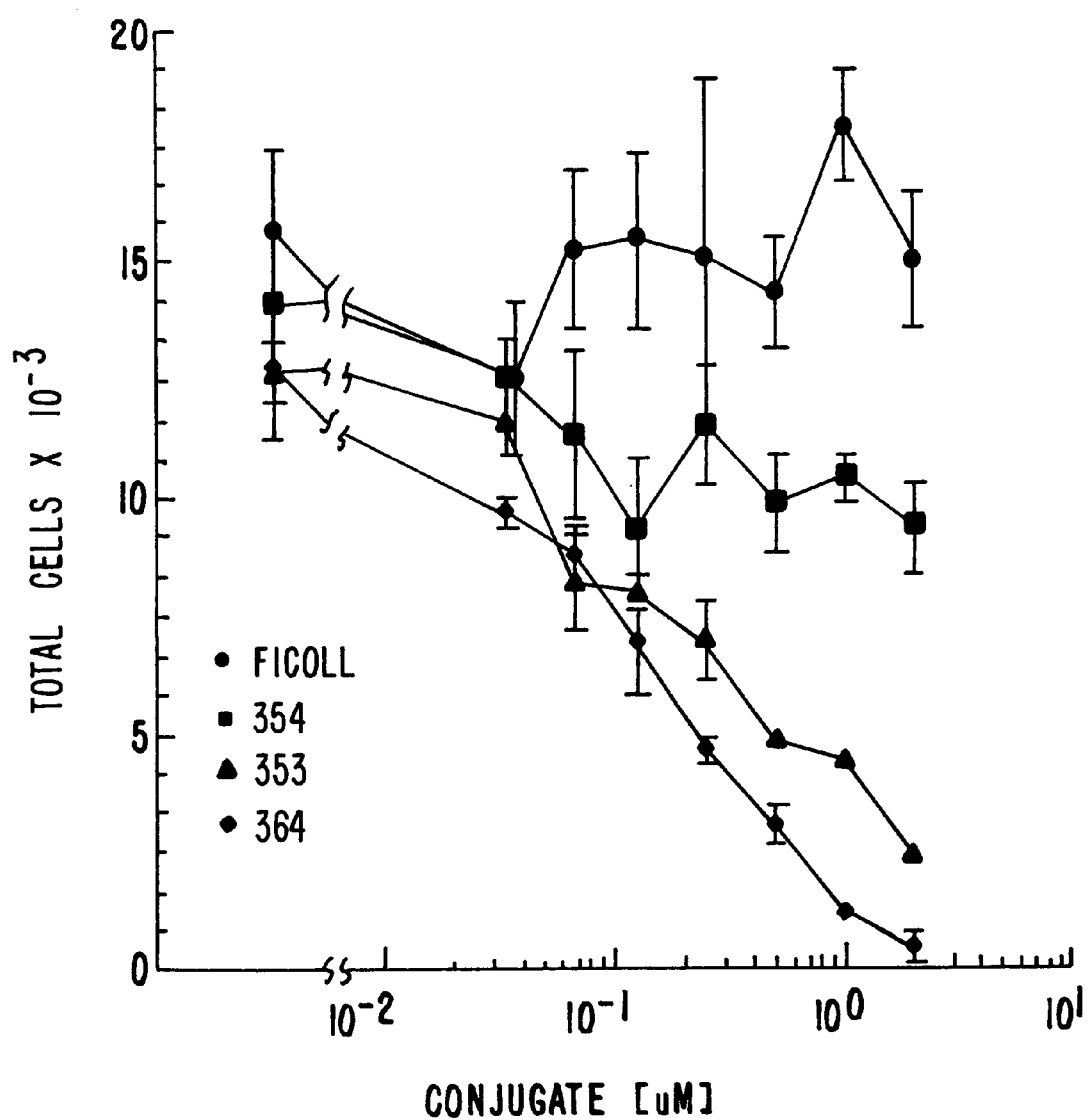
Figure 37:
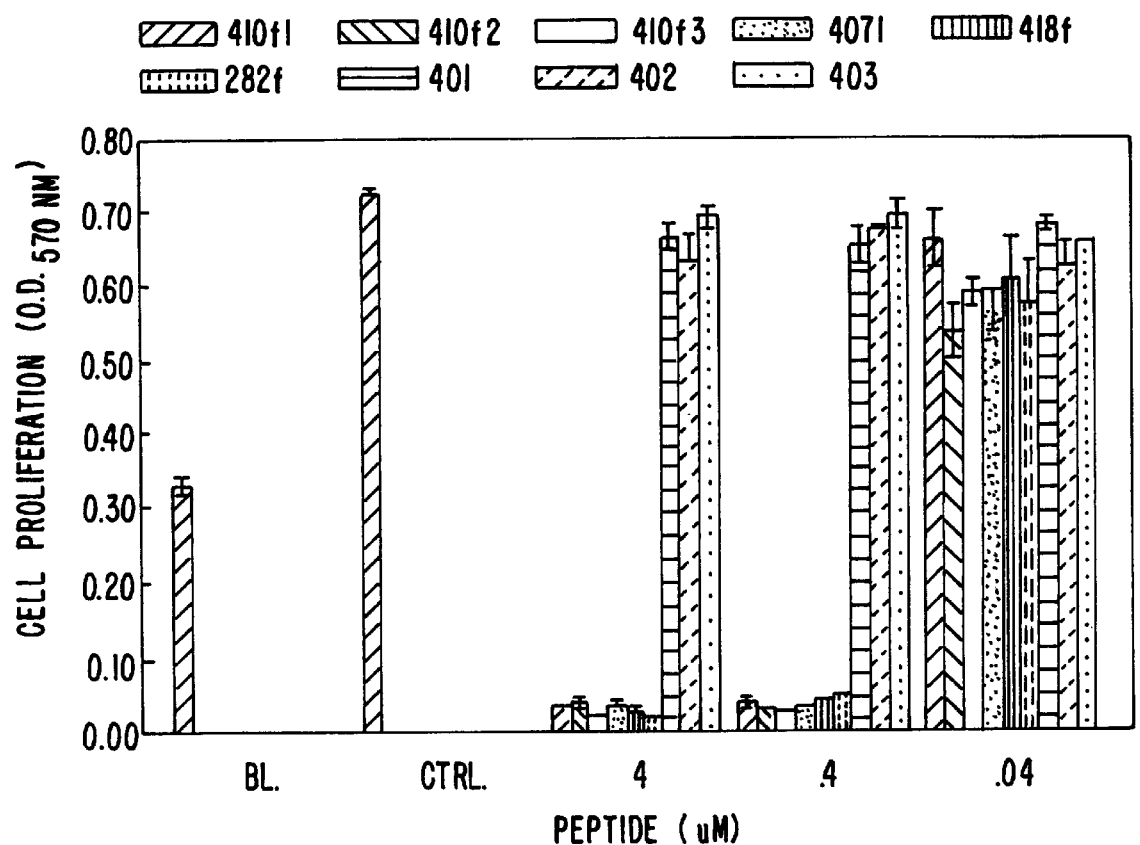

The inhibitory activity of thrombospondin on AIDS-KS cells was mimicked by a conjugate containing the peptide 364 (SEQ ID NO:30) with an $IC_{50}$ of $10^{-7}$ (FIG. 36). This inhibitory activity was primarily due to the WSXW motif (SEQ ID NO:73) as deletion of the amino-terminal basic amino acid residues (conjugate 353, SEQ ID NO:28) did not significantly decrease the inhibitory activity. However, conjugation of the same sequence through an amino-terminal cysteine thioether decreased the inhibitory activity (354, SEQ ID NO:29) unmodified FICOLL did not inhibit proliferation.

These observations were expanded in order to develop novel therapeutic agents for the treatment of AIDS-KS. Purification of TSP from platelets would be a costly way of obtaining enough TSP to treat an angiogenic process, e.g., KS. The results suggested that it was possible to evaluate smaller functional regions within the 140 kD fragment that mimics the biological effects observed.

As shown in FIG. 31, intravenous administration of the peptide conjugate (SEQ ID NO:30) strongly inhibited AIDS-KS lesion formation in the nude mouse model. This result demonstrates the activity of the peptide conjugates of the present invention for inhibiting pathological neovascularization in vivo.

H. Summary of Structural and Activity Results

Substitutions of the native TSP sequence can substantially increase heparin binding activity. Although 100-fold enhancement was observed of haparin binding activity based on TSP binding, only a 10-fold increase was observed based on inhibition of FGF-2 binding.

Activity of retro-inverso analogues demonstrates that the aminoacyl side chains are major contributors to the heparin-binding activity for the TSP peptide and that specific interactions with the peptide backbone or terminal charges are not crucial. Terminal charges in the forward peptide are similarly do not appear to be required. Accordingly, additional nonpeptide mimetics with potent heparin-binding activity may be prepared based on the aminoacyl substituents in the activity, according to the methods of the invention, and substantially as described herein.

The anti-proliferative activity of the thrombospondin peptide analogs is independent of the TGFβ activating sequence KRFK (SEQ ID NO:36), since peptides containing the inactive sequence KRAK (SEQ ID NO:37) had identical activity. However, these peptides still contain WSHW motif (SEQ ID NO:38) that were shown to inhibit TGFβ activation mediated by TSP which could result in inhibition of endothelial cell proliferation if this is mediated by conversion of latent to active TGF-β. The present data can not differentiate this possible mechanism of endothelial cell growth inhibition from that due to FGF-2 antagonism. However, inhibition of growth of tumor cells that are not sensitive to TGFβ by the peptides indicates that in this case, growth inhibition can be obtained independent of TGFβ activation.

III. Conjugates

In an additional embodiment, the invention provides a unique approach to constructing a water-soluble conjugate of peptides of the present invention, that exhibits a number of interesting and useful biological activities, most of which are expressed in high potency in conjugate form. Synthetic peptide segments from human thrombospondin Type I repeats have exhibited limited solubility in aqueous buffers owing to a marked tendency to aggregate. Disaggregation in very dilute solution following reconstitution from lyophilized powders has required up to several days as observed by slow release of biological activity and from aberrant characteristics of binding to known ligands.

Soluble conjugates of antigenic determinants and antibodies have been prepared with soluble, high molecular weight, hydrophilic polymers serving as carriers (see Inman, J. K. (1975) "Thymus-independent antigens: The preparation of covalent, hapten-FICOLL conjugates", J. Immunol. 114:704–709; Brunswick, et al. (1988) "Picogram quantities of anti-Ig antibodies coupled to dextran induce B cell proliferation", J. Immunol. 140:3364–3372; and Mongini, P. K. A. et al. (1992); "Membrane IgM-mediated signaling of human B cells—Effect of increased ligand binding site valency on the affinity and concentration requirements for inducing diverse stages of activation", J. Immunol. 148:3892–3901). These conjugates enhance biological activity through improved solubility and, in some cases, by multivalent presentation of active epitopes to cell surfaces. The conjugates have increased stability in body fluids and are resistant to proteases.

One aspect of the present invention is to store, aggregative peptides in concentrated form as solutions (or lyophilized powders) in a form which allows rapid expression of the desired in vitro and in vivo properties in experimental systems or in therapeutic applications. To this end, the present invention provides thrombospondin peptide segments covalently linked through stable bonds to suitably functionalized polymers, such as FICOLL™ and dextran.

An additional aspect of the invention is to provide compounds having increased the stability in body fluids, to decrease the sensitivity of the peptides to proteases and to decrease the clearance of the peptides from circulation, which is otherwise rapid for small peptides.

Polysucrose and dextran conjugated peptides of the invention have increased inhibitory activity for thrombospondin binding to heparin relative to the free peptides. The conjugates are potent inhibitors of tumor and endothelial cell proliferation in vitro. Thus, the conjugates are useful for in vitro applications involving inhibition of tumor or endothelial cell growth. These conjugates also are useful for the treatment of diseases associated with tumor growth or metastasis or abnormal vascular proliferation, including but not limited to hemangioma, diabetic retinopathy, and rheumatoid arthritis.

In a preferred embodiment the peptide conjugate comprises a water soluble polymer conjugated to at least one synthetic peptide having 4–30 amino acids, wherein said peptide comprises a subsequence Trp—$X_1$—$X_2$—Trp (SEQ ID NO:75) wherein $X_1$ is selected from Thr, Ala and Ser, $X_2$ is selected from Pro, Glu, His, Ala and Ser, and wherein said peptide conjugate has binding affinity for heparin or sulfated glycoconjugates. $X_1$ and $X_2$ may also may comprise modified forms of the above amino acids which are readily recognized by those of skill in the art such as N-blocked analogs and unnatural amino acid substitutions. In a preferred embodiment the water soluble polymer is a branched carbohydrate polymer. The carbohydrate polymer may include, for example polysucrose (such as FICOLL) or dextran.

In an alternative embodiment, the peptide conjugate includes a synthetic peptide which further comprises a sequence selected from the group consisting of —$B_1$—$B_2$—$X_3$—$B_3$— (SEQ ID NO:74) and —$B_1$—$X_3$—$B_2$—$X_4$—$B_3$— (SEQ ID NO:76), wherein $X_3$ and $X_4$ are independently any amino acid and $B_1$, $B_2$ and $B_3$ are independently selected from Lys, Arg and His.

Conjugation of FICOLL or dextran to the peptides of the invention may involve the use of buffers containing a dissociating agent for the combined steps of reconstituting the peptide, coupling the peptide to a particular polymer, and separating the resulting conjugate from unconjugated peptide, reagents and byproducts. A preferred dissociating agent is urea. Urea acts to mask noncovalent interactions between peptide molecules that cause low solubility and lead to the linking of aggregates of peptide to carrier sites rather than single species. Although urea is used in handling proteins and large peptides, it has not been used routinely in the chemical derivatization of small hydrophobic peptides.

The use of a water-soluble phosphine derivative to reduce disulfide bonds that form between cysteine peptides, exposed to atmospheric oxygen, has been reported (see Burns, J. A. (1991), *J. Org. Chem.* 56:2648–2650). This method permits subsequent alkylation of the released sulfhydryl groups by common SH-specific functions (e.g., as haloacetyl or maleimido groups) without having to remove the excess reagents or byproducts. This provides convenience of operations when working with small peptides. The use of tris(2-carboxyethyl) phosphine (TCEP) for reduction of cysteine peptides and subsequent site-directed coupling of cysteine peptides to a carrier bearing haloacetyl groups has not been previously reported.

In preferred embodiments, polysucrose such as FICOLL, a highly branched all-synthetic, polymerized sucrose of high molecular weight was chosen as a carrier, based on a unique combination of features, e.g., (1) ready functionalization by easily controlled chemical modification steps leading to a primary amine derivative; (2) very low (or absent) immunogenicity and no known toxicity; and (3) a highly branched carbohydrate structure which imparts greatly enhanced biological activity to coupled peptides as compared with similar conjugates prepared from a much less branched (mostly linear) polysaccharide carrier such as dextran.

Preferably the peptides of the invention are conjugated to the carbohydrate polymer through a site-specific thioether linkage. For instance, the synthetic peptides will typically have a free sulfhydryl group to conjugate with carriers or water soluble polymers which, in turn, bear sulfhydryl-selective electrophilic functions such as haloacetyl (preferably iodoacetyl) or maleimido groups. The polymer carriers preferably have a molecular weight greater than or equal to 20,000 kd. More preferred are polymer carriers having a molecular weight of at least 50,000.

The carriers preferably have one or more sulhydryl-selective functional groups at or near the end of a flexible spacing arm which serves to overcome steric hindrance by the carrier structure to presentation of peptide epitopes to their intended targets. The spacer arm between peptide epitopes and carrier matrix is typically of a length which minimizes stearic hindrance by the latter to interactions between epitopes and their intended targets. The spacer arm preferably has an 8–30 atom spacing structure, more preferably a 10 to 20 atom spacing structure, and most preferred are spacer arms having a 12-atom spacing structure.

In an additional embodiment, the water soluble polymer may be conjugated to one or more of the same or different peptides of the invention. For example, the polymer may be multiply substituted homogenously with a particular peptide of the invention, or alternatively, may be heterologously substituted with two or more peptides of the invention. For example, for those embodiments where the water soluble polymer is a polysucrose, it may be preferably conjugated to a range of about 1–50 peptides, having an average molecular weight of about 400,000. When the water soluble polymer is dextran, it may be preferably conjugated to a range of about 1–250 peptides, having an average nolecular weight of 2,000,000.

FIGS. 12–15 present an example of an approach to constructing a water-soluble conjugate of a peptide that exhibits a number of useful biological activities, which are expressed in high potency in conjugate form.

Figure 12:
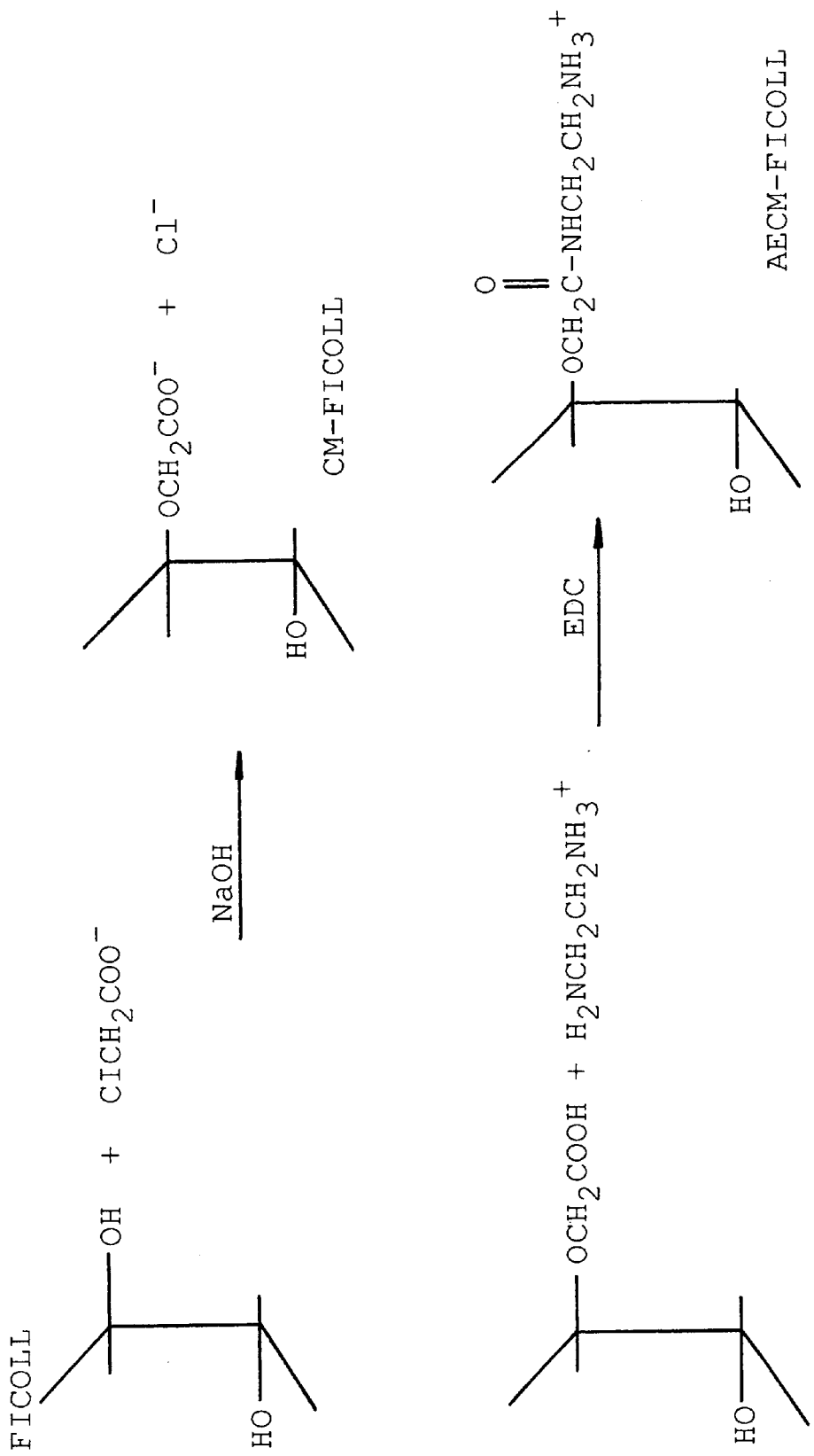
FIG. 12 outlines the initial functionalization of the polysaccharide carrier.
Figure 13:
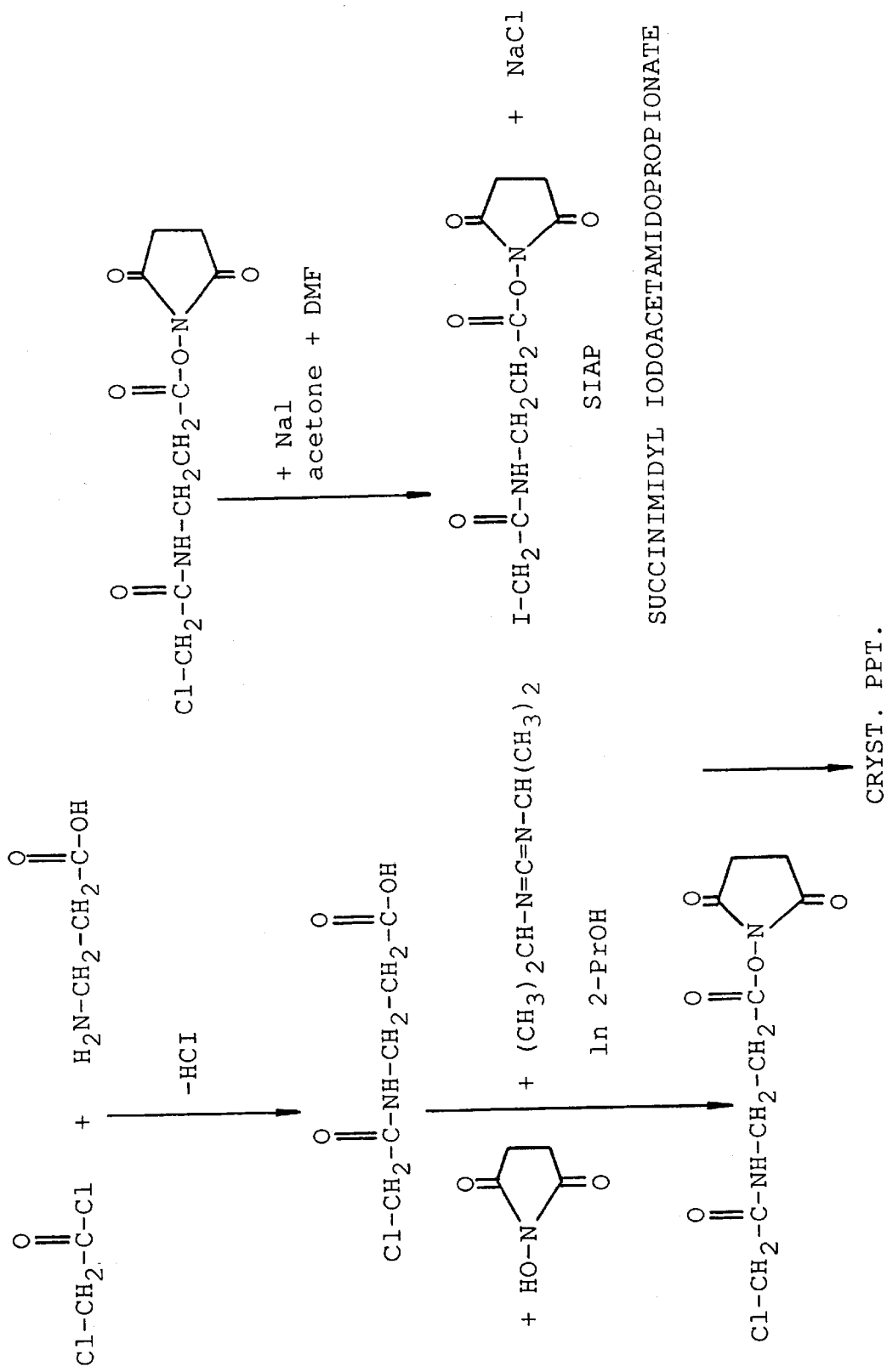
FIG. 13 presents the scheme for synthesizing the amine-specific iodoacetylating reagent, SIAP, that introduces additional spacing structure between peptide and carrier.

FIG. 12 outlines the initial functionalization of the polysaccharide carrier. FIG. 13 presents the scheme for synthesizing the amine-specific iodoacetylating reagent, SIAP, that also introduces additional spacing structure between peptide and carrier. A similar synthesis of the bromo analogue of SIAP, see Inman, J. K. et al. (1991), *Bioconjugate Chemistry* 2:458–463).

Figure 14:
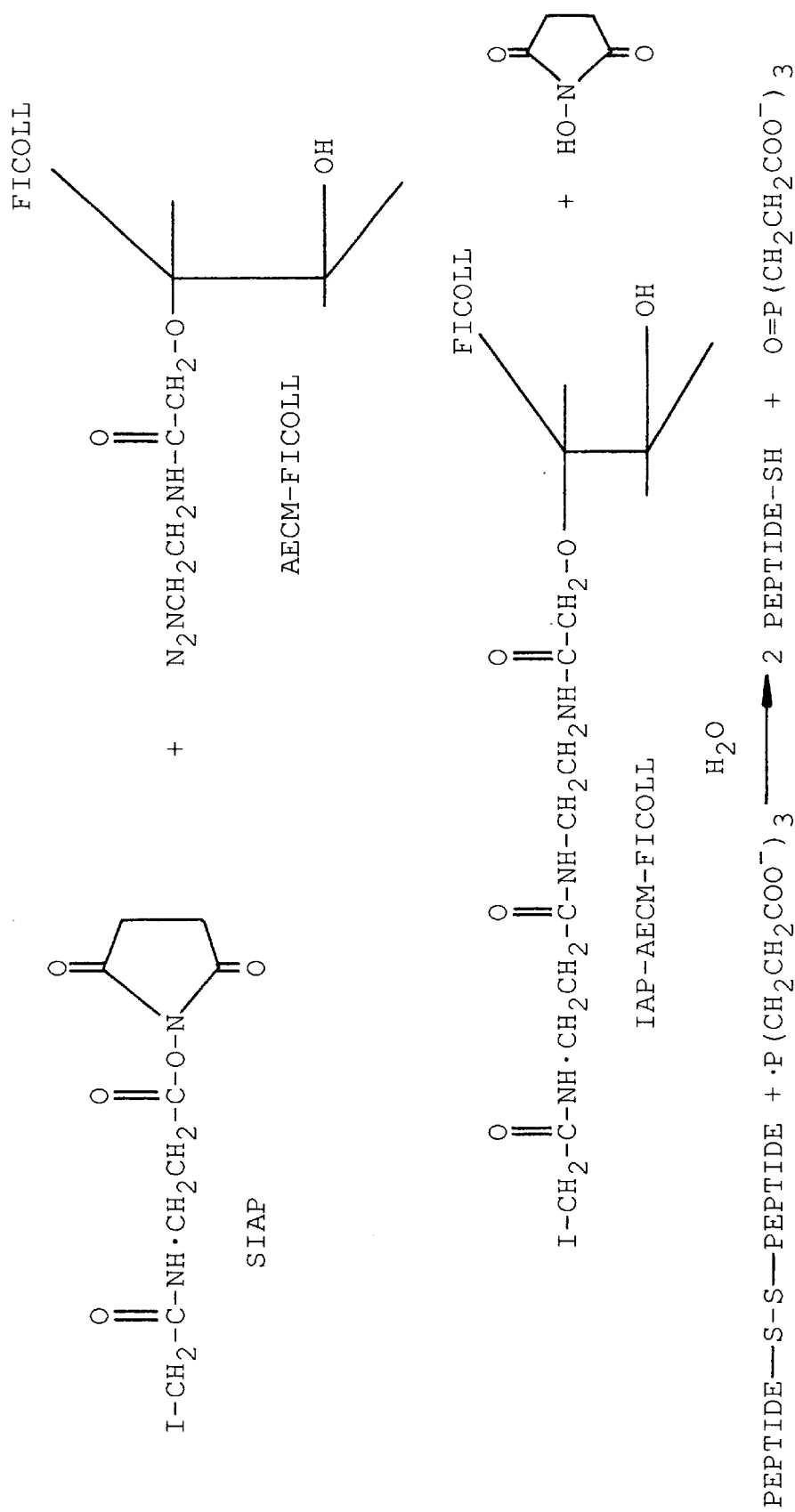
FIG. 14 illustrates how each component in the coupling reaction used in preparing the conjugate is rendered reactive for the formation of stable thioether linkages, namely, the reaction of SIAP with aminoethyl-carbamylmethylated (AECM) FICOLL and the reduction of disulfide bonds that have formed between deprotected, C-terminal cysteine residues of the peptide moiety.
Figure 15:
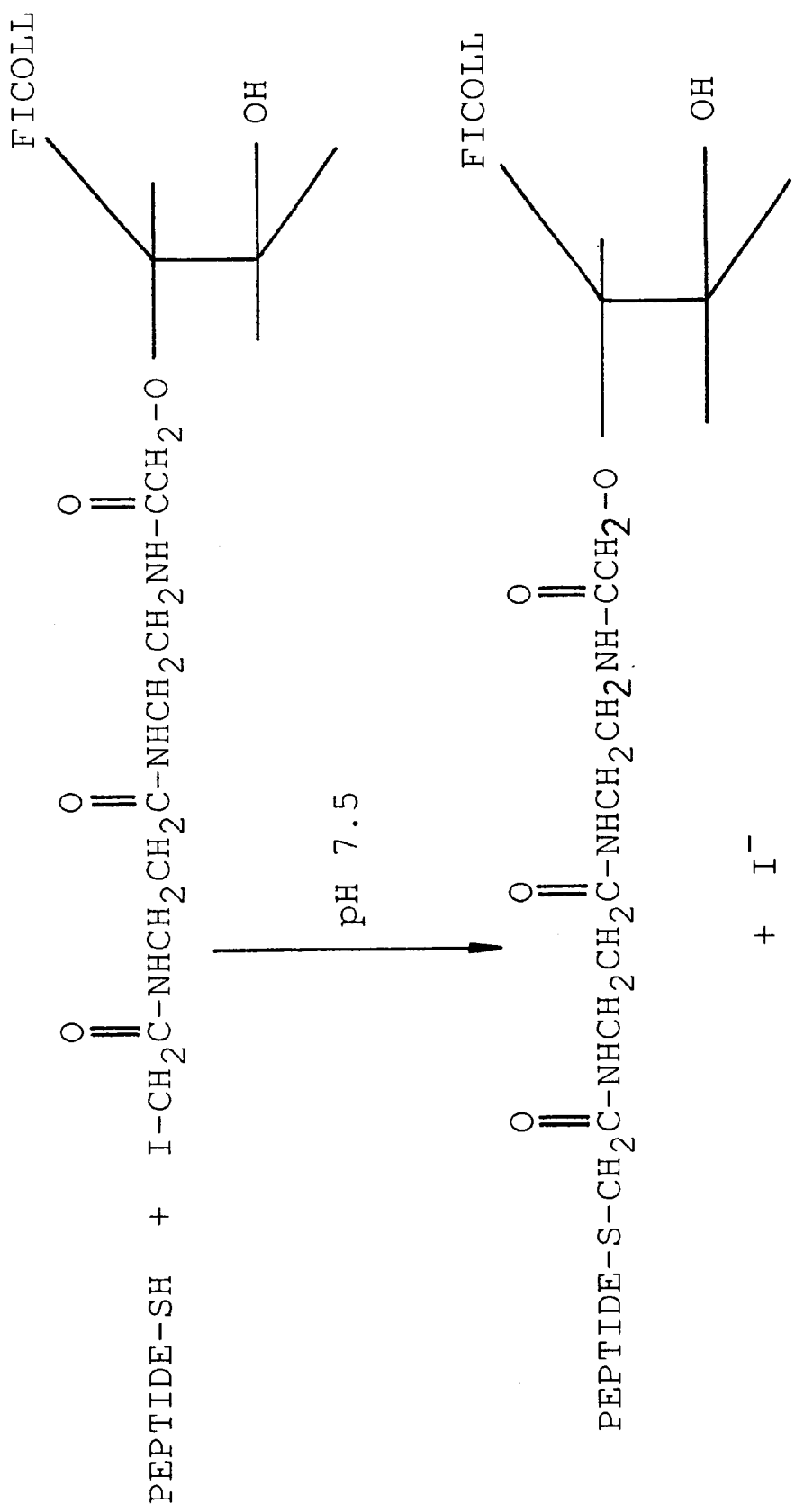
FIG. 15 depicts the thioether linkage reaction whereby multiple peptide molecules are coupled to a single molecular species of polysucrose (such as FICOLL). This method results in a bland, flexible, 12-atom spacing structure between peptide epitopes and carrier matrix that minimizes stearic hindrance by the latter to thrombospondin that lack the currently known heparin binding consensus sequences. The present data demonstrate that peptides from the type I repeats are potent heparin and sulfatide binding peptides that can inhibit interactions of three heparin binding proteins with sulfated glycoconjugates. These peptides may be general inhibitors of heparin-dependent adhesive proteins, growth factors, and coagulation enzymes. The peptides that inhibit binding to heparin strongly promote melanoma cell adhesion when immobilized on plastic. The peptides also inhibit some heparin-dependent interactions of laminin and thrombospondin with human melanoma cells. Although putative heparin binding sequences in the amino terminal domain of thrombospondin are not conserved in the recently identified second gene for thrombospondin (Bornstein et al., *J. Biol. Chem.* 266, 12821–12824, (1991)), the heparin binding sequences from the type I repeats identified here are conserved.

FIG. 14 illustrates how each component in the coupling reaction used in preparing the conjugate is rendered reactive for the formation of stable thioether linkages, namely, the reaction of SIAP with aminoethyl-carbamylmethylated (AECM) FICOLL and the reduction of disulfide bonds that have formed between deprotected, C-terminal cysteine residues of the peptide moiety. Finally, FIG. 15 depicts the thioether linkage reaction whereby multiple peptide molecules are coupled to a single molecular species of FICOLL. This method results in a bland, flexible, 12-atom spacing structure between peptide epitopes and carrier matrix that minimizes stearic hindrance by the latter to interactions between epitopes and their intended targets. Thus the invention also includes thiol derivatives of the peptides from the three type I repeats of human endothelial cell thrombospondin.

Table 9 shows examples of several peptides of the invention which are conjugated to FICOLL. Typically, where a peptide or analog or mimetic is conjugated to FICOLL, the peptide number will generally include an "f" adjacent to the number.

TABLE 8

Structures of Peptides Conjugated to FICOLL

| Peptide | Sequence |
| --- | --- |
| 353f | GGWSHWSPWSSC |
| 354f | CGGWSHWSPWSS |
| 224f, 364f, 387f, 407f | KRFKQDGGWSHWSPWSSC |
| 389f | KRFKQDGGASHASPASSC |
| 392f | KRFKQAGGWSHWSPWSSC |
| 416f | Ac(allD)CSSWPSWHSWGGDQKFRK-NH$_2$ |
| 419f | KRFKAAGGWSHWSPWSSC-NH$_2$ |

Aside from specific and special biological activities, a number of other unique features of the TSP peptide conjugates are also found. The use of highly cross-linked polysucrose (FICOLL) of high molecular weight (>25,000 Da) provides advantages as a carrier for covalently linked, biologically active peptides. For example, establishing stable thioether linkages between peptide and FICOLL with use of (a) an iodoacetamido-containing heterobifunctional reagent that features a bland spacing structure (e.g., the reagent, SIAP), and (b) use of a water-soluble phosphine derivative in situ during linkage reactions maximizes the availability of free, reactive sulfhydryl groups in the peptide. Also, the use of these polymers allows the linkage of peptides to the functionalized polymer carrier in a strongly disaggregative medium (e.g., 6 molar urea). This tactic includes pretreatment of the peptide under other, more strongly dissociative conditions that will break non-covalent interactions but not covalent bonds.

Conjugates of the thrombospondin peptides using FICOLL and dextran as carriers have been prepared and tested. In preliminary studies, the FICOLL conjugates had much greater activity than the dextran conjugates at similar levels of substitution. Several differences in the properties of the conjugates appear to account for the different activities, e.g., different relative size of the polymers, degree of branching of the polymers, accessibility of the coupled peptides, and/or effects of the carrier on peptide conformation. The existing conjugates were prepared using polymer with average molecular weight from about 20,000 to about 500,000 kD. Smaller FICOLL polymers may also be employed, and the degree of substitution may also be varied.

A brief description of the preparation of FICOLL conjugates follows, a more detailed description appears in the Examples section, below. FICOLL was carboxymethylated using chloroacetate. Carboxymethylated FICOLL was treated with an excess of ethylenediamine at pH 4.6 to 4.9 in the presence of 1-ethyl-3-(3-dimethylaminopropyl) carbodiimide to give aminoethyl-carbamylmethylated (AECM) FICOLL. AECM-FICOLL was treated with N-succimidyl 3-(2-iodoacetamido) propionate in dimethylformamide, and the purified product was coupled to the reduced thrombospondin peptides in the presence of 6 M urea. Unreacted iodoacetamido groups were capped by addition of 2-mercaptoethanol. The conjugate was purified by gel filtration in 6 M urea on Bio-Gel P60, dialyzed against phosphate buffered saline, and concentrated by ultrafiltration. The degree of modification was quantified by carbohydrate analysis and estimation of bound Trp using $\epsilon=5540$ $M^{-1}cm^{-1}$ per Trp residue.

The conjugates were tested in the in vitro binding assays and endothelial proliferation assays. As with the free peptides, the objective was to maximize the potency and specificity of the conjugates as antiproliferative agents. The conjugates were found to inhibit proliferation of breast carcinoma cells as well as endothelial cells.

IV. Pharmaceutical Compositions

While the peptides of the present invention are described primarily in terms of the free or conjugated peptides, analogs and mimetics ("peptides"), in some embodiments, the present invention also provides pharmaceutical composition comprising an effective amount of a peptide having a high binding affinity to heparin or related sulfated glycoconjugates, and said composition comprises a pharmaceutically acceptable excipient or carrier.

The term "effective amount" as used herein, typically refers to the amount of the active ingredient, e.g. the peptides of the invention, which are required to achieve the desired goal. For example, in therapeutic applications, an effective amount will be the amount required to be administered to a patient to result in treatment of the particular disorder for which treatment is sought. The term "treatment of a disorder" denotes the reduction or elimination of symptoms of a particular disorder. Effective amounts will typically vary depending upon the nature of the disorder, the peptides used, the mode of administration, and the size and health of the patient. Typically, effective amounts of the peptides of the invention will be in the range of from about 1 μg to about 1 g of polypeptide for a 70 kg patient, preferably from about 1 μg to about 100 μg.

Even more preferred is a pharmaceutical composition according to the invention, wherein the composition comprises an effective amount of a peptide having a sequence selected from the group consisting of SEQ ID NO:1, SEQ ID NO:2, SEQ ID NO:3, SEQ ID NO:14, and SEQ ID NO:19, and the sequences set forth in Table 3, in combination with a pharmaceutically acceptable excipient or carrier.

Also provided for is a pharmaceutical composition comprising the peptide conjugates of the invention and a pharmaceutically acceptable carrier. While it is possible to administer the peptide and peptide conjugates of the invention, alone, it is preferable to present it as part of a pharmaceutical formulation. Pharmaceutically acceptable carriers typically include carriers known to those of skill in the art, including pharmaceutical adjuvants. Generally these pharmaceutically acceptable carriers will include water, saline, buffers, and other compounds described, e.g., in the MERCK INDEX, Merck & Co., Rahway, N.J. See, also, *Bioreversible Carriers in Drug Design, Theory and Application,* Roche (ed.), Pergamon Press, (1987). These formulations typically comprise the pharmacological agent (i.e., the peptide or peptide conjugate) in a therapeutically or pharmaceutically effective dose together with one or more pharmaceutically or therapeutically acceptable carriers and optionally other therapeutic ingredients. Various considerations are described, e.g., in Gilman et al. (eds) (1990) *Goodman and Gilman's: The Pharmacological Bases of Therapeutics,* 8th Ed., Pergamon Press; *Novel Drug Delivery Systems,* 2nd Ed., Norris (ed.) Marcel Dekker Inc. (1989), and *Remington's Pharmaceutical Sciences,* the full disclosures of which are incorporated herein by reference. Methods for administration are discussed therein. In particular, the pharmaceutical conjugates of the invention may be administered intravenously, subcutaneously, orally, transdermally, such as in the method of (Prausnitz, M R, Bose, V G, Langer, R, Weaver, J C: Electroporation of Mammalian skin: a mechanism to enhance trans dermal drug delivery. *Pro. Nat. Acad. Science U.S.A.,* 90:10504–10508 (1993); and Wallace, B M, Lasker, J S: Stand and Deliver: getting peptide drugs into the body. *Science* 260:912-912 (1992). Liposomes may also be used to administer the conjugates of the invention (see Woodle, M C, Storm, G, Newman, M S, Jekot, J J, Collins, L R, Martin, F J, Szoka F C: Prolonged systemic delivery of peptide drugs by long circulating liposomes: illustration with vasopressin in the Brattleboro rat. *Pharmaceut. Res.* 9:260–265 (1992).

In alternate embodiments, the present invention also provides that the peptides according to the present invention may be immobilized on a suitable substrate either directly or after conjugation to a suitable carrier polymer or protein. Suitable substrates, carrier polymers, and carrier proteins are known to one of ordinary skill in the art. Such immobilized compositions are useful to promote adhesion and growth of anchorage-dependent cells. Particularly preferred is an embodiment wherein the immobilized peptide is peptide 246 (SEQ ID NO:19) or conjugates of peptides 353 (SEQ ID NO:28), 364 (SEQ ID NO:30), 392 (SEQ ID NO:32), 416, 419 (SEQ ID NO:34).

V. Diagnostic, Screening and Other Applications

In addition to the above described applications, the peptides, analogs and mimetics of the present invention are also particularly useful in a variety of other applications. In particular, as potent heparin binding compounds, the peptides of the present invention will find a variety of uses in diagnostic screening and affinity ligand applications.

As a specific example, the peptides, peptidomimetics and anlogs of the present invention may be used in methods for screening whether a compound is an agonist or antagonist of a heparin/thrombospondin interaction. In particular, the petides of the present invention, having been derived from TSP, and being capable of tightly binding heparin, provide an excellent model system of TSP-heparin interaction.

To assay for compounds that act as agonists or antagonists of TSP-heparin interaction, the particular peptide is incubated with heparin, in the presence of a test compound. Where the binding of the compound is increased or decreased in the presence of the test compound, it is an indication that the compound is an agonist or antagonist of TSP-heparin interaction, respectively. These methods can be used to screen a wide variety of compounds for potential therapeutic treatments.

In a further example, the compounds of the present invention may be useful as affinity ligands or probes from the detection, and or purification of heparin from within a sample. Affinity purification methods are generally well known in the art. For example, the compounds of the invention may be first immobilized upon a suitable solid support. Suitable solid supports will generally include agarose, cellulose, silica, dextran, and the like. Once immobilized, a sample may be contacted with the support bound peptide, whereby any heparin within the sample will selectively bind to the solid support. Bound heparin may then be readily eluted by altering the conditions to which the support is subjected, resulting in the release of the heparin (e.g. salt concentration, pH, and the like).

Alternatively, the peptides, analogs and peptidomimetics described herein may also be sued to identify heparin within a sample. In particular, these peptides, etc, may be used as affinity probes for the identification of heparin in a sample. Typically, these methods will involve the immobilization of the sample on a solid support followed by interogation with the heparin binding peptide. Typically, peptides used for this application will be labelled with a suitable detectable group, to allow for easier detection. Suitable detectable groups include, e.g., radiolabels, enzymatic labels, e.g., horse radish peroxidase, luciferase, and the like, binding complements, e.g. antibody-epitope pairs. Determination of binding between the peptide and a portion of the sample is then a matter of detecting the particular detectable group bound to the immobilized sample.

The present invention is further illustrated by the following examples. These examples are merely to illustrate aspects of the present invention and are not intended as limitations of this invention.

EXAMPLES

Example 1

General Procedures

Materials: Thrombospondin was purified from thrombin-stimulated human platelets as previously described (Roberts et al., *J. Biol. Chem.* 260, 9405–9411 (1985)). Recombinant heparin-binding fragments of thrombospondin, residues 1–175 ((28kD), and recombinant apolipodrotein E were provided by Biotechnology General, Ltd, Rehovot, Israel. Mouse laminin purified from the Engelbreth Holm Swarm tumor was provided by Dr. Lance Liotta, National Cancer Institute. Monoclonal antibodies to thrombospondin were provided by Dr. William Frazier (Washington University, St. Louis). Thrombospondin, its fragments, apolipoprotein E, BSA-peptide conjugates, and laminin were iodinated using Iodogen (Pierce Chemical Co., Rockford, Ill.) as previously described (Roberts et al., *J. Biol. Chem.* 260, 9405–9411 (1985)). Heparin-BSA conjugate was prepared by coupling bovine lung heparin (The Upjohn Co.) through the reducing terminus to BSA by reductive amination in the presence of $NaBH_3CN$ essentially as described (Funahashi et al., *Anal. Biochem.* 126, 414–421 (1982)). Bovine brain sulfatide was obtained from Supelco and dipalmitoylphosphatidylcholine and cholesterol were from Sigma.

Peptides were synthesized corresponding to portions of the three type I repeats of human thrombospondin as indicated in Table 1. Synthesis was done using art recognized methods for peptide synthesis. The peptides used in this study were synthesized on a Biosearch Model 9600 peptide synthesizer using standard Merrifield solid phase synthesis protocols and t-Boc chemistry. Peptides were analyzed by reverse-phase HPLC chromatography. Peptide solutions were neutralized by addition of dilute NaOH and stored in solution at −20°.

Adhesion Assays: Human melanoma cell line A2058 (Todaro et al., *Proc. Natl. Acad. Sci U.S.A.* 77, 5258–5262 (1980)) was maintained by monolayer culture at 37° with 5% carbon dioxide in RPMI 1640 medium containing 10% fetal bovine serum. For attachment assays, cells were removed using trypsin, passaged at $10^4$ $cells/cm^2$ and harvested between days 5 and 7. Attachment and spreading on thrombospondin-coated plastic was determined as previously described (Roberts et al., *J. Cell Biol.* 104, 131–139 (1987)). Inhibition was determined by adding the inhibitor diluted in 0.4 ml of bicarbonate-free RPMI 1640 medium, containing 1 mg/ml of bovine serum albumin (fatty acid free, Sigma), pH 7.3, to wells of a 24-well dish containing bacteriological polystyrene was coated with the indicated peptides at 200 µg/ml. Melanoma cells were harvested by incubation with phosphate buffered saline containing 2.5 mM EDTA for 20 minutes at 37°. The cells were centrifuged and viability (routinely >99%) was assessed by trypan blue exclusion. The cells were resuspended in medium and allowed to recover in suspension for 1 h. Melanoma cells (2×10$^5$) suspended in 100 µl of medium (approx. 10$^3$/mm$^2$) were added to each well and allowed to attach for 60 minutes at 37° C. in a humidified atmosphere. Adhesion was determined microscopically and is presented in FIG. 9 as the mean ±SD, n=6.

Figure 4A:
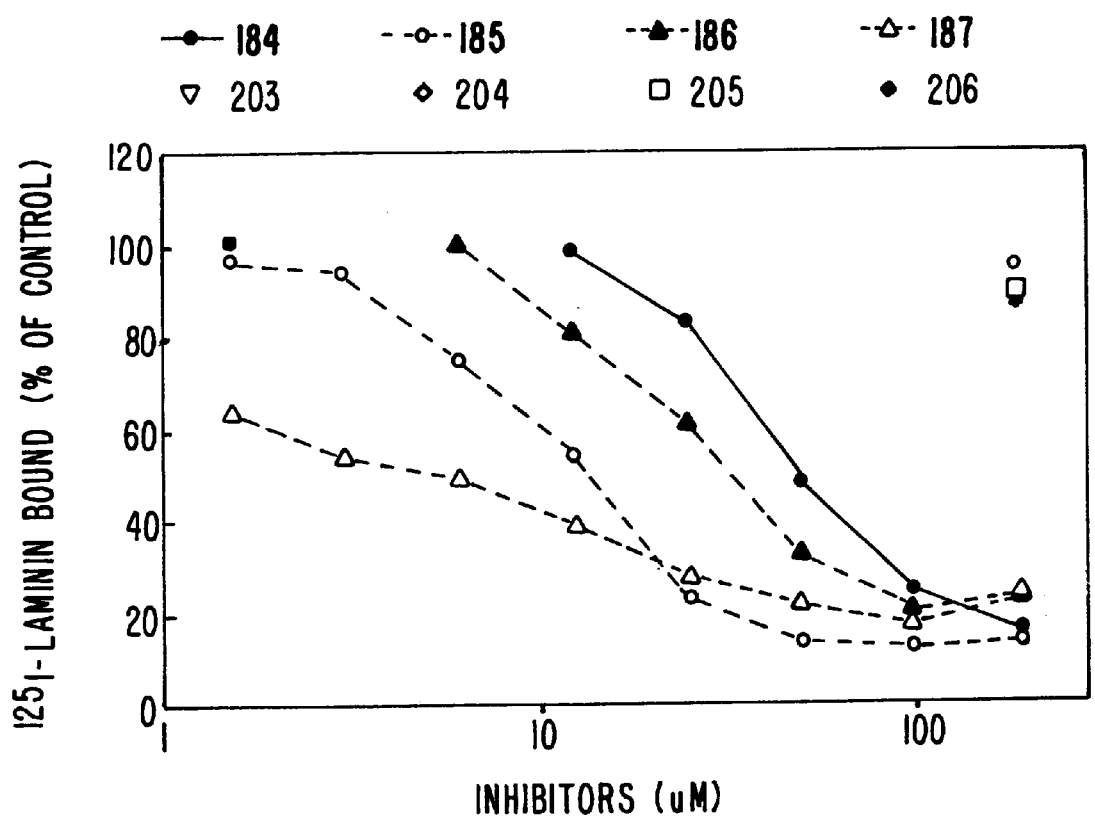
FIGS. 4A and 4B are graphs showing the inhibition of $^{125}$I-laminin binding to sulfated glycoconjugates by thrombospondin peptides.
Figure 4B:
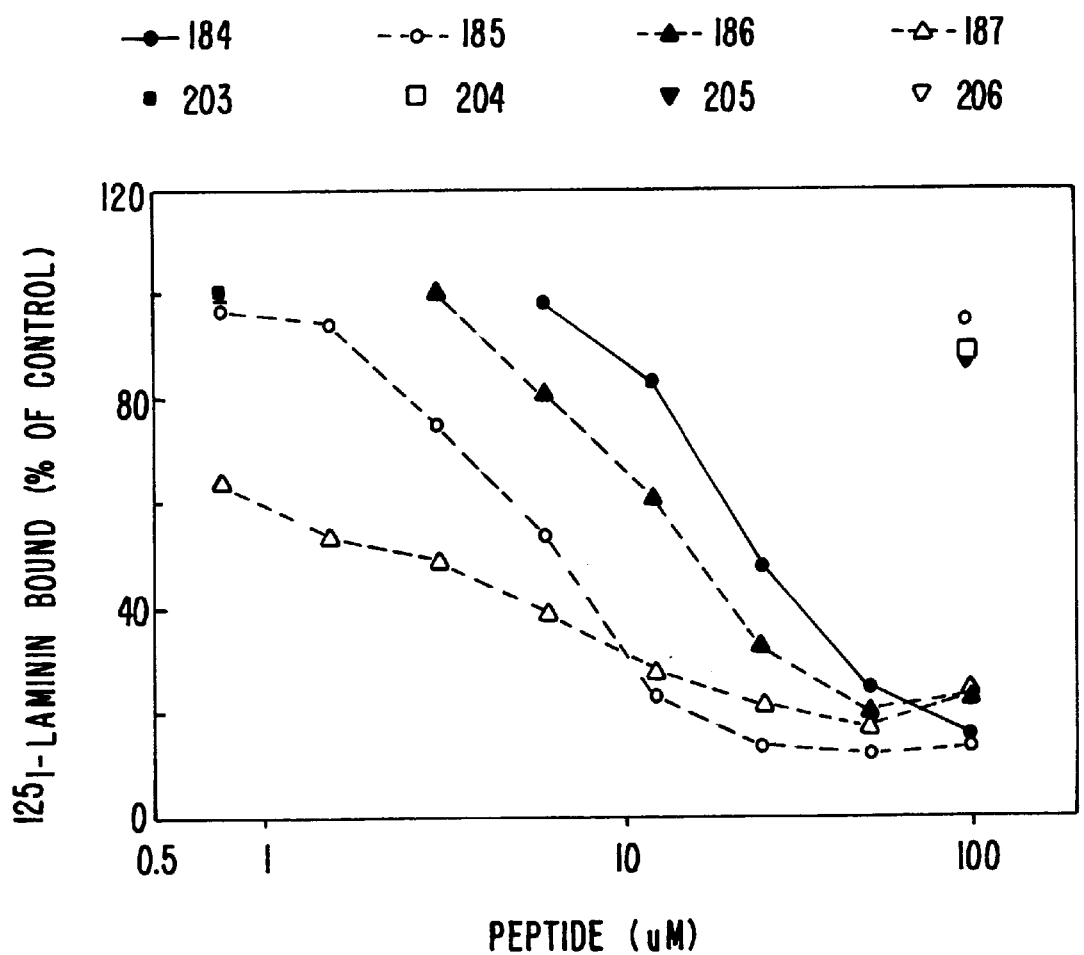

Sulfatide and Heparin Binding: The peptides were tested as inhibitors of laminin, thrombospondin or apolipoprotein E binding to a heparin-bovine serum albumen conjugate or to a sulfatide in a solid phase assay essentially following the procedure described in Zabrenetzky et al., *Cancer Res.,* Vol. 50, pages 5937–5942 (1990). Sulfatide (0.2 µg/well for thrombospondin binding, 0.6 µg/well for laminin binding) was immobilized in a mixture of 50 ng of phosdhatidyl choline, and 30 ng of cholesterol on polyvinyl chloride microtiter plates. Heparin-BSA (0.2 µg/well) was absorbed onto polyvinyl chloride microtiter plate wells by incubation of 50 µl of Dulbecco's PBS for 2 h at 37°. The wells were emptied and filled with 50 mM tris, pH 7.8 containing 150 mM NaCl, 1 mM CaCl$_2$, 0.025% NaN$_3$, and 1% BSA. After 30 minutes, the wells were emptied and 30 µl of various concentrations of potential inhibitory peptides diluted in the same buffer or buffer alone and 30 µl of $^{125}$I-labeled laminin, thrombospondin or apolipoprotein E (0.2 µg/ml) were added to each well. After 3 hours at 4°, the wells were washed 6 times with 0.15 M NaCl, cut from the plate and the bound radioactivity counted. FIGS. 1A–B and 2A–B show the level of thrombospondin binding to sulfatide and heparin-BSA, respectively, in the presence of increasing concentrations of the peptides listed. FIGS. 3 and 4A–B show the level of laminin binding to sulfatide and heparin-BSA, respectively, in the presence of increasing concentrations of the listed peptides.

A2058 Melanoma Cell Binding: Melanoma cells (1×10$^5$ in 0.2 ml) were incubated with 0.2 µg/ml labeled laminin alone or in the presence of 200 micrograms per ml of peptides from SEQ ID NO:1, SEQ ID NO:2, or SEQ ID NO:3, type-I repeats from thrombospondin (FIG. 5A). Melanoma cells were also incubated with labelled laminin or thrombospondin alone or in the presence of 10 µg/ml of peptides from the first (184, SEQ ID NO:1), second (185, SEQ ID NO:2 and 246, SEQ ID NO:19), or third type I repeat of thrombospondin (186, SEQ ID NO:3) or 1 µg/ml heparin (FIG. 5B). The cells were centrifuged through oil to separate the free laminin from the bound laminin followed by quantifying the radioactivity in the cell pellet by a gamma counter. The results are presented in FIGS. 5A and B, as a percent of control binding determined in the absence of peptide and is the mean of triplicate determinations ±the standard deviation.

Figure 6B:
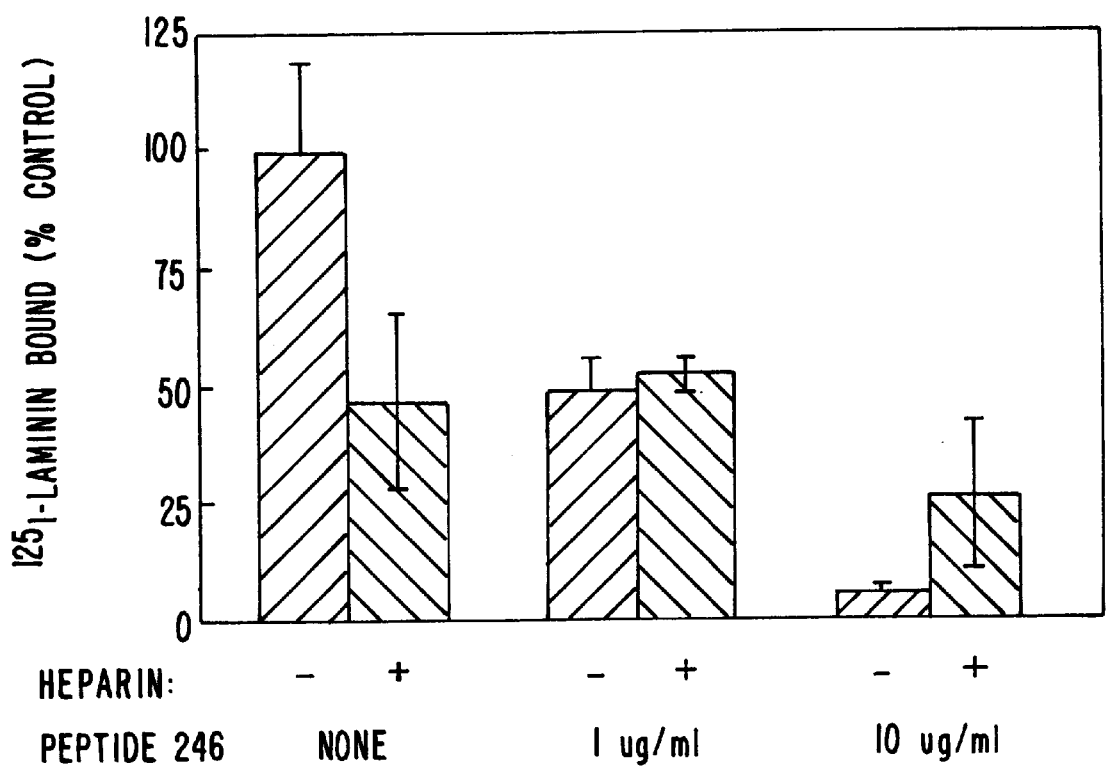

FIG. 6A shows a graph representing the inhibition of $^{125}$I-thrombospondin binding to A2058 melanoma cells by heparin and thrombospondin peptide SEQ ID NO:1. Melanoma cells (3×10$^5$ cells in 0.2 ml) were incubated with 0.2 µg/ml of labelled I$^{125}$-thrombospondin alone or in the presence of increasing concentrations of heparin or a peptide having the sequence according to SEQ ID NO:1 or a combination of the two inhibitors. Results are presented in FIG. 6 as percent of control binding in the absence of inhibitor and are the average of triplicate determination. FIG. 6B shows the inhibition of $^{125}$I-laminin binding to A2058 melanoma cells by heparin and thrombospondin peptide 246 (SEQ ID NO:19). Melanoma cells (2×10$^5$ cells in 0.2 ml) were incubated with 0.2 µg/ml of labelled laminin alone or in the presence of 0.1 µg/ml heparin or 1 or 10 µg/ml peptide 246 or a combination of the two inhibitors. Again, results are presented as percent of control binding in the absence of inhibitor and are the mean of triplicate determinations ±SD.

Example 2

Antibody Binding to Peptides: Inhibition of $^{125}$I-thrombospondin or laminin binding to cells A2058 melanoma cells were harvested as described above and suspended in Dulbecco's PBS containing 1 mg/ml BSA. In a final volume of 0.2 ml, 2×10$^5$ cells were preincubated for 15 minutes with potential inhibitors. Labeled protein was added and incubated on a rotating table for 1 h at 20°. The cell suspension was transferred to 0.4 ml polypropylene microfuge tubes (PGC) which were preincubated with tris BSA buffer. Oil (Nyosil-50, 0.2 ml) was added, and the tubes were centrifuged for 1 min at 10,000 rpm in a Beckman microcentrifuge B. The upper phase was removed and the oil layer was washed with 0.2 ml tris BSA buffer and recentrifuged. The supernatant fluid was aspirated, and the bottom of the tube was cut and counted.

Monoclonal antibody A4.1 binds to a 50 kDa fragment of thrombospondin (Prater et al., *J. Cell Biol.* 112, 1031–1040 (1991)) which contains the type I repeats that are conserved in several proteins including the circumsporozoite protein of Plasmodium falciparum. In a preliminary screening of thrombospondin antibody reactivity of antibody A4.1 with overlapping peptides from the circumsporozoite protein, we found that antibody A4.1 bound strongly to peptides containing the sequence SISTEWS (SEQ ID NO:39) (M. Seguin and D. Roberts, unpublished results). Peptides from the three type I repeats of thrombospondin homologous to this sequence (Table 1) were prepared and tested for binding to antibody A4.1 after conjugation to BSA. Specifically, peptides 184, 185, 186, 187, 203, 204, 205 and 206 (SEQ ID NOS:1–8, respectively) were tested for antibody binding ability. Antibody A4.1 bound strongly to peptide 184 (SEQ ID NO:1) from the first type I repeat and weakly to peptides 185 and 186 (SEQ ID NO:2 and SEQ ID NO:3) from the second and third repeats but not to a series of peptides containing flanking sequences adjacent to the active sequences. Using peptides directly coated on plastic, antibody A4.1 bound best to the peptide 185 (SEQ ID NO:2) from the second repeat and less to the peptides from the first and third repeats. Thus, antibody A4.1 binds specifically to three dodecapeptides (12 amino acids in each chain) from the type I repeats of thrombospondin, although it is not clear from the present results whether the antibody distinguishes between the three repeats.

Figure 2A:
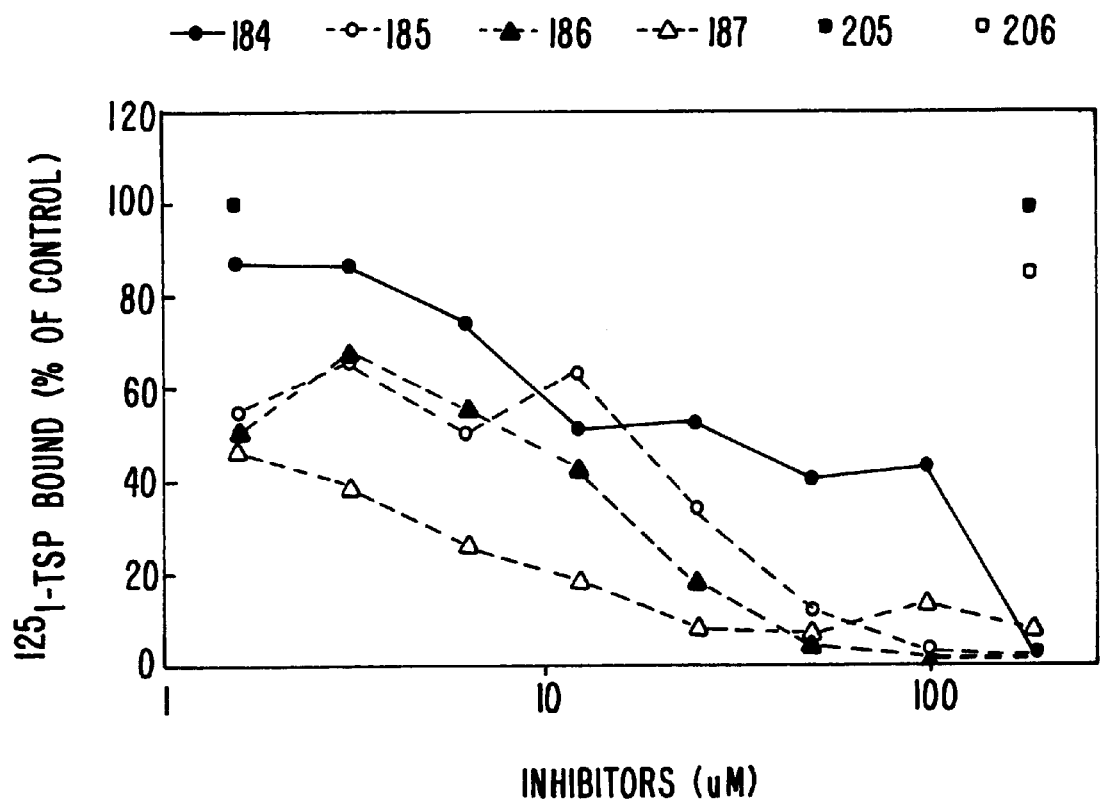
FIGS. 2A and 2B are graphs illustrating the inhibition of $^{125}$I-thrombospondin binding to sulfated glycoconjugates by thrombospondin peptides.
Figure 2B:
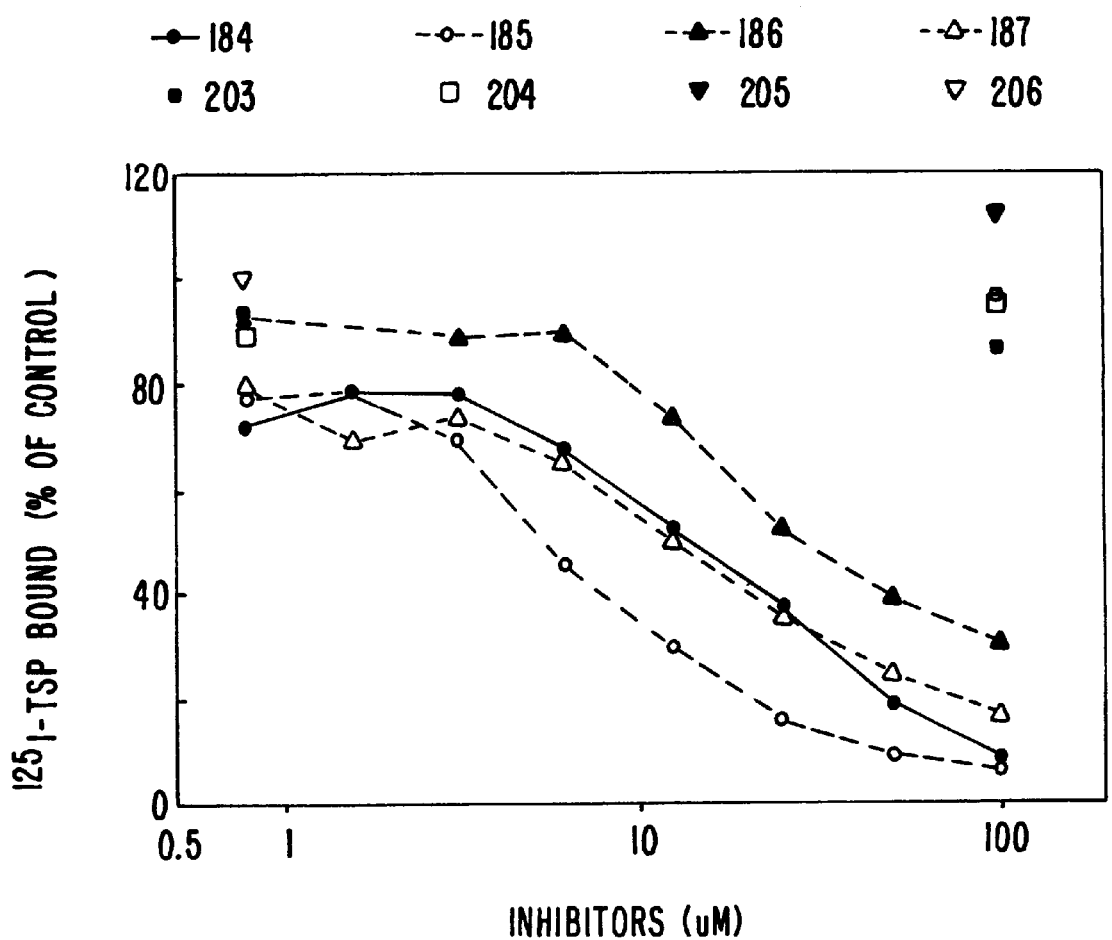
Figure 7:
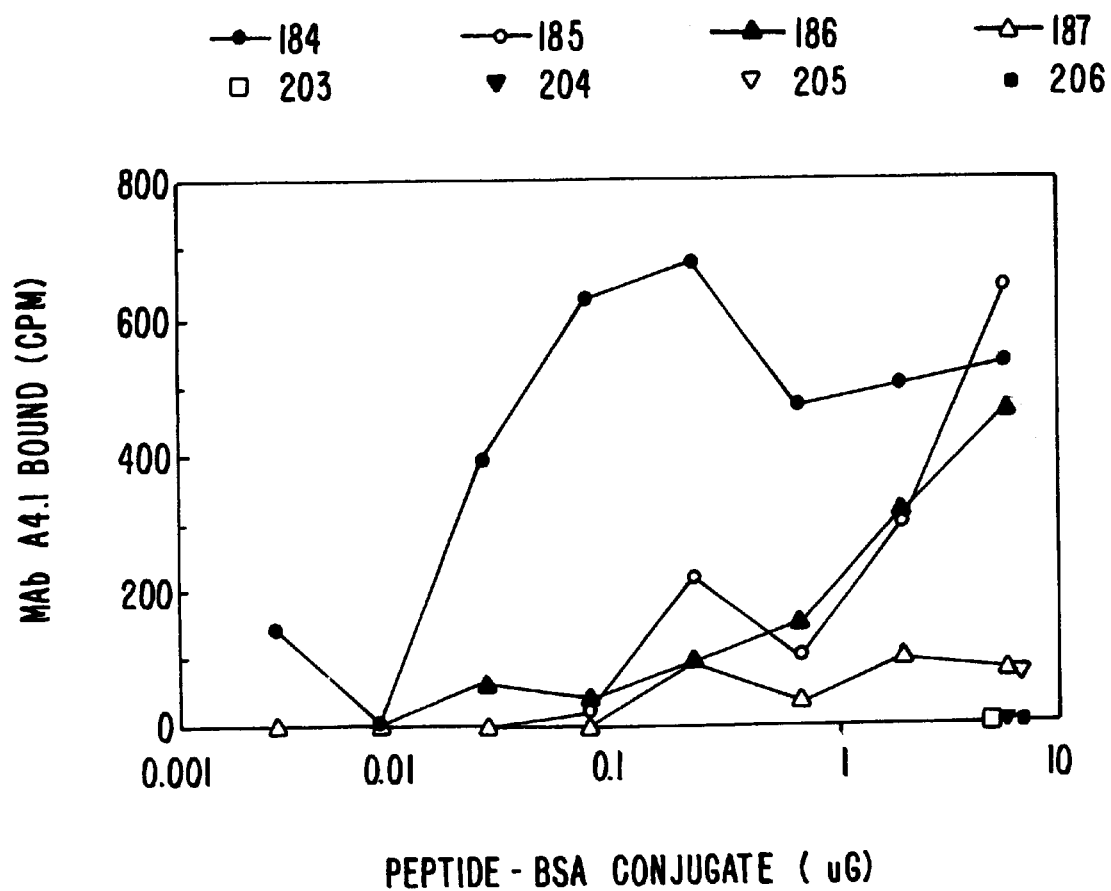
FIG. 7 is a graph representing the binding of anti-thrombospondin antibody A4.1 to thrombospondin peptides.

Because adhesion of cells on the 50 kD fragment of thrombospondin is partially inhibited by sulfated polysaccharides (Prater et al., *J. Cell Biol.* 112, 1031–1040 (1991)), several peptides from the type I repeats were tested for inhibition of thrombospondin binding to heparin and sulfatide (FIG. 7). The peptides chosen flanked the VTCG sequence (SEQ ID NO:5) identified as an adhesive motif by Rich and coworkers (Rich et al., *Science* 249, 1574–1577 (1990)), but in most cases lacked clusters of basic amino acids needed for the predicted heparin binding consensus sequence. Surprisingly, the sequences amino-terminal to the VTCG sequence (SEQ ID NO:5) were most active. Dodecapeptides from all three repeats (SEQ ID NO:1, SEQ ID NO:2 and SEQ ID NO:30) inhibited thrombospondin binding to both heparin and sulfatide with $IC_{50}$ values ranging from 6 to 50 $\mu$M. The peptide from the third repeat (SEQ ID NO:3) was the most active inhibitor of heparin binding followed by the second and first (SEQ ID NO:1) repeats. The order of inhibition was different for thrombospondin binding to sulfatide, where the second repeat peptide (SEQ ID NO:2) was the most potent inhibitor (FIG. 2B). Two peptides from the amino terminal heparin binding domain of thrombospondin were tested which contain consensus sequences for heparin binding, resides 23 to 32 and 77 to 83 respectively. Only the former peptide inhibited thrombospondin binding to heparin, with an $IC_{50}$ value of 60 $\mu$M. These peptides, however, did not inhibit thrombospondin binding to sulfatide.

Example 3

Determination of effect of peptides and peptide conjugates on binding of $^{125}$I-thrombospondin to heparin-BSA Microtiter plate wells were coated with heparin-BSA. Heparin-BSA (0.2 $\mu$g/well) was adsorbed by incubation in 50 $\mu$l of Dulbecco's PBS for 2 h at 37°. The wells were emptied, filled with tris-BSA, and incubated for 30 to 60 minutes. The buffer was removed, and labelled thrombospondin was added and incubated in the wells for 3 h at 40. The wells were emptied and washed 4 times with saline. The bottoms of the wells were cut from the plate and counted to quantify thrombospondin binding. Inhibition of thrombospondin binding was determined using peptides diluted in 30 $\mu$l of 50 mM tris buffer, pH 7.8, containing 110 mM NaCl, 1 mM $CaCl_2$, 0.025% $NaN_3$, and 1% BSA or buffer alone and 30 $\mu$l of $^{125}$I-labeled TSP (0.2 $\mu$g/ml). Free peptides p353 (SEQ ID NO:28) and p354 (SEQ ID NO:29) and peptides 246 (SEQ ID NO:19), 297 (SEQ ID NO:40), and FICOLL conjugated peptides (353 (SEQ ID NO:28), 354 (SEQ ID NO:29), and four preparations of 364 (SEQ ID NO:30) (224, 364, 364R1, 364R2) were tested for inhibition of thrombospondin binding at the indicated concentrations. The peptide conjugates preferably have a binding affinity for heparin or sulfated glycoconjugates which is in the range of $10^{10}$–$10^4$ molar$^{-1}$.

Figure 16:
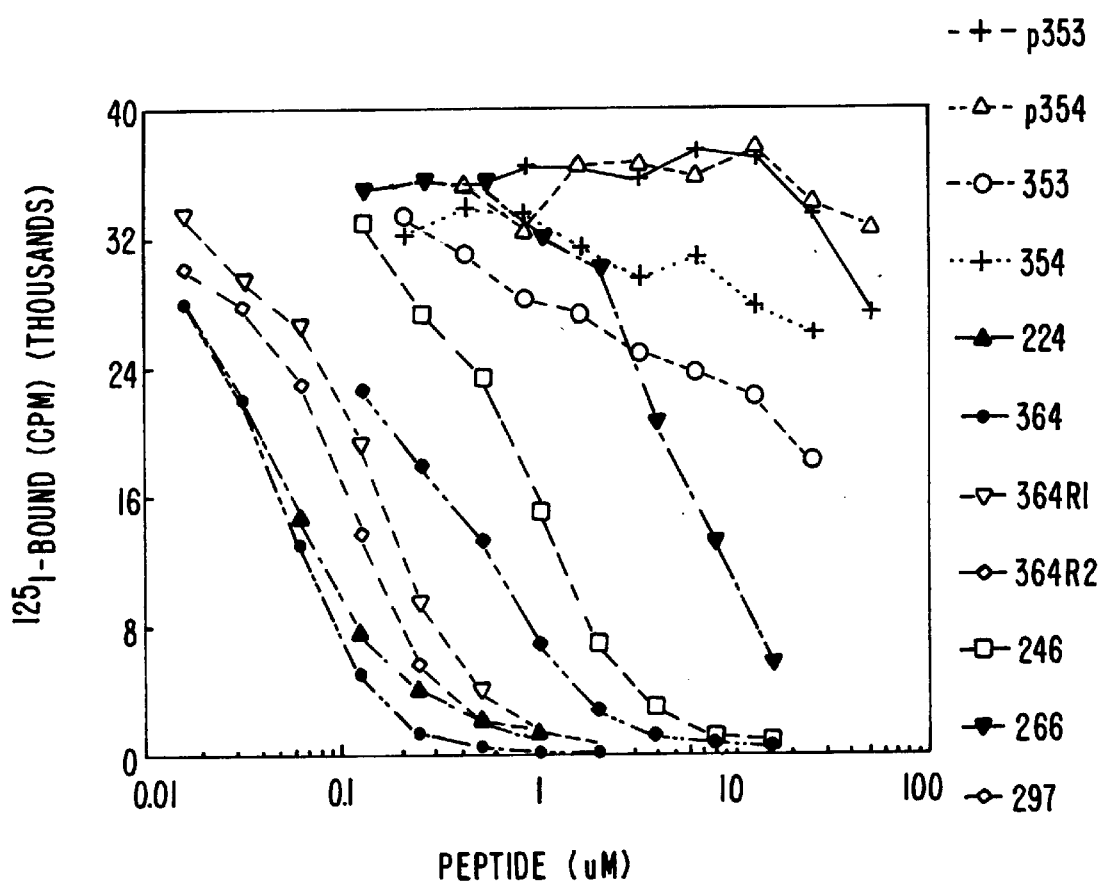
Figure 17A:
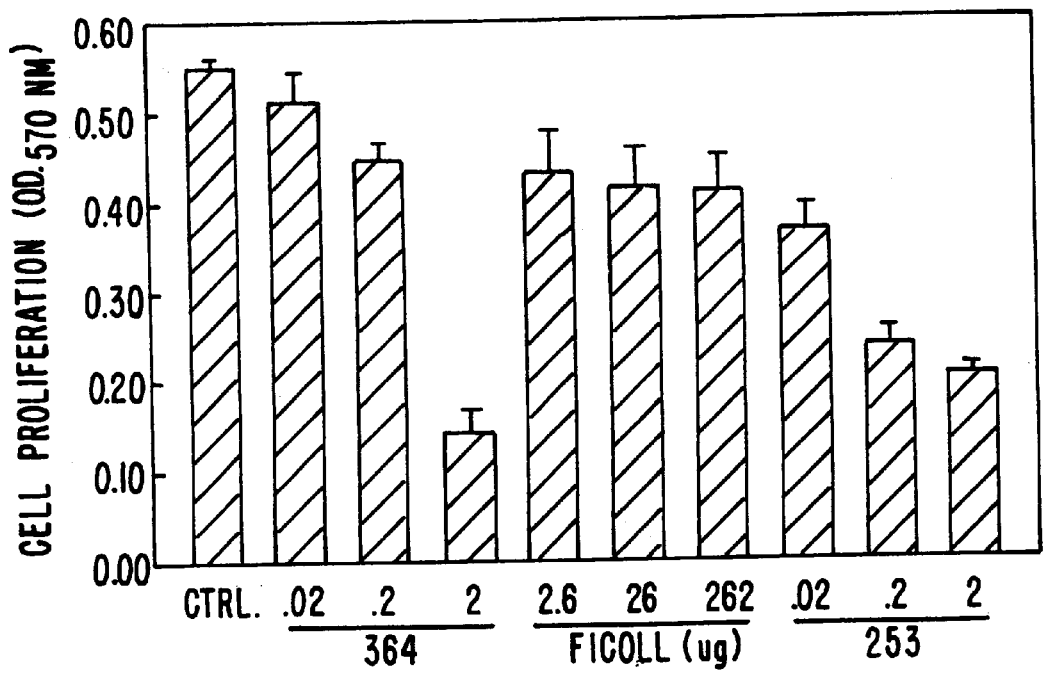
Figure 17B:
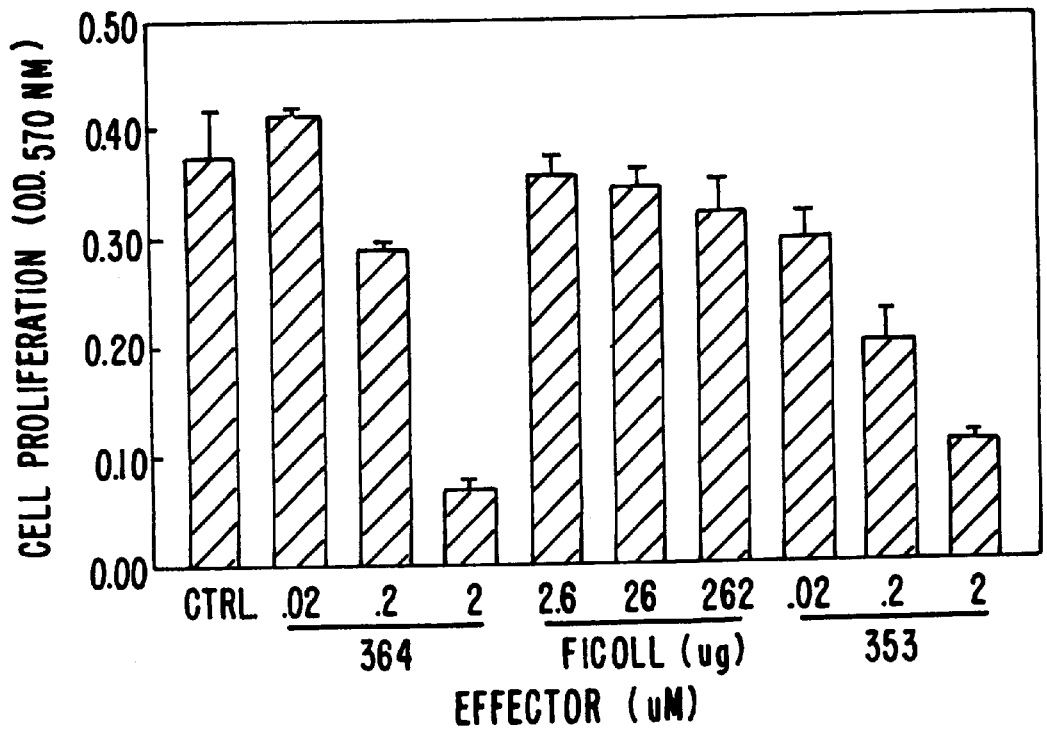
Figure 18:
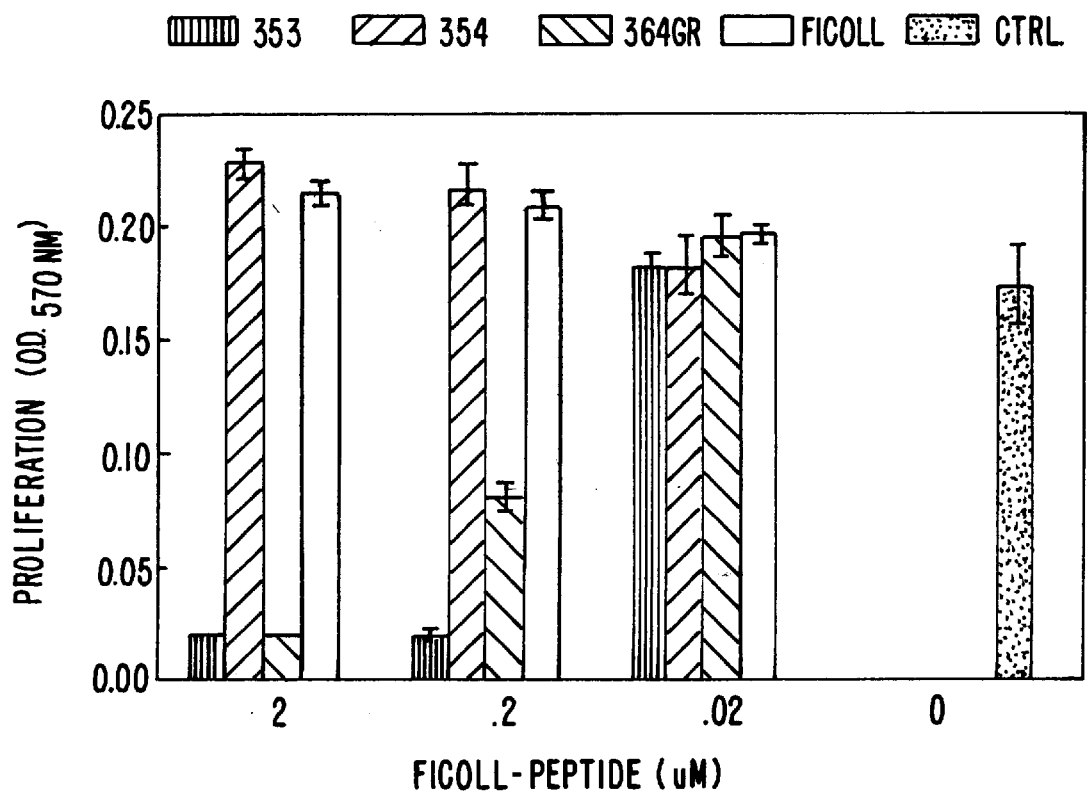
Figure 19:
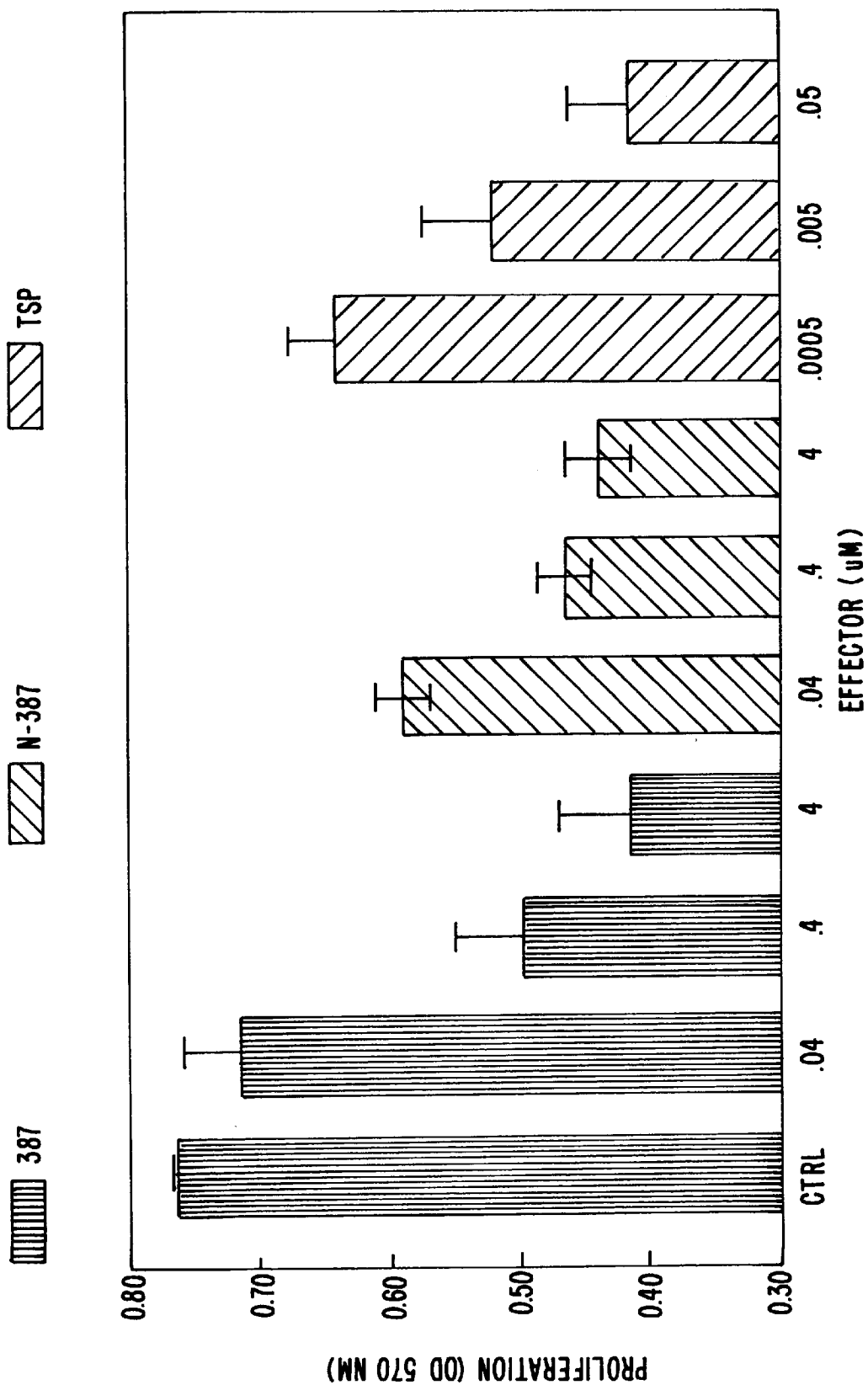
Figure 20:
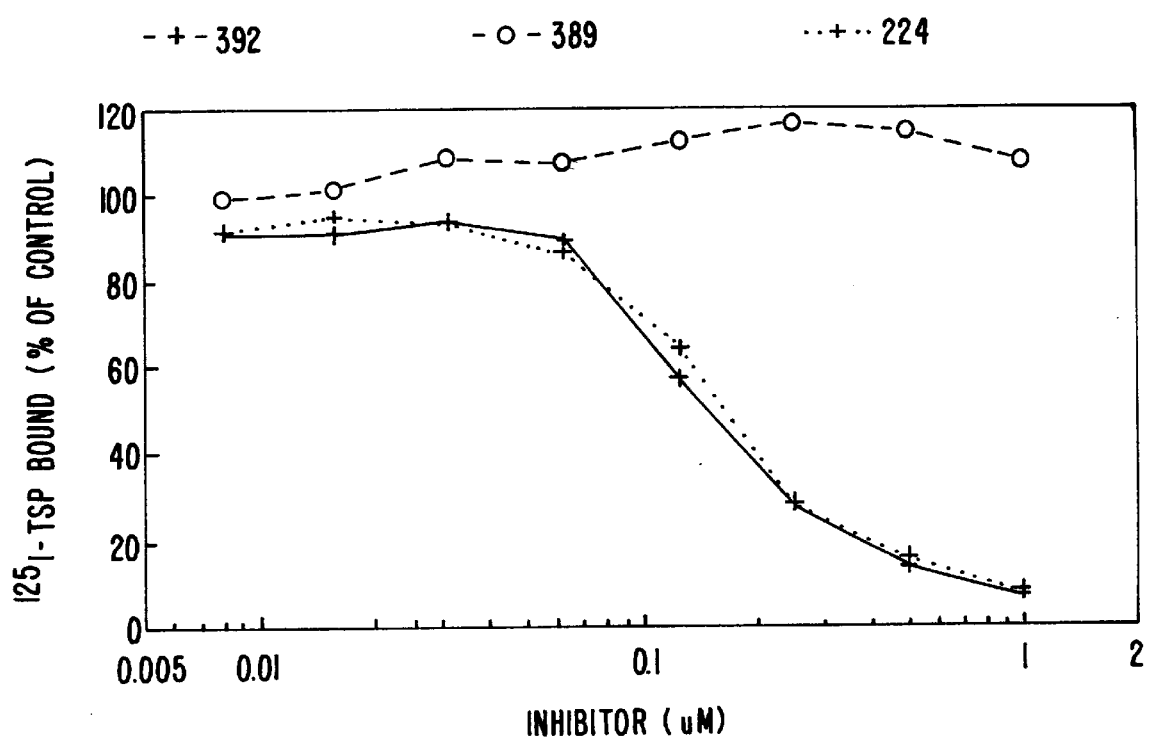

Peptides conjugated to FICOLL were more active than the corresponding free peptides (FIG. 16). Activity of peptide 246 (SEQ ID NO:19) was increased approximately 10-fold following conjugation to the carrier. Three independent preparations of the conjugate varied approximately 3-fold in activity. A conjugate of peptide 353 (SEQ ID NO:28), which contains the WSXW motif (SEQ ID NO:73) but lacks the basic amino acid motif of peptides 364 (SEQ ID NO:30) (see Table 3), was less active than the conjugate of peptide 364 (SEQ ID NO:30) but more active than the 354 conjugate SEQ ID NO:29 with the same sequence linked through a cysteine residue at the amino terminus. Both the peptide 353 (SEQ ID NO:28) and 364 (SEQ ID NO:30) conjugates were linked through a Cys residue at the carboxyl terminus. The conjugate of 364-FICOLL contained 9.1 peptides per molecule of polymer and the conjugate of 387-dextran contained 44 peptides per polymer. In order to determine the effect of modification of Trp residues and Asp residue on binding of FICOLL conjugates to heparin, binding of $^{125}$I-thrombospondin to immobilized heparin-BSA was also determined in the presence of the indicated concentrations of FICOLL-peptide conjugates: peptide 392 (SEQ ID NO:32) (+, KRFKQAGGWSHWSPWSSC), 389 (SEQ ID NO:31) (o, KRFKQDGGASHASPASSC), or 224, (SEQ ID NO:30), (+,KRFKQDGGWSHWSPWSSC). Results are presented in FIG. 20 as a percent of control binding determined in the absence of inhibitor. From the data, it appears that the Trp residues are important to the heparin binding activity, as the conjugates containing the basic residues alone are inactive. Furthermore, the Asp residue can be modified to Ala with no loss of activity.

Figure 21:
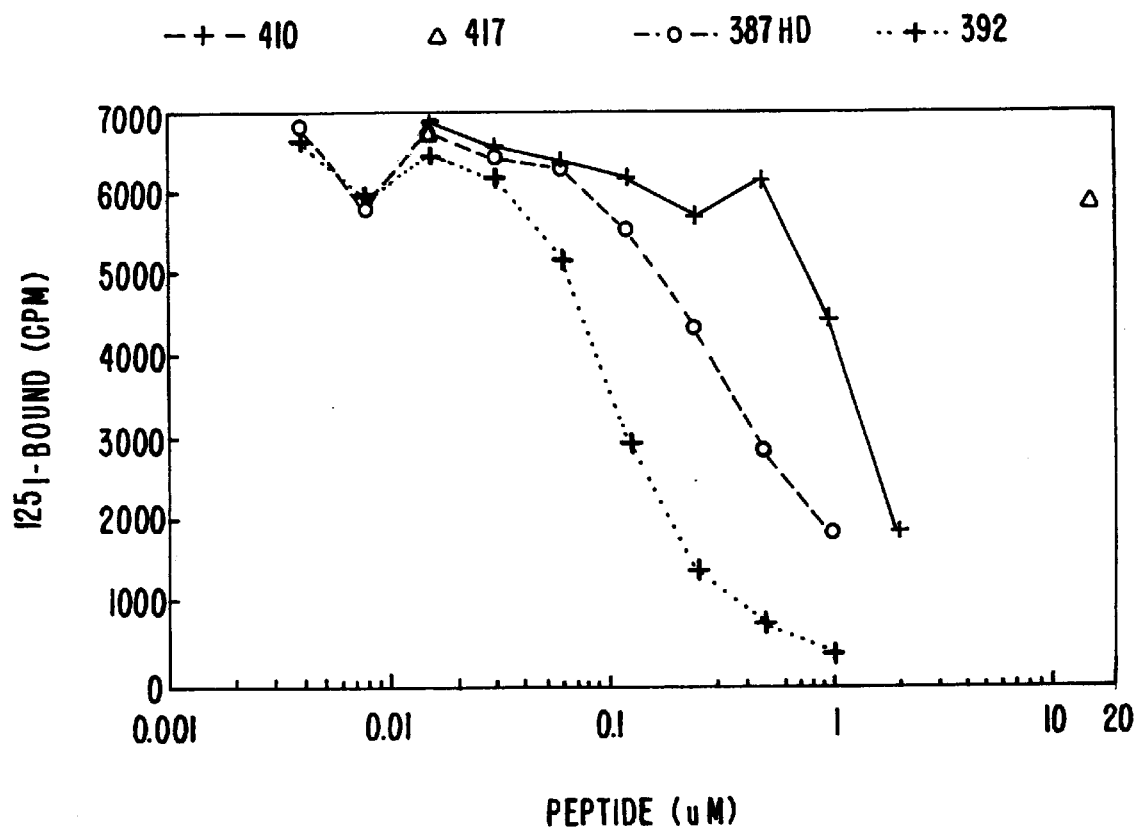

Free retro-inverso peptide Ac-allD-CSSWPSWHSWGGDQKFRK-$NH_2$ (+, 416) control peptide RCD(thioP)C ($\Delta$,417) or peptides 387 (SEQ ID NO:30) or conjugated peptide 392 (SEQ ID NO:32), were tested for inhibiting binding of thrombospondin to heparin, and the results are shown in FIG. 21. The data indicates that the retro-inverso modified peptide retains heparin-binding activity. Its activity however, is approximately three-fold less than the native sequence.

Figure 22:
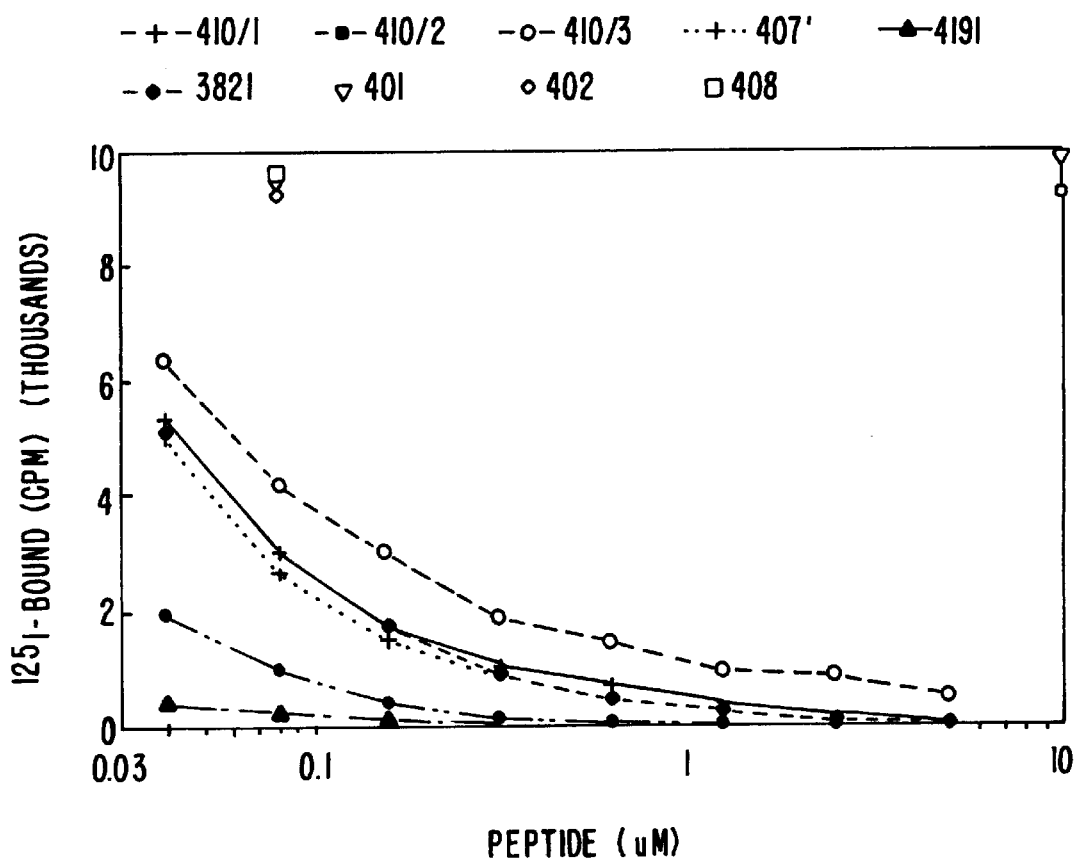
Figure 23:
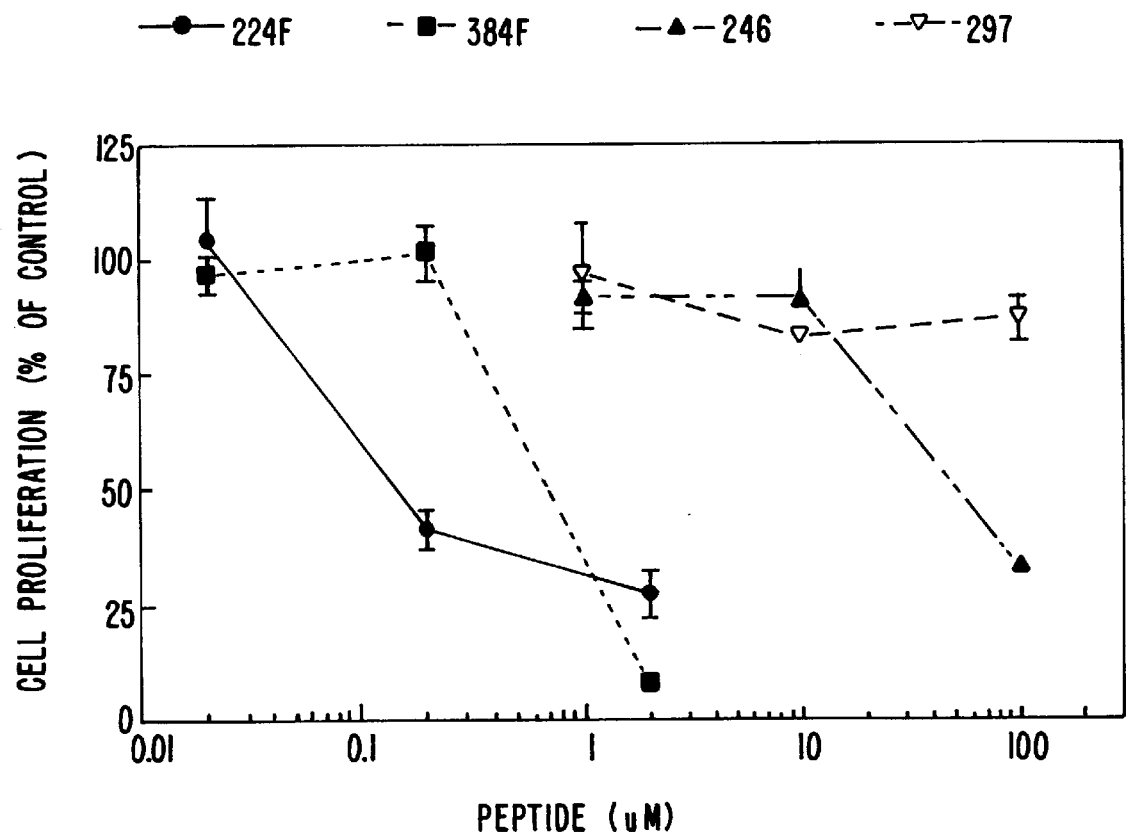
Figure 24A:
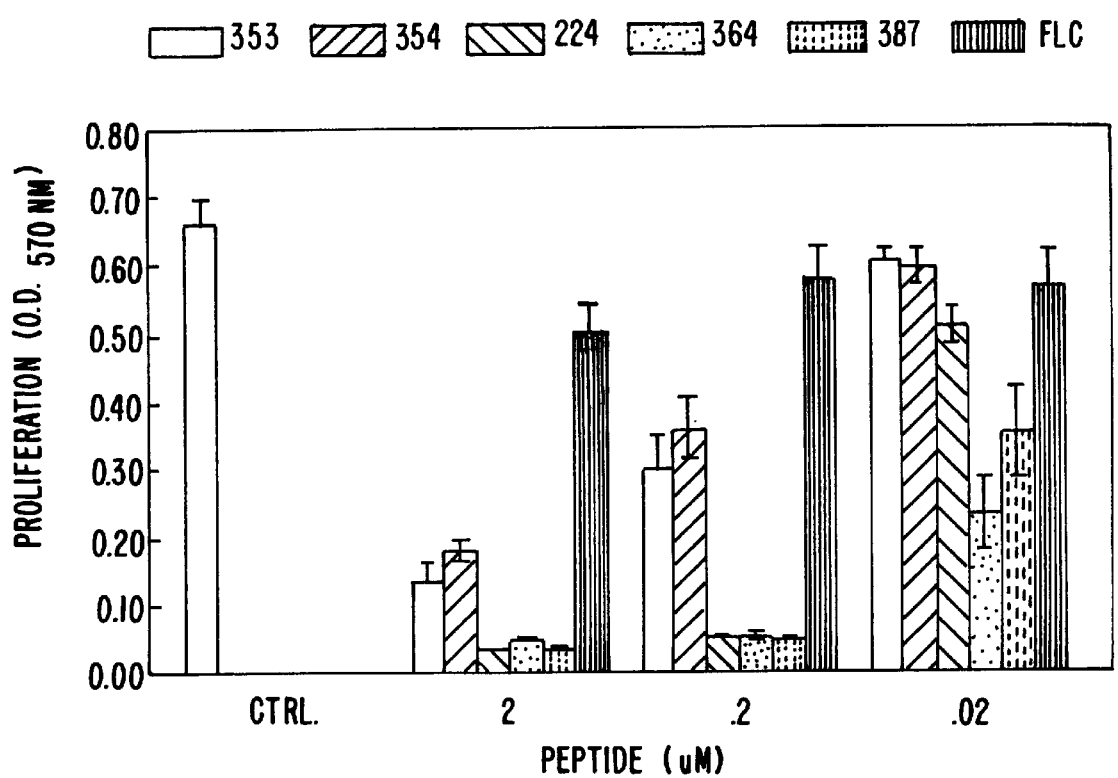
Figure 24B:
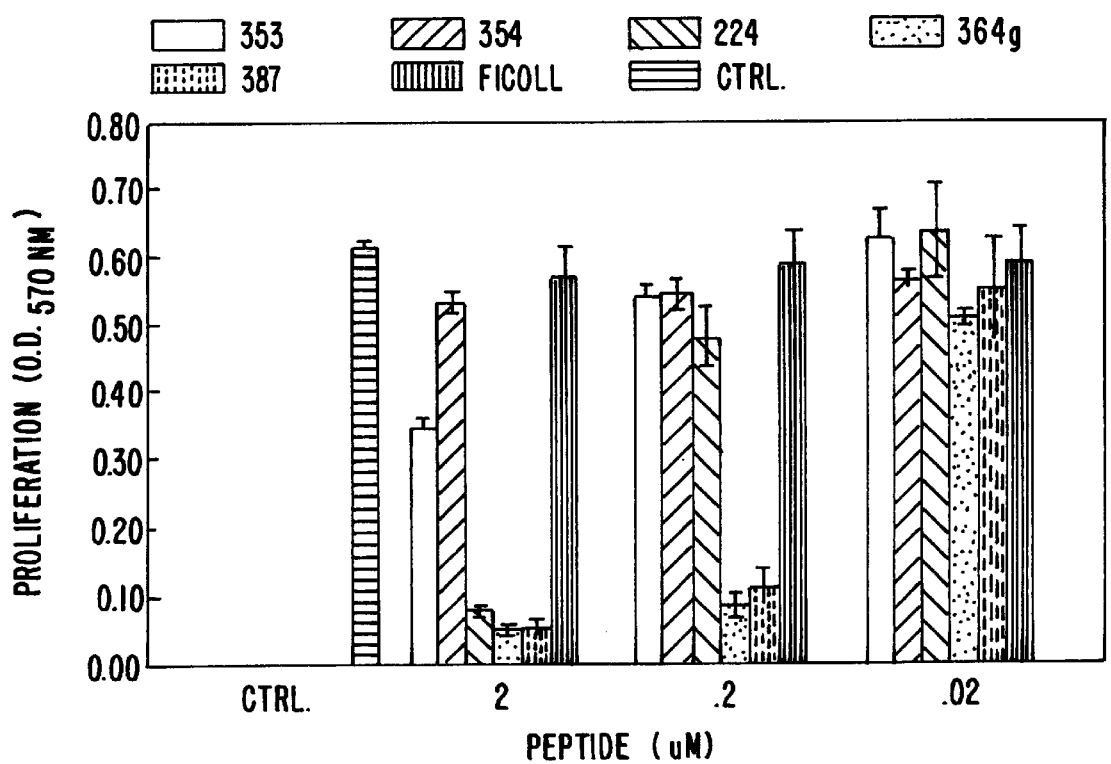

Several peptide conjugates 416, 407 (SEQ ID NO:30), 419 (SEQ ID NO:34) and 392 (SEQ ID NO:32) or free peptides 401 (SEQ ID NO:35), 402 (SEQ ID NO:36), 408 (SEQ ID NO:37) were tested for inhibiting thrombospondin binding to heparin, and the results are shown in FIG. 22. The structures 416f1, f2, f3 were three syntheses of Ac-allD-CSSWPSWHSWGGDQKFRK-$NH_2$ conjugated to FICOLL; 407f was an independent synthesis of the native sequence KRFKQDGGWSHWSPWSSC (SEQ ID NO:30) conjugated to FICOLL; 419f is KRFKAAGGWSHWSPWSSC-$NH_2$ (SEQ ID NO:33) conjugated to FICOLL, and 392 is KRFKQAGGWSHWSPWSSC (SEQ ID NO:32) conjugated to FICOLL. The free peptides are 401 (KRFKQDGG, SEQ ID NO:35), 402 (KRFK, SEQ ID NO:36), and 408 (KRAK, SEQ ID NO:37). The data indicates that retro-inverso conjugates to FICOLL are active. The 419 structure enables amide modified peptides of the invention. The free peptides show lack of activity of BBXB (SEQ ID NO:74) peptides without the WSXW motif (SEQ ID NO:73).

Example 4

Figure 40A:
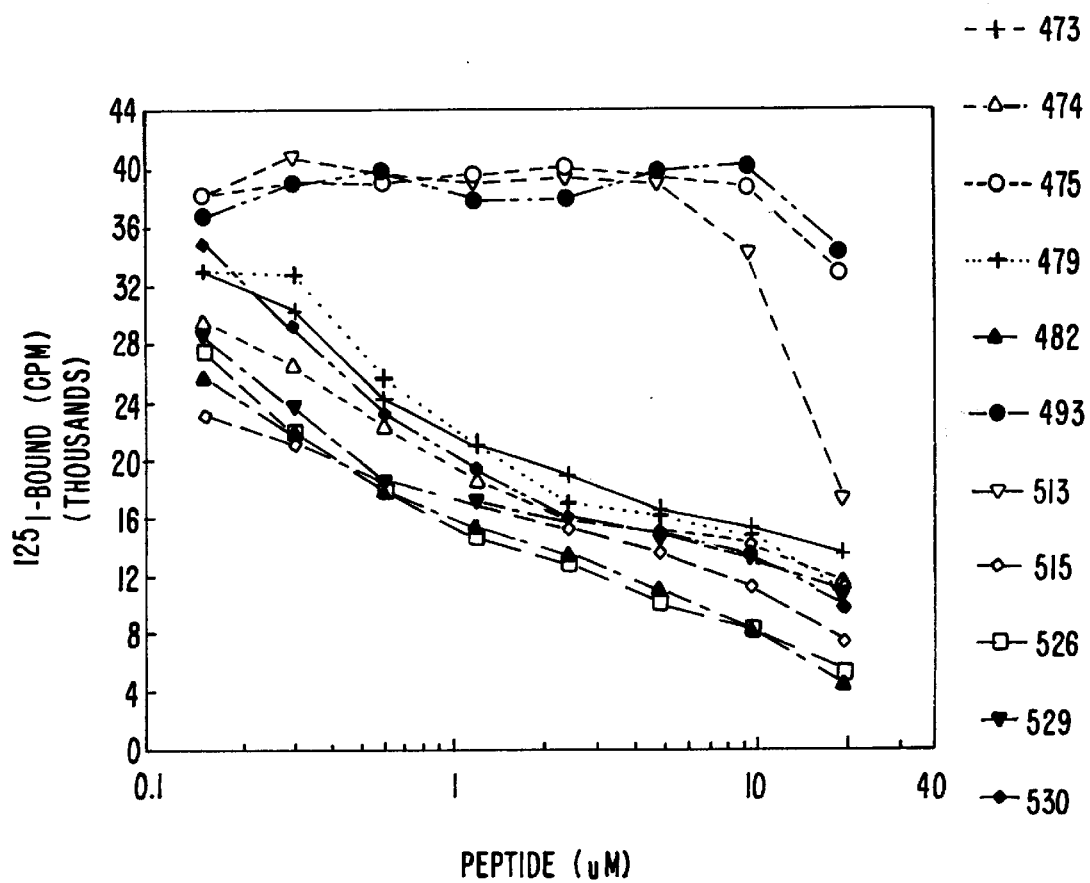
Figure 40B:
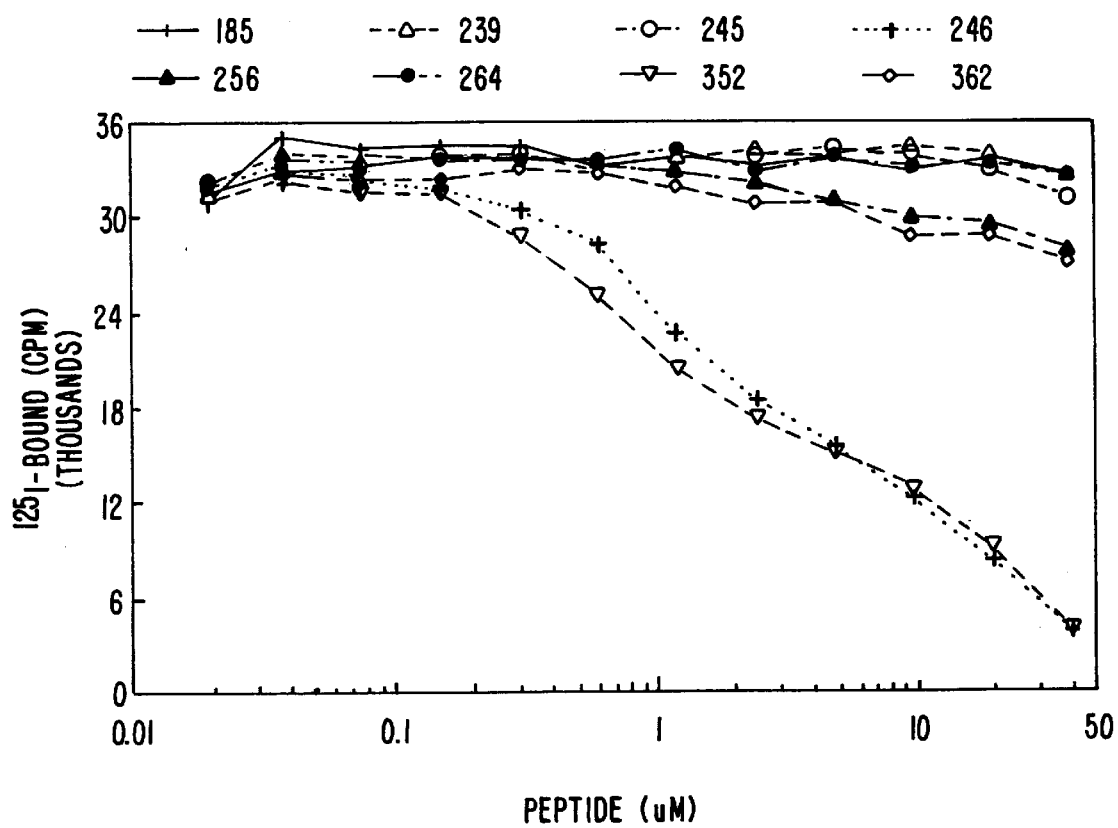
Figure 40C:
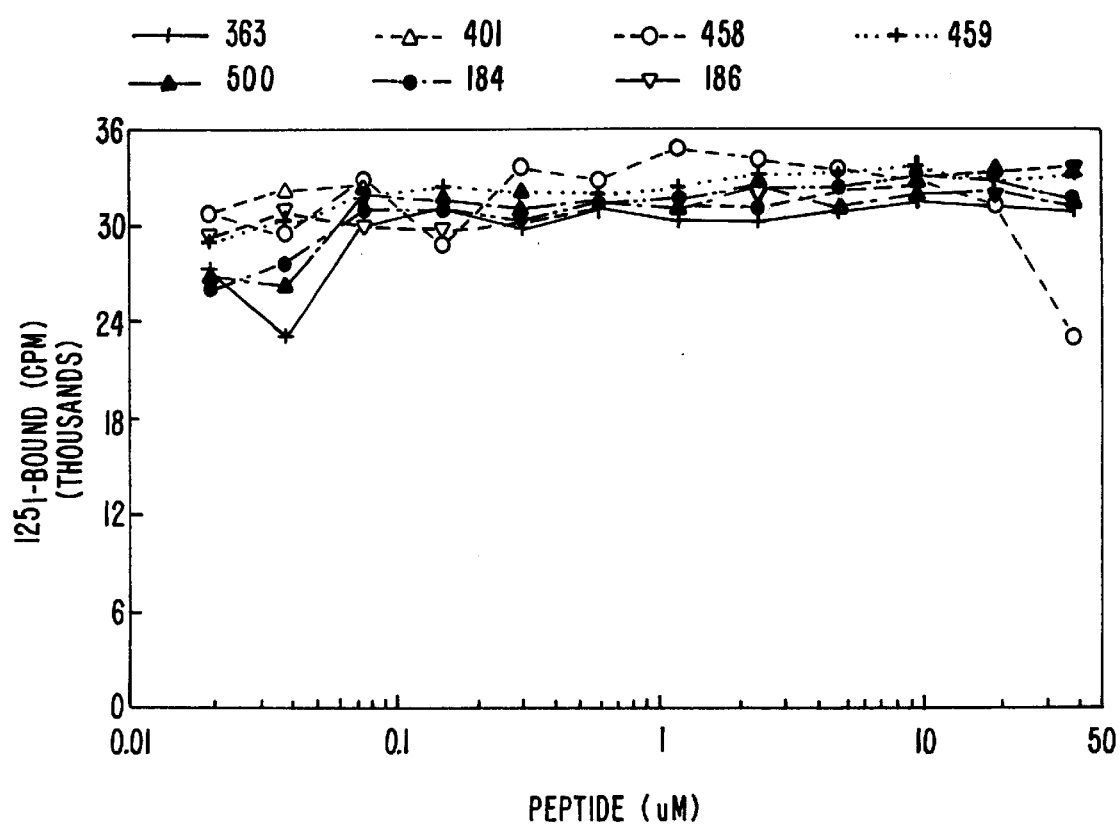

Determination of Inhibition of bFGF binding to heparin using TSP peptide analogs Binding of $^{125}$I-bFGF to heparin was determined using an immobilized heparin-BSA conjugate as previously described (Guo, et al. (1992) Proc. Nat'l Acad. Sci. 89:3040–3044). $^{125}$I-bFGF, prepared as described by Neufeld, et al, (1985), J. Biol. Chem. 260:13860–13868, was added described above, and incubated for 2 hours at 25° C. Bound radioactivity was determined after washing and cutting the wells from the plate. FIGS. 40A, B and C show the inhibition of $^{125}$I-bFGF binding to heparin by a number of TSP peptide analogs.

Example 5

Preparation of Conjugated Peptides

Polysucrose of average molecular weight 70,000 or 400,000 was obtained from Pharmacia (FICOLL™). Unless otherwise specified, chemicals were obtained from Sigma Chemical Co. Solvents and common inorganics were reagent grade. Diisopropylcarbodiimide and dimethylformamide were purchased from Aldrich Chemical Co.

Preparation of $AECM_{71}$-FICOLL(400):

Carboxymethylated (CM) FICOLL. To solution of 13.3 g FICOLL (Av. MW 70 or 400 kDa) in 170 ml water was added 75 ml of 10.0 M NaOH. The mixture was cooled to 14.5°, and 0.25 mole of chloroacetic acid (using equiv. wt. by titration) was added. The temperature rose to approximately 25° where it was maintained for 3 h. At this time, 2.0 g of $NaH_2PO_4.H_2O$ were added, and the mixture was titrated with 5.0 N HCl (93 ml) to pH 6–7 (glass electrode). The neutral solution was dialyzed (12–14 kDa MWCO tubing) in the cold against 4-liter changes of 0.2 M NaCl, once or twice daily for 4 days. The dialysis tubes were hung in a stream of air to reduce volume by ⅓ to ½ (perevaporation).

Aminoethyl-carbamylmethylated (AECM) FICOLL:

To the dialyzed, concentrated solution of CM-FICOLL was added solid ethylenediamine dihydrochloride to the extent of 20 g per 100 ml. The pH was adjusted to 4.6–4.9 with 1N HCl or NaOH and maintained there during the addition (15 min) of 1.5 g/100 ml of 1-ethyl-30 (dimethylaminopropyl)carbodiimide hydrochloride (EDC). The pH of the reaction mixture was kept in this range for 4 h and then adjusted to 6.1 with 2 N NaOH. The resulting solution was dialyzed as above, then dialyzed for 2 days against distilled water. The dialyzate was reduced 2 fold in volume by perevaporation, lyophilized and stored at −20°.

Amino group content of the AECM-FICOLL was determined by a modification of the method of Snyder and Sobocinski (*Anal. Biochem.* 64, 284–288, 1975): Briefly, samples were dissolved in 0.1 M sodium borate, pH 9.3, and treated with an excess of 2,4,6-trinitrobenzene-sulfonic acid for several hours in parallel with standards of 4-aminobutyric acid in the same buffer. Absorbencies were read at the isobestic point of 366 nm for the several chromophores produced (see *J. Immunol. Methods,* 86:155 (1986).

Synthesis of N-succinimidyl 3-(2-iodoacetamido) propionate (SIAP): N-Chloroacetyl-β-alanine: Chloroacetyl chloride in dioxane was added to an excess of β-alanine dissolved in water. The addition was carrier out dropwise while maintaining the temperature below 10° and the pH near 9 by simultaneously adding 5 N NaOH. The reaction mixture was acidified to pH 1.8, saturated with NaCl, and extracted three times with ethyl acetate. The upper layers were collected, pooled and reduced to 13% of their volume by rotary evaporation. Product was recovered by addition of an equal volume of hexane and inducing crystallization. Recrystallization was carried out from ethyl acetate-hexane 3:2 v/v to +5°.

N-Succinimidyl 3-(2-chloroacetamido)propionate: 1,3 Diisopropylcarbodiimide (41 m mole) was added to a solution of N-chloroacetyl-β-alanine (40 m mol) and N-hydroxysuccinimide (46 mmol) in 120 mol of 2-propanol at 5° C. crystallization was induced when product began precipitating. Product was collected after allowing the mixture to stand overnight at room temperature. Recrystallization was carried out from 60 ml of absolute ethanol.

SIAP: N-Succinimidyl 3-(2-chloroacetamido) propionate (10 mmol) was dissolved in a mixture of acetone (15 ml) and N,N-dimethyl-formamide (3.6 ml). A solution of sodium iodide (30 m mol) in 15 ml of acetone was added, and the flask was flushed with nitrogen, stoppered and allowed to stand in the dark at room temperature overnight. Solvent was removed by flash evaporation, and the residue was extracted with dichloromethane and water (containing a small amount of sodium thiosulfate). The organic layer was washed twice with water, dried over anhydrous sodium sulfate and filtered. Solvent was removed, and the residue was crystallized twice from 19–25 ml of 2-propanol.

Conjugation of Peptide #387 to AECM-FICOLL:

Peptide #387 (SEQ ID NO:30) (HCK) has the same sequence as #364 (SEQ ID NO:30) and #246C:, namely, H-KRFKQDGGWSHWSPWSSC-OH, and linkage to carrier is through the C-terminal cysteine side chain.

Step 1: N-Iodoacetamidopropionyl-AECM-FICOLL. $AECM_{71}$-FICOLL(400) (250 mg) was dissolved in 7.4 ml of HE buffer (0.15 M HEPES, 0.075 M NaOH, 1.0 mM EDTA, pH 7.5). N-succinimidyl 3-(2-iodoacetamido) propionate (SIAP) (60 mg) was dissolved in 0.6 ml N,N-dimethylformamide and added to the AECM-FICOLL. The mixture was allowed to stand at room temperature for 1–2 h and then passed through a column (2.5×22 cm) of desalting gel (Bio-Rad, P-6DG). The column was equilibrated and run with HE/5 (HE buffer diluted 5 fold). Fractions (2.66 ml) were collected and their absorbencies at 280 nm were read undiluted. Five fractions from the first emerging peak (IAP-AECM-FICOLL) were pooled and weighed. Solid urea was added to make a final concentration of just slightly over 6.0 M by adding 0.5 g urea per gram of pool (6.65 g).

Step 2: Reduction of disulfide bonds in peptide material. Tris(2-carboxyethyl)phosphine hydrochloride (TCEP from Pierce Chemical Co.) (21.5 mg) was dissolved in 14.0 ml of HE/5, 6.0 M urea. Immediately thereafter, 60 mg of peptide #387 (SEQ ID NO:30) were layered on top of this solution and allowed to dissolve by gentle magnetic stirring. The pH was adjusted to 7.5 by adding of 1.0 M $Na_2CO_3$ (0.45 ml) and monitoring the solution with nonbleeding pH strips. The reaction mixture was allowed to stand for 15 min.

Step 3: Coupling reaction and separation of conjugate. The peptide solution was added dropwise with stirring to the IAP-AECM-FICOLL. The pH was adjusted back to 7.5 with 40 $\mu$l of 1.0 M $Na_2CO_3$. The mixture was stirred under $N_2$ for 2 h, sealed off , and allowed to stand at room temperature for 42 h. Unreacted iodoacetamido groups were capped by addition of 22 $\mu$l of 2-mercaptoethanol. After standing several hours, the mixture was passed through a 5.0×46-cm column of Bio-Rad, Bio-Gel P-60 (medium), packed and run with HE/5, 6.0 M urea (rate 60 ml/h). $A_{280}$ readings (undiluted) of 10-ml fractions were used to locate the first emerging peak. Six fractions from this peak were pooled and dialyzed in Spectra/Por tubing (MWCO 12–14 kDa) against daily 2-liter changes of phosphate-buffered saline for 4 days. The dialyzate was concentrated 2.5 fold using Filtron MAC-ROSEP™ 50K centrifugal concentrators. The peptide concentration of the conjugate solution was estimated from the absorbance at 280 nm (10 times that of a 10-fold diluted sample) by employing the average molar absorptivity of a tryptophan residue in globular proteins (5540 $M^{-1}$ $cm^{-1}$) as reported by H. Mach et al. (*Anal. Biochem.* 200, 74–80, 1992). Thus, with 3 Trp residues in peptide #387 (SEQ ID NO:30), its concentration is calculated as $C(\mu M)=A_{280}/0.01662$. This procedure yielded 24 ml of conjugate solution in PBS having a peptide concentration of 117 $\mu$M. In conjugating dextran to the peptides of the invention, this example is repeated substituting dextran for FICOLL.

Alternate Conjugate Preparation Method: Polysucrose was obtained and first functionalized with amino groups, as described above. The AECM FICOLL derivative (50 mg) was iodoacetylated in 1.35 ml of 0.15 M HEPES-NaOH buffer at pH 7.5, containing 1 mM EDTA by addition of 9.6 mg of iodoacetic acid N-hydroxysuccinimide ester (Sigma) dissolved in 0.15 ml of dimethylformamide. After about 15 minutes of reaction, the solution was passed over a desalting column to obtain the iodoacetylated AECM-FICOLL. Nine $\mu$moles of peptide (e.g., peptide 517) were dissolved in 1.8 ml distilled water, and 250 $\mu$l of a 50 mM solution of tris-(2-carboxyethyl) phosphine-HCl (Pierce Chemical)) in water was added to the peptide solution. The pH was adjusted to 7.1 to 7.8 by addition of 1M $Na_2CO_3$. After 30–60 minutes, the resulting solution was passed through a column packed with 1.4 ml of io-Rad AG1—X8 anion exchange resin in the acetate form. The column effluent was led into the iodoacetylatedAECM-Ficoll solution and the solution was stirred overnight at room temperature. The resulting solution was dialyzed overnight against phosphate buffered saline with several changes in a 12–14 kD molecular weight cut-off tubing. Peptide concentration of the resulting solution was determined by measuring its absorbance at 280 nm, then determining the actual concentration by dividing this value by the extinction coefficient 0.01108.

Example 6
Determination of the effect of peptide conjugates on proliferation of bovine corneal endothelial cells Corneal bovine endothelial cells (BCE cells) were used at passages 2 through 8 (Munjal et al., 1990). BCE cell cultures were maintained in DMEM (low glucose), containing 10% FCS, 4 mM glutamine, 2.5 µg/ml amphotericin B, and 500 U/ml each of penicillin G potassium and streptomycin sulfate (all media components were from Biofluids Inc., Rockville, Md.). BCE cells were grown at 34° in 5% $CO_2$. The media were changed every 2–3 days.

Endothelial cell proliferation was measured using the CELL TITER 96™ assay (Promega, Madison, Wis.). $5\times10^3$ cells were plated into each well of a 96-well culture plate in 0.5 or 5% FCS-containing medium together with the indicated concentrations of growth effectors. After 72 h, 15 µl of dye solution was added to each well, and the plates were incubated for an additional 4 h. Solubilization solution was added, and absorbance at 570 nm was determined after 24 h as described by the manufacturer.

The peptide 364 (SEQ ID NO:30) conjugate was a potent inhibitor of endothelial cell proliferation, with an $IC_{50}$ consistently less than 1 µM. The FICOLL carrier without peptide was inactive. The conjugate of peptide 353 (SEQ ID NO:28), which lacks the amino terminal basic amino acid sequence, was also strongly active for inhibiting proliferation of endothelial cells. Similar inhibitory activities were observed using cells grown in 0.5% of 5% fetal calf serum (FIGS. 22A and 22B). In addition, peptides 224, 364 (SEQ ID NO:30) and 246 (SEQ ID NO:19) are KRFKQDGGW-SHWSPWSSC conjugated to FICOLL (224F, 364F) or as free peptide 246 (SEQ ID NO:19) were also tested (FIG. 23). 297 is a control peptide from the carboxyl terminal domain of thrombospondin (TAYRWRLSHRPKTGFIRV) (SEQ ID NO:40). The free peptide 246 (SEQ ID NO:19) inhibits proliferation with an IC50=40 µM. Two preparations of FICOLL conjugated peptide 224 (SEQ ID NO:30) and 364 (SEQ ID NO:30) are 40 to 200-fold more active for inhibiting proliferation than the free peptide. A peptide from the carboxyl terminus is not active.

Figure 25:
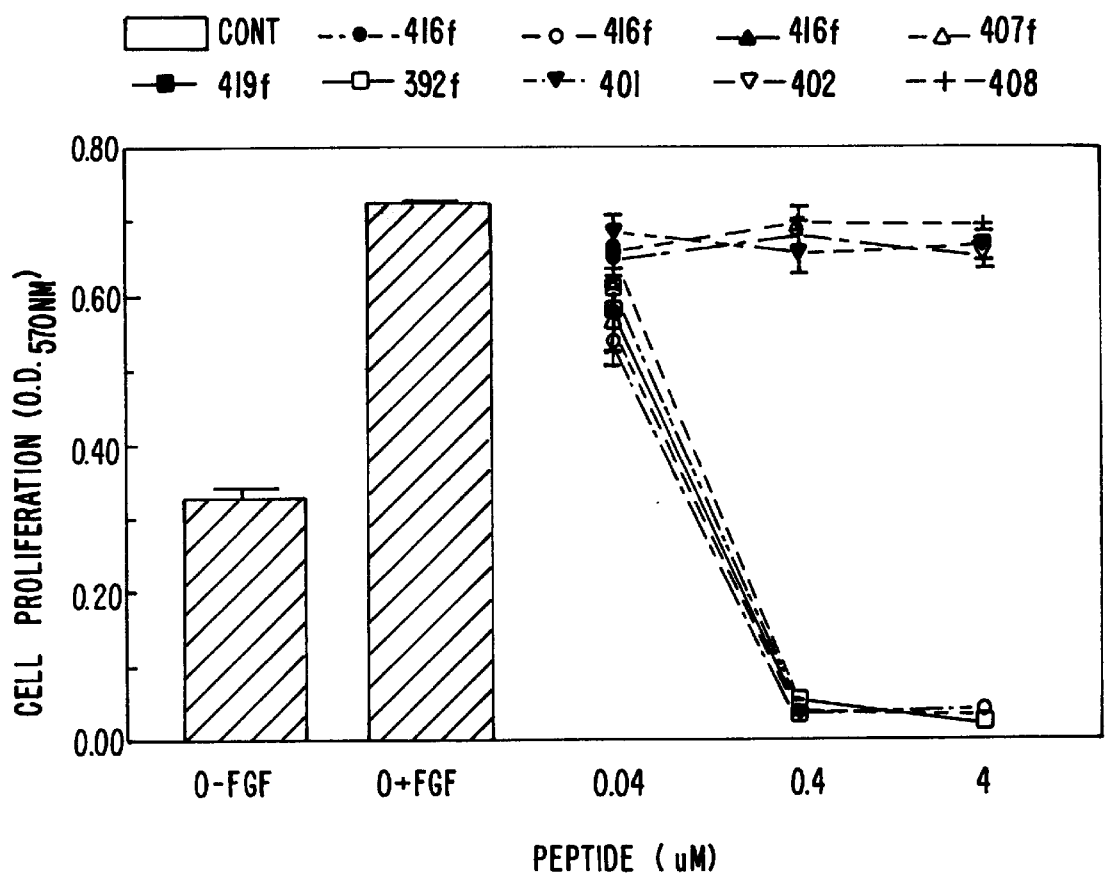

Example 7
Determination of the effect of peptide conjugates on proliferation of bovine aortic endothelial cells FICOLL conjugates of peptide 353 (SEQ ID NO:28) (GGWSHWSPWSSC), 354 (SEQ ID NO:29) (CGGWSHWSPWSS), 224 364 g (SEQ ID NO:30) and 387 (SEQ ID NO:30) (three syntheses of KRFKQDGGWSHWSPWSSC), or free FICOLL were tested at the indicated concentrations as inhibitors of proliferation of bovine aortic endothelial cells in DMEM medium containing 0.5% (FIG. 24A) or 5 % (FIG. 24B) fetal calf serum. The conjugates also inhibit proliferation of aortic endothelial cells. Therefore, the conjugates are general inhibitors of both large and small vessel endothelial cell proliferation. Inhibition by the optimal sequences is not strongly reduced at high serum concentration. This contrasts with existing inhibitors of endothelial cell proliferation, which are fully active only at low serum concentrations. This Figure also shows activity of peptide conjugates without the basic residues (353, SEQ ID NO:28). Its activity shows more serum sensitivity. Also the results verify that unconjugated FICOLL is inactive for these cells. Also tested for the ability to inhibit proliferation of bovine aortic endothelial cells were peptide conjugates 416f1, f2 and f3 (three preparations of the retro-inverso peptide Ac-allD-CSSWPSWHSWGGDQKFRK-$NH_2$ coupled to FICOLL) 407 (SEQ ID NO:30) (an independent synthesis of peptide KRFKQDGGWSHWSPWSSC conjugated to FICOLL) 419 (SEQ ID NO:34) (KRFKAAGGWSHWSPWSSC coupled to FICOLL, where the Q and D of the native sequence were replaced with Ala residues) 392 (KRFKQAGGWSHWSPWSSC (SEQ ID NO:32) where the D is replaced with an Ala residue). The results are shown in FIG. 25. D to A and QD to AA substitutions do not alter the antiproliferative activities of the peptide conjugates. The retro-inverso peptide conjugate is highly active for inhibiting aortic endothelial cell proliferation. In all cases, bFGF-stimulated proliferation was inhibited by the active conjugates.

Figure 38:
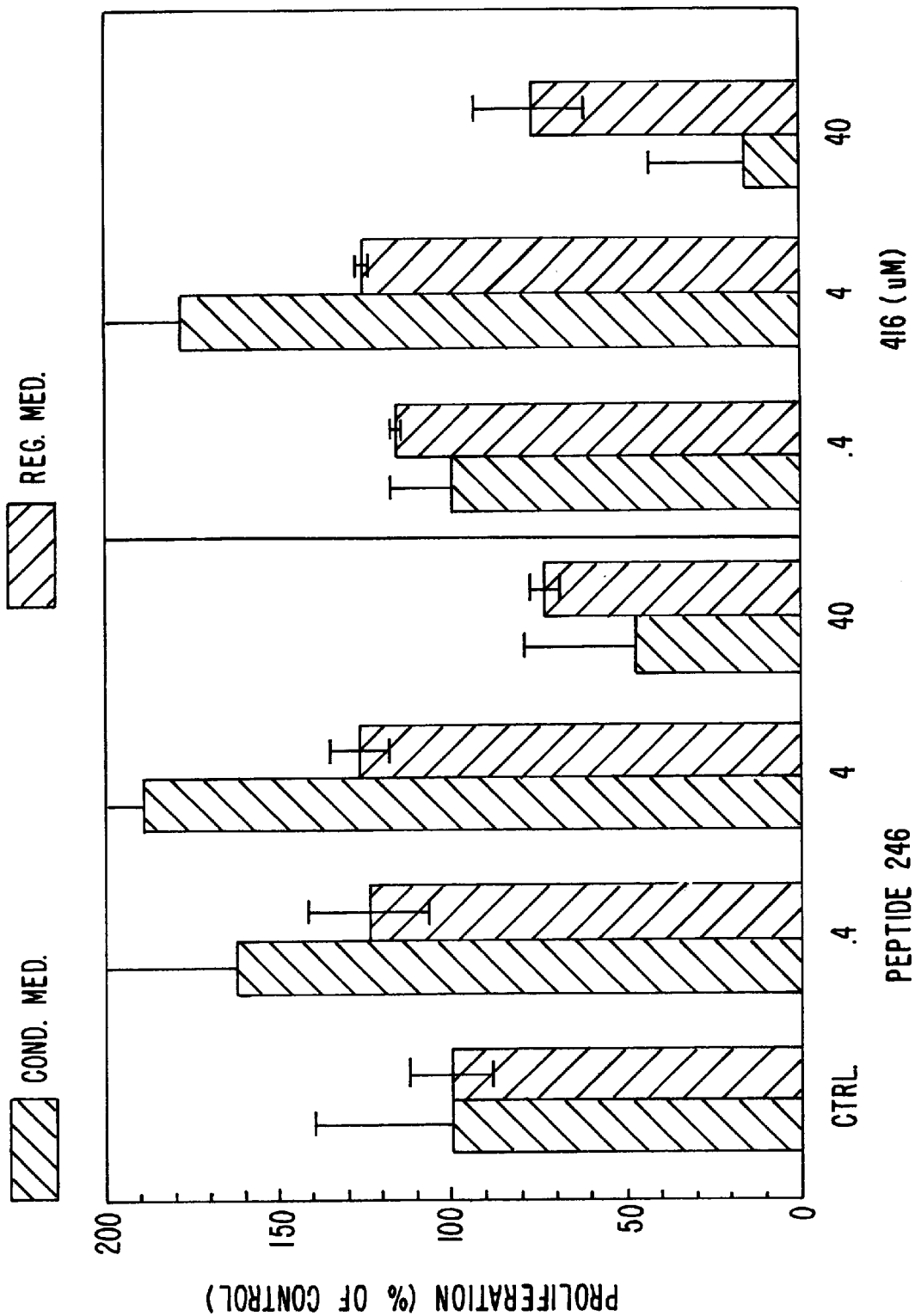
Figure 39A:
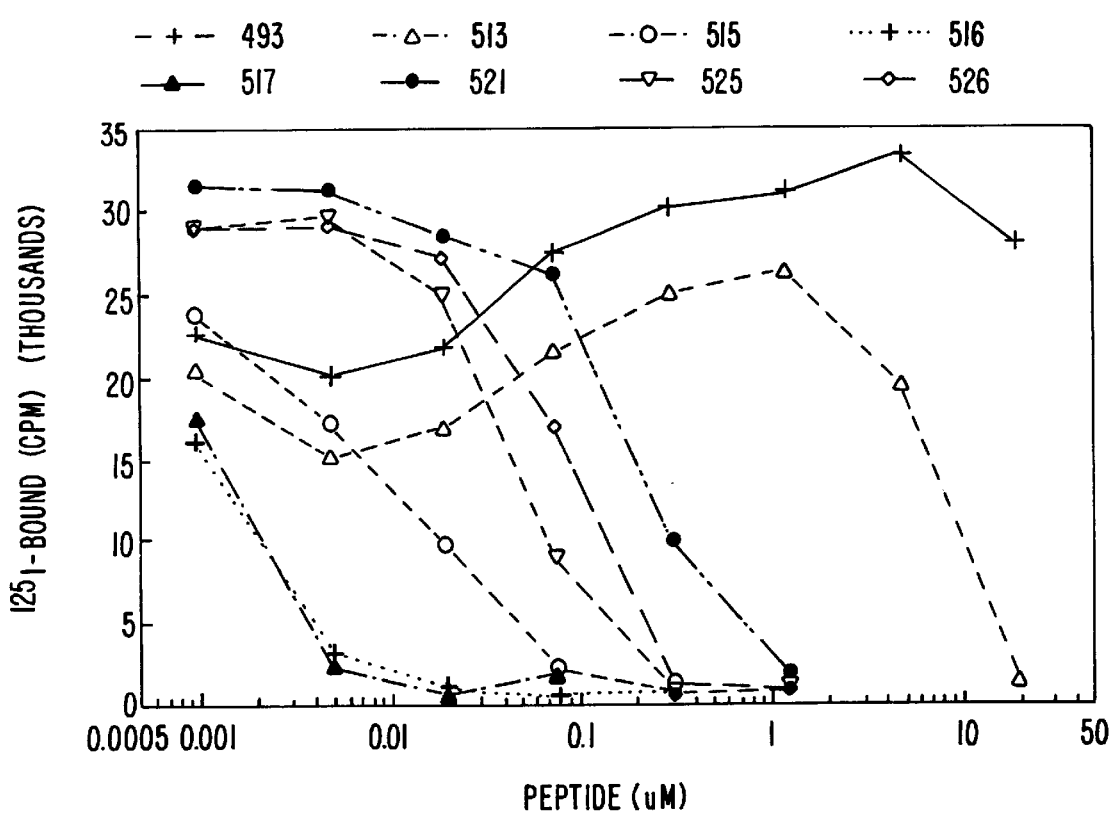
Figure 39B:
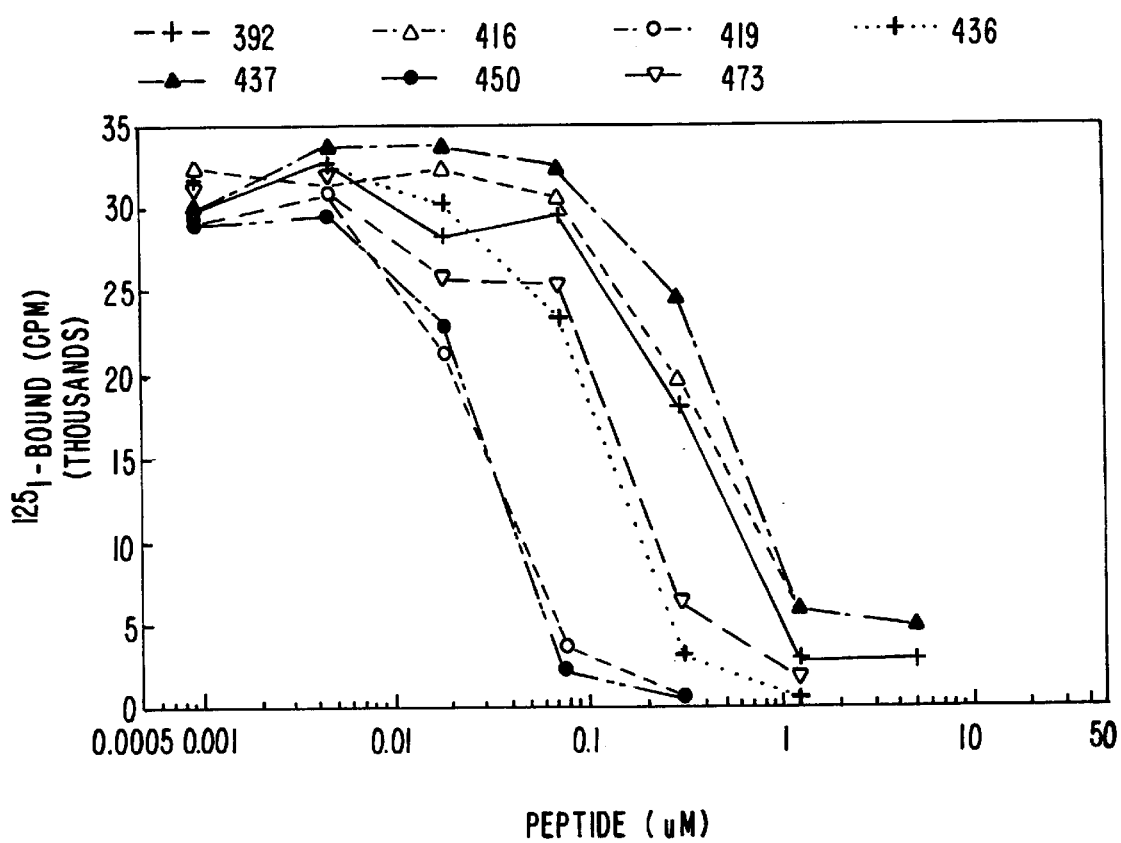
Figure 39C:
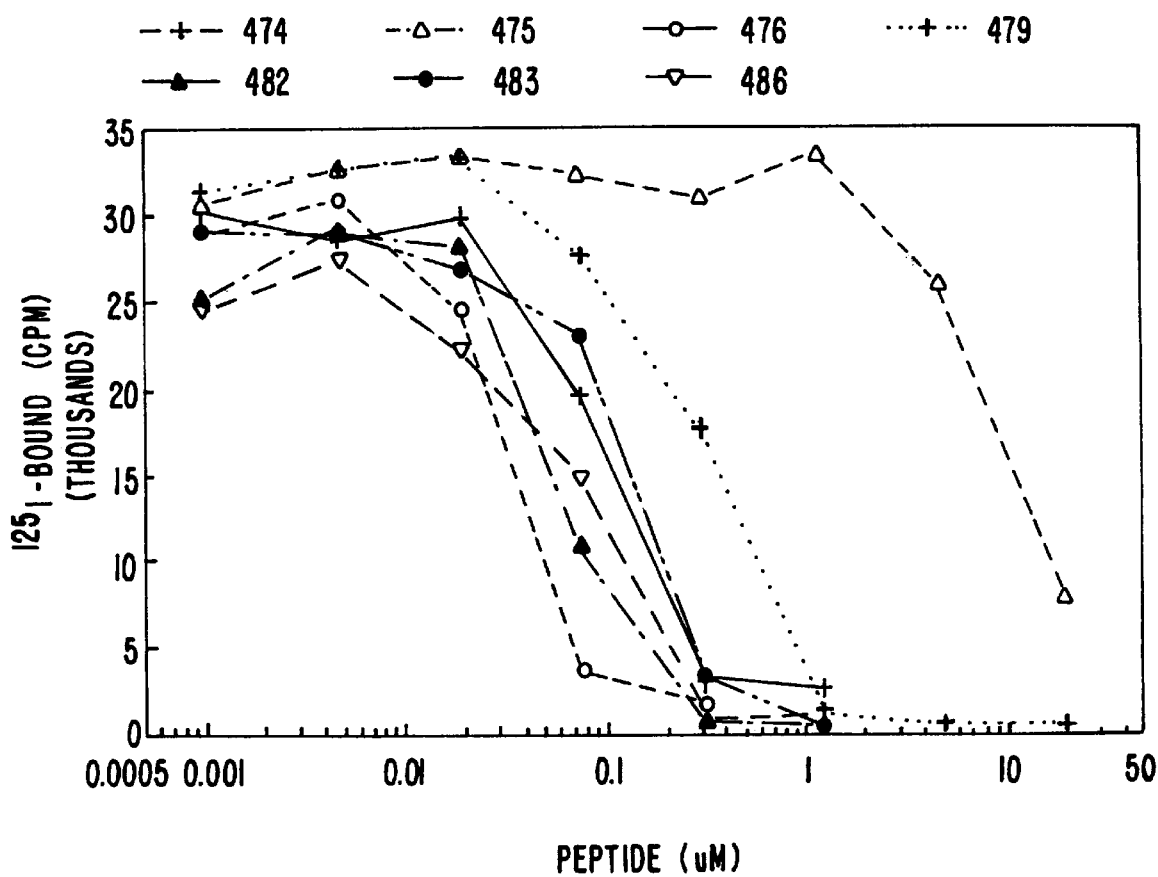
Figure 41A:
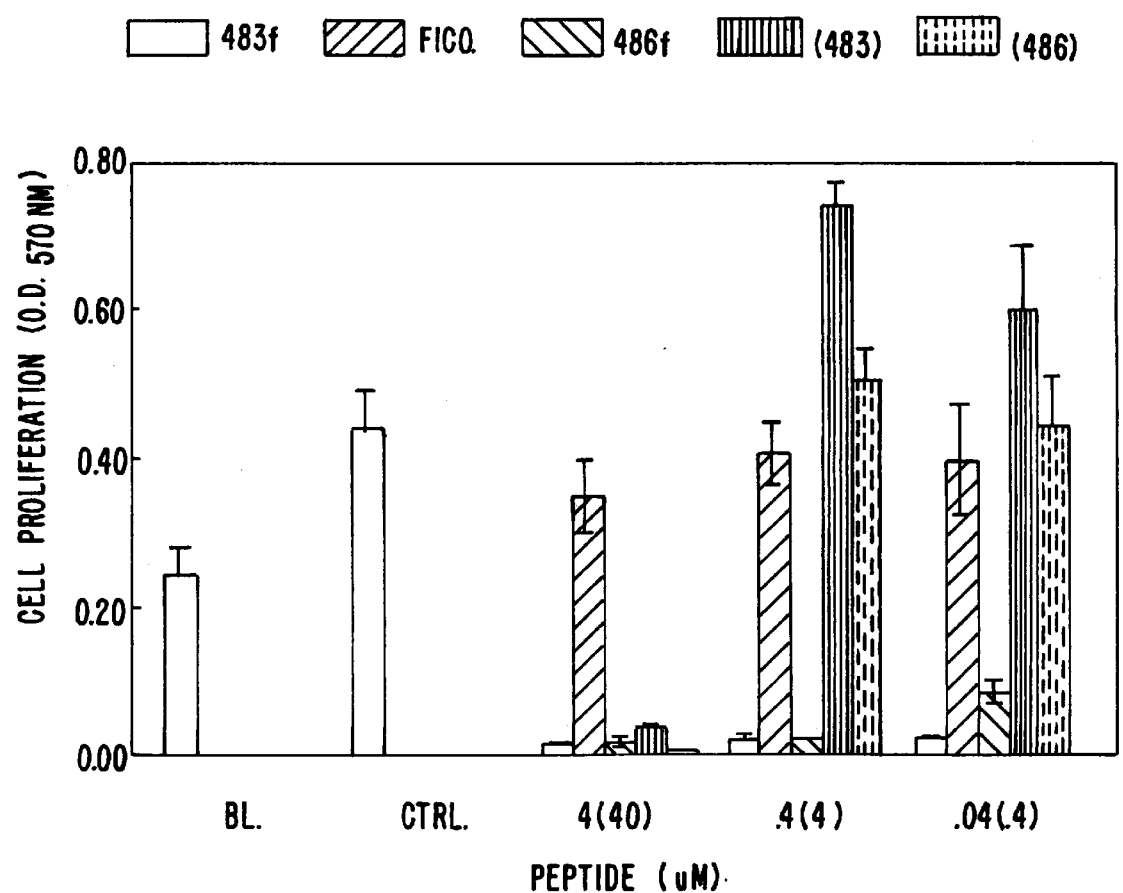
Figure 41B:
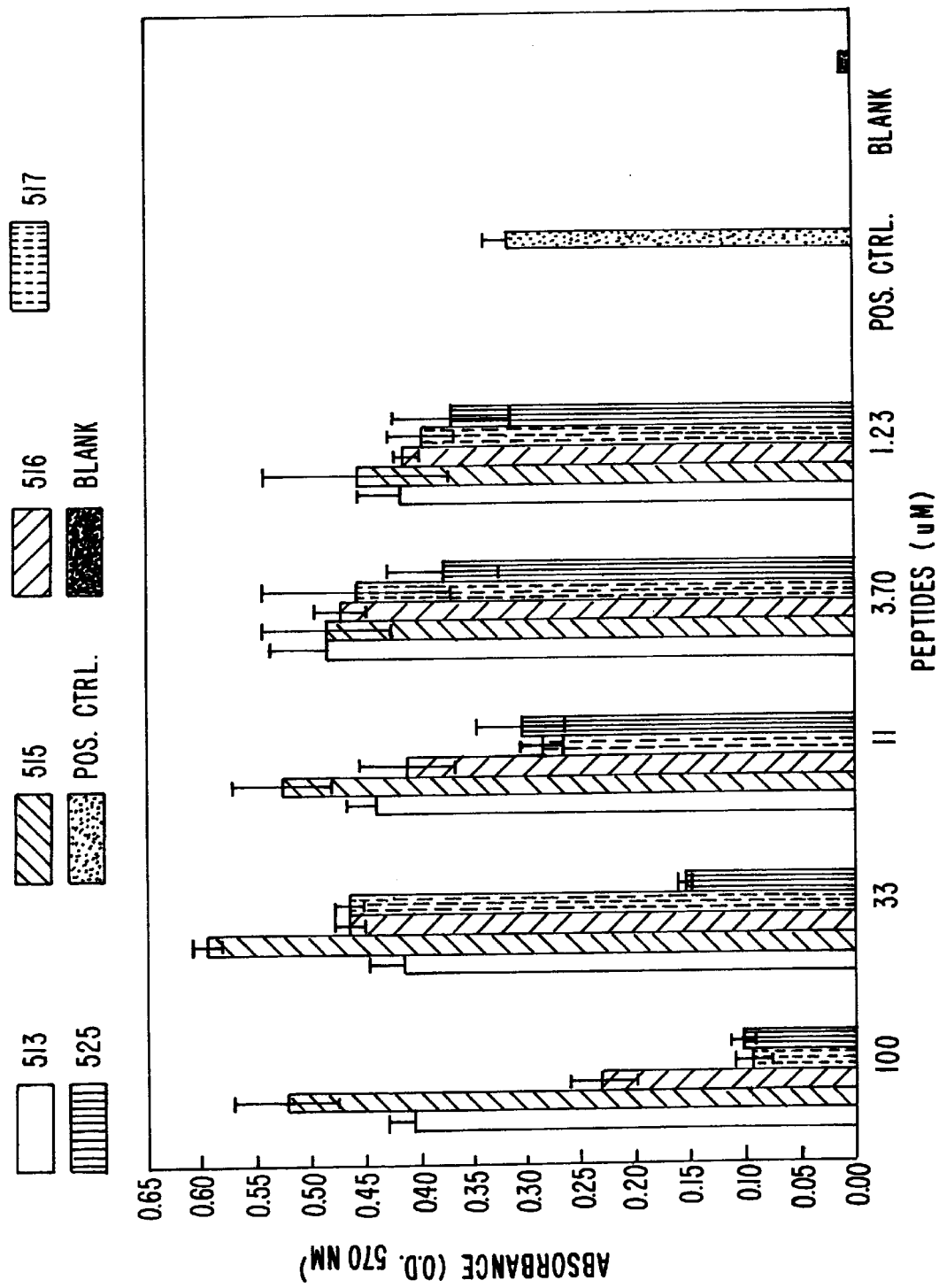
Figure 42:
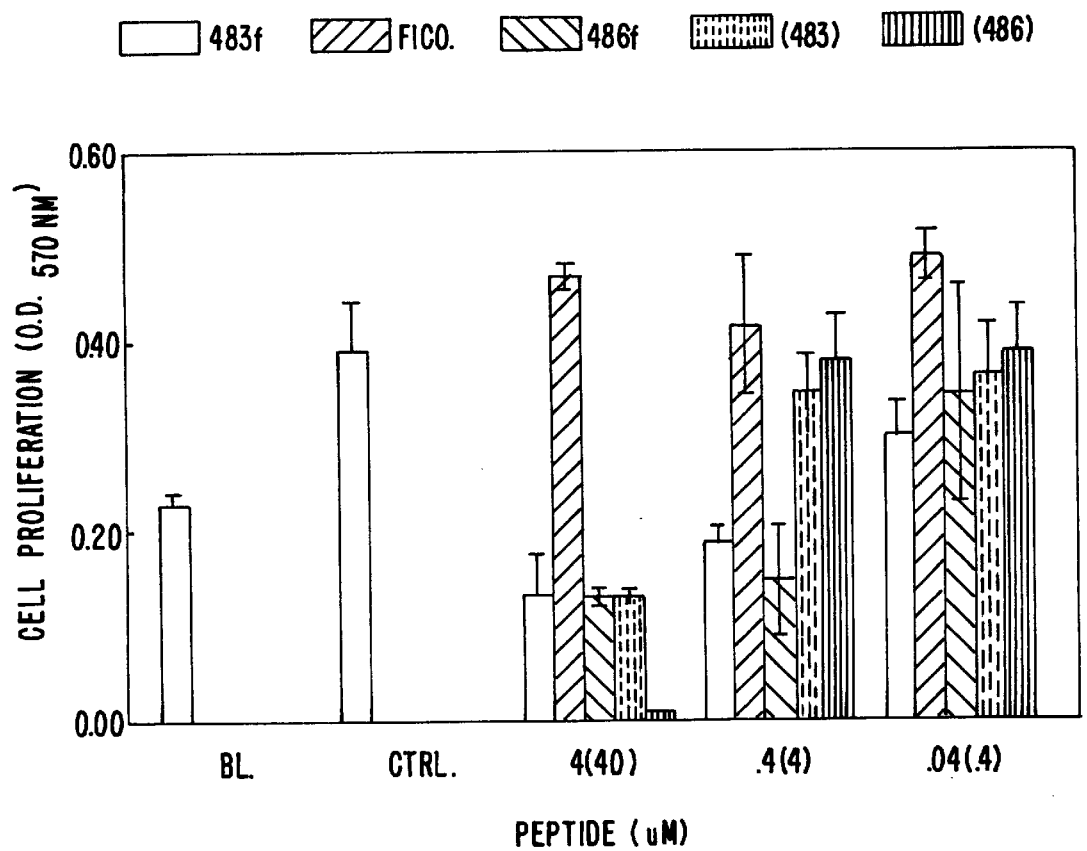

Proliferation of bovine aortic endothelial cells was also determined for cells grown in the presence of the indicated concentrations of peptide 246 (KRFKQDGGWSHWSPWSS) (SEQ ID NO:19) or peptide 416 (retro-inverso) in RPMI-HITES (reg medium) or corresponding conditioned medium from MDA 435 breast carcinoma cells. The results are shown in FIG. 38. At 40 µM, both the free peptides significantly inhibit proliferation of endothelial cells. Therefore, retro-inverso analogs of the thrombospondin peptides also have antiproliferative activity as a free peptide. Inhibition is greater for cells grown in conditioned medium from breast carcinoma cells than from unconditioned medium. FIGS. 41A, B and C show additional examples of the inhibition of BAEC using a number of TSP peptide analogs and polysucrose conjugates.

Example 8
Inhibition of melanoma cell proliferation by conjugated peptides

Human A2058 melanoma cells (31C) or murine K1735 melanoma cells, clone 19 (31A) and TK (31B), were plated in 96 well plates at 5000 cells per well in RPMI medium containing 5% fetal calf serum (31A panel) or 0.5% fetal calf serum (31B panel) alone (control) or in the presence of the indicated concentrations of FICOLL peptide conjugates. Cell proliferation was measured using the CellTiter 96™ assay (Promega, Madison, Wis.). After 72 h, 15 µl of dye solution was added to each well, and the plates were incubated for an additional 4 h. Solubilization solution was added, absorbance at 570 nm was determined. Peptide conjugates: 416F (Ac-allD-CSSWPSWHSWGGDQKFRK-$NH_2$), 407F (SEQ ID NO:30) (KRFKQDGGWSHWSPWSSC), 419F (SEQ ID NO:34) (KFKAAGGWSHWSPWSSC), 392F (SEQ ID NO:32) (KRFKQAGGWSHWSPWSSC), 353F (SEQ ID NO:28) (GGWSHWSPWSSC). The results are shown in FIGS. 26A, B and C.

The data indicates that both human and murine melanoma cell lines are inhibited by the thrombospondin and related peptide conjugates. The retro-inverso conjugate is active in all cases. A conjugate of peptide 353 (SEQ ID NO:28), without the basic residues, is inactive or weakly active. Therefore peptides containing both the basic sequence and the WSXW motif (SEQ ID NO:73) are preferred for optimal activity to inhibit melanoma proliferation.

Figure 44A:
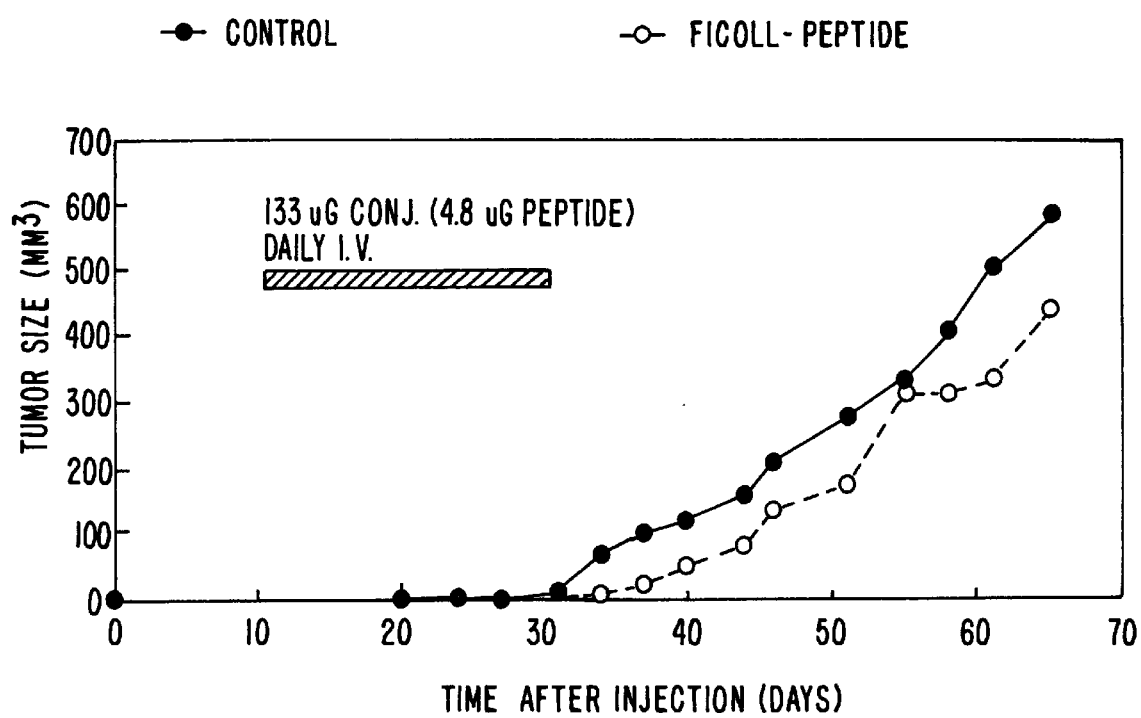

Example 9
Determination of the effect of peptide conjugates on human breast carcinoma cell proliferation Human breast carcinoma cells MDA MB435 (American Type Culture Collection) were grown in RPMI 1640 medium containing 10% fetal calf serum. Proliferation was determined as described in FIG. 18 and 44A, B and C.

Figure 44B:
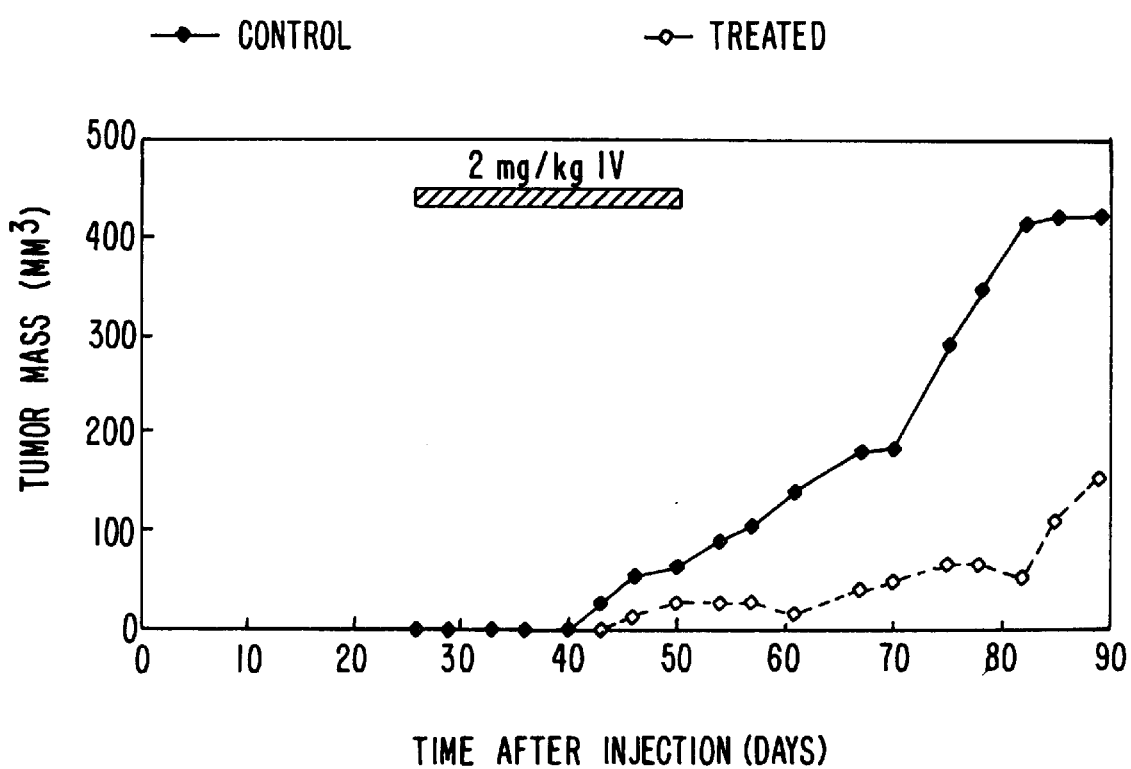
Figure 44C:
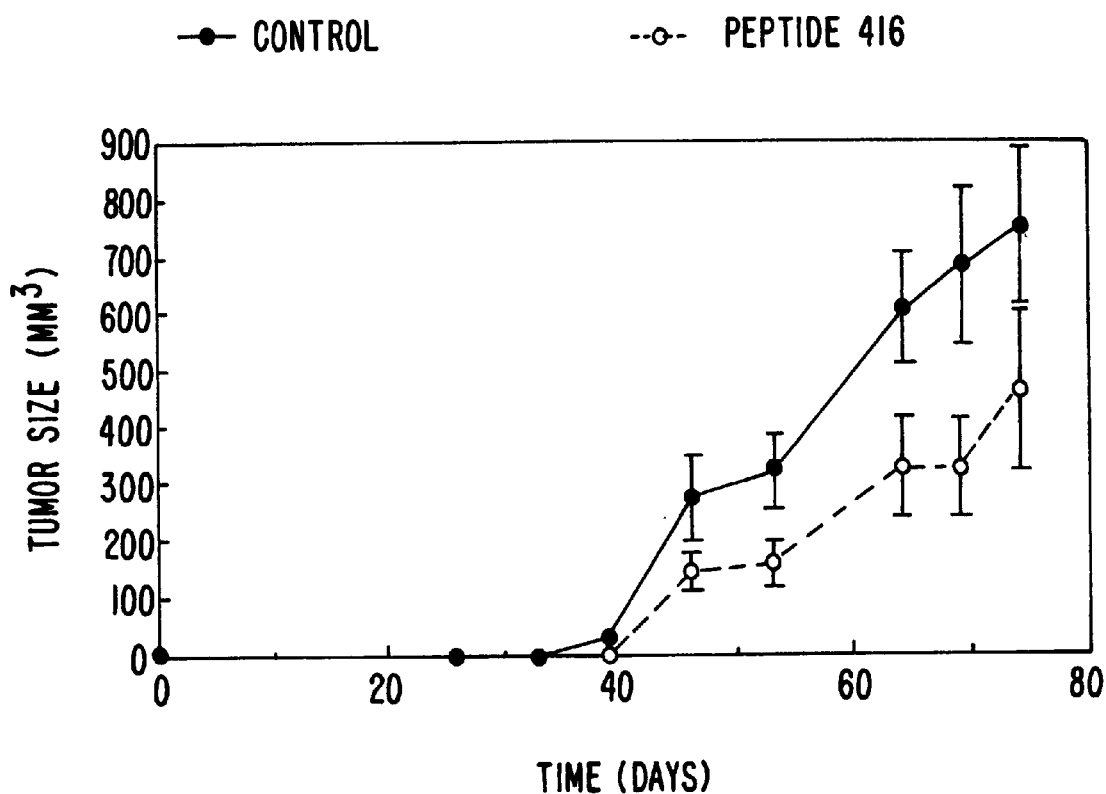

The FICOLL conjugate of peptide 364 (SEQ ID NO:30) strongly inhibited proliferation of MDA435 breast carcinoma cells. FICOLL alone was inactive. The shorter peptide without basic residues was active if coupled through a carboxy-terminal Cys residue (peptide 353 SEQ ID NO:28) but not when coupled through an amino-terminal Cys residue (peptide 354 SEQ ID NO:29). The TSP peptide analog ri-amKRFKQDGGWSHWSPWSSCac (416) showed substantial inhibition of MDA cell proliferation (FIGS. 44B and C).

Example 10
Inhibition of human breast carcinoma cell proliferation using thrombospondin or a peptide conjugate Human breast carcinoma cells MDA MB435 (American Type Culture Collection) were grown in RPMI 1640 medium containing 10% fetal calf serum. Proliferation was determined in the presence of 0.5% fetal calf serum and bFGF as described in FIG. 19.

Two preparations of the peptide 387 (SEQ ID NO:30) gave similar inhibition curves. Inhibition of proliferation by intact native thrombospondin is also presented. Based on the dose response curves, the peptide conjugates are approximately 10-fold less active than the native protein. Expressed on a subunit molar basis, however, the conjugates are only about three-fold less active than the native protein.

Example 11
Determination of Effect of Peptide Conjugates on In Vivo Tumor Formation Further studies were conducted using the MDA435 breast carcinoma model in nude mice (FIG. 27). Tumorigenesis and spontaneous metastasis are determined after orthotopic injection of the tumor cells in mammary fat pads. An alternative formulation involves intraperitoneal injections of the conjugates, incorporation of conjugates or free peptides in liposomes (Woodle M D, Storm G, Newman M S, Jekot J J, Collins; L R, Martin F J, Szoka F C (1992): Prolonged delivery of peptide drugs by long-circulating liposomes: illustration with vasopressin in the brattleboro rat. *Pharm. Res.* 9:260–265), or implantation of encapsulated conjugates in controlled release pellets (obtained from Innovative Research of America) to achieve the desired effective dosage.

From preliminary data, it was found that the FICOLL peptide conjugates are nontoxic when 0.1 ml of conjugate containing 20 $\mu$M bound peptide was injected IV in nude mice for up to 20 days. Based on published studies of related peptide conjugates (Braatz J A, Yashuda Y, Olden K, Yamada K M, Heifetz A H (1993): Functional peptide-polyurethane conjugates with extended circulatory half lives. Bioconjugate Chem 4:262–267), the conjugates are predicted have circulating half lives on the order of 10 hours. Free peptides usually have circulating half lives of less than 10 minutes, based on published results. The short half lives were due to clearance or stability of the peptides in plasma. Use of nonhydrolyzable amino acid analogs or capping modifications of the peptides decreases sensitivity to degradation.

The presented experiment consisted of two groups of animals. The objective was to test a peptide conjugate for effects on breast carcinoma growth. The treated animals were injected with MDA435 cells alone on day one and then injected intravenously with drugs from day 10 through approximately day 30. Tumor growth and frequency of metastasis were determined in both groups.

NIH Nu/Nu mice, approximately eight weeks of age are injected with $10^5$ MDA MB435 cells by the mammary fat pad route. Mice were anesthetized with 150–200 $\mu$l i.p. of a 1:80 dilution in PBS of a solution containing 25 g. tribromoethanol in 12.5 ml tertiary amyl alcohol. The mammary fat pad was cleaned with ethanol and a 10 mm incision was made directly above the site of injection. Mammary fat pad #4 could be observed beneath the skin after the incision was made. Using a 0.1 ml Hamilton syringe and 27 gauge ½" needle, 10 $\mu$l of cell suspension, $1\times10^5$ cells in HBSS, are injected into the fat pad. The incision is closed using 1–2 Autoclips (90 mm, Clay Adams). Autoclips are removed 7 days post-injection and scarring is minimal.

Six animals were injected for each condition, per experiment. Animals were earpunched after injection for subsequent identification. Beginning at day 10 and continuing every day until approximately day 30, the experimental animals were injected i.v. (tail vein) with 0.1 ml of the FICOLL conjugate. Primary tumor size was determined twice weekly by length×width×height measurement, and the animals are observed daily for general health. When the primary tumor of any animal exceeded 20 mm in any dimension, all of the animals were sacrificed. The presence of metastases was determined by gross autopsy and examination of H & E stained sections of any suspicious organ and step sections of the lungs and draining lymph nodes. The primary tumors were removed, stripped free of other tissues, and weighed. At any time during the experiment, animals suspected of being in distress were sacrificed and examined as above.

FIG. 27 shows the inhibition of human breast carcinoma tumor growth in nude mice. The graph shows mean tumor size for each treated and control groups of 6 mice. The MDA435s cells were implanted orthotopically in the mammary fat pads of female Nu/Nu mice on day 0. The 387-FICOLL (SEQ ID NO:30) conjugate was administered intravenously daily from day 10 through day 30. Tumor dimensions are presented as a function of time. Intravenous treatment with the peptide conjugate delays tumor growth in the mouse model. The conjugates were not toxic to the animals.

Example 12
Determination of Effect of Thrombospondin and Functional Domains on Proliferation and Chemotaxis of Kaposi's Sarcoma Cells AIDS-KS cell strains were cultured as previously described (Nakamura, S. et al. "Kaposi's Sarcoma Cells: Long-Term Culture with Growth Factor From Retrovirus-Infected CD4+ T Cells", *Science*, (1988) 242:426; and Salahuddin, S. Z. et al. "Angiogenic Properties of kaposi's Sarcoma-Derived Cells After Long-Term Culture In Vitro", *Science* (1988) 242:430). TSP was purified from thrombin-stimulated human platelets as described. TSP peptides and peptide conjugates were synthesized corresponding to sequences of human TSP as described.

For the cell proliferation assays $1\times10^3$ cells/well were seeded in triplicate in 24 well flat bottom plates (Falcon, Franklin Lakes, N.J.) that contained the required dilutions of TSP, TSP peptide-FICOLL conjugates, and growth factors: 1) Oncostatin M (OSM) (PreProtech) at 25 ng/ml, or 2) activated lymphocyte conditioned medium (AL—CM) at 20%. After 7 days, the cells were trypsinized and counted using a Coulter $Z_m$ Cell Counter (Coulter Corporation). The values are triplicate determinations and the bars indicate standard deviations, n=3.

Directed migration (chemotaxis) and general migration (chemokinesis) of AIDS-KS cells in culture was measured by the modified Boyden chamber assay using fibronectin coated 8 nm Nucleopore filters as previously described. In brief, the AIDS-KS cells, were trypsinized then resuspended in RPMI 1640 containing 105 FBS (GIBCO-BRL) and 20% activated lymphocyte conditioned medium. The trypsinized cells were allowed to recover in suspension for 2 hours, then the cells were recovered by centrifugation and resuspended in RPMI 1640 containing 0.1% BS at $5 \times 10^5$ cells/ml prior to adding 100 µl to the upper wells in the chemotaxis chamber. Migration to BSA (0.1%) and OSM was performed in the presence of the indicated concentrations of TSP, and TSP peptide-FICOLL conjugates. After 3 hours incubation at 37° C. filters were stained with Diff Quick (Merz-Dade, Dudingen, Switzerland), and the migrated cells in ten high-power fields were counted. The values are triplicate determinations and the bars indicate standard deviations, n=3. See FIG. 33.

For determination of In vivo Angiogenesis, $2 \times 10^6$ AIDS-KS cells suspended in phosphate buffered saline without calcium and magnesium (PBS w/o), passage 6–8, were transplanted subcutaneously on day 0 of the flanks of male Balb/c nu/nu athymic mice. The animals were injected intravenously with increasing dilutions of TSP peptide-FICOLL conjugates or the equivalent concentrations of FICOLL mixed in PBS w/o as a control from days 1–5. On day 6 the angiogenic lesions were observed, measured, fixed in 10% formalin, and stained with hematoxylin-eosin.

FIG. 31 shows the inhibition of formation of Kaposi's sarcoma angiogenic lesions in mice treated intravenously for 4 days with daily injections of 0.1 ml of FICOLL-conjugated peptide KRFKQDGGWSHWSPWSSC (SEQ ID NO:30) containing 10.5 or 21 µM bound peptide.

Figure 32:
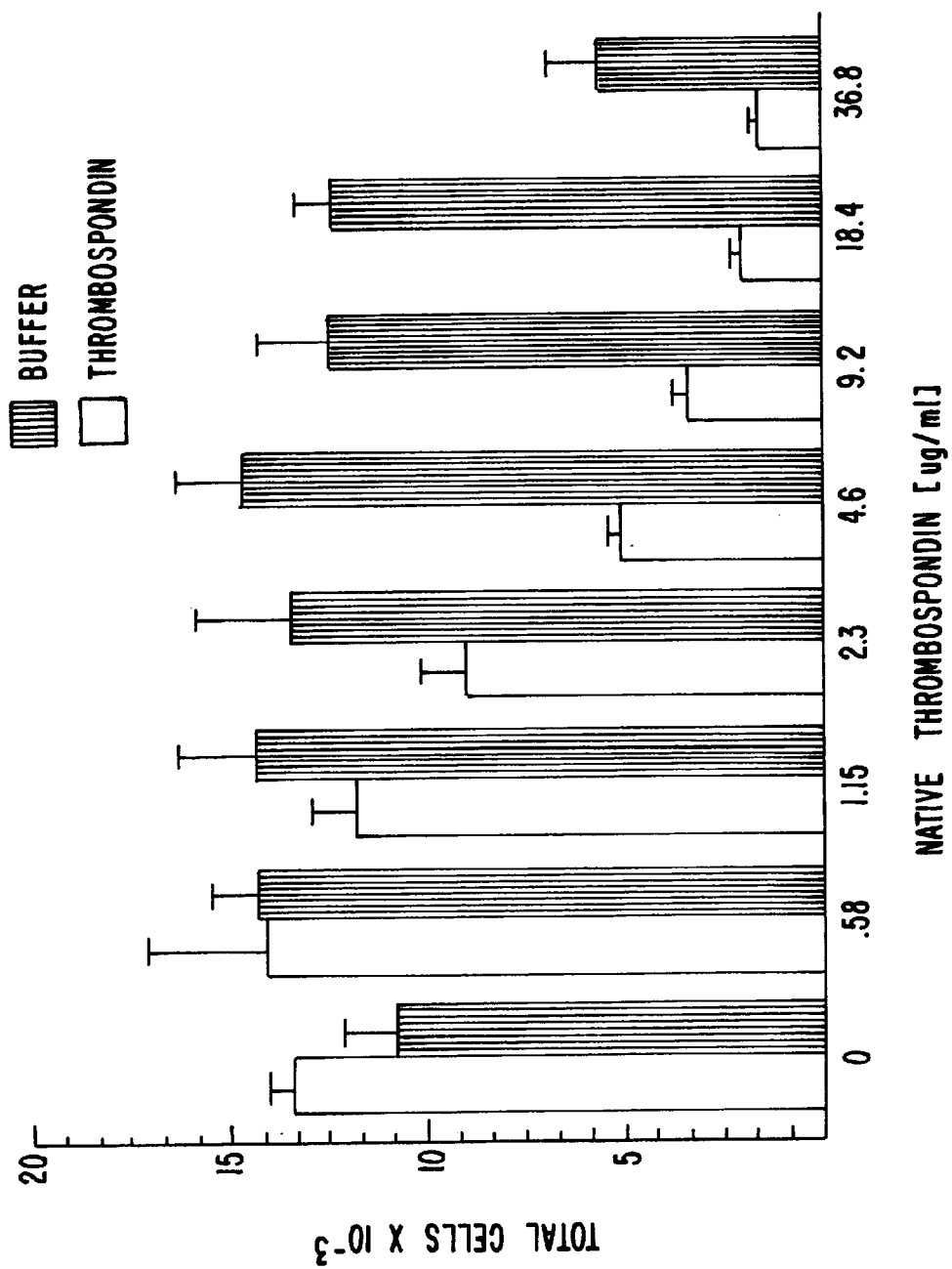

Inhibition of AIDS-KS cell Proliferation by TSP: The effect that TSP had on the growth of the AIDS-KS cells was determined. When AIDS-KS cells were cultured with increasing concentrations of TSP we observed a concentration dependent decrease in cell number with increasing concentrations of TSP (FIG. 32). No morphological changes in the AIDS-KS cells when grown in the presence of TSP were observed. This was in contrast to the cell rounding observed with other heparin-binding proteins, e.g., apolipoprotein E, that inhibit these cells.

Figure 33:
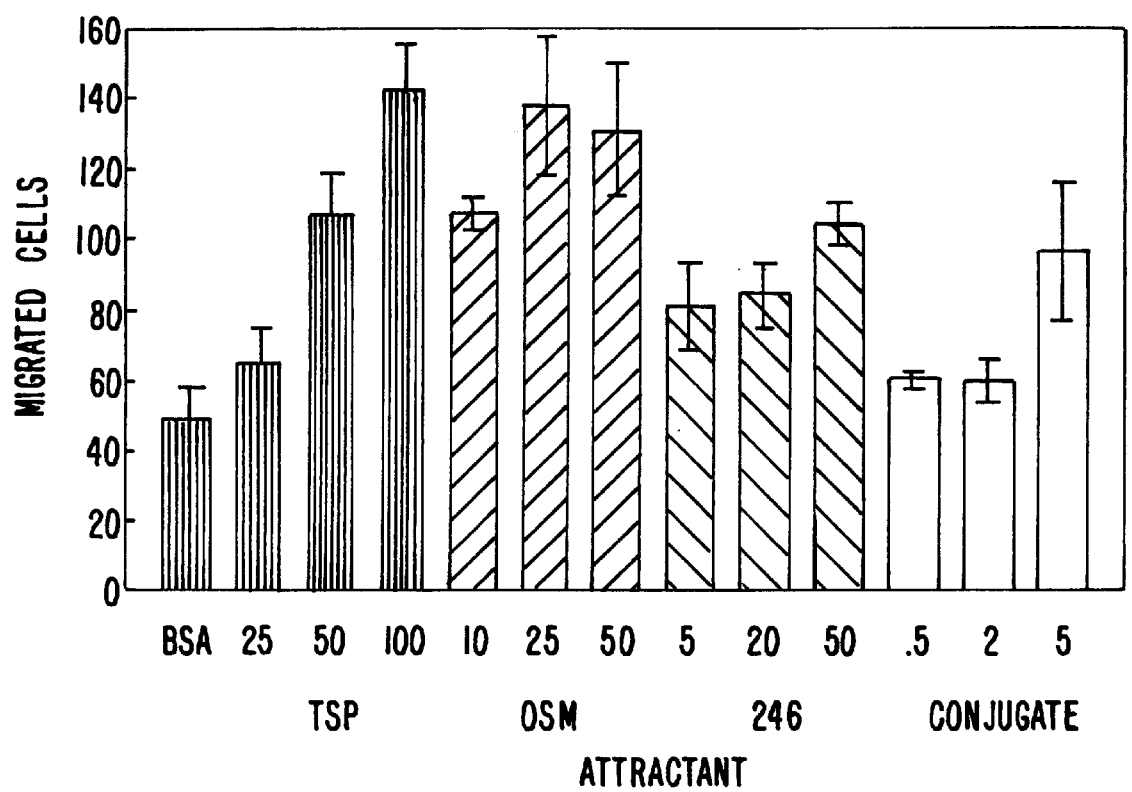
Figure 34:
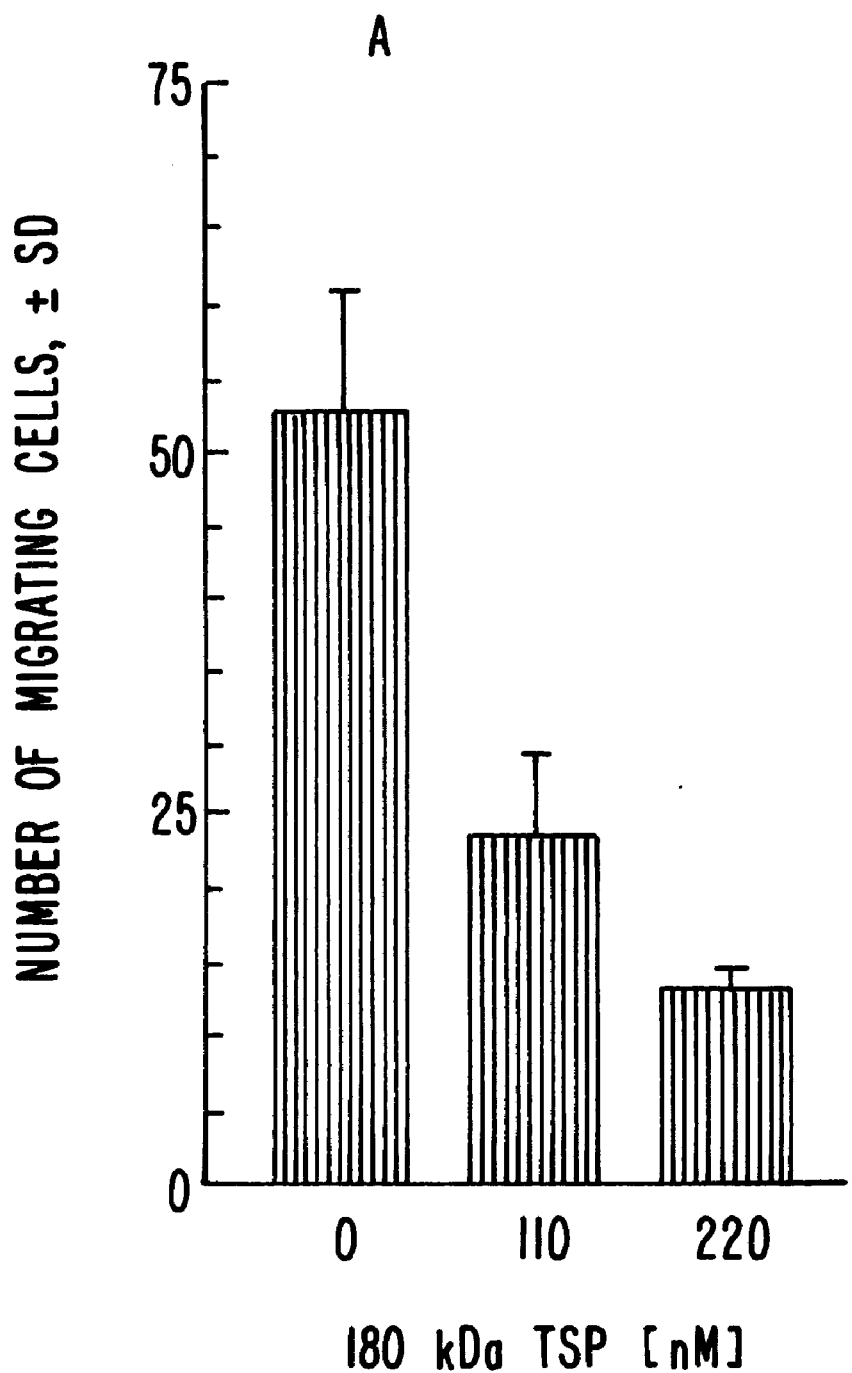
Figure 35:
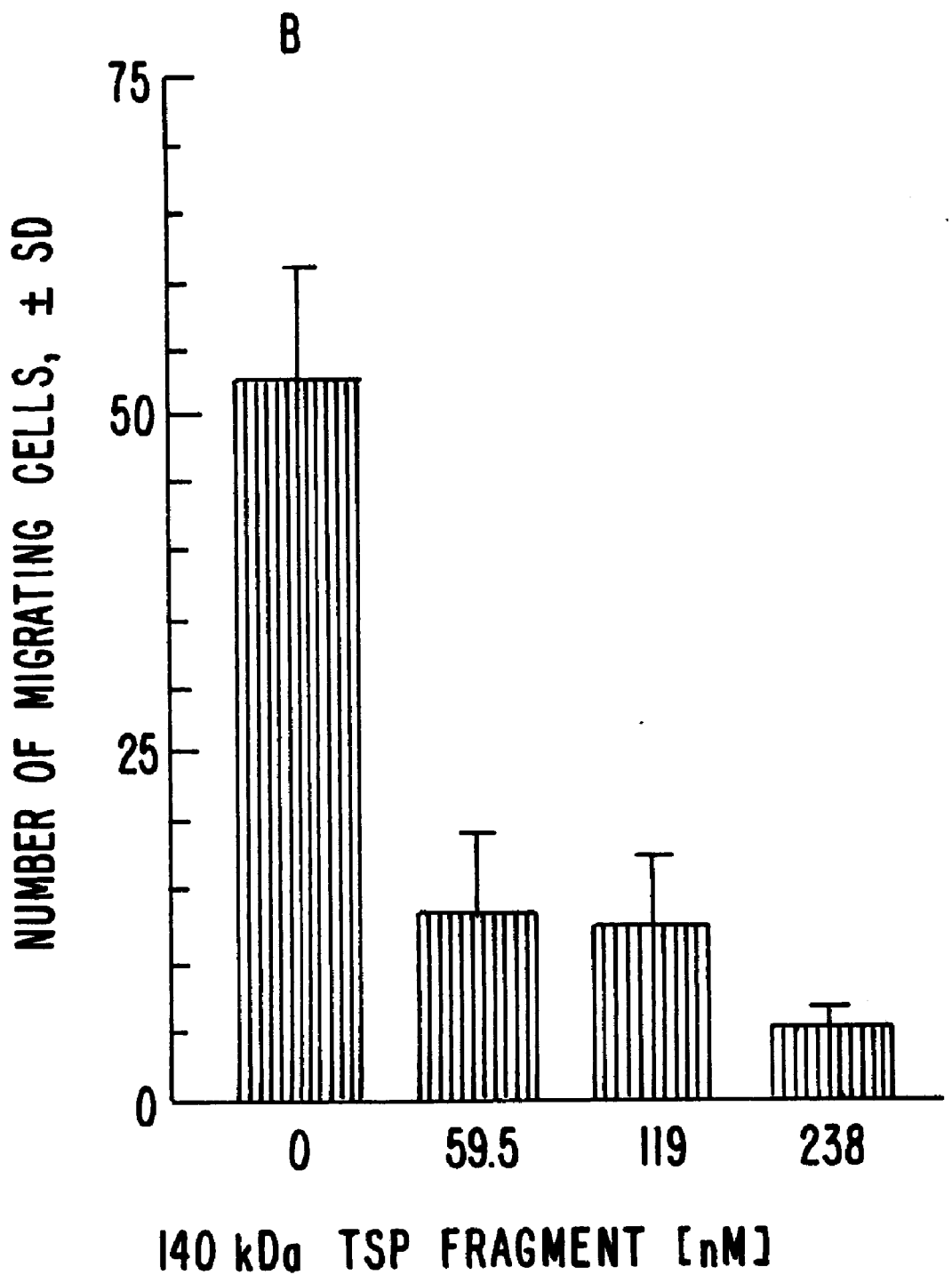

TSP, oncostatin M, and peptide conjugates stimulat chemotaxis of AIDS-KS cells: Additions of TSP in the lower well of a modified Boyden chamber induced a dose-dependent stimulation of AIDS-KS cell motility (FIG. 32). The growth factor oncostatin M also simulated motility Both a free peptide from thrombospondin 246, (SEQ ID NO:19) and the corresponding peptide conjugate also induced increased motility of the cells (FIG. 33).

TSP Inhibits OSM Stimulated Migration of AIDS-KS Cells: In previous studies it was reported that oncostatin M (OSM) is a potent mitogen from the AIDS-KS-spindle cells, but also stimulates chemotaxis and migration of these cells as well. Chemotaxis in response to angiogenic factors is an important aspect of the angiogenic process. Chemotaxis assays were performed to determine what effect TSP has on OSM stimulated chemotaxis. When TSP was added in the lower chamber along with OSM, however, OSM stimulated migration was inhibited (FIG. 34) at an $IC_{50}<110$ nfM. When these assays were performed using the 140 kD fragment of TSP that lacks the heparin binding amino terminus (FIG. 35), this region was found to be highly active with an $IC_{50}$ of <59 nm (this fragment does contain the three type I repeat sequences). This region also inhibited cell proliferation. Although TSP is a large complex molecule with many functional domains through the studies with the 140 kDa TSP fragment we were able to map a region of TSP that inhibited cell proliferation and migration of the AIDS-KS-spindle cells.

Example 13

Cellular DNA Fragmentation ELISA

Target cells (BAEC or MDA or MCF7) (10 ml; $2 \times 10^5$ cells/ml) were incubated with 10 µM BrdU; (=100 µl of BrdU added to 10 ml cell culture) overnight at 37° C. in a humidified atmosphere. After labeling, the cells were trypsinized and centrifuged at 250× g for 10 minutes and resuspended in culture medium. The cell concentration was adjusted to $1 \times 10^5$ cells/ml and 100 µl/well were transferred to a microtiter plate (tissue grade, 96-well flat bottom plate) to replicate wells containing either peptide solution or culture medium only (100 µl/well) to yield a final volume of 200 µl/well. The cells were incubated for certain periods of time (24–72 hours) at 37° C. in humidified atmosphere (5% $CO_2$).

After incubation, the cells in the microtiter plates were lysed by addition of 20 µl of washing buffer (10×) for 30 minutes at room temperature. The plates were then centrifuged at 250× g for 10 minutes. 100 µl of supernatent was then transferred into the wells of separate microtiter plates, precoated with anti-DNA antibody. The samples were incubated for 90 minutes at room temperature. After washing, the samples were denatured and fixed by microwave irradiation for 5 minutes. After cooling the microtiter plates for 10 minutes at −20° C., anti-BrdU peroxidase conjugate solution was added and incubated for an additional 90 minutes at room temperature. After washing, immunocomplexed anti-BrdU peroxidase was detected by TMB substrate (reaction time 10 minutes at room temperature, in the dark). 450 nm color absorbance was detected on an ELISA plate reader.

Figure 43:
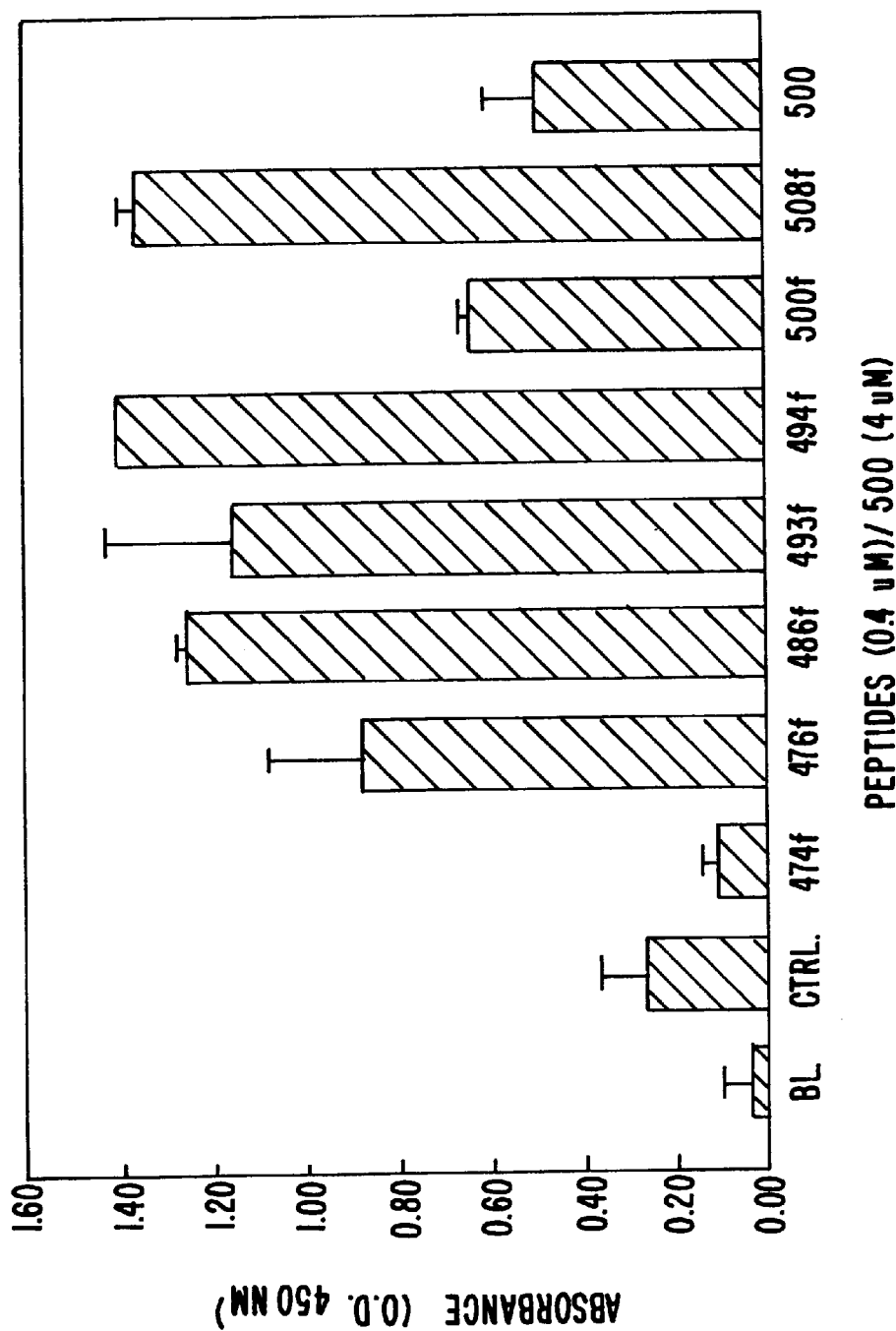

FIG. 43 shows the DNA fragment analysis of BAEC, following treatment with a number of different peptide analogs. Peptide analogs 476f, 486f, 493f, 494f, 500f, 508f and 500f all showed substantially higher levels of DNA fragmnetation than the control.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of a disclosed embodiment. It is to be understood that the phraseology or terminology employed herein is for the purposes of description only and not of limitation. All publications and patent documents cited in this application are incorporated by reference in their entirety for all purposes to the same extent as if each individual publication or patent document were so individually denoted.

What is claimed is:

1. A peptide having an amino acid sequence KRFKAAGGWSHWSPWSSC-NH$_2$ (Peptide 419) (SEQ ID NO:33).

2. A peptide having an amino acid sequence KRFKQAGGWSHWSPWSSC (Peptide 392) (SEQ ID NO:32).

3. A substantially pure peptide from 11 to 30 amino acids in length, wherein said peptide comprises the sequences (SEQ ID NO:106 through SEQ ID NO:113):

$X_5$—R—F—K—$X_9$—$X_{10}$—$(X_{11})_m$—$(G)_n$—W—S—$X_{12}$—W—$(S$—$X_{13}$—$W)_z$—$X_{14}$—$X_{15}$ where $X_5$ is selected independently from R, K, acR and acK;

$X_9$ is Q or A;

$X_{10}$ is D or A;

$X_{11}$ is G or delta-amino-valeric acid and m is 1 or 0;

n is 1 or 0;

$X_{12}$ is H or P; and $X_{13}$ is H or P and z is 1 or 0;

$X_{15}$ is selected independently from the group consisting of S, A and amides thereof; and $X_{14}$ is A.

4. A substantially pure peptide selected from the group consisting of: KRFKQDGGWSWHSPWSSC (SEQ ID NO:41); KRFKQAGGWSHWSPWSSC (SEQ ID NO:32); KRFKAAGGWSHWSPWSSCam (SEQ ID NO:33); acK-RAKAAGGWSHWSPWSSCam (SEQ ID NO:43); acK-RAKQAGGWSHWAACam (SEQ ID NO:44); KRAKQDUWSHWSP (SEQ ID NO:45); KRAKQDGGW-SHWSP; and KRAKQDUWSHWSP (SEQ ID NO:46), where am is a carboxy-terminal amide, ac is an amino-terminal acetyl, and U is delta-amino-valeric acid.

5. A method of inhibiting heparin or heparan sulfate interaction in a sample, without activating latent TGF-β present in the sample, comprising contacting the sample with an effective amount of a peptide of claim 1, 2, 3 or 4.

6. A method of inhibiting interaction of heparin or heparan sulfate with FGF-2 in a sample, comprising contacting the sample with an effective amount of a peptide of claim 1, 2, 3 or 4.

7. A method of inhibiting endothelial cell proliferation, comprising contacting the endothelial cells with an effective amount of a peptide of claim 1, 2, 3 or 4.

8. A method of inhibiting tumor growth in a patient, comprising administering to said patient, an effective amount of a peptide of claim 1, 2, 3 or 4.

9. A pharmaceutical composition comprising a peptide of claim 1, 2, 3 or 4 in combination with a pharmaceutically acceptable carrier.

* * * * *

SEQUENCE LISTING (1) GENERAL INFORMATION:

(iii) NUMBER OF SEQUENCES: 113

(2) INFORMATION FOR SEQ ID NO:1:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Ser Pro Trp Ser Glu Trp Thr Ser Cys Ser Thr Ser
1               5                   10

(2) INFORMATION FOR SEQ ID NO:2:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Ser His Trp Ser Pro Trp Ser Ser Cys Ser Val Thr
1               5                   10

(2) INFORMATION FOR SEQ ID NO:3:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Gly Pro Trp Ser Pro Trp Asp Ile Cys Ser Val Thr
1               5                   10

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Cys Ser Val Thr Cys Gly
1               5

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS:
        (D) TOPOLOGY: linear

```
        (ii) MOLECULE TYPE: peptide (xi) SEQUENCE DESCRIPTION: SEQ ID NO:5:

Val Thr Cys Gly
1

(2) INFORMATION FOR SEQ ID NO:6:

(i) SEQUENCE CHARACTERISTICS:
              (A) LENGTH: 10 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:6:

Val Thr Cys Gly Gly Gly Val Gln Lys Arg
1               5                   10

(2) INFORMATION FOR SEQ ID NO:7:

(i) SEQUENCE CHARACTERISTICS:
              (A) LENGTH: 10 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:7:

Val Thr Cys Gly Asp Gly Val Ile Thr Arg
1               5                   10

(2) INFORMATION FOR SEQ ID NO:8:

(i) SEQUENCE CHARACTERISTICS:
              (A) LENGTH: 10 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:8:

Thr Ser Cys Gly Asn Gly Ile Gln Gln Arg
1               5                   10

(2) INFORMATION FOR SEQ ID NO:9:

(i) SEQUENCE CHARACTERISTICS:
              (A) LENGTH: 4 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:9:

Cys Ser Val Thr
1

(2) INFORMATION FOR SEQ ID NO:10:

(i) SEQUENCE CHARACTERISTICS:
              (A) LENGTH: 4 amino acids
              (B) TYPE: amino acid
              (C) STRANDEDNESS:
```

(D) TOPOLOGY: linear (ii) MOLECULE TYPE: peptide (xi) SEQUENCE DESCRIPTION: SEQ ID NO:10:

Ser Ser Val Thr
1

(2) INFORMATION FOR SEQ ID NO:11:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:11:

Ala Ser Val Thr
1

(2) INFORMATION FOR SEQ ID NO:12:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:12:

Ser Ser Val Thr Cys Gly
1               5

(2) INFORMATION FOR SEQ ID NO:13:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:13:

Ser Ser Cys Ser Val Thr
1               5

(2) INFORMATION FOR SEQ ID NO:14:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:14:

Ser His Trp Ser Pro Trp Ser Ser
1               5

(2) INFORMATION FOR SEQ ID NO:15:

(i) SEQUENCE CHARACTERISTICS:
            (A) LENGTH: 8 amino acids
            (B) TYPE: amino acid (C) STRANDEDNESS:
            (D) TOPOLOGY: linear (ii) MOLECULE TYPE: peptide (xi) SEQUENCE DESCRIPTION: SEQ ID NO:15:

Trp Ser Pro Trp Ser Ser Cys Ser
1               5

(2) INFORMATION FOR SEQ ID NO:16:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:16:

Trp Ser Pro Trp Ser Ser Cys Ser Val Thr
1               5                  10

(2) INFORMATION FOR SEQ ID NO:17:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:17:

Ser His Ala Ser Pro Ala Ser Ser
1               5

(2) INFORMATION FOR SEQ ID NO:18:

(i) SEQUENCE CHARACTERISTICS:
            (A) LENGTH: 13 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:18:

Val Thr Cys Gly Gly Gly Val Gln Lys Arg Ser Arg Leu
1               5                  10

(2) INFORMATION FOR SEQ ID NO:19:

(i) SEQUENCE CHARACTERISTICS:
            (A) LENGTH: 17 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:19:

Lys Arg Phe Lys Gln Asp Gly Gly Trp Ser His Trp Ser Pro Trp Ser
1               5                  10                 15

Ser (2) INFORMATION FOR SEQ ID NO:20:

```
        (i) SEQUENCE CHARACTERISTICS:
             (A) LENGTH: 7 amino acids
             (B) TYPE: amino acid
             (C) STRANDEDNESS:
             (D) TOPOLOGY: linear (ii) MOLECULE TYPE: peptide (xi) SEQUENCE DESCRIPTION: SEQ ID NO:20:

Arg Gln Met Lys Lys Thr Arg
1               5

(2) INFORMATION FOR SEQ ID NO:21:

(i) SEQUENCE CHARACTERISTICS:
             (A) LENGTH: 10 amino acids
             (B) TYPE: amino acid
             (C) STRANDEDNESS:
             (D) TOPOLOGY: linear (ii) MOLECULE TYPE: peptide (xi) SEQUENCE DESCRIPTION: SEQ ID NO:21:

Arg Lys Gly Ser Gly Arg Arg Leu Val Lys
1               5                   10

(2) INFORMATION FOR SEQ ID NO:22:

(i) SEQUENCE CHARACTERISTICS:
             (A) LENGTH: 11 amino acids
             (B) TYPE: amino acid
             (C) STRANDEDNESS:
             (D) TOPOLOGY: linear (ii) MOLECULE TYPE: peptide (xi) SEQUENCE DESCRIPTION: SEQ ID NO:22:

Gly Gly Trp Ser His Trp Ser Pro Trp Ser Ser
1               5                   10

(2) INFORMATION FOR SEQ ID NO:23:

(i) SEQUENCE CHARACTERISTICS:
             (A) LENGTH: 6 amino acids
             (B) TYPE: amino acid
             (C) STRANDEDNESS:
             (D) TOPOLOGY: linear (ii) MOLECULE TYPE: peptide (xi) SEQUENCE DESCRIPTION: SEQ ID NO:23:

Ser His Trp Trp Ser Ser
1               5

(2) INFORMATION FOR SEQ ID NO:24:

(i) SEQUENCE CHARACTERISTICS:
             (A) LENGTH: 7 amino acids
             (B) TYPE: amino acid
             (C) STRANDEDNESS:
             (D) TOPOLOGY: linear (ii) MOLECULE TYPE: peptide (xi) SEQUENCE DESCRIPTION: SEQ ID NO:24:

Ser His Trp Ser Trp Ser Ser
1               5

(2) INFORMATION FOR SEQ ID NO:25:
```

(i) SEQUENCE CHARACTERISTICS:
    (A) LENGTH: 11 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:25:

Gly Gly Trp Ser His Ala Ser Pro Trp Ser Ser
1               5                   10

(2) INFORMATION FOR SEQ ID NO:26:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:26:

Ser His Trp Ser Ser Pro Trp Ser Ser
1               5

(2) INFORMATION FOR SEQ ID NO:27:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

Ser His Trp Ala Pro Trp Ser Ser
1               5

(2) INFORMATION FOR SEQ ID NO:28:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

Gly Gly Trp Ser His Trp Ser Pro Trp Ser Ser Cys
1               5                   10

(2) INFORMATION FOR SEQ ID NO:29:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

Cys Gly Gly Trp Ser His Trp Ser Pro Trp Ser Ser
1               5                   10

(2) INFORMATION FOR SEQ ID NO:30:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

```
Lys Arg Phe Lys Gln Asp Gly Gly Trp Ser His Trp Ser Pro Trp Ser
1               5                   10                  15
Ser Cys
```

(2) INFORMATION FOR SEQ ID NO:31:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

```
Lys Arg Phe Lys Gln Asp Gly Gly Ala Ser His Ala Ser Pro Ala Ser
1               5                   10                  15
Ser Cys
```

(2) INFORMATION FOR SEQ ID NO:32:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

```
Lys Arg Phe Lys Gln Ala Gly Gly Trp Ser His Trp Ser Pro Trp Ser
1               5                   10                  15
Ser Cys
```

(2) INFORMATION FOR SEQ ID NO:33:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 18
        (D) OTHER INFORMATION: /product= "OTHER"
            /note= "Xaa = cysteinamide"

(xi) SEQUENCE DESCRIPTION: SEQ ID NO:33:

```
Lys Arg Phe Lys Ala Ala Gly Gly Trp Ser His Trp Ser Pro Trp Ser
1               5                   10                  15
Ser Xaa
```

(2) INFORMATION FOR SEQ ID NO:34:

(i) SEQUENCE CHARACTERISTICS:
              (A) LENGTH: 18 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:34:

Lys Arg Phe Lys Ala Ala Gly Gly Trp Ser His Trp Ser Pro Trp Ser
1               5                   10                  15
Ser Cys (2) INFORMATION FOR SEQ ID NO:35:

(i) SEQUENCE CHARACTERISTICS:
              (A) LENGTH: 8 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:35:

Lys Arg Phe Lys Gln Asp Gly Gly
1               5

(2) INFORMATION FOR SEQ ID NO:36:

(i) SEQUENCE CHARACTERISTICS:
              (A) LENGTH: 4 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:36:

Lys Arg Phe Lys
1

(2) INFORMATION FOR SEQ ID NO:37:

(i) SEQUENCE CHARACTERISTICS:
              (A) LENGTH: 4 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:37:

Lys Arg Ala Lys
1

(2) INFORMATION FOR SEQ ID NO:38:

(i) SEQUENCE CHARACTERISTICS:
              (A) LENGTH: 4 amino acids
              (B) TYPE: amino acid
              (C) STRANDEDNESS:
              (D) TOPOLOGY: linear (ii) MOLECULE TYPE: peptide (xi) SEQUENCE DESCRIPTION: SEQ ID NO:38:

Trp Ser His Trp
1

(2) INFORMATION FOR SEQ ID NO:39:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

Ser Ile Ser Thr Glu Trp Ser
1               5

(2) INFORMATION FOR SEQ ID NO:40:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:40:

Thr Ala Tyr Arg Trp Arg Leu Ser His Arg Pro Lys Thr Gly Phe Ile
1               5                  10                  15

Arg Val (2) INFORMATION FOR SEQ ID NO:41:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

Lys Arg Phe Lys Gln Asp Gly Gly Trp Ser Trp His Ser Pro Trp Ser
1               5                  10                  15

Ser Cys (2) INFORMATION FOR SEQ ID NO:42:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:42:

Lys Arg Ala Lys Ala Ala Gly Gly Trp Ser His Trp Ser Pro Trp Ser
1               5                  10                  15

Ser Cys (2) INFORMATION FOR SEQ ID NO:43:

(i) SEQUENCE CHARACTERISTICS:
        (A) LENGTH: 18 amino acids
        (B) TYPE: amino acid
        (C) STRANDEDNESS:
        (D) TOPOLOGY: linear

```
    (ii) MOLECULE TYPE: peptide (ix) FEATURE:
         (A) NAME/KEY: Modified-site
         (B) LOCATION: 1
         (D) OTHER INFORMATION: /product= "OTHER"
             /note= "Xaa = alpha-N-acetyl-lysine"

(ix) FEATURE:
         (A) NAME/KEY: Modified-site
         (B) LOCATION: 18
         (D) OTHER INFORMATION: /product= "OTHER"
             /note= "Xaa = cysteinamide"

(xi) SEQUENCE DESCRIPTION: SEQ ID NO:43:

Xaa Arg Ala Lys Ala Ala Gly Gly Trp Ser His Trp Ser Pro Trp Ser
1               5                   10                  15

Ser Xaa (2) INFORMATION FOR SEQ ID NO:44:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
             /note= "Xaa = alpha-N-acetyl-lysine"

(ix) FEATURE:
         (A) NAME/KEY: Modified-site
         (B) LOCATION: 15
         (D) OTHER INFORMATION: /product= "OTHER"
             /note= "Xaa = cysteinamide"

(xi) SEQUENCE DESCRIPTION: SEQ ID NO:44:

Xaa Arg Ala Lys Gln Ala Gly Gly Trp Ser His Trp Ala Ala Xaa
1               5                   10                  15

(2) INFORMATION FOR SEQ ID NO:45:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 7
         (D) OTHER INFORMATION: /product= "OTHER"
             /note= "Xaa = delta-amino-valeric acid"

(xi) SEQUENCE DESCRIPTION: SEQ ID NO:45:

Lys Arg Ala Lys Gln Asp Xaa Trp Ser His Trp Ser Pro
1               5                   10

(2) INFORMATION FOR SEQ ID NO:46:

(i) SEQUENCE CHARACTERISTICS:
        (A) LENGTH: 14 amino acids
        (B) TYPE: amino acid
        (C) STRANDEDNESS:
```

```
        (D) TOPOLOGY: linear (ii) MOLECULE TYPE: peptide (xi) SEQUENCE DESCRIPTION: SEQ ID NO:46:

Lys Arg Ala Lys Gln Asp Gly Gly Trp Ser His Trp Ser Pro
1               5                   10

(2) INFORMATION FOR SEQ ID NO:47:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = alpha-N-acetyl-lysine"

(ix) FEATURE:
        (A) NAME/KEY: Modified-site
        (B) LOCATION: 16
        (D) OTHER INFORMATION: /product= "OTHER"
            /note= "Xaa = cysteinamide"

(xi) SEQUENCE DESCRIPTION: SEQ ID NO:47:

Xaa Lys Arg Ala Lys Ala Ala Gly Gly Trp Ser His Trp Ala Ser Xaa
1               5                   10                  15

(2) INFORMATION FOR SEQ ID NO:48:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:48:

Lys Arg Phe Lys Gln Ala Gly Gly Trp Ser His Trp Ser Pro Trp
1               5                   10                  15

(2) INFORMATION FOR SEQ ID NO:49:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:49:

Lys Arg Phe Lys Asp Asp Gly Gly Trp Ser His Trp Ser Pro Trp Ser
1               5                   10                  15

Ser Cys (2) INFORMATION FOR SEQ ID NO:50:

(i) SEQUENCE CHARACTERISTICS:
        (A) LENGTH: 12 amino acids
        (B) TYPE: amino acid
        (C) STRANDEDNESS:
        (D) TOPOLOGY: linear
```

(ii) MOLECULE TYPE: peptide (xi) SEQUENCE DESCRIPTION: SEQ ID NO:50:

Lys Arg Phe Lys Gln Asp Gly Gly Trp Ser His Trp
1               5                   10

(2) INFORMATION FOR SEQ ID NO:51:

(i) SEQUENCE CHARACTERISTICS:
            (A) LENGTH: 12 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:51:

Thr Arg Ile Arg Gln Asp Gly Gly Trp Ser His Trp
1               5                   10

(2) INFORMATION FOR SEQ ID NO:52:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:52:

Gly Gly Trp Ser His Trp
1               5

(2) INFORMATION FOR SEQ ID NO:53:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:53:

Ser His Trp Ser Pro Trp Ser Ser Cys
1               5

(2) INFORMATION FOR SEQ ID NO:54:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:54:

Trp Ser Pro Trp Ser
1               5

(2) INFORMATION FOR SEQ ID NO:55:

(i) SEQUENCE CHARACTERISTICS:
            (A) LENGTH: 4 amino acids
            (B) TYPE: amino acid
            (C) STRANDEDNESS:

(D) TOPOLOGY: linear (ii) MOLECULE TYPE: peptide (xi) SEQUENCE DESCRIPTION: SEQ ID NO:55:

Arg Gly Asp Ser
1

(2) INFORMATION FOR SEQ ID NO:56:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:56:

Ile Lys Val Ala Val
1               5

(2) INFORMATION FOR SEQ ID NO:57:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa = Arg, Lys,
                alpha-N-acetyl-arginine, or
                alpha-N-acetyl-lysine"

(ix) FEATURE:
            (A) NAME/KEY: Modified-site
            (B) LOCATION: 2
            (D) OTHER INFORMATION: /note= "Xaa = Arg or Lys"

(ix) FEATURE:
            (A) NAME/KEY: Modified-site
            (B) LOCATION: 3
            (D) OTHER INFORMATION: /note= "Xaa = Phe or Ala"

(ix) FEATURE:
            (A) NAME/KEY: Modified-site
            (B) LOCATION: 4
            (D) OTHER INFORMATION: /note= "Xaa = Arg or Lys"

(ix) FEATURE:
            (A) NAME/KEY: Modified-site
            (B) LOCATION: 5
            (D) OTHER INFORMATION: /note= "Xaa = Gln or Ala"

(ix) FEATURE:
            (A) NAME/KEY: Modified-site
            (B) LOCATION: 6
            (D) OTHER INFORMATION: /note= "Xaa = Asp or Ala"

(ix) FEATURE:
            (A) NAME/KEY: Modified-site
            (B) LOCATION: 7
            (D) OTHER INFORMATION: /note= "Xaa = Gly or
                delta-amino-valeric acid"

(ix) FEATURE:
            (A) NAME/KEY: Modified-site
            (B) LOCATION: 11
            (D) OTHER INFORMATION: /note= "Xaa = His or Pro"

```
    (ix) FEATURE:
          (A) NAME/KEY: Modified-site
          (B) LOCATION: 14
          (D) OTHER INFORMATION: /note= "Xaa = His or Pro"

(xi) SEQUENCE DESCRIPTION: SEQ ID NO:57:

Xaa Xaa Xaa Xaa Xaa Xaa Xaa Gly Trp Ser Xaa Trp Ser Xaa Trp
 1               5                  10                  15

(2) INFORMATION FOR SEQ ID NO:58:

(i) SEQUENCE CHARACTERISTICS:
          (A) LENGTH: 12 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /note= "Xaa = Arg, Lys,
              alpha-N-acetyl-arginine, or
              alpha-N-acetyl-lysine"

(ix) FEATURE:
          (A) NAME/KEY: Modified-site
          (B) LOCATION: 2
          (D) OTHER INFORMATION: /note= "Xaa = Arg or Lys"

(ix) FEATURE:
          (A) NAME/KEY: Modified-site
          (B) LOCATION: 3
          (D) OTHER INFORMATION: /note= "Xaa = Phe or Ala"

(ix) FEATURE:
          (A) NAME/KEY: Modified-site
          (B) LOCATION: 4
          (D) OTHER INFORMATION: /note= "Xaa = Arg or Lys"

(ix) FEATURE:
          (A) NAME/KEY: Modified-site
          (B) LOCATION: 5
          (D) OTHER INFORMATION: /note= "Xaa = Gln or Ala"

(ix) FEATURE:
          (A) NAME/KEY: Modified-site
          (B) LOCATION: 6
          (D) OTHER INFORMATION: /note= "Xaa = Asp or Ala"

(ix) FEATURE:
          (A) NAME/KEY: Modified-site
          (B) LOCATION: 7
          (D) OTHER INFORMATION: /note= "Xaa = Gly or
              delta-amino-valeric acid"

(ix) FEATURE:
          (A) NAME/KEY: Modified-site
          (B) LOCATION: 11
          (D) OTHER INFORMATION: /note= "Xaa = His or Pro"
    (xi) SEQUENCE DESCRIPTION: SEQ ID NO:58:

Xaa Xaa Xaa Xaa Xaa Xaa Xaa Gly Trp Ser Xaa Trp
 1               5                  10

(2) INFORMATION FOR SEQ ID NO:59:

(i) SEQUENCE CHARACTERISTICS:
          (A) LENGTH: 14 amino acids
          (B) TYPE: amino acid
          (C) STRANDEDNESS:
          (D) TOPOLOGY: linear (ii) MOLECULE TYPE: peptide
```

```
    (ix) FEATURE:
         (A) NAME/KEY: Modified-site
         (B) LOCATION: 1
         (D) OTHER INFORMATION: /note= "Xaa = Arg, Lys,
             alpha-N-acetyl-arginine, or
             alpha-N-acetyl-lysine"

(ix) FEATURE:
         (A) NAME/KEY: Modified-site
         (B) LOCATION: 2
         (D) OTHER INFORMATION: /note= "Xaa = Arg or Lys"

(ix) FEATURE:
         (A) NAME/KEY: Modified-site
         (B) LOCATION: 3
         (D) OTHER INFORMATION: /note= "Xaa = Phe or Ala"

(ix) FEATURE:
         (A) NAME/KEY: Modified-site
         (B) LOCATION: 4
         (D) OTHER INFORMATION: /note= "Xaa = Arg or Lys"

(ix) FEATURE:
         (A) NAME/KEY: Modified-site
         (B) LOCATION: 5
         (D) OTHER INFORMATION: /note= "Xaa = Gln or Ala"

(ix) FEATURE:
         (A) NAME/KEY: Modified-site
         (B) LOCATION: 6
         (D) OTHER INFORMATION: /note= "Xaa = Asp or Ala"

(ix) FEATURE:
         (A) NAME/KEY: Modified-site
         (B) LOCATION: 7
         (D) OTHER INFORMATION: /note= "Xaa = Gly or
             delta-amino-valeric acid"

(ix) FEATURE:
         (A) NAME/KEY: Modified-site
         (B) LOCATION: 10
         (D) OTHER INFORMATION: /note= "Xaa = His or Pro"

(ix) FEATURE:
         (A) NAME/KEY: Modified-site
         (B) LOCATION: 13
         (D) OTHER INFORMATION: /note= "Xaa = His or Pro"

(xi) SEQUENCE DESCRIPTION: SEQ ID NO:59:

Xaa Xaa Xaa Xaa Xaa Xaa Xaa Trp Ser Xaa Trp Ser Xaa Trp
1               5                   10

(2) INFORMATION FOR SEQ ID NO:60:

(i) SEQUENCE CHARACTERISTICS:
         (A) LENGTH: 14 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "Xaa = Arg, Lys,
             alpha-N-acetyl-arginine, or
             alpha-N-acetyl-lysine"

(ix) FEATURE:
         (A) NAME/KEY: Modified-site
         (B) LOCATION: 2
         (D) OTHER INFORMATION: /note= "Xaa = Arg or Lys"

(ix) FEATURE:
         (A) NAME/KEY: Modified-site
         (B) LOCATION: 3
```

(D) OTHER INFORMATION: /note= "Xaa = Phe or Ala"

(ix) FEATURE:
           (A) NAME/KEY: Modified-site
           (B) LOCATION: 4
           (D) OTHER INFORMATION: /note= "Xaa = Arg or Lys"

(ix) FEATURE:
           (A) NAME/KEY: Modified-site
           (B) LOCATION: 5
           (D) OTHER INFORMATION: /note= "Xaa = Gln or Ala"

(ix) FEATURE:
           (A) NAME/KEY: Modified-site
           (B) LOCATION: 6
           (D) OTHER INFORMATION: /note= "Xaa = Asp or Ala"

(ix) FEATURE:
           (A) NAME/KEY: Modified-site
           (B) LOCATION: 10
           (D) OTHER INFORMATION: /note= "Xaa = His or Pro"

(ix) FEATURE:
           (A) NAME/KEY: Modified-site
           (B) LOCATION: 13
           (D) OTHER INFORMATION: /note= "Xaa = His or Pro"

(xi) SEQUENCE DESCRIPTION: SEQ ID NO:60:

Xaa Xaa Xaa Xaa Xaa Xaa Gly Trp Ser Xaa Trp Ser Xaa Trp
1               5                   10

(2) INFORMATION FOR SEQ ID NO:61:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /note= "Xaa = Gln or Ala"

(ix) FEATURE:
          (A) NAME/KEY: Modified-site
          (B) LOCATION: 2
          (D) OTHER INFORMATION: /note= "Xaa = Asp or Ala"

(ix) FEATURE:
          (A) NAME/KEY: Modified-site
          (B) LOCATION: 3
          (D) OTHER INFORMATION: /note= "Xaa = Gly or
              delta-amino-valeric acid"

(ix) FEATURE:
          (A) NAME/KEY: Modified-site
          (B) LOCATION: 7
          (D) OTHER INFORMATION: /note= "Xaa = His or Pro"

(ix) FEATURE:
          (A) NAME/KEY: Modified-site
          (B) LOCATION: 10
          (D) OTHER INFORMATION: /note= "Xaa = His or Pro"

(xi) SEQUENCE DESCRIPTION: SEQ ID NO:61:

Xaa Xaa Xaa Gly Trp Ser Xaa Trp Ser Xaa Trp
1               5                   10

(2) INFORMATION FOR SEQ ID NO:62:

(i) SEQUENCE CHARACTERISTICS:
          (A) LENGTH: 8 amino acids

```
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa = Gln or Ala"

(ix) FEATURE:
            (A) NAME/KEY: Modified-site
            (B) LOCATION: 2
            (D) OTHER INFORMATION: /note= "Xaa = Asp or Ala"

(ix) FEATURE:
            (A) NAME/KEY: Modified-site
            (B) LOCATION: 3
            (D) OTHER INFORMATION: /note= "Xaa = Gly or
                delta-amino-valeric acid"

(ix) FEATURE:
            (A) NAME/KEY: Modified-site
            (B) LOCATION: 7
            (D) OTHER INFORMATION: /note= "Xaa = His or Pro"

(xi) SEQUENCE DESCRIPTION: SEQ ID NO:62:

Xaa Xaa Xaa Gly Trp Ser Xaa Trp
1               5

(2) INFORMATION FOR SEQ ID NO:63:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa = Gln or Ala"

(ix) FEATURE:
            (A) NAME/KEY: Modified-site
            (B) LOCATION: 2
            (D) OTHER INFORMATION: /note= "Xaa = Asp or Ala"

(ix) FEATURE:
            (A) NAME/KEY: Modified-site
            (B) LOCATION: 3
            (D) OTHER INFORMATION: /note= "Xaa = Gly or
                delta-amino-valeric acid"

(ix) FEATURE:
            (A) NAME/KEY: Modified-site
            (B) LOCATION: 6
            (D) OTHER INFORMATION: /note= "Xaa = His or Pro"

(ix) FEATURE:
            (A) NAME/KEY: Modified-site
            (B) LOCATION: 9
            (D) OTHER INFORMATION: /note= "Xaa = His or Pro"

(xi) SEQUENCE DESCRIPTION: SEQ ID NO:63:

Xaa Xaa Xaa Trp Ser Xaa Trp Ser Xaa Trp
1               5                   10

(2) INFORMATION FOR SEQ ID NO:64:

(i) SEQUENCE CHARACTERISTICS:
            (A) LENGTH: 11 amino acids
```

```
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa = Arg, Lys,
                alpha-N-acetyl-arginine, or
                alpha-N-acetyl-lysine"

(ix) FEATURE:
            (A) NAME/KEY: Modified-site
            (B) LOCATION: 2
            (D) OTHER INFORMATION: /note= "Xaa = Arg or Lys"

(ix) FEATURE:
            (A) NAME/KEY: Modified-site
            (B) LOCATION: 3
            (D) OTHER INFORMATION: /note= "Xaa = Phe or Ala"

(ix) FEATURE:
            (A) NAME/KEY: Modified-site
            (B) LOCATION: 4
            (D) OTHER INFORMATION: /note= "Xaa = Arg or Lys"

(ix) FEATURE:
            (A) NAME/KEY: Modified-site
            (B) LOCATION: 5
            (D) OTHER INFORMATION: /note= "Xaa = Gln or Ala"

(ix) FEATURE:
            (A) NAME/KEY: Modified-site
            (B) LOCATION: 6
            (D) OTHER INFORMATION: /note= "Xaa = Asp or Ala"

(ix) FEATURE:
            (A) NAME/KEY: Modified-site
            (B) LOCATION: 10
            (D) OTHER INFORMATION: /note= "Xaa = His or Pro"

(xi) SEQUENCE DESCRIPTION: SEQ ID NO:64:

Xaa Xaa Xaa Xaa Xaa Xaa Gly Trp Ser Xaa Trp
1               5                   10

(2) INFORMATION FOR SEQ ID NO:65:

(i) SEQUENCE CHARACTERISTICS:
            (A) LENGTH: 13 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa = Arg, Lys,
                alpha-N-acetyl-arginine, or
                alpha-N-acetyl-lysine"

(ix) FEATURE:
            (A) NAME/KEY: Modified-site
            (B) LOCATION: 2
            (D) OTHER INFORMATION: /note= "Xaa = Arg or Lys"

(ix) FEATURE:
            (A) NAME/KEY: Modified-site
            (B) LOCATION: 3
            (D) OTHER INFORMATION: /note= "Xaa = Phe or Ala"

(ix) FEATURE:
            (A) NAME/KEY: Modified-site
            (B) LOCATION: 4
```

(D) OTHER INFORMATION: /note= "Xaa = Arg or Lys"

(ix) FEATURE:
          (A) NAME/KEY: Modified-site
          (B) LOCATION: 5
          (D) OTHER INFORMATION: /note= "Xaa = Gln or Ala"

(ix) FEATURE:
          (A) NAME/KEY: Modified-site
          (B) LOCATION: 6
          (D) OTHER INFORMATION: /note= "Xaa = Asp or Ala"

(ix) FEATURE:
          (A) NAME/KEY: Modified-site
          (B) LOCATION: 9
          (D) OTHER INFORMATION: /note= "Xaa = His or Pro"

(ix) FEATURE:
          (A) NAME/KEY: Modified-site
          (B) LOCATION: 12
          (D) OTHER INFORMATION: /note= "Xaa = His or Pro"

(xi) SEQUENCE DESCRIPTION: SEQ ID NO:65:

Xaa Xaa Xaa Xaa Xaa Xaa Trp Ser Xaa Trp Ser Xaa Trp
1               5                   10

(2) INFORMATION FOR SEQ ID NO:66:

(i) SEQUENCE CHARACTERISTICS:
          (A) LENGTH: 10 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /note= "Xaa = Gln or Ala"

(ix) FEATURE:
          (A) NAME/KEY: Modified-site
          (B) LOCATION: 2
          (D) OTHER INFORMATION: /note= "Xaa = Asp or Ala"

(ix) FEATURE:
          (A) NAME/KEY: Modified-site
          (B) LOCATION: 6
          (D) OTHER INFORMATION: /note= "Xaa = His or Pro"

(ix) FEATURE:
          (A) NAME/KEY: Modified-site
          (B) LOCATION: 9
          (D) OTHER INFORMATION: /note= "Xaa = His or Pro"

(xi) SEQUENCE DESCRIPTION: SEQ ID NO:66:

Xaa Xaa Gly Trp Ser Xaa Trp Ser Xaa Trp
1               5                   10

(2) INFORMATION FOR SEQ ID NO:67:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /note= "Xaa = Arg, Lys,
               alpha-N-acetyl-arginine, or alpha-N-acetyl-lysine"

(ix) FEATURE:
    (A) NAME/KEY: Modified-site
    (B) LOCATION: 2
    (D) OTHER INFORMATION: /note= "Xaa = Arg or Lys"

(ix) FEATURE:
    (A) NAME/KEY: Modified-site
    (B) LOCATION: 3
    (D) OTHER INFORMATION: /note= "Xaa = Phe or Ala"

(ix) FEATURE:
    (A) NAME/KEY: Modified-site
    (B) LOCATION: 4
    (D) OTHER INFORMATION: /note= "Xaa = Arg or Lys"

(ix) FEATURE:
    (A) NAME/KEY: Modified-site
    (B) LOCATION: 5
    (D) OTHER INFORMATION: /note= "Xaa = Gln or Ala"

(ix) FEATURE:
    (A) NAME/KEY: Modified-site
    (B) LOCATION: 6
    (D) OTHER INFORMATION: /note= "Xaa = Asp or Ala"

(ix) FEATURE:
    (A) NAME/KEY: Modified-site
    (B) LOCATION: 7
    (D) OTHER INFORMATION: /note= "Xaa = Gly or
        delta-amino-valeric acid"

(ix) FEATURE:
    (A) NAME/KEY: Modified-site
    (B) LOCATION: 10
    (D) OTHER INFORMATION: /note= "Xaa = His or Pro"

(xi) SEQUENCE DESCRIPTION: SEQ ID NO:67:
Xaa Xaa Xaa Xaa Xaa Xaa Xaa Trp Ser Xaa Trp
 1               5                   10

(2) INFORMATION FOR SEQ ID NO:68:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Arg, Lys,
            alpha-N-acetyl-arginine, or
            alpha-N-acetyl-lysine"

(ix) FEATURE:
        (A) NAME/KEY: Modified-site
        (B) LOCATION: 2
        (D) OTHER INFORMATION: /note= "Xaa = Arg or Lys"

(ix) FEATURE:
        (A) NAME/KEY: Modified-site
        (B) LOCATION: 3
        (D) OTHER INFORMATION: /note= "Xaa = Phe or Ala"

(ix) FEATURE:
        (A) NAME/KEY: Modified-site
        (B) LOCATION: 4
        (D) OTHER INFORMATION: /note= "Xaa = Arg or Lys"

(ix) FEATURE:
        (A) NAME/KEY: Modified-site
        (B) LOCATION: 5
        (D) OTHER INFORMATION: /note= "Xaa = Gln or Ala"

```
    (ix) FEATURE:
         (A) NAME/KEY: Modified-site
         (B) LOCATION: 6
         (D) OTHER INFORMATION: /note= "Xaa = Asp or Ala"

(ix) FEATURE:
         (A) NAME/KEY: Modified-site
         (B) LOCATION: 9
         (D) OTHER INFORMATION: /note= "Xaa = His or Pro"

(xi) SEQUENCE DESCRIPTION: SEQ ID NO:68:

Xaa Xaa Xaa Xaa Xaa Xaa Trp Ser Xaa Trp
1               5                   10

(2) INFORMATION FOR SEQ ID NO:69:

(i) SEQUENCE CHARACTERISTICS:
         (A) LENGTH: 7 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "Xaa = Gln or Ala"

(ix) FEATURE:
         (A) NAME/KEY: Modified-site
         (B) LOCATION: 2
         (D) OTHER INFORMATION: /note= "Xaa = Asp or Ala"

(ix) FEATURE:
         (A) NAME/KEY: Modified-site
         (B) LOCATION: 3
         (D) OTHER INFORMATION: /note= "Xaa = Gly or
             delta-amino-valeric acid"

(ix) FEATURE:
         (A) NAME/KEY: Modified-site
         (B) LOCATION: 6
         (D) OTHER INFORMATION: /note= "Xaa = His or Pro"

(xi) SEQUENCE DESCRIPTION: SEQ ID NO:69:

Xaa Xaa Xaa Trp Ser Xaa Trp
1               5

(2) INFORMATION FOR SEQ ID NO:70:

(i) SEQUENCE CHARACTERISTICS:
         (A) LENGTH: 7 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /note= "Xaa = Gln or Ala"

(ix) FEATURE:
         (A) NAME/KEY: Modified-site
         (B) LOCATION: 2
         (D) OTHER INFORMATION: /note= "Xaa = Asp or Ala"

(ix) FEATURE:
         (A) NAME/KEY: Modified-site
         (B) LOCATION: 6
         (D) OTHER INFORMATION: /note= "Xaa = His or Pro"
```

(xi) SEQUENCE DESCRIPTION: SEQ ID NO:70:

Xaa Xaa Gly Trp Ser Xaa Trp
1               5

(2) INFORMATION FOR SEQ ID NO:71:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Gln or Ala"

(ix) FEATURE:
        (A) NAME/KEY: Modified-site
        (B) LOCATION: 2
        (D) OTHER INFORMATION: /note= "Xaa = Asp or Ala"

(ix) FEATURE:
        (A) NAME/KEY: Modified-site
        (B) LOCATION: 5
        (D) OTHER INFORMATION: /note= "Xaa = His or Pro"

(ix) FEATURE:
        (A) NAME/KEY: Modified-site
        (B) LOCATION: 8
        (D) OTHER INFORMATION: /note= "Xaa = His or Pro"

(xi) SEQUENCE DESCRIPTION: SEQ ID NO:71:

Xaa Xaa Trp Ser Xaa Trp Ser Xaa Trp
1               5

(2) INFORMATION FOR SEQ ID NO:72:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Gln or Ala"

(ix) FEATURE:
        (A) NAME/KEY: Modified-site
        (B) LOCATION: 2
        (D) OTHER INFORMATION: /note= "Xaa = Asp or Ala"

(ix) FEATURE:
        (A) NAME/KEY: Modified-site
        (B) LOCATION: 5
        (D) OTHER INFORMATION: /note= "Xaa = His or Pro"

(xi) SEQUENCE DESCRIPTION: SEQ ID NO:72:

Xaa Xaa Trp Ser Xaa Trp
1               5

(2) INFORMATION FOR SEQ ID NO:73:

(i) SEQUENCE CHARACTERISTICS:
        (A) LENGTH: 4 amino acids
        (B) TYPE: amino acid
        (C) STRANDEDNESS:

(D) TOPOLOGY: linear (ii) MOLECULE TYPE: peptide (ix) FEATURE:
        (A) NAME/KEY: Modified-site
        (B) LOCATION: 3
        (D) OTHER INFORMATION: /note= "Xaa = any amino acid"

(xi) SEQUENCE DESCRIPTION: SEQ ID NO:73:

Trp Ser Xaa Trp
1

(2) INFORMATION FOR SEQ ID NO:74:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Lys, Arg, or His"

(ix) FEATURE:
        (A) NAME/KEY: Modified-site
        (B) LOCATION: 2
        (D) OTHER INFORMATION: /note= "Xaa = Lys, Arg, or His"

(ix) FEATURE:
        (A) NAME/KEY: Modified-site
        (B) LOCATION: 3
        (D) OTHER INFORMATION: /note= "Xaa = any amino acid"

(ix) FEATURE:
        (A) NAME/KEY: Modified-site
        (B) LOCATION: 4
        (D) OTHER INFORMATION: /note= "Xaa = Lys, Arg, or His"

(xi) SEQUENCE DESCRIPTION: SEQ ID NO:74:

Xaa Xaa Xaa Xaa
1

(2) INFORMATION FOR SEQ ID NO:75:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Xaa = Ser, Thr, or Ala"

(ix) FEATURE:
        (A) NAME/KEY: Modified-site
        (B) LOCATION: 3
        (D) OTHER INFORMATION: /note= "Xaa = Pro, Glu, Ala, His,
            or Ser"

(xi) SEQUENCE DESCRIPTION: SEQ ID NO:75:

Trp Xaa Xaa Trp
1

(2) INFORMATION FOR SEQ ID NO:76:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Lys, Arg, or His"

(ix) FEATURE:
        (A) NAME/KEY: Modified-site
        (B) LOCATION: 2
        (D) OTHER INFORMATION: /note= "Xaa = any amino acid"

(ix) FEATURE:
        (A) NAME/KEY: Modified-site
        (B) LOCATION: 3
        (D) OTHER INFORMATION: /note= "Xaa = Lys, Arg, or His"

(ix) FEATURE:
        (A) NAME/KEY: Modified-site
        (B) LOCATION: 4
        (D) OTHER INFORMATION: /note= "Xaa = any amino acid"

(ix) FEATURE:
        (A) NAME/KEY: Modified-site
        (B) LOCATION: 5
        (D) OTHER INFORMATION: /note= "Xaa = Lys, Arg, or His"

(xi) SEQUENCE DESCRIPTION: SEQ ID NO:76:

Xaa Xaa Xaa Xaa Xaa
1               5

(2) INFORMATION FOR SEQ ID NO:77:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /note= "Xaa = any amino acid"

(xi) SEQUENCE DESCRIPTION: SEQ ID NO:77:

Trp Ser Xaa Trp Ser
1               5

(2) INFORMATION FOR SEQ ID NO:78:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /note= "Xaa = Pro, Glu, Ala, His,
            or Ser"

(xi) SEQUENCE DESCRIPTION: SEQ ID NO:78:

```
Trp Ser Xaa Trp
1
```

(2) INFORMATION FOR SEQ ID NO:79:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Lys, Arg, or His"

(ix) FEATURE:
        (A) NAME/KEY: Modified-site
        (B) LOCATION: 2
        (D) OTHER INFORMATION: /note= "Xaa = any amino acid"

(ix) FEATURE:
        (A) NAME/KEY: Modified-site
        (B) LOCATION: 3
        (D) OTHER INFORMATION: /note= "Xaa = Lys, Arg, or His"

(ix) FEATURE:
        (A) NAME/KEY: Modified-site
        (B) LOCATION: 4
        (D) OTHER INFORMATION: /note= "Xaa = Lys, Arg, or His"

(xi) SEQUENCE DESCRIPTION: SEQ ID NO:79:

```
Xaa Xaa Xaa Xaa
1
```

(2) INFORMATION FOR SEQ ID NO:80:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Lys or
            alpha-N-acetyl-lysine"

(xi) SEQUENCE DESCRIPTION: SEQ ID NO:80:

```
Xaa Lys Phe Lys
1
```

(2) INFORMATION FOR SEQ ID NO:81:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Lys or
            alpha-N-acetyl-lysine"

(ix) FEATURE:

(A) NAME/KEY: Modified-site
        (B) LOCATION: 5
        (D) OTHER INFORMATION: /note= "Xaa = Gln or Ala"

(ix) FEATURE:
        (A) NAME/KEY: Modified-site
        (B) LOCATION: 6
        (D) OTHER INFORMATION: /note= "Xaa = Asp or Ala"

(ix) FEATURE:
        (A) NAME/KEY: Modified-site
        (B) LOCATION: 7
        (D) OTHER INFORMATION: /note= "Xaa = Gly or
            delta-amino-valeric acid"

(ix) FEATURE:
        (A) NAME/KEY: Modified-site
        (B) LOCATION: 11
        (D) OTHER INFORMATION: /note= "Xaa = His or Pro"

(ix) FEATURE:
        (A) NAME/KEY: Modified-site
        (B) LOCATION: 14
        (D) OTHER INFORMATION: /note= "Xaa = His or Pro"

(xi) SEQUENCE DESCRIPTION: SEQ ID NO:81:

Xaa Lys Phe Lys Xaa Xaa Xaa Gly Trp Ser Xaa Trp Ser Xaa Trp
1               5                   10                  15

(2) INFORMATION FOR SEQ ID NO:82:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Lys or
            alpha-N-acetyl-lysine"

(ix) FEATURE:
        (A) NAME/KEY: Modified-site
        (B) LOCATION: 5
        (D) OTHER INFORMATION: /note= "Xaa = Gln or Ala"

(ix) FEATURE:
        (A) NAME/KEY: Modified-site
        (B) LOCATION: 6
        (D) OTHER INFORMATION: /note= "Xaa = Asp or Ala"

(ix) FEATURE:
        (A) NAME/KEY: Modified-site
        (B) LOCATION: 7
        (D) OTHER INFORMATION: /note= "Xaa = Gly or
            delta-amino-valeric acid"

(ix) FEATURE:
        (A) NAME/KEY: Modified-site
        (B) LOCATION: 11
        (D) OTHER INFORMATION: /note= "Xaa = His or Pro"

(xi) SEQUENCE DESCRIPTION: SEQ ID NO:82:

Xaa Lys Phe Lys Xaa Xaa Xaa Gly Trp Ser Xaa Trp
1               5                   10

(2) INFORMATION FOR SEQ ID NO:83:

(i) SEQUENCE CHARACTERISTICS:
        (A) LENGTH: 14 amino acids
        (B) TYPE: amino acid

```
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /note= "Xaa = Lys or
              alpha-N-acetyl-lysine"

(ix) FEATURE:
          (A) NAME/KEY: Modified-site
          (B) LOCATION: 5
          (D) OTHER INFORMATION: /note= "Xaa = Gln or Ala"

(ix) FEATURE:
          (A) NAME/KEY: Modified-site
          (B) LOCATION: 6
          (D) OTHER INFORMATION: /note= "Xaa = Asp or Ala"

(ix) FEATURE:
          (A) NAME/KEY: Modified-site
          (B) LOCATION: 7
          (D) OTHER INFORMATION: /note= "Xaa = Gly or
              delta-amino-valeric acid"

(ix) FEATURE:
          (A) NAME/KEY: Modified-site
          (B) LOCATION: 10
          (D) OTHER INFORMATION: /note= "Xaa = His or Pro"

(ix) FEATURE:
          (A) NAME/KEY: Modified-site
          (B) LOCATION: 13
          (D) OTHER INFORMATION: /note= "Xaa = His or Pro"

(xi) SEQUENCE DESCRIPTION: SEQ ID NO:83:

Xaa Lys Phe Lys Xaa Xaa Xaa Trp Ser Xaa Trp Ser Xaa Trp
1               5                   10

(2) INFORMATION FOR SEQ ID NO:84:

(i) SEQUENCE CHARACTERISTICS:
          (A) LENGTH: 14 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /note= "Xaa = Lys or
              alpha-N-acetyl-lysine"

(ix) FEATURE:
          (A) NAME/KEY: Modified-site
          (B) LOCATION: 5
          (D) OTHER INFORMATION: /note= "Xaa = Gln or Ala"

(ix) FEATURE:
          (A) NAME/KEY: Modified-site
          (B) LOCATION: 6
          (D) OTHER INFORMATION: /note= "Xaa = Asp or Ala"

(ix) FEATURE:
          (A) NAME/KEY: Modified-site
          (B) LOCATION: 10
          (D) OTHER INFORMATION: /note= "Xaa = His or Pro"

(ix) FEATURE:
          (A) NAME/KEY: Modified-site
          (B) LOCATION: 13
          (D) OTHER INFORMATION: /note= "Xaa = His or Pro"
```

(xi) SEQUENCE DESCRIPTION: SEQ ID NO:84:

Xaa Lys Phe Lys Xaa Xaa Gly Trp Ser Xaa Trp Ser Xaa Trp
1               5                   10

(2) INFORMATION FOR SEQ ID NO:85:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Lys or
            alpha-N-acetyl-lysine"

(ix) FEATURE:
        (A) NAME/KEY: Modified-site
        (B) LOCATION: 5
        (D) OTHER INFORMATION: /note= "Xaa = Gln or Ala"

(ix) FEATURE:
        (A) NAME/KEY: Modified-site
        (B) LOCATION: 6
        (D) OTHER INFORMATION: /note= "Xaa = Asp or Ala"

(ix) FEATURE:
        (A) NAME/KEY: Modified-site
        (B) LOCATION: 7
        (D) OTHER INFORMATION: /note= "Xaa = Gly or
            delta-amino-valeric acid"

(ix) FEATURE:
        (A) NAME/KEY: Modified-site
        (B) LOCATION: 10
        (D) OTHER INFORMATION: /note= "Xaa = His or Pro"

(xi) SEQUENCE DESCRIPTION: SEQ ID NO:85:

Xaa Lys Phe Lys Xaa Xaa Xaa Trp Ser Xaa Trp
1               5                   10

(2) INFORMATION FOR SEQ ID NO:86:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Lys or
            alpha-N-acetyl-lysine"

(ix) FEATURE:
        (A) NAME/KEY: Modified-site
        (B) LOCATION: 5
        (D) OTHER INFORMATION: /note= "Xaa = Gln or Ala"

(ix) FEATURE:
        (A) NAME/KEY: Modified-site
        (B) LOCATION: 6
        (D) OTHER INFORMATION: /note= "Xaa = Asp or Ala"

(ix) FEATURE:
        (A) NAME/KEY: Modified-site
        (B) LOCATION: 10
        (D) OTHER INFORMATION: /note= "Xaa = His or Pro"

(xi) SEQUENCE DESCRIPTION: SEQ ID NO:86:

Xaa Lys Phe Lys Xaa Xaa Gly Trp Ser Xaa Trp
1               5                   10

(2) INFORMATION FOR SEQ ID NO:87:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Lys or
            alpha-N-acetyl-lysine"

(ix) FEATURE:
        (A) NAME/KEY: Modified-site
        (B) LOCATION: 5
        (D) OTHER INFORMATION: /note= "Xaa = Gln or Ala"

(ix) FEATURE:
        (A) NAME/KEY: Modified-site
        (B) LOCATION: 6
        (D) OTHER INFORMATION: /note= "Xaa = Asp or Ala"

(ix) FEATURE:
        (A) NAME/KEY: Modified-site
        (B) LOCATION: 9
        (D) OTHER INFORMATION: /note= "Xaa = His or Pro"

(ix) FEATURE:
        (A) NAME/KEY: Modified-site
        (B) LOCATION: 12
        (D) OTHER INFORMATION: /note= "Xaa = His or Pro"

(xi) SEQUENCE DESCRIPTION: SEQ ID NO:87:

Xaa Lys Phe Lys Xaa Xaa Trp Ser Xaa Trp Ser Xaa Trp
1               5                   10

(2) INFORMATION FOR SEQ ID NO:88:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Lys or
            alpha-N-acetyl-lysine"

(ix) FEATURE:
        (A) NAME/KEY: Modified-site
        (B) LOCATION: 5
        (D) OTHER INFORMATION: /note= "Xaa = Gln or Ala"

(ix) FEATURE:
        (A) NAME/KEY: Modified-site
        (B) LOCATION: 6
        (D) OTHER INFORMATION: /note= "Xaa = Asp or Ala"

(ix) FEATURE:
        (A) NAME/KEY: Modified-site
        (B) LOCATION: 9
        (D) OTHER INFORMATION: /note= "Xaa = His or Pro"

(xi) SEQUENCE DESCRIPTION: SEQ ID NO:88:

Xaa Lys Phe Lys Xaa Xaa Trp Ser Xaa Trp
1               5                   10

(2) INFORMATION FOR SEQ ID NO:89:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Lys or
            alpha-N-acetyl-lysine"

(xi) SEQUENCE DESCRIPTION: SEQ ID NO:89:

Xaa Arg Ala Lys
1

(2) INFORMATION FOR SEQ ID NO:90:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Lys or
            alpha-N-acetyl-lysine"

(ix) FEATURE:
        (A) NAME/KEY: Modified-site
        (B) LOCATION: 5
        (D) OTHER INFORMATION: /note= "Xaa = Gln or Ala"

(ix) FEATURE:
        (A) NAME/KEY: Modified-site
        (B) LOCATION: 6
        (D) OTHER INFORMATION: /note= "Xaa = Asp or Ala"

(ix) FEATURE:
        (A) NAME/KEY: Modified-site
        (B) LOCATION: 7
        (D) OTHER INFORMATION: /note= "Xaa = Gly or
            delta-amino-valeric acid"

(ix) FEATURE:
        (A) NAME/KEY: Modified-site
        (B) LOCATION: 11
        (D) OTHER INFORMATION: /note= "Xaa = His or Pro"

(ix) FEATURE:
        (A) NAME/KEY: Modified-site
        (B) LOCATION: 14
        (D) OTHER INFORMATION: /note= "Xaa = His or Pro"

(xi) SEQUENCE DESCRIPTION: SEQ ID NO:90:

Xaa Arg Ala Lys Xaa Xaa Xaa Gly Trp Ser Xaa Trp Ser Xaa Trp
1               5                   10                  15

(2) INFORMATION FOR SEQ ID NO:91:

(i) SEQUENCE CHARACTERISTICS:
                (A) LENGTH: 12 amino acids
                (B) TYPE: amino acid
                (C) STRANDEDNESS:
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /note= "Xaa = Lys or
                    alpha-N-acetyl-lysine"

(ix) FEATURE:
                (A) NAME/KEY: Modified-site
                (B) LOCATION: 5
                (D) OTHER INFORMATION: /note= "Xaa = Gln or Ala"

(ix) FEATURE:
                (A) NAME/KEY: Modified-site
                (B) LOCATION: 6
                (D) OTHER INFORMATION: /note= "Xaa = Asp or Ala"

(ix) FEATURE:
                (A) NAME/KEY: Modified-site
                (B) LOCATION: 7
                (D) OTHER INFORMATION: /note= "Xaa = Gly or
                    delta-amino-valeric acid"

(ix) FEATURE:
                (A) NAME/KEY: Modified-site
                (B) LOCATION: 11
                (D) OTHER INFORMATION: /note= "Xaa = His or Pro"

(xi) SEQUENCE DESCRIPTION: SEQ ID NO:91:

Xaa Arg Ala Lys Xaa Xaa Xaa Gly Trp Ser Xaa Trp
1               5                   10

(2) INFORMATION FOR SEQ ID NO:92:

(i) SEQUENCE CHARACTERISTICS:
                (A) LENGTH: 14 amino acids
                (B) TYPE: amino acid
                (C) STRANDEDNESS:
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /note= "Xaa = Lys or
                    alpha-N-acetyl-lysine"

(ix) FEATURE:
                (A) NAME/KEY: Modified-site
                (B) LOCATION: 5
                (D) OTHER INFORMATION: /note= "Xaa = Gln or Ala"

(ix) FEATURE:
                (A) NAME/KEY: Modified-site
                (B) LOCATION: 6
                (D) OTHER INFORMATION: /note= "Xaa = Asp or Ala"

(ix) FEATURE:
                (A) NAME/KEY: Modified-site
                (B) LOCATION: 7
                (D) OTHER INFORMATION: /note= "Xaa = Gly or
                    delta-amino-valeric acid"

(ix) FEATURE:
                (A) NAME/KEY: Modified-site
                (B) LOCATION: 10
                (D) OTHER INFORMATION: /note= "Xaa = His or Pro"

(ix) FEATURE:

-continued (A) NAME/KEY: Modified-site
              (B) LOCATION: 13
              (D) OTHER INFORMATION: /note= "Xaa = His or Pro"

(xi) SEQUENCE DESCRIPTION: SEQ ID NO:92:

Xaa Arg Ala Lys Xaa Xaa Xaa Trp Ser Xaa Trp Ser Xaa Trp
1               5                   10

(2) INFORMATION FOR SEQ ID NO:93:

(i) SEQUENCE CHARACTERISTICS:
              (A) LENGTH: 14 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /note= "Xaa = Lys or
                   alpha-N-acetyl-lysine"

(ix) FEATURE:
              (A) NAME/KEY: Modified-site
              (B) LOCATION: 5
              (D) OTHER INFORMATION: /note= "Xaa = Gln or Ala"

(ix) FEATURE:
              (A) NAME/KEY: Modified-site
              (B) LOCATION: 6
              (D) OTHER INFORMATION: /note= "Xaa = Asp or Ala"

(ix) FEATURE:
              (A) NAME/KEY: Modified-site
              (B) LOCATION: 10
              (D) OTHER INFORMATION: /note= "Xaa = His or Pro"

(ix) FEATURE:
              (A) NAME/KEY: Modified-site
              (B) LOCATION: 13
              (D) OTHER INFORMATION: /note= "Xaa = His or Pro"

(xi) SEQUENCE DESCRIPTION: SEQ ID NO:93:

Xaa Arg Ala Lys Xaa Xaa Gly Trp Ser Xaa Trp Ser Xaa Trp
1               5                   10

(2) INFORMATION FOR SEQ ID NO:94:

(i) SEQUENCE CHARACTERISTICS:
              (A) LENGTH: 11 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /note= "Xaa = Lys or
                   alpha-N-acetyl-lysine"

(ix) FEATURE:
              (A) NAME/KEY: Modified-site
              (B) LOCATION: 5
              (D) OTHER INFORMATION: /note= "Xaa = Gln or Ala"

(ix) FEATURE:
              (A) NAME/KEY: Modified-site
              (B) LOCATION: 6
              (D) OTHER INFORMATION: /note= "Xaa = Asp or Ala"

(ix) FEATURE:

(A) NAME/KEY: Modified-site
              (B) LOCATION: 7
              (D) OTHER INFORMATION: /note= "Xaa = Gly or
                  delta-amino-valeric acid"

(ix) FEATURE:
              (A) NAME/KEY: Modified-site
              (B) LOCATION: 10
              (D) OTHER INFORMATION: /note= "Xaa = His or Pro"

(xi) SEQUENCE DESCRIPTION: SEQ ID NO:94:

Xaa Arg Ala Lys Xaa Xaa Xaa Trp Ser Xaa Trp
1               5                   10

(2) INFORMATION FOR SEQ ID NO:95:

(i) SEQUENCE CHARACTERISTICS:
              (A) LENGTH: 11 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /note= "Xaa = Lys or
                  alpha-N-acetyl-lysine"

(ix) FEATURE:
              (A) NAME/KEY: Modified-site
              (B) LOCATION: 5
              (D) OTHER INFORMATION: /note= "Xaa = Gln or Ala"

(ix) FEATURE:
              (A) NAME/KEY: Modified-site
              (B) LOCATION: 6
              (D) OTHER INFORMATION: /note= "Xaa = Asp or Ala"

(ix) FEATURE:
              (A) NAME/KEY: Modified-site
              (B) LOCATION: 10
              (D) OTHER INFORMATION: /note= "Xaa = His or Pro"

(xi) SEQUENCE DESCRIPTION: SEQ ID NO:95:

Xaa Arg Ala Lys Xaa Xaa Gly Trp Ser Xaa Trp
1               5                   10

(2) INFORMATION FOR SEQ ID NO:96:

(i) SEQUENCE CHARACTERISTICS:
              (A) LENGTH: 13 amino acids
              (B) TYPE: amino acid
              (C) STRANDEDNESS:
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /note= "Xaa = Lys or
                  alpha-N-acetyl-lysine"

(ix) FEATURE:
              (A) NAME/KEY: Modified-site
              (B) LOCATION: 5
              (D) OTHER INFORMATION: /note= "Xaa = Gln or Ala"

(ix) FEATURE:
              (A) NAME/KEY: Modified-site
              (B) LOCATION: 6
              (D) OTHER INFORMATION: /note= "Xaa = Asp or Ala"

(ix) FEATURE:
            (A) NAME/KEY: Modified-site
            (B) LOCATION: 9
            (D) OTHER INFORMATION: /note= "Xaa = His or Pro"

(ix) FEATURE:
            (A) NAME/KEY: Modified-site
            (B) LOCATION: 12
            (D) OTHER INFORMATION: /note= "Xaa = His or Pro"

(xi) SEQUENCE DESCRIPTION: SEQ ID NO:96:

Xaa Arg Ala Lys Xaa Xaa Trp Ser Xaa Trp Ser Xaa Trp
 1               5                  10

(2) INFORMATION FOR SEQ ID NO:97:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa = Lys or
                alpha-N-acetyl-lysine"

(ix) FEATURE:
            (A) NAME/KEY: Modified-site
            (B) LOCATION: 5
            (D) OTHER INFORMATION: /note= "Xaa = Gln or Ala"

(ix) FEATURE:
            (A) NAME/KEY: Modified-site
            (B) LOCATION: 6
            (D) OTHER INFORMATION: /note= "Xaa = Asp or Ala"

(ix) FEATURE:
            (A) NAME/KEY: Modified-site
            (B) LOCATION: 9
            (D) OTHER INFORMATION: /note= "Xaa = His or Pro"

(xi) SEQUENCE DESCRIPTION: SEQ ID NO:97:

Xaa Arg Ala Lys Xaa Xaa Trp Ser Xaa Trp
 1               5                  10

(2) INFORMATION FOR SEQ ID NO:98:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa = Arg, Lys,
                alpha-N-acetyl-arginine, or
                alpha-N-acetyl-lysine"

(ix) FEATURE:
            (A) NAME/KEY: Modified-site
            (B) LOCATION: 5
            (D) OTHER INFORMATION: /note= "Xaa = Gln or Ala"

(ix) FEATURE:
            (A) NAME/KEY: Modified-site
            (B) LOCATION: 6
            (D) OTHER INFORMATION: /note= "Xaa = Asp or Ala"

(ix) FEATURE:
              (A) NAME/KEY: Modified-site
              (B) LOCATION: 7
              (D) OTHER INFORMATION: /note= "Xaa = Gly or
                   delta-amino-valeric acid"

(ix) FEATURE:
              (A) NAME/KEY: Modified-site
              (B) LOCATION: 11
              (D) OTHER INFORMATION: /note= "Xaa = His or Pro"

(ix) FEATURE:
              (A) NAME/KEY: Modified-site
              (B) LOCATION: 14
              (D) OTHER INFORMATION: /note= "Xaa = His or Pro"

(xi) SEQUENCE DESCRIPTION: SEQ ID NO:98:

Xaa Lys Ala Lys Xaa Xaa Xaa Gly Trp Ser Xaa Trp Ser Xaa Trp
1               5                   10                  15

(2) INFORMATION FOR SEQ ID NO:99:

(i) SEQUENCE CHARACTERISTICS:
          (A) LENGTH: 12 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /note= "Xaa = Arg, Lys,
               alpha-N-acetyl-arginine, or
               alpha-N-acetyl-lysine"

(ix) FEATURE:
          (A) NAME/KEY: Modified-site
          (B) LOCATION: 5
          (D) OTHER INFORMATION: /note= "Xaa = Gln or Ala"

(ix) FEATURE:
          (A) NAME/KEY: Modified-site
          (B) LOCATION: 6
          (D) OTHER INFORMATION: /note= "Xaa = Asp or Ala"

(ix) FEATURE:
          (A) NAME/KEY: Modified-site
          (B) LOCATION: 7
          (D) OTHER INFORMATION: /note= "Xaa = Gly or
               delta-amino-valeric acid"

(ix) FEATURE:
          (A) NAME/KEY: Modified-site
          (B) LOCATION: 11
          (D) OTHER INFORMATION: /note= "Xaa = His or Pro"

(xi) SEQUENCE DESCRIPTION: SEQ ID NO:99:

Xaa Lys Ala Lys Xaa Xaa Xaa Gly Trp Ser Xaa Trp
1               5                   10

(2) INFORMATION FOR SEQ ID NO:100:

(i) SEQUENCE CHARACTERISTICS:
          (A) LENGTH: 14 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site (B) LOCATION: 1
            (D) OTHER INFORMATION: /note= "Xaa = Arg, Lys,
                alpha-N-acetyl-arginine, or
                alpha-N-acetyl-lysine"

(ix) FEATURE:
            (A) NAME/KEY: Modified-site
            (B) LOCATION: 5
            (D) OTHER INFORMATION: /note= "Xaa = Gln or Ala"

(ix) FEATURE:
            (A) NAME/KEY: Modified-site
            (B) LOCATION: 6
            (D) OTHER INFORMATION: /note= "Xaa = Asp or Ala"

(ix) FEATURE:
            (A) NAME/KEY: Modified-site
            (B) LOCATION: 7
            (D) OTHER INFORMATION: /note= "Xaa = Gly or
                delta-amino-valeric acid"

(ix) FEATURE:
            (A) NAME/KEY: Modified-site
            (B) LOCATION: 10
            (D) OTHER INFORMATION: /note= "Xaa = His or Pro"

(ix) FEATURE:
            (A) NAME/KEY: Modified-site
            (B) LOCATION: 13
            (D) OTHER INFORMATION: /note= "Xaa = His or Pro"

(xi) SEQUENCE DESCRIPTION: SEQ ID NO:100:

Xaa Lys Ala Lys Xaa Xaa Xaa Trp Ser Xaa Trp Ser Xaa Trp
1               5                   10

(2) INFORMATION FOR SEQ ID NO:101:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa = Arg, Lys,
                alpha-N-acetyl-arginine, or
                alpha-N-acetyl-lysine"

(ix) FEATURE:
            (A) NAME/KEY: Modified-site
            (B) LOCATION: 5
            (D) OTHER INFORMATION: /note= "Xaa = Gln or Ala"

(ix) FEATURE:
            (A) NAME/KEY: Modified-site
            (B) LOCATION: 6
            (D) OTHER INFORMATION: /note= "Xaa = Asp or Ala"

(ix) FEATURE:
            (A) NAME/KEY: Modified-site
            (B) LOCATION: 10
            (D) OTHER INFORMATION: /note= "Xaa = His or Pro"

(ix) FEATURE:
            (A) NAME/KEY: Modified-site
            (B) LOCATION: 13
            (D) OTHER INFORMATION: /note= "Xaa = His or Pro"

(xi) SEQUENCE DESCRIPTION: SEQ ID NO:101:

Xaa Lys Ala Lys Xaa Xaa Gly Trp Ser Xaa Trp Ser Xaa Trp
1               5                   10

(2) INFORMATION FOR SEQ ID NO:102:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Arg, Lys,
            alpha-N-acetyl-arginine, or
            alpha-N-acetyl-lysine"

(ix) FEATURE:
        (A) NAME/KEY: Modified-site
        (B) LOCATION: 5
        (D) OTHER INFORMATION: /note= "Xaa = Gln or Ala"

(ix) FEATURE:
        (A) NAME/KEY: Modified-site
        (B) LOCATION: 6
        (D) OTHER INFORMATION: /note= "Xaa = Asp or Ala"

(ix) FEATURE:
        (A) NAME/KEY: Modified-site
        (B) LOCATION: 7
        (D) OTHER INFORMATION: /note= "Xaa = Gly or
            delta-amino-valeric acid"

(ix) FEATURE:
        (A) NAME/KEY: Modified-site
        (B) LOCATION: 10
        (D) OTHER INFORMATION: /note= "Xaa = His or Pro"

(xi) SEQUENCE DESCRIPTION: SEQ ID NO:102:

```
Xaa Lys Ala Lys Xaa Xaa Xaa Trp Ser Xaa Trp
1               5                   10
```

(2) INFORMATION FOR SEQ ID NO:103:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Arg, Lys,
            alpha-N-acetyl-arginine, or
            alpha-N-acetyl-lysine"

(ix) FEATURE:
        (A) NAME/KEY: Modified-site
        (B) LOCATION: 5
        (D) OTHER INFORMATION: /note= "Xaa = Gln or Ala"

(ix) FEATURE:
        (A) NAME/KEY: Modified-site
        (B) LOCATION: 6
        (D) OTHER INFORMATION: /note= "Xaa = Asp or Ala"

(ix) FEATURE:
        (A) NAME/KEY: Modified-site
        (B) LOCATION: 10
        (D) OTHER INFORMATION: /note= "Xaa = His or Pro"

(xi) SEQUENCE DESCRIPTION: SEQ ID NO:103:

```
Xaa Lys Ala Lys Xaa Xaa Gly Trp Ser Xaa Trp
1               5                   10
```

(2) INFORMATION FOR SEQ ID NO:104:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Arg, Lys,
            alpha-N-acetyl-arginine, or
            alpha-N-acetyl-lysine"

(ix) FEATURE:
        (A) NAME/KEY: Modified-site
        (B) LOCATION: 5
        (D) OTHER INFORMATION: /note= "Xaa = Gln or Ala"

(ix) FEATURE:
        (A) NAME/KEY: Modified-site
        (B) LOCATION: 6
        (D) OTHER INFORMATION: /note= "Xaa = Asp or Ala"

(ix) FEATURE:
        (A) NAME/KEY: Modified-site
        (B) LOCATION: 9
        (D) OTHER INFORMATION: /note= "Xaa = His or Pro"

(ix) FEATURE:
        (A) NAME/KEY: Modified-site
        (B) LOCATION: 12
        (D) OTHER INFORMATION: /note= "Xaa = His or Pro"

(xi) SEQUENCE DESCRIPTION: SEQ ID NO:104:

```
Xaa Lys Ala Lys Xaa Xaa Trp Ser Xaa Trp Ser Xaa Trp
1               5                   10
```

(2) INFORMATION FOR SEQ ID NO:105:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Arg, Lys,
            alpha-N-acetyl-arginine, or
            alpha-N-acetyl-lysine"

(ix) FEATURE:
        (A) NAME/KEY: Modified-site
        (B) LOCATION: 5
        (D) OTHER INFORMATION: /note= "Xaa = Gln or Ala"

(ix) FEATURE:
        (A) NAME/KEY: Modified-site
        (B) LOCATION: 6
        (D) OTHER INFORMATION: /note= "Xaa = Asp or Ala"

(ix) FEATURE:
        (A) NAME/KEY: Modified-site
        (B) LOCATION: 9
        (D) OTHER INFORMATION: /note= "Xaa = His or Pro"

(xi) SEQUENCE DESCRIPTION: SEQ ID NO:105:

Xaa Lys Ala Lys Xaa Xaa Trp Ser Xaa Trp
1               5                   10

(2) INFORMATION FOR SEQ ID NO:106:

(i) SEQUENCE CHARACTERISTICS:
           (A) LENGTH: 17 amino acids
           (B) TYPE: amino acid
           (C) STRANDEDNESS:
           (D) TOPOLOGY: linear (ii) MOLECULE TYPE: peptide (ix) FEATURE:
           (A) NAME/KEY: Modified-site
           (B) LOCATION: 1
           (D) OTHER INFORMATION: /note= "Xaa = Arg, Lys,
                alpha-N-acetyl-arginine, or
                alpha-N-acetyl-lysine"

(ix) FEATURE:
           (A) NAME/KEY: Modified-site
           (B) LOCATION: 5
           (D) OTHER INFORMATION: /note= "Xaa = Gln or Ala"

(ix) FEATURE:
           (A) NAME/KEY: Modified-site
           (B) LOCATION: 6
           (D) OTHER INFORMATION: /note= "Xaa = Asp or Ala"

(ix) FEATURE:
           (A) NAME/KEY: Modified-site
           (B) LOCATION: 7
           (D) OTHER INFORMATION: /note= "Xaa = Gly or
                delta-amino-valeric acid"

(ix) FEATURE:
           (A) NAME/KEY: Modified-site
           (B) LOCATION: 11
           (D) OTHER INFORMATION: /note= "Xaa = His or Pro"

(ix) FEATURE:
           (A) NAME/KEY: Modified-site
           (B) LOCATION: 14
           (D) OTHER INFORMATION: /note= "Xaa = His or Pro"

(ix) FEATURE:
           (A) NAME/KEY: Modified-site
           (B) LOCATION: 16
           (D) OTHER INFORMATION: /note= "Xaa = Ser or Ala"

(ix) FEATURE:
           (A) NAME/KEY: Modified-site
           (B) LOCATION: 17
           (D) OTHER INFORMATION: /note= "Xaa = Ser, Ala, serinamide,
                or alaninamide"

(xi) SEQUENCE DESCRIPTION: SEQ ID NO:106:

Xaa Arg Phe Lys Xaa Xaa Xaa Gly Trp Ser Xaa Trp Ser Xaa Trp Xaa
1               5                   10                  15

Xaa (2) INFORMATION FOR SEQ ID NO:107:

(i) SEQUENCE CHARACTERISTICS:
           (A) LENGTH: 14 amino acids
           (B) TYPE: amino acid
           (C) STRANDEDNESS:
           (D) TOPOLOGY: linear (ii) MOLECULE TYPE: peptide (ix) FEATURE:

```
          (A) NAME/KEY: Modified-site
          (B) LOCATION: 1
          (D) OTHER INFORMATION: /note= "Xaa = Arg, Lys,
              alpha-N-acetyl-arginine, or
              alpha-N-acetyl-lysine"

(ix) FEATURE:
          (A) NAME/KEY: Modified-site
          (B) LOCATION: 5
          (D) OTHER INFORMATION: /note= "Xaa = Gln or Ala"

(ix) FEATURE:
          (A) NAME/KEY: Modified-site
          (B) LOCATION: 6
          (D) OTHER INFORMATION: /note= "Xaa = Asp or Ala"

(ix) FEATURE:
          (A) NAME/KEY: Modified-site
          (B) LOCATION: 7
          (D) OTHER INFORMATION: /note= "Xaa = Gly or
              delta-amino-valeric acid"

(ix) FEATURE:
          (A) NAME/KEY: Modified-site
          (B) LOCATION: 11
          (D) OTHER INFORMATION: /note= "Xaa = His or Pro"

(ix) FEATURE:
          (A) NAME/KEY: Modified-site
          (B) LOCATION: 13
          (D) OTHER INFORMATION: /note= "Xaa = Ser or Ala"

(ix) FEATURE:
          (A) NAME/KEY: Modified-site
          (B) LOCATION: 14
          (D) OTHER INFORMATION: /note= "Xaa = Ser, Ala, serinamide
              or alaninamide"

(xi) SEQUENCE DESCRIPTION: SEQ ID NO:107:

Xaa Arg Phe Lys Xaa Xaa Xaa Gly Trp Ser Xaa Trp Xaa Xaa
1               5                   10

(2) INFORMATION FOR SEQ ID NO:108:

(i) SEQUENCE CHARACTERISTICS:
          (A) LENGTH: 16 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /note= "Xaa = Arg, Lys,
              alpha-N-acetyl-arginine, or
              alpha-N-acetyl-lysine"

(ix) FEATURE:
          (A) NAME/KEY: Modified-site
          (B) LOCATION: 5
          (D) OTHER INFORMATION: /note= "Xaa = Gln or Ala"

(ix) FEATURE:
          (A) NAME/KEY: Modified-site
          (B) LOCATION: 6
          (D) OTHER INFORMATION: /note= "Xaa = Asp or Ala"

(ix) FEATURE:
          (A) NAME/KEY: Modified-site
          (B) LOCATION: 7
          (D) OTHER INFORMATION: /note= "Xaa = Gly or
              delta-amino-valeric acid"

(ix) FEATURE:
          (A) NAME/KEY: Modified-site
```

(B) LOCATION: 10
            (D) OTHER INFORMATION: /note= "Xaa = His or Pro"

(ix) FEATURE:
            (A) NAME/KEY: Modified-site
            (B) LOCATION: 13
            (D) OTHER INFORMATION: /note= "Xaa = His or Pro"

(ix) FEATURE:
            (A) NAME/KEY: Modified-site
            (B) LOCATION: 15
            (D) OTHER INFORMATION: /note= "Xaa = Ser or Ala"

(ix) FEATURE:
            (A) NAME/KEY: Modified-site
            (B) LOCATION: 16
            (D) OTHER INFORMATION: /note= "Xaa = Ser, Ala, serinamide,
                or alaninamide"

(xi) SEQUENCE DESCRIPTION: SEQ ID NO:108:

Xaa Arg Phe Lys Xaa Xaa Xaa Trp Ser Xaa Trp Ser Xaa Trp Xaa Xaa
1               5                   10                  15

(2) INFORMATION FOR SEQ ID NO:109:

(i) SEQUENCE CHARACTERISTICS:
            (A) LENGTH: 16 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa = Arg, Lys,
                alpha-N-acetyl-arginine, or
                alpha-N-acetyl-lysine"

(ix) FEATURE:
            (A) NAME/KEY: Modified-site
            (B) LOCATION: 5
            (D) OTHER INFORMATION: /note= "Xaa = Gln or Ala"

(ix) FEATURE:
            (A) NAME/KEY: Modified-site
            (B) LOCATION: 6
            (D) OTHER INFORMATION: /note= "Xaa = Asp or Ala"

(ix) FEATURE:
            (A) NAME/KEY: Modified-site
            (B) LOCATION: 10
            (D) OTHER INFORMATION: /note= "Xaa = His or Pro"

(ix) FEATURE:
            (A) NAME/KEY: Modified-site
            (B) LOCATION: 13
            (D) OTHER INFORMATION: /note= "Xaa = His or Pro"

(ix) FEATURE:
            (A) NAME/KEY: Modified-site
            (B) LOCATION: 15
            (D) OTHER INFORMATION: /note= "Xaa = Ser or Ala"

(ix) FEATURE:
            (A) NAME/KEY: Modified-site
            (B) LOCATION: 16
            (D) OTHER INFORMATION: /note= "Xaa = Ser, Ala, serinamide,
                or alaninamide"

(xi) SEQUENCE DESCRIPTION: SEQ ID NO:109:

Xaa Arg Phe Lys Xaa Xaa Gly Trp Ser Xaa Trp Ser Xaa Trp Xaa Xaa
1               5                   10                  15

(2) INFORMATION FOR SEQ ID NO:110:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Arg, Lys,
            alpha-N-acetyl-arginine, or
            alpha-N-acetyl-lysine"

(ix) FEATURE:
        (A) NAME/KEY: Modified-site
        (B) LOCATION: 5
        (D) OTHER INFORMATION: /note= "Xaa = Gln or Ala"

(ix) FEATURE:
        (A) NAME/KEY: Modified-site
        (B) LOCATION: 6
        (D) OTHER INFORMATION: /note= "Xaa = Asp or Ala"

(ix) FEATURE:
        (A) NAME/KEY: Modified-site
        (B) LOCATION: 7
        (D) OTHER INFORMATION: /note= "Xaa = Gly or
            delta-amino-valeric acid"

(ix) FEATURE:
        (A) NAME/KEY: Modified-site
        (B) LOCATION: 10
        (D) OTHER INFORMATION: /note= "Xaa = His or Pro"

(ix) FEATURE:
        (A) NAME/KEY: Modified-site
        (B) LOCATION: 12
        (D) OTHER INFORMATION: /note= "Xaa = Ser or Ala"

(ix) FEATURE:
        (A) NAME/KEY: Modified-site
        (B) LOCATION: 13
        (D) OTHER INFORMATION: /note= "Xaa = Ser, Ala, serinamide,
            or alaninamide"

(xi) SEQUENCE DESCRIPTION: SEQ ID NO:110:

```
Xaa Arg Phe Lys Xaa Xaa Xaa Trp Ser Xaa Trp Xaa Xaa
1               5                   10
```

(2) INFORMATION FOR SEQ ID NO:111:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Arg, Lys,
            alpha-N-acetyl-arginine, or
            alpha-N-acetyl-lysine"

(ix) FEATURE:
        (A) NAME/KEY: Modified-site
        (B) LOCATION: 5
        (D) OTHER INFORMATION: /note= "Xaa = Gln or Ala"

(ix) FEATURE:
        (A) NAME/KEY: Modified-site

```
        (B) LOCATION: 6
        (D) OTHER INFORMATION: /note= "Xaa = Asp or Ala"

(ix) FEATURE:
        (A) NAME/KEY: Modified-site
        (B) LOCATION: 10
        (D) OTHER INFORMATION: /note= "Xaa = His or Pro"

(ix) FEATURE:
        (A) NAME/KEY: Modified-site
        (B) LOCATION: 12
        (D) OTHER INFORMATION: /note= "Xaa = Ser or Ala"

(ix) FEATURE:
        (A) NAME/KEY: Modified-site
        (B) LOCATION: 13
        (D) OTHER INFORMATION: /note= "Xaa = Ser, Ala, serinamide,
            or alaninamide"

(xi) SEQUENCE DESCRIPTION: SEQ ID NO:111:

Xaa Arg Phe Lys Xaa Xaa Gly Trp Ser Xaa Trp Xaa Xaa
1               5                   10

(2) INFORMATION FOR SEQ ID NO:112:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Arg, Lys,
            alpha-N-acetyl-arginine, or
            alpha-N-acetyl-lysine"

(ix) FEATURE:
        (A) NAME/KEY: Modified-site
        (B) LOCATION: 5
        (D) OTHER INFORMATION: /note= "Xaa = Gln or Ala"

(ix) FEATURE:
        (A) NAME/KEY: Modified-site
        (B) LOCATION: 6
        (D) OTHER INFORMATION: /note= "Xaa = Asp or Ala"

(ix) FEATURE:
        (A) NAME/KEY: Modified-site
        (B) LOCATION: 9
        (D) OTHER INFORMATION: /note= "Xaa = His or Pro"

(ix) FEATURE:
        (A) NAME/KEY: Modified-site
        (B) LOCATION: 12
        (D) OTHER INFORMATION: /note= "Xaa = His or Pro"

(ix) FEATURE:
        (A) NAME/KEY: Modified-site
        (B) LOCATION: 14
        (D) OTHER INFORMATION: /note= "Xaa = Ser or Ala"

(ix) FEATURE:
        (A) NAME/KEY: Modified-site
        (B) LOCATION: 15
        (D) OTHER INFORMATION: /note= "Xaa = Ser, Ala, serinamide,
            or alaninamide"

(xi) SEQUENCE DESCRIPTION: SEQ ID NO:112:

Xaa Arg Phe Lys Xaa Xaa Trp Ser Xaa Trp Ser Xaa Trp Xaa Xaa
1               5                   10                  15
```

-continued (2) INFORMATION FOR SEQ ID NO:113:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Arg, Lys,
            alpha-N-acetyl-arginine, or
            alpha-N-acetyl-lysine"

(ix) FEATURE:
        (A) NAME/KEY: Modified-site
        (B) LOCATION: 5
        (D) OTHER INFORMATION: /note= "Xaa = Gln or Ala"

(ix) FEATURE:
        (A) NAME/KEY: Modified-site
        (B) LOCATION: 6
        (D) OTHER INFORMATION: /note= "Xaa = Asp or Ala"

(ix) FEATURE:
        (A) NAME/KEY: Modified-site
        (B) LOCATION: 9
        (D) OTHER INFORMATION: /note= "Xaa = His or Pro"

(ix) FEATURE:
        (A) NAME/KEY: Modified-site
        (B) LOCATION: 11
        (D) OTHER INFORMATION: /note= "Xaa = Ser or Ala"

(ix) FEATURE:
        (A) NAME/KEY: Modified-site
        (B) LOCATION: 12
        (D) OTHER INFORMATION: /note= "Xaa = Ser, Ala, serinamide,
            or alaninamide"

(xi) SEQUENCE DESCRIPTION: SEQ ID NO:113:

Xaa Arg Phe Lys Xaa Xaa Trp Ser Xaa Trp Xaa Xaa
1                 5                    10